United States Patent [19]

Ueno et al.

[11] Patent Number: 5,225,439
[45] Date of Patent: Jul. 6, 1993

[54] PROSTAGLANDINS E AND ANTI ULCERS CONTAINING SAME

[75] Inventors: Ryuzo Ueno, Nishinomiya; Ryuji Ueno, Kyoto; Ichie Kato, Kawanishi; Tomio Oda, Itami, all of Japan

[73] Assignee: K.K. Ueno Seiyaku Oyo Kenkyujo, Osaka, Japan

[21] Appl. No.: 681,031

[22] Filed: Apr. 5, 1991

Related U.S. Application Data

[63] Continuation of Ser. No. 460,830, Sep. 12, 1989, abandoned, which is a continuation-in-part of Ser. No. 149,445, Jan. 28, 1988, abandoned.

[30] Foreign Application Priority Data

Jan. 28, 1987 [JP] Japan .................................. 62-18820
Mar. 18, 1987 [JP] Japan .................................. 62-65352

[51] Int. Cl.$^5$ .................. C07C 177/00; A61K 31/557
[52] U.S. Cl. ..................................... 514/530; 514/573; 560/121; 562/503
[58] Field of Search ........................ 500/121; 562/503; 514/530, 573

[56] References Cited

U.S. PATENT DOCUMENTS 3,830,578 9/1974 Samuelsson .......................... 560/14
5,166,174 11/1992 Ueno .................................. 514/530

Primary Examiner—Robert Gerstl
Attorney, Agent, or Firm—Sughrue, Mion, Zinn Macpeak & Seas

[57] ABSTRACT

The novel 13, 14-dihydro-15-keto prostaglandins E of the invention have remarkable preventive effects against ulcers. Further, the novel 13,14-dihydro-15-keto-prostaglandins E of the invention have an advatage that they have none of side effects which prostaglandin E intrinsically has, or can remarkably reduce such effects of the prostaglandin E. Therefore, the novel 13, 14-dihydro-15-keto prostaglandins E of the invention are effective for animal and human use for treatment and prevention of ulcers, such as duodenal ulcer and gastric ulcer.

22 Claims, 57 Drawing Sheets

PROSTAGLANDINS E AND ANTI ULCERS CONTAINING SAME

This is a continuation of application Ser. No. 07/460,830 filed Sep. 12, 1989, now abandoned which is a continuation-in-part of application Ser. No. 07/149,445 filed Jan. 28, 1988, now abandoned.

BACKGROUND OF THE INVENTION

The present invention relates to a novel type of prostaglandin E and ulcer preventive agents containing the same.

Prostaglandin is a generic term for various prostanoic acids and is classified into various groups, such as E, F, A, B, C, D, and H, according to the manner in which keto and/or hydroxyl groups are introduced in five-membered ring portions. Prostaglandins will stimulate the uterine muscle and, in addition, they have various physiological and pharmacological actions, such as vasodilation, inhibition of platelet aggregation, and inflammatory action.

Prostaglandin E (hereinafter referred to as PGE), as a substance with a five-membered ring structure, has a group represented by:

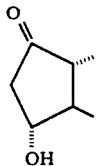

Broadly, there are known two types of PGE, namely, $PGE_1$ in which the carbon-carbon bond at the 5- and 6-positions ($C_5$-$C_6$ bond) is a single bond:

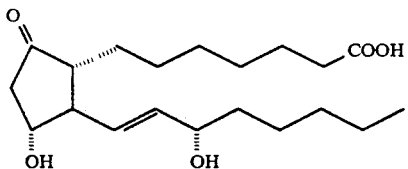

and $PGE_2$ in which the $C_5$-$C_6$ bond is a double bond:

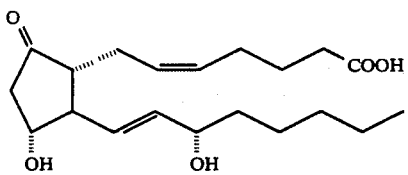

$PGE_2$, for example, is known as having antiulcer activity on one hand, but on the other hand it has such actions as uterine contraction, intestine contraction, and vasodilation; further it is recognized as having side effects, such as severe alvine flux. Therefore, it is unsuitable or impossible to use $PGE_2$ as antiulcers.

Whilst, it has been recognized that in human or animal metabolites there are present free substances similar to prostaglandin E in which $C_{13}$-$C_{14}$ bond is saturated and in which the carbon at the 15-position forms a carbonyl group. These substances, or species of 13,14-dihydro-15-keto prostaglandin E are:

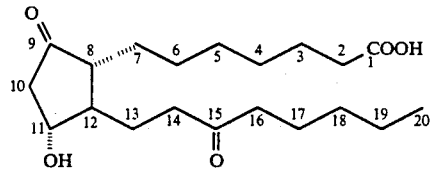

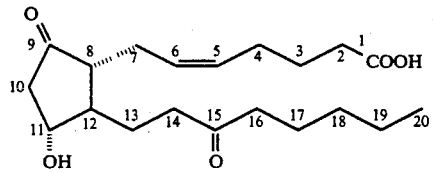

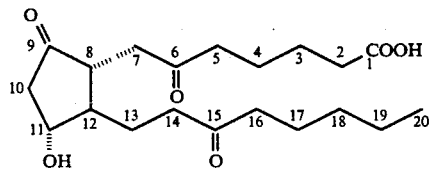

These corresponds to $PGE_1$, $PGE_2$, and 6-keto $PGE_1$ respectively, and they are known as substances which are naturally metabolically produced in vivo through enzymic metabolic reaction. These species of 13,14-dihydro-15-keto PGE have been reported as physiologically and pharmacologically inactive metabolic products which exhibit little of the various physiological activities of PGE (Acta Physiologica Scandinavica, Vol 66, p. 509~, 1966), and has been regarded as such. Therefore, little has been expected of the pharmacological effect of these metabolic products and compounds similar to them.

SUMMARY OF THE INVENTION

While evaluating the pharmacological activities of derivatives of the aforesaid metabolic products, the present inventor found that the derivatives, such as esters salts, one having a protective group on the carboxyl group as well as one having free carboxyl group, one having substituent groups at the 16-, 17-, 19-, and/or 20-positions, one in which the carbon at the 11-position has a methyl group or a hydroxymethyl group, and one having an alkoxy group at the terminal of a ω chain, exhibited antiulcer activities, and that they showed no trace or a significantly reduced degree of such central and peripheral physiological effects as were simultaneously appeared as a side effect and were inherent to known or common PGE which had been recognized as having antiulcer activities.

DETAILED DESCRIPTION OF THE INVENTION

Figure 1:
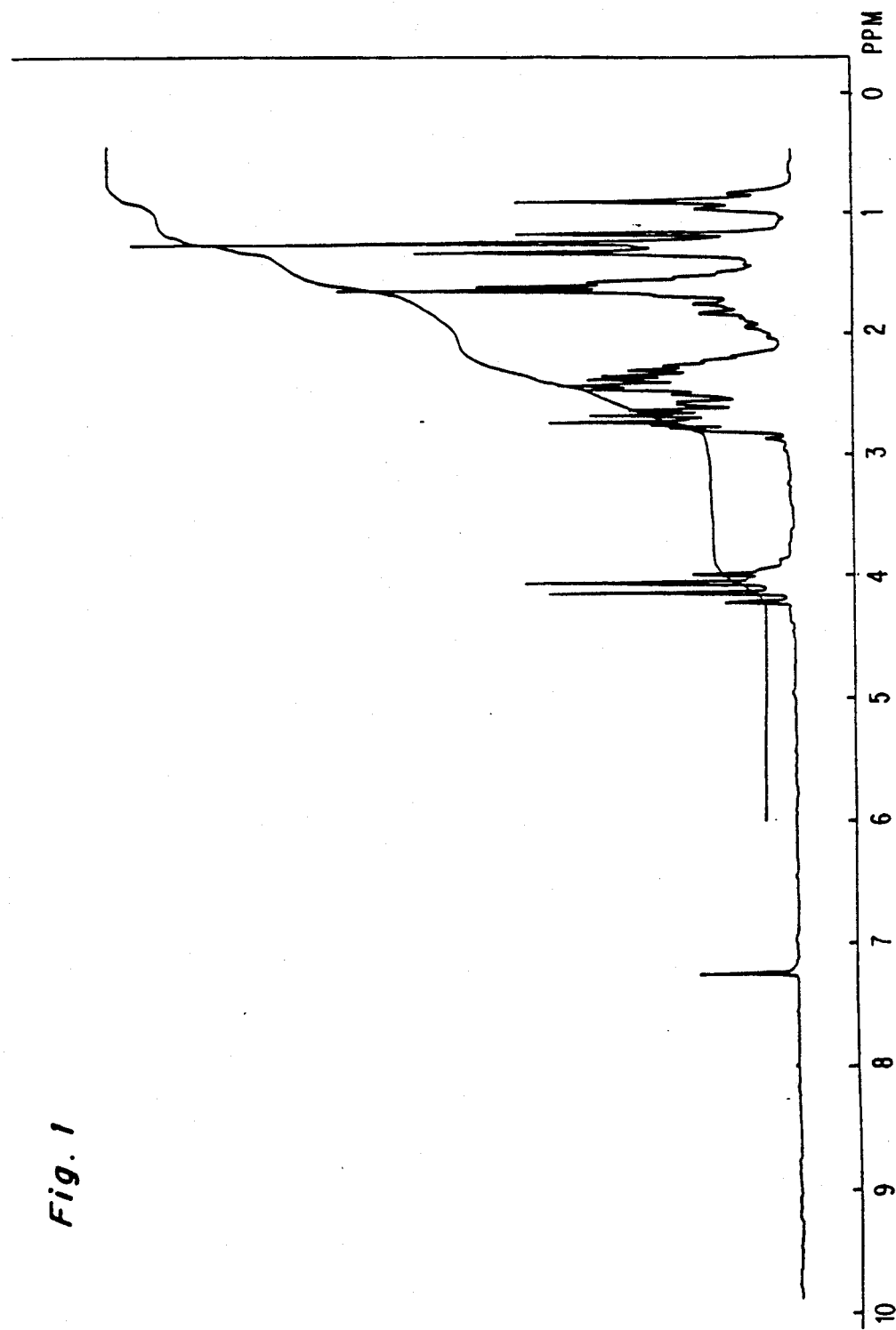
FIG. 1-57 show n.m.r. spectra of the prostagrandins obtained in the present invention.

The present invention relates to 13,14-dihydro-15-keto prostaglandins E represented by the general formula:

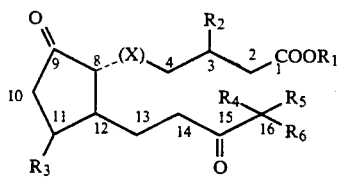

(in which
X represents:

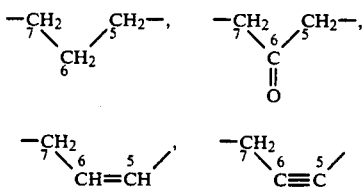

$R_1$ represents: hydrogen atom, physiologically acceptable salts, physiologically acceptable protective group $C_1$-$C_4$ alkyl, benzyl, hydroxyalkyl, or alkoxyalkyl group;

$R_2$ represents: hydrogen atom or a methyl group;

$R_3$ represents: a hydroxyl, methyl, or hydroxymethyl group;

$R_4$ and $R_5$, each represents: hydrogen atom, or a methyl, hydroxyl group, or halogen atom (provided that $R_4$ and $R_5$ may be identical with or different from each other); and $R_6$ represents: $C_1$-$C_9$ alkyl group which may have a branch or a double bond, or $C_1$-$C_9$ alkyl group having an alkoxy-substituent group, in which $C_2$-$C_3$ bond may be a double bond)

and antiulcers containing the same.

In the general formula (I), (X)— has any of the above shown structures.

A compound where —(X)— is

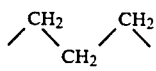

is a prostaglandin belonging to the PGE$_1$ group, and a compound where —(X)— is

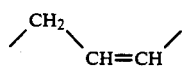

is a prostaglandin to the PGE$_2$. Therefore, a compound where —(X)— is

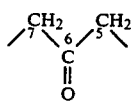

is a prostaglandin to the 6-keto PGE$_1$.

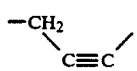

is a prostaglandins E belonging to 5,6-dehydro-PGE$_2$.

$R_1$ in the general formula (I) represents hydrogen atom an alkyl, benzyl, hydroxyalkyl, alkoxyalkyl group having 1-4 carbon atoms, a physiologically acceptable salt residue, or a physiologically acceptable protective group.

The alkyl group may be a cycloalkyl group, e.g., a cyclopropyl group, a cyclopentyl group, or an alkyl group having a side chain or a double bond structure, such as, for example, isopropyl group, tert-butyl group, or allyl group. Preferably, however, it is a straight chain saturated alkyl group, or more specifically a methyl or ethyl group. Examples of the hydroxyalkyl group are hydroxyethyl and hydroxyisopropyl groups. Or, it may be an alkoxyalkyl group, such as methoxyethyl group or alkoxyalkyl group.

$R_2$ represents hydrogen or a methyl group, in which the carbons at the 2- and 3-positions may have a double bond.

The carboxyl group may be free, a salt residue, or a protective group. As the salt may be a physiologically acceptable salt, for example, alkaline metal salt such as sodium salt, potassium salt and the like; alkaline earth metal salt such as calcium, magnesium salt; ammonium salt; a physiologically acceptable amine salt such as salt of methylamine, dimethylamin, cyclopentylamine, benzylamine, pyperidine, monoethanolamine, diethanolamine, monomethylmonoethanolamine, tromethamine, lysine, tetraalkylammonium and the like. The protective group may include alkylsilicon such as trimethylsilicon, triethylsilicon and the like; tetrahydroxypyran and the like.

$R_3$ represents a hydroxyl, methyl, or ethyl group, in which the steric configuration relating to the carbon at the 11-position may take the form of $\alpha$, $\beta$, or a mixture thereof. Especially, one in which such steric configuration takes the $\alpha$-position.

$R_4$ and $R_5$ are independently hydrogen, methyl or hydroxyl groups, or halogens. $R_4$ and $R_5$ may be identical or different, but preferably at least one of them is a methyl group or a halogen, or more particularly fluorine atom.

$R_6$ is a saturated or unsaturated $C_1$~$C_9$ alkyl group, or a $Cl_1$~$C_9$ alkyl group having an alkoxy-substituent group. For the alkyl group, one having $C_4$~$C_9$ is particularly preferred. For such $C_4$~$C_9$ alkyl group, a straight-chain alkyl group or an alkyl group having one methyl group branch is particularly preferred. In the alkyl group having an alkoxy substituent, the alkoxy group is preferably methoxy or ethoxy, and for the alkyl group, one having $C_2$~$C_6$ is suitable.

Typical examples of the compounds according to the invention are:

13,14-dihydro-15-keto-PGE$_2$ alkyl ester;
13,14-dihydro-15-keto-PGE$_2$ cycloalkyl ester;
13,14-dihydro-15-keto-PGE$_2$ hydroxy alkyl ester;
13,14-dihydro-15-keto-PGE$_2$ benzyl ester;
13,14-dihydro-15-keto-PGE$_1$ alkyl ester;
13,14-dihydro-6,15-diketo-PGE$_1$ alkyl ester;
13,14-dihydro-15-keto-18-methoxy-19, 20-dinor-PGE$_2$ or alkylester;
13,14-dihydro-15-keto-18-methoxy-PGE$_2$ or alkylester;
13,14-dihydro-15-keto-$\Delta^2$-PGE$_2$ or alkyl ester;
13,14-dihydro-15-keto-20-methoxy-$\Delta^2$-PGE$_2$ or alkyl ester;
13,14-dihydro-15-keto-3R,S-methyl-PGE$_2$ or alkyl ester;
13,14-dihydro-15-keto-3R,S-methyl-20-methoxy-PGE$_2$ or alkyl ester;
13,14-dihydro-15-keto-11-dehydroxy-11R-methyl-PGE$_2$ or alkyl ester;

13,14-dihydro-15-keto-16R,S-fluoro-11-dehydroxy-11R-methyl-PGE$_2$ or alkyl ester;
13,14-dihydro-15-keto-16R,S-hydroxy-PGE$_2$ or alkyl ester;
13,14-dihydro-15-keto-16R,S-fluoro-PGE$_2$ or alkyl ester;
13,14-dihydro-15-keto-16R,S-methyl-PGE$_2$ or alkyl ester;
13,14-dihydro-15-keto-16,16-dimethyl-PGE$_2$ or alkyl ester;
13,14-dihydro-15-keto-16,16-dimethyl-20-methoxy-PGE$_2$ or alkyl ester;
13,14-dihydro-15-keto-17S-methyl-PGE$_2$ or alkyl ester;
13,14-dihydro-15-keto-19-methy-PGE$_2$ or alkyl ester;
13,14-dihydro-15-keto-20-isopropylidene PGE$_2$ or alkyl ester;
13,14-dihydro-15-keto-20-ethyl-PGE$_2$ or alkyl ester;
13,14-dihydro-15-keto-20-ethyl-11-dehydroxy-11R-methyl-PGE$_2$ or alkyl ester;
13,14-dihydro-15-keto-20-n-propyl-PGE$_2$ or alkyl ester;
13,14-dihydro-15-keto-20-ethyl-PGE$_1$ or alkyl ester;
13,14-dihydro-6,15-diketo-16R,S-fluoro-PGE$_1$ or alkyl ester;
13,14-dihydro-6,15-diketo-16R,S-fluoro-11-dehydroxy-11R-methyl-PGE$_1$ or alkyl ester;
13,14-dihydro-6,15-diketo-16R,S-methyl-PGE$_1$ or alkyl ester;
13,14-dihydro-6,15-diketo-16,16-dimethyl-PGE$_1$ or alkyl ester;
13,14-dihydro-6,15-diketo-19-methyl-PGE$_1$ or alkyl ester;
13,14-dihydro-6,15-diketo-20-methyl-PGE$_1$ or alkyl ester;
13,14-dihydro-6,15-diketo-11-dehydroxy-11R-methyl-PGE$_1$ or alkyl ester; and
13, 14-dihydro-6,15-diketo-11-dehydroxy-11R-hydroxymethyl PGE$_1$ alkyl ester.
13,14-dihydro-15-keto-20-methyl-PGE$_1$ or alkyl ester;
13,14-dihydro-15-keto-$\Delta^2$-PGE$_1$ or alkyl ester
13,14-dihydro-15-keto-16R,S-fluoro-20-methyl-PGE$_2$ or alkyl ester,
13,14-dihydro-15-keto-16,16-difluoro-PGE$_2$ or alkyl ester,
13,14-dihydro-15-keto-5,6-dehydro-20-methoxy-PGE$_2$ or alkyl ester.

The prostaglandins E of the present invention can be synthesized in such way as shown illustrated in Examples and the accompanying synthesis charts (I)~(XXI). That is, a commercially available (−) or (±) Corey lactone (1) may be used as the starting material, and then collins-oxidized to give an aldehyde (2); the aldehyde (2) may be reacted with dimethyl (2-oxoalkyl) phosphonate to give an α, β-unsaturated ketone 3), which is then reduced. The resulting unsaturated ketone (4) is protected with respect to its carbonyl group. A hydroxyl group after protective group, p-phenylbenzoate being removed is protected with THP. After lactone (7) is reduced to lactol (8), an α chain is introduced by Wittig reaction.

The PGE$_2$ in which —(X)— is

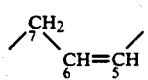

can be obtained by reducing the lactone (7) to lactol (8), then subjecting the lactol (8) to reaction with (4-carboxybutyl) triphenylphosphonium bromide.

The PGE$_1$ in which —(X)— is

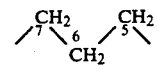

can be obtained through reduction of the PGE$_2$.

The 6-keto PGE$_1$ in which —(X)— is

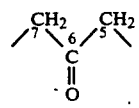

can be obtained by adding bromine or iodine atom on C$_5$–C$_6$ double bond of

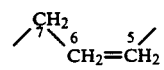

using N-bromosuccinimide or iodine atom, and simultaneously cyclizing the C$_6$-carbon and the hydroxyl group at the 9-position to give a bromide or a iodide, and then the bromide or iodide is treated with DBU to ketonize the carbon at the 6-position.

5,6-Dehydro-PGE$_2$s in which (X) is:

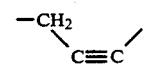

may be prepared by treating copper enolate which can be prepared by adding a monoalkyl-copper complex or a dialkylcopper complex of following formula on 1,4-position of 4R-t-butyldimethylsilyloxy-2-cyclopentene-1-on (167):

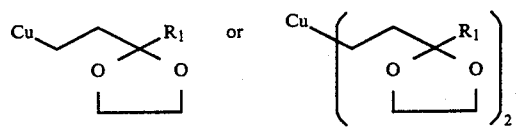

with 6-carboalkoxy-1-iodo-2-hexine or its derivatives.

The compound in which R$_3$ is a methyl group can be obtained by Jones- oxidizing the hydroxyl group at the 9-position in 11-tosylate to form an PGA-type, then subjecting it to the action of a dimethyl copper complex. Alternatively, the compound can be synthesized by protecting the carbonyl group of the saturated ketone (4) obtained by reduction of the unsaturated ketone (3), turning into tosylate the alcohol obtained after release of P-phenylbenzoyl group, treating the tosylate with DBU, turning the resulting unsaturated lactone into lactol, introducing an o-chain into the lactol through Wittig reaction, oxidizing the resulting alcohol (9-position) to form an PGA-type, to which a dimethyl copper complex is reacted, then introducing a methyl group into the 11-position.

The compound in which R$_3$ is hydroxymethyl group can be obtained by applying benzophenone as a photosensitizer to the A-type prostaglandin (PGA) obtained in manner as above described, then adding methanol.

For the synthesis of the PGE in which either $R_4$ or $R_5$ is a group other than hydrogen atom, and of the PGE in which $R_6$ is other than n-butyl, the compound used in obtaining the α, β-unsaturated ketone (3), namely, dimethyl (2-oxoalkyl) phosphonate should be correspondingly replaced by other suitable compound. For example, where $R_4$ is fluorine atom, $R_6$ is n-butyl, and $R_5$ is hydrogen atom, dimethyl (3-fluoro-2-oxopeptyl) phosphonate may be used. Where $R_4$ and $R_5$ are hydrogen atom, and $R_6$ is an isopentyl group, dimethyl (6-methyl-2-oxoheptyl) phosphonate may be used.

The synthesis of the compounds of the invention is not limited to the foregoing. For protection of individual functional groups and for oxidation-reduction, suitable procedures may be applied as required.

The prostaglandins E of the present invention may be used as medicines for animal and human. Usually, they are used systemically or locally in various ways, such as oral administration, intravenous injection, and subcutaneous injection. The dosage varies according to the subject for administration, animal or human, age, weight, symptoms, efficacy of treatment, method of administration, and time of treatment.

Where the compounds of the invention are used in the form of solid compositions for oral administration, they include tablets, powder, and granules. In such solid composition, one or more active substances are mixed with at least one kind of inactive diluent, for example, lactose, mannitol, grape sugar, hydroxypropyl cellulose, crystallite cellulose, starch, polycinyl pyrrolidone, or magnesium metasilicoaluminate. Such composition may, according to the conventional procedure, contain some additive other than said inactive diluent, e.g., lubricant, such as magnesium stearate, decomposer, such as calcium fibrogluconate, etherified cyclodextrin, such as α, β- or γ-cyclodextrin, dimethyl-α-, dimethyl-β-, or hydroxypropyl-β-cyclodextrin, branched cyclodextrin, such as glucosyl-, or maltosylcyclodextrin, or stabilizer, such as formylated cyclodextrin, sulfur-containing cyclodextrin, misoprotol, or phospholipid. The aforesaid cyclodextrins may provide increased stability. The stability may be improve by forming liposome with a phospholipid.

Tablets or pills may be coated or covered with a gastrically soluble material, such as refined sugar, gelatin, hydroxypropyl cellulose, or hydroxypropyl methyl cellulose phthalate, or a film of such matereial in one or more layers. Also, they may be encapsulized with an absorbable material, such as gelatin.

In the form of liquid compositions for oral administration, the compounds of the invention include medically allowable emulsions, solutions, suspensions, syrups, and elixers. They may contain inactive diluents conventionally used, such as, for example, refined water, ethanol, and coconut oil. In addition to such inactive diluent, the compositions may contain wetting agents, auxiliary agents, such as suspensions, edulcorants, flavors, aromatics, and preservatives. The liquid compositions may be encapsulated as such in soft capsules and the like.

Other forms of compositions for oral administration include sprays prepared per se according to the usual known procedures which may contain one or more kinds of active substances.

The compounds of the invention in the form of injections for non-oral administration include sterile aqueous and non-aqueous solvents, suspensions, emulsions, and detergents.

The aqueous solutions and suspensions include, for example, distilled water and physiologic salt solution. The non- aqueous solutions and suspensions include, for example, vegetable oils, such as polyethylene glycol and olive oil, alcohols, such as ethanol, and Polysorbate. Such composition may contain auxiliaries, such as presevatives, wetting agents, emulsions, and dispersions. These compositions are sterilized by being passed through bacteria retaining filters or by incorporation of bactericides, or by light irradiation. It is also possible to first prepare a germ-free solid composition and dissolve same in a germ-free injection solvent before using it as an injection.

EXAMPLE 1

1) Preparation of Dimethyl (3R,S-Fluoro-z-oxoheptyl)phosphonate:

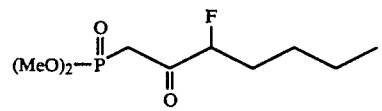

1-1 Methyl 2-R,S-Fluorocaproate

Methyl 2R,S-bromocaproate (40 g) waŠ added to anhydrous potassium fluoride (23 g) in acetoamide (23 g) kept at 105° C. The mixture was vigorously stirred at 105° C. for 6h. A crude product obtained after the usual work-up, was distilled under reduced pressure. Yield 20 g (71%), b.p. 66° C./20 mmHg.

1-2 Dimethyl (3R,S-Fluoro-2-oxoheptyl) phosphonate

Dimethyl methylphosphonate (8.38 g) was dissolved in dry THF (200 ml), and the resulting solution was cooled to −78° C. n-Butyl lithium (1.6-M, 42ml) was added dropwise to the solution, and 10 min later 10 ml of the THF solution of methyl 2R, S-fluorocaproate (20 g) was added dropwise. After the addition, the reaction solution was stirred at −78° C. for 45 min, and then at room temperature for 45 min. A crude product obtained after the usual work-up was chromatographed (hexane:ethyl acetate=1:1). Yield 5.04 g (62%).

2) Preparation of Dimethyl (3R,S-Methyl-2-oxoheptyl)phosphonate

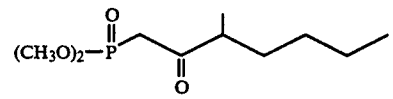

2-1 Methyl 2R,S-Methylcaproate

A THF (50 ml) solution of dissopropylamine (12.9 ml) was cooled to −78° C. and n-BuLi (1.6-M, 57,6 ml) was added dropwise over 1.5 h (preparation of LDA). A solution of methyl caproate (10 g) in THE (50 ml) was added dropwise to the prepared LDA over 50 min. After stirring for 2 h, a solution of methyl iodide (6.2 ml) in THF (20 ml) was added dropwise over 40 min. The reaction solution was stirred at −78° C. for 1 h, and then at room temperature overnight.

After the usual work-up, the resulting residue was distilled under reduced pressure, and thus 3.15 g of methyl 2R,S-methylcaproate (b.p. 44° C./10 mmHg) was obtained.

2-2 Dimethyl (3-Methyl-2-oxoheptyl) phosphonate

To a THF (120 ml) solution of dimethyl methylphosphonate (5.04 g) at −60° C. was added dropwise n-BuLi (1.6-M, 25.4 ml), and the mixture was stirred for 30 min. A THF (50 ml) solution of methyl 2R,S-methylcaproate (3.15 g) was added dropwise. The mixture was stirred at −60° C. for 1 h, then at room temperature for 1.5 h, and thereafter acetic acid (2 ml) was added at 0° C. A crude product obtained after the usual work-up was chromatographed (hexane:ethyl acetate=1:5). Yeild: 2,85 g (58%).

3) Preparation of Dimethyl (6-Methyl-2-oxoheptyl)phosphonate

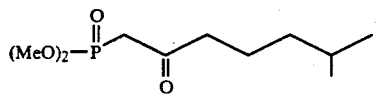

3-1 Methyl 5-methylcaproate

Sodium ethoxide was prepared from sodium metal (9.1 g) and freshly distilled absolute ethanol (250 ml). Diethyl malonate (63.5 g) was added to sodium ethoxide in ethanol, and the mixture was stirred at 60°–70° C. for 50 min. Isoamyl bromide (60 g) was added, and the reaction mixture was heated under reflux overnight. After the usual work-up, the resulting crude product was distilled under reduced pressure to give diethyl isoamylmalonate. Yield: 71.7 g (78%).

Diethyl isoamylmalonate (71.7 g) was added to a 50% aqueous solution of sodium hydroxide (60 ml), and the mixture was heated under reflux for 6 h. After cooling, the mixture was extracted with ether; the water layer was acidified with hydrochloric acid and, after saturation with sodium chloride, was extracted with ether. The extracts from the acidic aqueous layer were concentrated under reduced pressure to give isoamylmalonic acid. The obtained dicaboxylic acid was heated at 180° C. for 2 h. After distillation under reduced pressure, 5-mehyl-caproic acid was obtained. Yield: 30 g (75%), b.p. 107°–108° C./11 mmHg.

The 5-methyl-caproic acid (30 g) was treated with methanol (600 ml) and sulfuric acid (3 ml), and thus methyl 5-methylcaproate was obtained. Yield: 27 g (81%).

3-2 Dimethyl (6-Methyl-2-oxoheptyl)phosphonate

Dimethyl (6-methyl-2-oxoheptyl)phosphonate was prepared from methyl 5-methylcaproate and dimethyl methylphosphonate according to the known method.

4) Preparation of Dimethyl (3,3-Dimethyl-7-methoxy-2-oxoheptyl)phosphonate

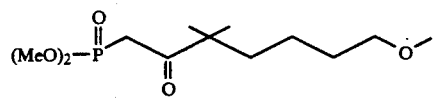

4-1 Methyl 2,2-Dimethyl-6-methoxy caproate 1,4-Butanediol (50 g) was treated with sodium hydride (NaH) (60%, 26,6 g) and methyl iodide (250 g) in THF (150 ml) to give 4-methoxy-1-butanol. Yield: 21.8 g (38%), b.p. 135/760 mmHg.

4-Methoxyl-1-butanol (8.49 g) was treated with p-toluenesulfonyl chloride and 4-dimethylaminopyridine in methylene chloride (150 ml) to give 4-methoxy-butyl-1-tosylate. Yield: 16.1 g (77%).

4-Methoxy-butyl-1-tosylate (16.1 g), together with NaI (18.7 g), was agitated in acetone (80 ml) at room temperature for 3 h to give 1-iodo-4-methoxy-butane (9.05 g, 68%).

To N-isopropylcyclohexylamine (5.96 ml) in THF (30 ml) was added dropwise n-BuLi (1,6-M, 22.7 ml) at −78° C., and the mixture was stirred for 30 min, to which a THF (5 ml) solution of methyl isobutyrate (3.43 g) was added, and stirred at −78° C. for 45 min. Then, a HMPA (6.3 ml) solution of 1-iodo-4-methoxy-butane (9.05 g) was added to the mixture, and stirred at room temperature for 1 h to give methyl 2,2-dimethyl-6-methoxycaproate (4.81 g, 85%) after usual work-up.

4-2 Dimethyl (3,3-Dimethyl-7-methoxy-2-oxoheptyl)phosphonate

Prepared from methyl 2,2-dimethyl-6-methoxycaproate and dimethyl methylphosphonate according to the known method.

5) Preparation of Dimethyl (3-(2-Tetrahydropyranyl)oxy-2-oxoheptyl)phosphonate

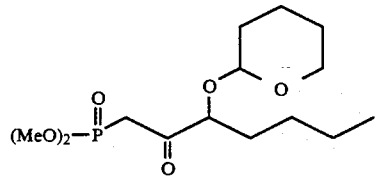

5-1 Methyl 2-(2-Tetrahydropyranyl)oxycaproate

A tetrahydropyranyl ether was prepared from commercially available methyl 2R,S-hydroxycaproate according to the usual method. (Yield 71%).

5-2 Dimethyl (3-(2-Tetrahydropyranyl)oxy-2-oxoheplyl)phosphonate

Prepared from methyl 2-(2-tetrahydropyranyl) oxycaproate and dimethyl methylphoriate according to the known method. (Yield 48%).

6) Preparation of Dimethyl(4S-methyl-2-oxoheptyl)phosphonate

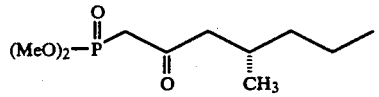

6-1 Ethyl 3S-Methyl-caproate

Sodium ethoxide was prepared from sodium metal (7.61 g) and absolute ethanol (200 ml). Diethyl malonate (50.3 ml) was added dropwise to the ethanol containing sodium ethoxide. After heating to 80° C., 2-bromopentane (50 g) was added and the mixture was reflued for 24 h. Diethyl (2-pentyl)malonate (62.7 g) was obtained after the usual work-up. Diethyl (2-pentyl)malonate was added to a 50% potassium hydroxide solution and the mixture was heated for 3 h while water/ethanol being distilled off. After cooling, the solution was acidified with concentrated hydrochloric acid. Then, the solution was extracted with ethyl acetate. The extract was concentrated under reduced pressure, and the resulting product was heated to 180° C. until bubbling ceased. After distillation, colorless 3R,S-methy-caproic acid was obtained. Yield: 27.7 g (35%), b.p. 200° C./760 mmHg.

3R,S-Methyl-caproic acid was dissolved in ehanol 160 ml) and cinchonidine (64 g) was added and dissolved under heating.

The solution was concentrated under reduced pressure, and the resulting salt was recrystallized from 60% methanol six times to give needle crystals. Yield: 14.4 g, $(\alpha)_D^{31} = -3.3$ (C=13.6 (benzene) literature value—3.1 )

3S-Methyl-caproic acid (3.94 g) was converted to the corresponding ethyl ester with using ethanol and catalytic amount of sulfuric acid. Yield: 4.04 g (84%).

6-2 Dimethyl (4S-Methyl-2-oxoheptyl)phosphonate

This compound was prepared from ethyl 3S-methyl-caproate and dimethyl methylphosphonate according to the known method.

7) Preparation of Dimethyl (3,3-Dimethyl-2-oxoheptyl)phosphonate

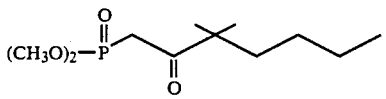

7-1 Ethyl 2,2-Dimethyl-caproate

To LDA prepared at −78° C. in the usual manner was added ethyl isobutyrate (45 g) in THF, and stirred for 1 h. A dry HMPA solution of butyl iodide (107 g) was added, and the mixture was stirred at −78° C. for 1 h and then at room temperature for additional 1 h.

A crude product obtained after the usual work-up was distilled. Yield: 50 g (75%), b.p. 68° C. / 25 mmHg.

7-2 Dimethyl(3,3-Dimethyl-2-oxoheptyl) phosphonate

Prepared from ethyl 2,2-dimethyl-caproate and dimethyl methylphosphonate according to the usual method.

8) Preparation of (3R,S-Methyl-4-carboxybutyl) triphenylphosphonium bromide

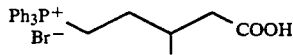

In ether (300 ml), 3-methyl-1,5-pentanediol (23.3 g) was converted to 5-acetoxy-3-methyl-1-pentanol with pyridine (16 ml) and acetyl chloride (14 ml) at 0° C. Yield: 18.4 g.

5-Acetoxy-3-methyl-1-pentanol was oxidized with Jones reagent in acetone (200 ml) at −20° C. to give 5-acetoxy-3R,S-methyl valeric acid. Yield: 8.2 g (24%).

To 5-acetoxy-3R,S-methyl valeric acid (8.2 g) was added hydrobromic acid (40 ml) and concentrated sulfuric acid (10 ml), and the mixture was agitated at 90° C. overnight. Thereafter, the solution was poured into iced water. A crude product obtained after the usual work-up was chromatographed (ethyl acetate:hexane=1.5), and thus 8.0 g of 5-bromo-3R,S-methyl valeric acid (87%) was obtained.

5-Bromo-3R,S-methyl valeric acid with triphenyl phosphine (21.5 g) was reflued in acetonitrile (100 ml) for 2 days. The reaction solution was poured into ether and the resulting precepitate was separated by filtration. Thus, (3-R,S-methyl-4-carboxybutyl)triphenylphosphonium bromide was obtained. Yield: 9.78 g (52%).

EXAMPLE 2 (See Chart I)

Preparation of 13,14-Dihydro-6,15-diketo-PGE₁ ethyl ester (15), R:Et 2-1 Preparation of 1S-2-Oxa-3-oxo-6R-(3-oxo-1-trans-octenyl)-7R-(4-phenylbenzoyl)oxy-cis-bicychlo(3, 3, 0) octane (3)

To the suspension of sodium hydride (NaH) 60%, 250 mg) in THF (40 ml) was added dropwise dimethyl(2-oxoheptyl)phosphonate, and the reaction solution was stirred for 30 min. A THF solution (40 ml) of the aldehyde (2) previously prepared by Collins oxidization of (−)-Corey lactone (1) (2 g) was added. Reaction was maintained at room temperature overnight, and then acetic acid was added. After the usual work-up, an α,β-unsaturated ketone (3) was obtained. Yield: 1.95 g (50%).

2-2 Preparation of IS-2-Oxa-3-oxo-6R-(3,3-ethylenedioxyoctanyl)-7R-(4-phenylbenzoyl)oxy-cis-bicyclo (3,3,0) octane (5)

The unsaturated ketone (3) was hydrogenated in ethyl acetate (100 ml) with using 5% paradium-carbon (100 mg) and hydrogen to give the corresponding saturated ketone (4).

The ketone (4) (1.95 g) was dissolved in toluene 150 ml), and ethylene glycol and p-toluenesulfonic acid (catalytic amount) were added. The solution was heated under reflux overnight while water produced was distilled off. After the usual work-up, ketal (5) was obtained. Yield: 1.8 g 84%).

2-3 Preparation of IS-2-Oxa-3-oxo-6R-(3,3-ethylenedioxy-1-octanyl)-7R-hydroxy-cis-bicyclo (3,3,0) octane (6)

The compound (5) (1.8 g) was dissolved in methanol (80 ml) and THF (20 ml), and after addition of potassium carbonate (0.563 g), the solution was stirred at room temperature for 7 h. A crude product obtained by a usual manner was chromatographed (ethyl acetate-hexane=1:3→1:1) to give alcohol (6). Yield: 0.95 g (82%).

2-4 Preperation of tetrahydropyranyl ether (7)

The compound (6) (0.95 g) was dissolved in dichloromethane (100 ml) and then dihydropyran (0.76 g) and p-toluene sulfonate (catalytic amount) were added. The resulting solution was stirred overnight. After the usual work-up and purification, tetrahydropyranyl ether (7) was obtained. Yield: 1.06 g (88%).

2-5 Preparation of lactol (8)

To the tetrahydropyranyl ether (7) (1.06 g) in dry toluene (30 ml) at −78° C. was added dropwise diisobutylaluminum hydride (DIBAL-H) (1.5 M, 2.3 ml) and stirred for 60 min. Lactol (8) was obtained after the usual work-up.

2-6 Preparation of 13,14-Dihydro-11-(2-tetrahydropyranyl)oxy-15,15-ethylenedioxy PGF$_{2\alpha}$ (9)

Sodium hydride (60%, 0.86 g), washed with pentane, was suspended in DMSO (50 ml), and stirred for 90 min at 60°~70° C. After the reaction solution was cooled to room temperature, (4-carboxybutyl)triphenylphosphonium bromide in DMSO was added, and agitated for 30 min, to which lactol (8) in DMSO (10ml) was added. After stirred overnight, the reaction solution was poured into ice-water, made basic with addition of 20% sodium hydroxide solution, and extracted with ether. The aqueous layer was adjusted to pH 4~5 with 4N-hydrochloric acid and extracted with ethyl acetate. The ethyl acetate layer was washed with water, then with saturated sodium chloride solution, and was dried over magnesium sulfate. Thereafter, the solvent was distilled off. Ether was added and insolubles were separated by filtration. The filtrate was concentrated under reduced pressure to give the compound (9).

2-7 Esterification of the Compound (9)

Preparation of the compound (10), R=Et

The carboxylic acid (9) was dissolved in dry acetonitrile (50 ml) and then DBU (0.48 g) and ethyl iodide (1.76 g) were added. The solution was stirred at room temperature overnight. A crude product was obtained after the usual work-up, and was column-chromatographed (ethyl acetate-hexane 1:3). Thus, 1.04 g of ethylester (10) was obtained. (Yield: 76% from (7)).

2-8 Preparation of the Compound (11)

The alcohol (10) (1.04 g) was dissolved in dry tetrahydrofuran (3.4 ml) and dry methylene chloride (26.4 ml), and after addition of NBS (0.364 g) at 0° C., the reaction solution was stirred for 5 min. A crude product was obtained after the usual work-up, and chromatographed (ethyl acetate-hexane=1:3) to give the compound (11). Yield: 0.61 g (51%).

2-9 Preparation of 13,14-Dihydro-15,15-ethylenedioxy-6-keto-11-(2-tetrahydropyranyl)oxy-PGF$_{1\alpha}$ethyl ester (13)

The bromoether (11) (0.61 g) was dissolved in dry toluene (30 ml), and then DBU (25 ml) was added. The solution was agitated at 40° C. overnight. After the end of the period, the solution was cooled with ice and 1 N-hydrochloric acid was added to acidify the solution, and agitated for 10 minutes. Subsequently, the solution was extracted with ethyl acetate. A crude product was obtained after the usual work-up, and then chromatographed (ethyl acetate-hexane=1:3→1:1) to give the compound (13). Yield: 0.332 g (61%).

2-10 Preparation of 13,14-Dihydro-15,15-ethylenedioxy-6-keto-11-(2-tetrapyranyl)oxy-PGE$_1$ ethyl ester (14)

The alcohol (13) (0.332 g) was oxidized in acetone (20 ml) at −20° C. with Jones reagent (2.67 M, 0.36 ml). A crude product obtained after the usual work-up was chromatographed (ethyl acetate-hexane=1:3) to give the compound (14). Yield: 0.198 g (58%).

2-11 Preparation of 13,14-Dihydro-6,15-diketo-PGE$_1$ ethyl ester (15)

The tetrahydropyranyl ether (14) (0.198 g) was dissolved in a mixed solvent (14 ml) of acetic acid:water:THF (4:2:1), and the solution was stirred for 1 h at 45° C. Benzene was added, and the solvent was removed under reduced pressure. The resulting crude product was chromatographed (ethyl acetate-hexane=1:3) to give 13,14-dihydro-6,15-diketo-PGE$_1$ ethyl ester (15). Yield: 0.098 g (65%).

The n. m. r. spectrum of 13,14-dihydro-6,15-diketo-PGE$_1$ ethyl ester (15) is shown in FIG. 1.

Mass (SIMS) m/z: 397 (M+H)$^{30}$, 379 ((M+H)$^{30}$−18), 287, 157, 111, 99.

EXAMPLE 3 (See Chart I)

Preparation of (±) 13,14-Dihydro-6,15-diketo-PGE$_1$ ethyl ester (15), R:Et

Preparation of the title compound was carried out using (±)-Corey lactone (1) and a similar manner to the Example 1.

Figure 2:
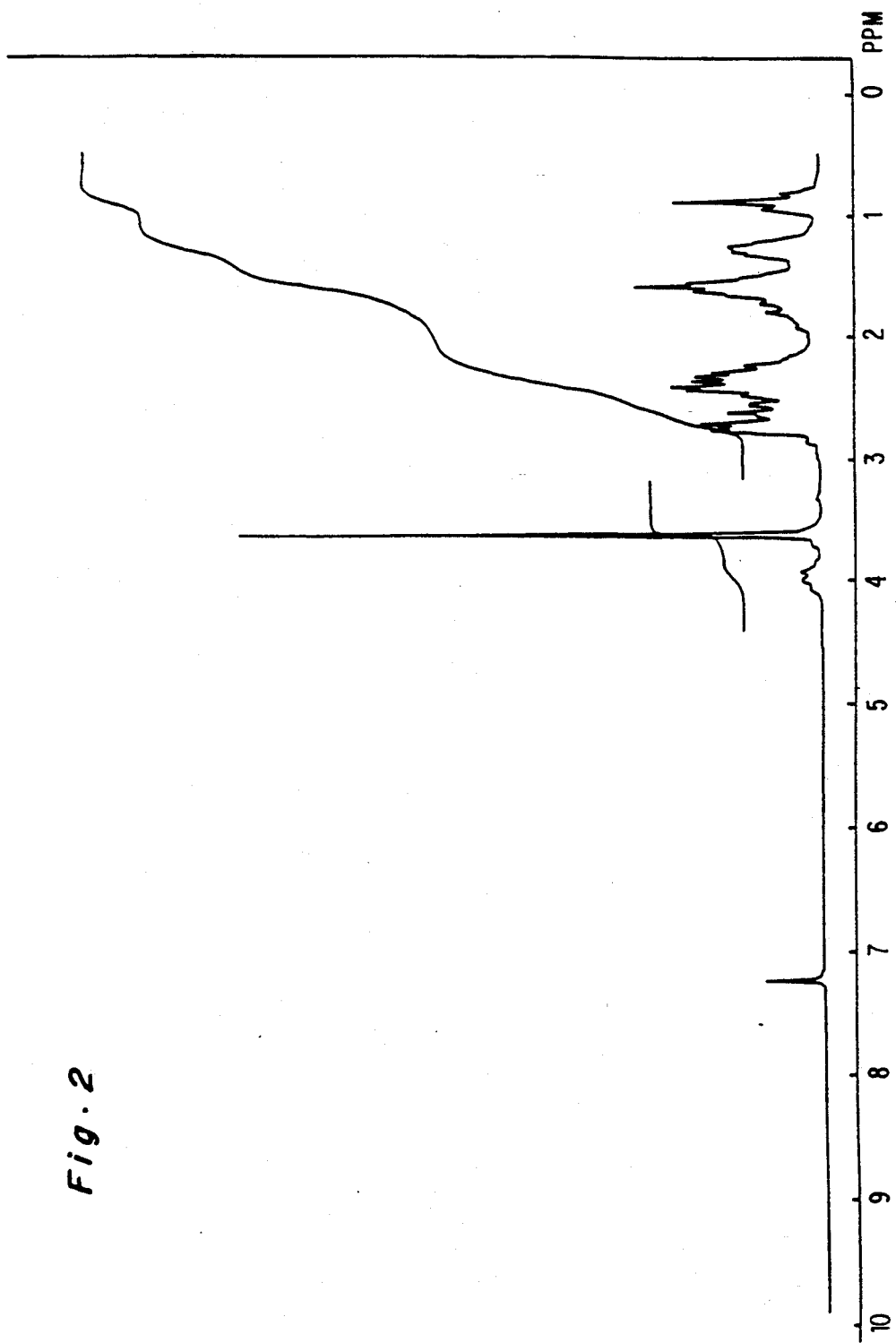

The n. m. r. spectrum of (±)-13,14-dihydro-6,15-diketo-PGE$_1$ ethyl ester (15) is shown in FIG. 2.

Mass (SIMS) m/z: 397 (M+H)$^+$, 379 ((M+H)$^{30}$−18), 287, 157, 111, 99.

EXAMPLE 4 (See Chart I)

Preparation of 13,14-Dihydro-6,15-diketo-PGE$_1$ methyl ester (15), R:Me

Preparation of the title compound was carried out in the same way as in Examples 2 and 3, except that (−)-Corey lactone (1) was used, and that the carboxylic acid (9) was methylated with diazomethane to give the compound (10) (R=CH$_3$)

The n. m. r. spectrum of the 13,14-dihydro-6,15-diketo-PGE$_1$ methyl ester (15) is shown in FIG. 2.

Mass (SIMS) m/z: 405 (M+H)$^{30}$, 383 ((M+H)$^+$ −18), 365, 287, 143, 121, 111, 99.

EXAMPLE 5 (See Charts I and II)

Preparation of 13,14-Dihydro-15-keto-3R,S-methyl-PGE$_2$ methyl ester (19)

Sodium hydride (60%, 1.72 g), washed with pentane, was suspended in dry DMSO, and the suspension was agitated for 45 min at 70° C. After the reaction solution was ice-cooled, a DMSO solution of (3R,S-methyl-4-carboxybutyl)triphenylphosphonium bromide was added. The reaction was stood at room temperature. Then, a DMSO solution of lactol (8) produced from (−)-Corey lactone with the procedure shown in Examples 2 to 4 was added, and agitated for 2 h. The resultant was diluted with a mixed solvent of ether and ethyl acetate (1:1), and poured into 5% potassium carbonate solution. After vigorous stirring, separated organic layer was extracted with aqueous potassium carbonate solution twice. The combined basic aqueous layers were acidified with hydrochloric acid at 0° C., and then were extracted with ethyl acetate three times. The combined ethyl acetate layers were washed with sodium chloride solution, and then concentrated under reduce pressure. The residue thus obtained was dissolved in ether and insolubles were filtered off. The filtrate was partially concentrated and was treated with diazomethane. After subseqent concentration, a crude product was obtained, and was chromatographed (ethyl acetate-hexane=2:5) to give a colorless oily substance (17) (2.15 g, 56%).

The alcoholic substance (17) (2.15 g) was oxidized in acetone (60 ml) at −30° C. with Jones reagent (2.67-M) (2.20 ml).

A residue obtained after the usual work-up was chromatographed (ethyl acetate:hexane=1:3) to give a colorless oily substance (18) (1.64 g, 77%).

The tetrahydropyranyl ether (18) (1.64 g) was dissolved into a mixed solvent (50 ml) of acetic acid:water:THF (4:2:1), and agitated for 3 h at 45° C. The reaction solution was concentrated under reduced pressure, and the resulting crude product was chromatographed (ethyl acetate:benzene=4:5) to give a colorless oily substance, 13,14-dihydro-15-keto-3R,S-methyl-PGE$_2$ methyl ester (19). Yield: 0.98 g (80%).

Figure 3:
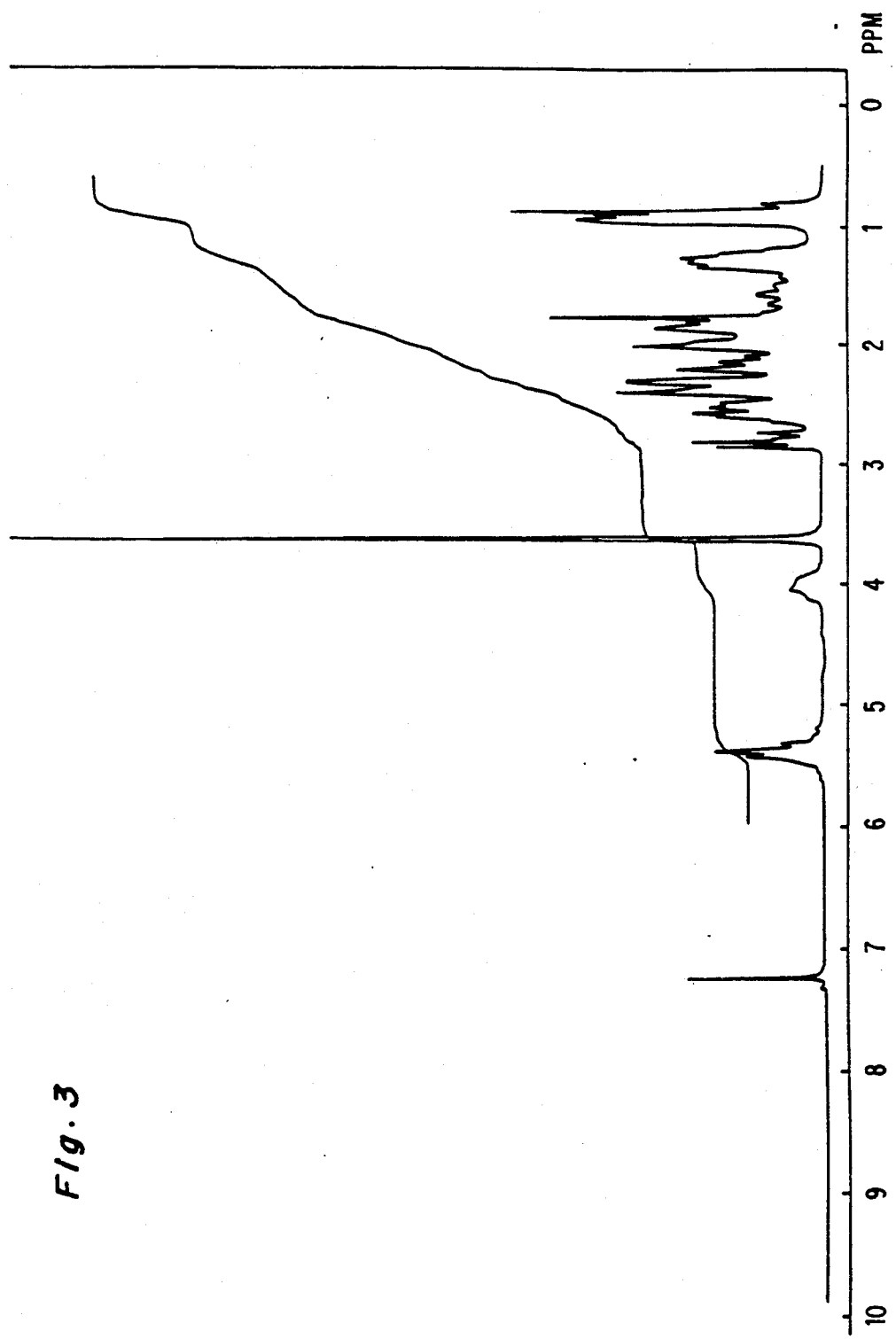

The n. m. r. spectrum of 13,14-dihydro-15-keto-3R,S-methyl-PGE$_2$ methyl ester (19) is shown in FIG. 3.

Mass (D I) m/z: 380 ($M^{30}$), 362 ($M^+ - 18$), 208, 109, 94, 81.

EXAMPLE 6 (See Chart III)

Preparation of 13,14-Dihydro-15-keto-16R,S-methyl-PGE$_2$ ethyl ester (29), R=Et

6-1 Preparation of 1S-2-Oxa-3-oxo-6R-(4R,S-methyl-3-oxo-1-trans-octenyl)-7R-(4-phenyl) benzoyloxy-cis-bicyclo (3, 3, 0) octane (20)

Sodium hydride (60%, 0.228 g) was suspended in anhydrous THF (40 ml), and a THF (30 ml) solution of dimethyl (3R,S-methyl-2-oxoheptyl)phosphonate (1.4 g) was added with agitation for 30 min. To the resultant was added a THF solution (30 ml) of the aldehyde (2) obtained after collins oxidation of (−)-Corey lactone. The reaction was kept at room temperature for 2 h, and then acetic acid was added to neutralize the reaction. An α,β-unsaturated ketone (20) was obtained after the usual work-up and the purification. Yield: 1.606 g (61%).

6-2 Preparation of 1S-2-Oxa-3-oxo-6R-(3,3-ethylenedioxy-4R,S-methyl-1-octanyl)-7R-(4-phenyl) benzoyloxy-cis-bicyclo (3, 3, 0) octane (22)

The α,β-unsaturated ketone (20) was hydrogenated in ethyl acetate with 5% palladium-carbon (0.150 g), and hydrogen. The saturated ketone (21) thus obtained was dissolved in anhydrous benzene (150 ml), to which p-toluenesulfonic acid (in catalytic amount) and ethylene glycol (10 ml) were added, and refluxed overnight while water was distilled off. Ketal (22) was obtained after the usual work-up. Yield: 1.538 g (87%).

6-3 Transesterification of the ketal (22): Synthesis of alcohol (23)

The ketal (22) (1.538 g) was dissolved in absolute methanol (100 ml), and K$_2$CO$_3$ (0.503 g) was added, the reaction was stirred for 5 h.

The reaction solution was neutralized with addition of acetic acid.

A crude product obtained after the usual work-up was chromatographed (ethyl acetate:hexane=1:2) to give the alcohol (23). Yield: 0.8682 g (88%).

6-4 Preparation of Tetrahydropyranyl ether (24)

The compound (23) (0.8682 g) was dissolved in dry CH$_2$Cl$_2$ (100 ml), and dihydropyran (5 ml) and p-toluenesulfonic acid (catalytic amount) were added. The reaction solution was stirred for 20 min. A crude product obtained after the usual work-up was chromatographed (hexane:ethyl acetate=5:1) to give the tetrahydropyranyl ether (24). Yield: 1.040 g (94%).

6-5 Preparation of lactol (25)

The tetrahydropyranyl ether (24) was treated with DIBAL-H (1.5-M, 5 ml) in dry toluene (30 ml) at −78° C. to give the lactol (25). Yield: 1.030 g.

6-6 Preparation of 13,14-Dihydro-15,15-ethylenedioxy-16R,S-methyl-11-(2-tetrahydropyranyl) oxy-PGF$_{2\alpha}$ (26)

Sodium hydride (50%, 0.600 g) washed with dry ether was suspended in DMSO (8 ml), and the suspension was heated at 60° C. for 1 h with agitation. A DMSO (10 ml) solution of (4-carboxybutyl)triphenylphosphonium bromide (3.3 g) was added dropwise. Deep red ylide was obtained, to which the above lactol (25) in DMSO (8 ml) was added. The reaction was kept overnight at room temperature with stirring, and then poured into an ice-water, the aqueous solution was adjusted to pH 12 with 10% sodium hydroxide solution. The basic aqueous solution was extracted with ethyl acetate. The aqueous layer was adjusted to pH 6 with 1N hydrochloric acid at 0° C., and was extracted with ethyl acetate, and the combined organic extract were washed with brine. After drying, the extract was concentrated under reduced pressure to give the carboxylic acid (26). Yield: 1.299 g.

6-7 Preparation of ethyl ester (27), R=Et:Esterification of the compound (26)

The carboxylic acid (26) (1.299 g) was dissolved in dry acetonitrile (50 ml). To the solution were added ethyl iodide (0.6 g) and DBU (0.4750 g). The mixture was kept at 0° C. for 2 h. A crude product obtained after the usual work-up, was chromatographed (hexane:ethyl acetate=2:1) to give 0.6226 g of the ethyl ester (27). (Yield: 48%, from (24)).

6-8 Preparation of ketone (28)

The ethyl ester (27) (0.6226 g) was oxidized with Jones reagent (2.67-M, 0.45 ml) in acetone (40 ml) at −40° C.

A crude product obtained after the usual work-up was chromatographed (hexane-ethyl acetate=3:1). Yield: 0.3942 g (63%).

6-9 Preparation of 13,14-Dihydro-15-keto-16R,S-methyl-PGE$_2$ ethyl ester (29)

Figure 4:
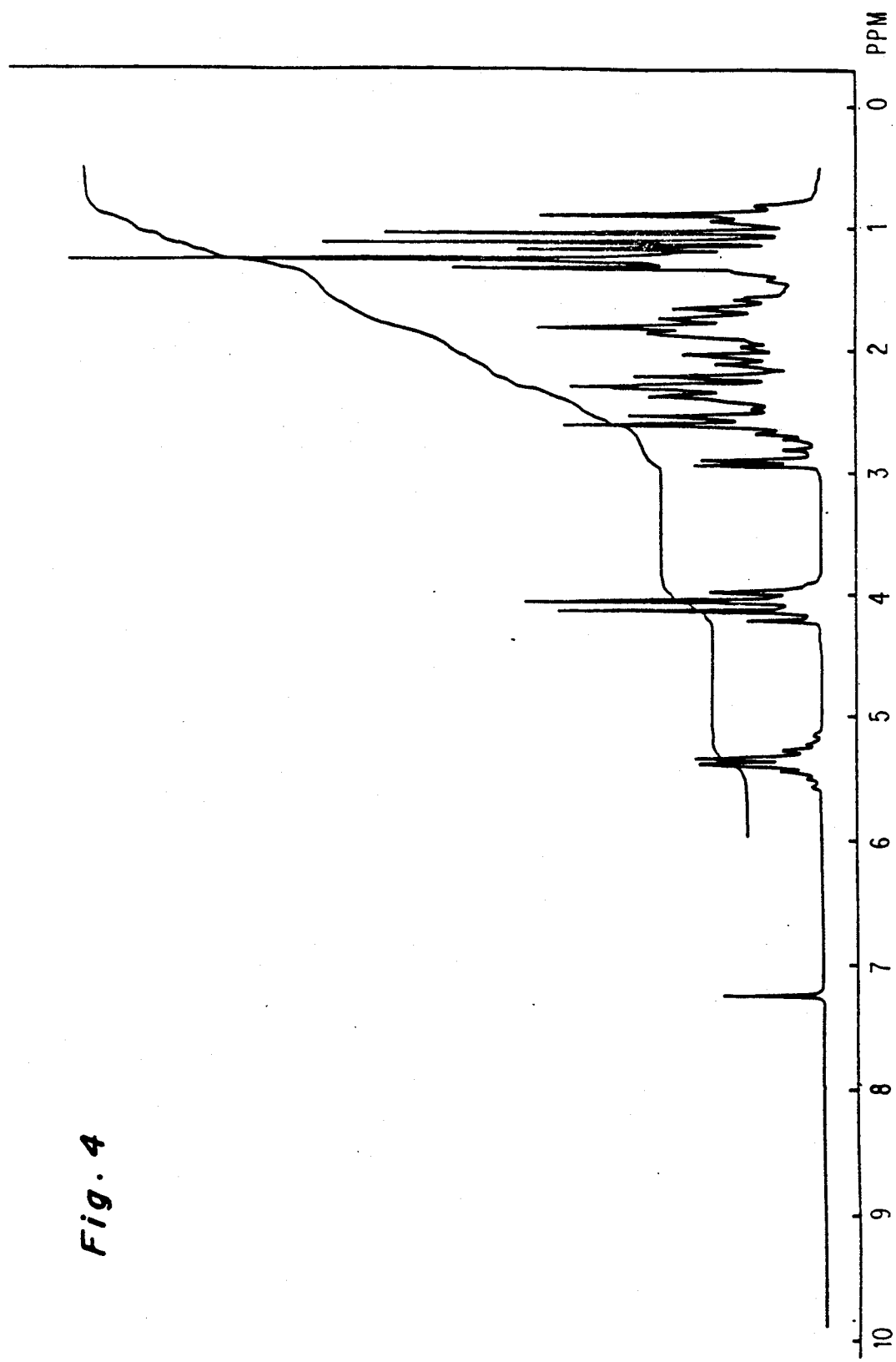
Figure 5:
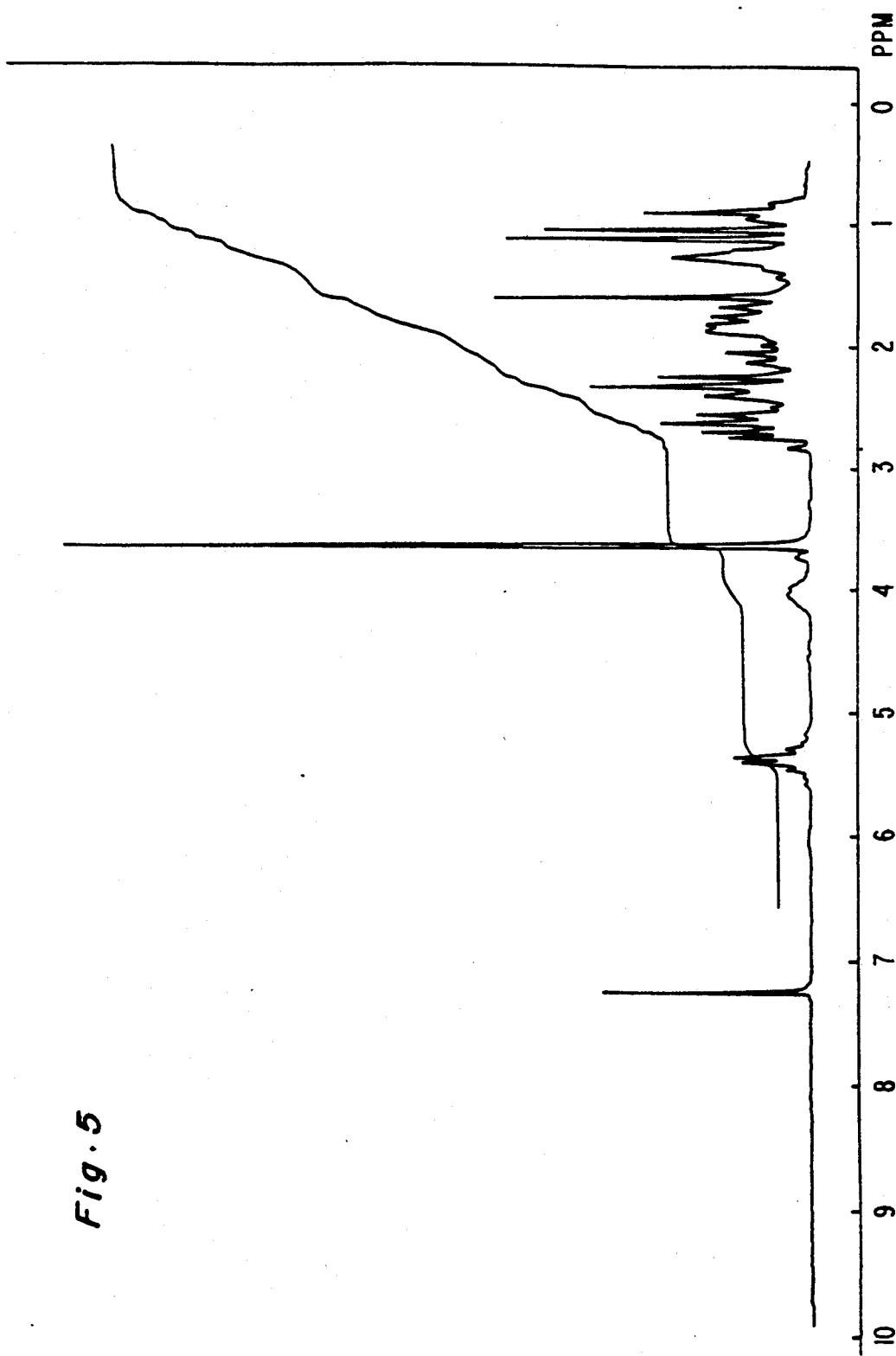

The ketone (28) (0.3942 g) was dissolved in a mixted solvent (10 ml) of acetic acid:water:THF (3:1:1), and the solution was kept at 40° C. for 4 h. A crude product obtained after the usual work-up was chromatographed (hexane-ethyl acetate=4:1) to give 13,14-dihydro-15-keto-16R,S-methyl-PGE$_2$ ethyl ester (29). Yield: 0.1559 g (53%). The n. m. r. spectrum of the 13,14-Dihydro-15-keto-16R,S-methyl-PGE$_2$ ethyl ester (29) is shown in FIG. 4.

Mass (SIMS) m/z: 395 $(M+H)^+$, 377 $((M+H)^+ - 18)$ 331, 203, 109, 85.

EXAMPLE 7 (See Chart III)

Synthesis of 13,14-Dihydro-15-keto-16R,S-methyl-PGE$_2$ methyl ester (29), R=Me The title compound (29) was prepared in the same manner as in Example 6 except that the carboxylic acid (26) was methylated with diazomethane.

Figure 6:
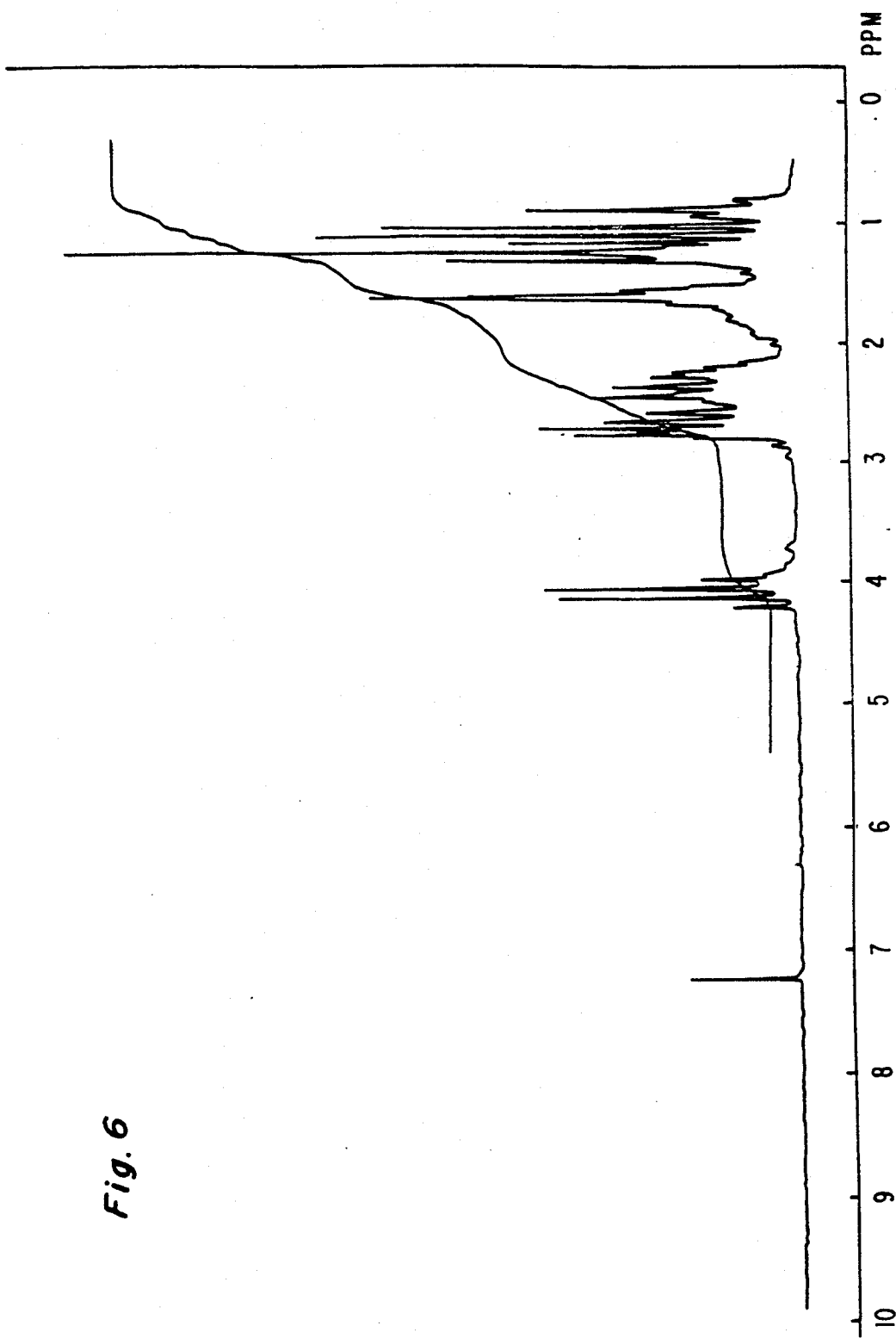

The n. m. r. spectrum of the 13,14-dihydro-15-keto-16R,S-methyl-PGE$_2$ methyl ester (29) is shown in FIG. 6.

Mass (D I) m/z: 380 (M+), 362 ((M+ −18), 331, 249, 234, 222, 137, 109.

EXAMPLE 8 (See Chart IV)

Synthesis of 13,14-Dihydro-6,15-diketo-16R,S-methyl-PGE$_1$ ethyl ester (33), R=Et

8-1 Preparation of bromide (30) R=Et

PGF$_2$-ethyl ester derivative (27) (1.405 g) was dissolved in a mixed solvent (50 ml) of THF-CH$_2$Cl$_2$ (2:5). To the solution was added a THF-CH$_2$Cl$_2$ (2:5; 20 ml) solution of NBS (0.5250 g) at 0° C., which was agitated for 20 min. A crude product obtained after the usual work-up was chromatographed (hexane:ethyl acetate=3:1) to give the bromide (30). Yield: 1.592 g (98%).

8-2 Preparation of 13,14-Dihydro-15,15-ethylenedioxy-6-keto-16R,S-methyl-11-(2-tetrahydropyranyl)oxy-PGF$_{2\alpha}$ ethyl ester (31)

The bromide (30) (1.592 g) was dissolved in toluene (4 ml) and DBU (3.5 ml), and the solution was stirred at 50° C. overnight. After cooled, the solution was diluted with ether, and washed with sodium hydrogensulfite solution. A crude product obtained after the usual work-up was chromatographed (hexane:ethyl acetate=1.5:1) to give the compound (31). Yield: 1.031 g (72%).

8-3 Preparation of ketone (32)

The 6-keto-PGF derivative (31) (0.5012 g) was oxidized with Jones reagent (2.67-M:1.2 ml) in acetone (35 ml) at −25° C. A crude product obtained after the usual work-up was chromatographed (hexane:ethyl acetate=1:1) to give the ketone (32). Yield: 0.3907 g (78%).

8-4 Preparation of 13,14-Dihydro-6,15-diketo-16R,S-methyl-PGE$_1$ ethyl ester (33):

The 6-keto-PGF derivative (32) (0.3907 g) was dissolved in a mixed solvent (24 ml) of acetic acid:water:THF (3:1:1), and the solution was kept at 50° C. for 3.5 h. After cooled, the solution was concentrated under reduced pressure. The resulting crude product was chromatographed (hexane:ethyl acetate=1:1) to give 13,14-dihydro-6,15-diketo-16R,S-methyl-PGE$_1$ ethyl ester (33). Yield: 0.2100 g (71%).

The n. m. r. spctrum of 13,14-dihydro-6,15-diketo-16R,S-methyl-PGE$_1$ ethyl ester (33) R ; Et, is shown in FIG. 6.

Mass (SIMS) m/z: 411 (M+H)+, 393 ((M+H)+ −18), 375, 347, 301, 149, 130.

EXAMPLE 9 (See Chart IV)

Synthesis of 13,14-Dihydro-6,15-diketo-16R,S-methyl-PGE$_1$ methyl ester (33), R=Me The title compound (33) was prepared from the methyl ester (27) following the same manner as the preparation of 13,14-dihydro-6,15-diketo-16R,S-methyl-PGE$_1$ ethyl ester (33).

Figure 7:
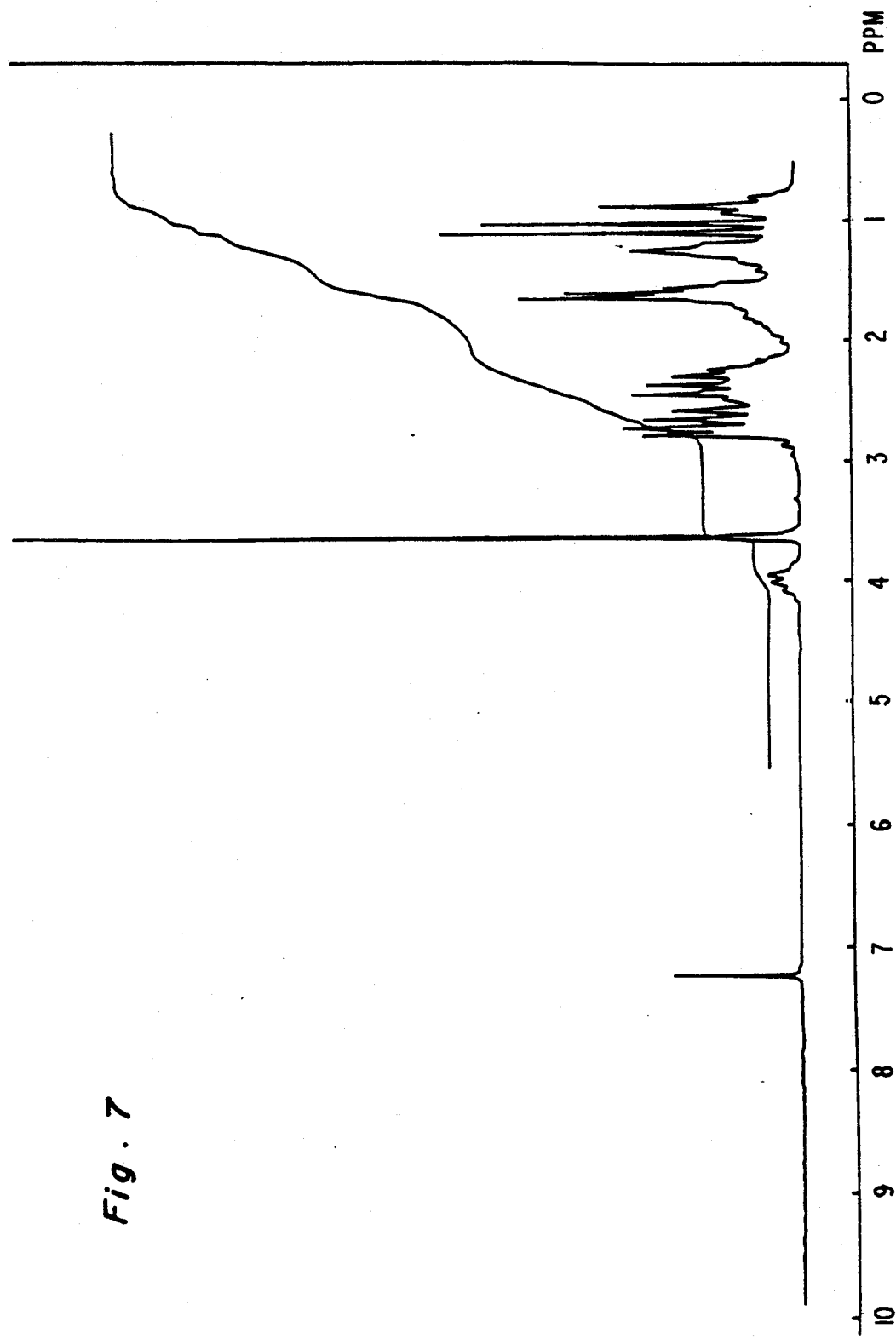

The n. m. r. spctrum of the 13,14-dihydro-6,15-diketo-16R,S-methyl-PGE$_1$ methyl ester (33) is shown in FIG. 7.

Mass (SIMS) m/z: 397 (M+H)+, 379 ((M+H)+ −18) 365, 347, 301, 143, 121, 111.

EXAMPLE 10 (See Chart V)

Preparation of 13,14-Dihydro-15-keto-3R,S,16R,S-dimethyl-PGE$_2$ methyl ester (36)

10-1 Preparation of 13,14-Dihydro-15,15-ethylenedioxy-3R,S,16R,S-dimethyl-11-(2-tetrahydropyranyl)oxy-PGE$_2$ methyl ester (34)

Sodium hydride (60%, 0.4660 g), washed with dry ether, was suspended in dry DMSO (8 ml), and the suspension was stirred at 60° C. for 1 h. A DMSO solution of (3R,S-methyl-4-carboxybutyl)triphenylphosphonium bromide (2.66 g) was added to sodium methylsulfinyl carbonion to give deep red ylide. After addition, the reaction solution was stirred for 15 minutes. A DMSO solution (10 ml) of lactol (25) (0.8 g) was added dropwise, and the mixture was agitated overnight. The reaction solution was poured in ice-water and adjusted to pH 12 with 10% sodium hydroxide solution, and then extracted with ether. The aqueous layer was adjusted to pH 5-6 with 1-N hydrochrolic acid and then extracted with ether. The organic extract of the acidic aqueous solution was dried, and concentrated under reduced pressure. The crude product thus obtained was esterified with diazomethane and then was chromatographed to give 13,14-dihydro-3R,S, 16R,S-dimethyl-15,15-ethylenedioxy-11-(2-tetrahydropyranyl)oxy-PGE$_2$ methyl ester (34). Yield: 0.7483 g.

10-2 Preparation of 13,14-Dihydro-15-keto-3R,S, 16R,S-dimethyl-PGE$_2$ methyl ester (36):

According to the manner analogous to the Examples 2 to 9 with using the PGF$_2$ derivative (34), 13,14-dihydro-15-keto-3R,S-16R,S-dimethyl-PGE$_2$ methyl ester (36) was (36) was produced.

Figure 8:
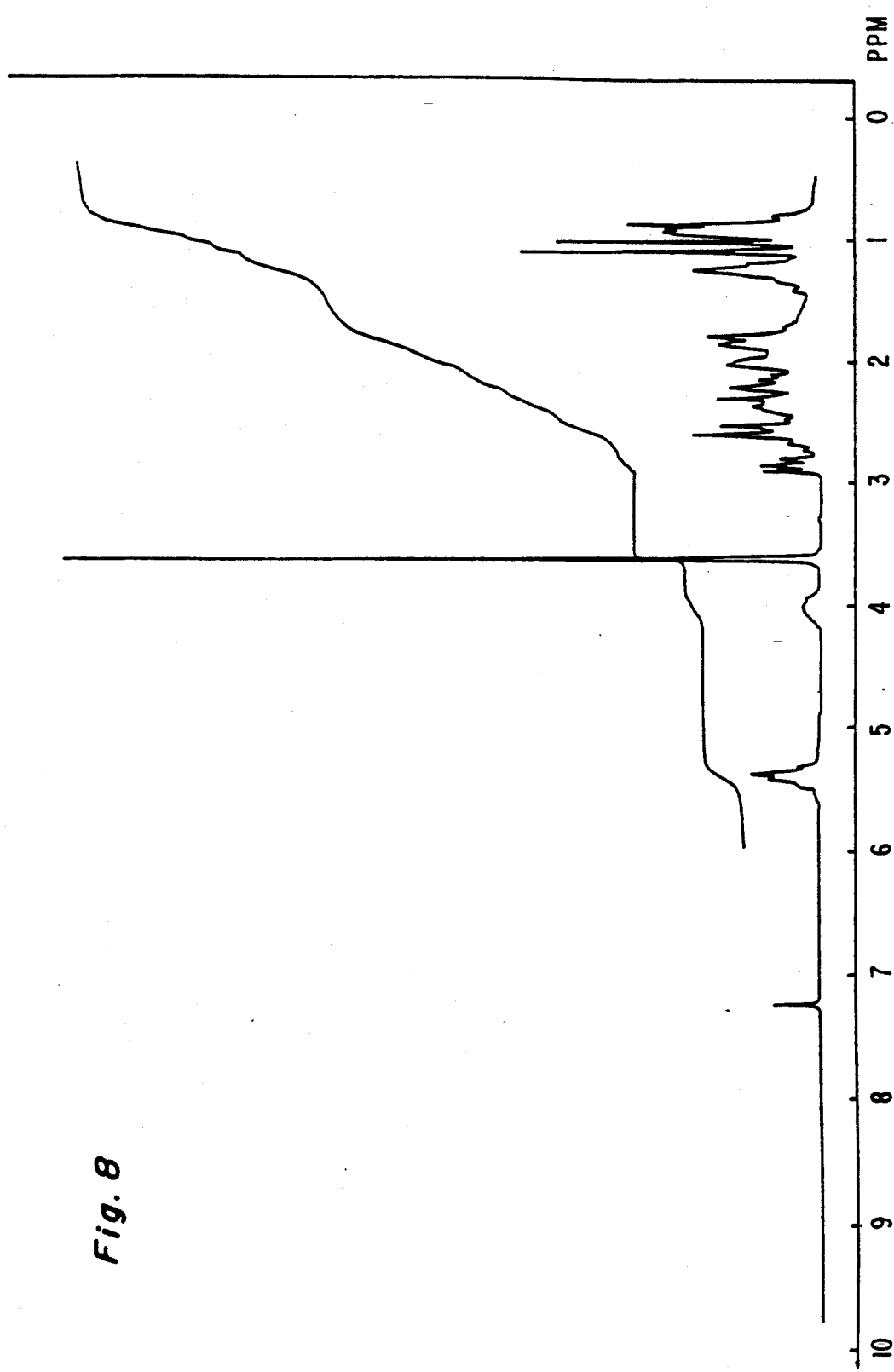

The n. m. r. spectrum of 13,14-dihydro-15-keto-3R,S-16R,S-dimethyl-PGE$_2$ methyl ester (36) is shown in FIG. 8.

Mass (SIMS) m/z: 395 (M+H)+, 377 ((M+H)+ −18), 345, 121, 109, 95.

EXAMPLE 11 (See Chart VI)

Preparation of 13,14-Dihydro-6,15-diketo-16R,S-fluoro-PGE$_1$ ethyl ester (50)

11-1 Preparation of 1S-2-Oxa-3-oxo-6R-(4R, S-fluoro-3-oxo-1-trans-octenyl)-7R-(4-phenylbenzoyl)oxy-cis-bicyclo (3, 3, 0) octane (37)

Sodium hydride (60%, 1.70 g) was suspended in THF, and a THF solution of dimethyl(3R,S-fluoro-2-oxoheptyl)phosphonate (4) (10.23 g) was added to the suspension, and agitated at room temperature for 20 min. To the mixture was added a THF solution of aldehyde (2) which was obtained after Collins-oxidation of the (−)-lactone (1) (−)-lactone (1) (15.00 g).

After 2 h agitation at room temperature, the reaction solution was neutralized with acetic acid (15 ml). Thereafter, a residue obtained after the usual work-up was purified by column-chromatography (ethyl acetate:hexane=1:2) to give a colorless oily enone (37) Yield: 10.45 g (53%).

11-2 Preparation of 1S-2-Oxa-3-oxo-6R-(4R,S-fluoro-3R,S-hydroxy-1-octyl)-7R-(4-phenylbenzoyl-)oxy-cisbicyclo (3, 3, 0) octane (39)

The enone (37) (10.45 g) was hydrogenated with 5% palladium or carbon (1.0 g) and hydrogen in ethyl acetate (50 to give ketone (38). Yield: 9.35 g (89%).

The ketone (38) (9.35 g) was reduced with sodium borohydride (1.15%) in absolute methanol 200 ml) to give a g colorless oily substance (39). Yield: 6.50 g (69%).

11-3 Preparation of 1S-2-Oxa-3-oxo-6R-(4R,S-fluoro-3R,S-t-butyldimethyl-silyloxy-1-octyl)-7R-hydroxy-cisbicyclo(3, 3, 0)octane (41):

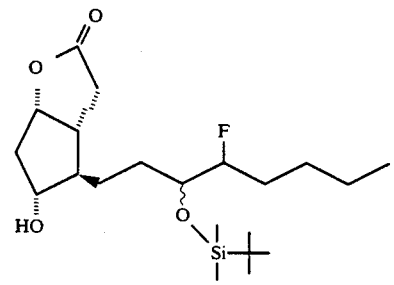

(41)

The alcohol (39) (6.50 g) was converted with t-butyldimethylsilyl chloride (6.27 g) and imidazole (5.67 g) in dry DMF (30 ml) to the corresponding t-butyldimethylsilyl ether (40).

Yield: 8.80 g (100%)

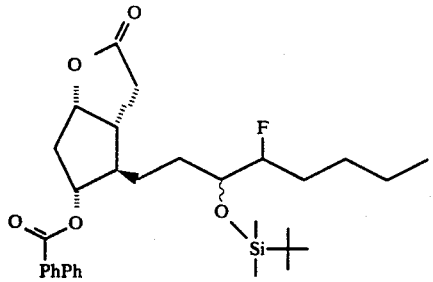

(40)

The t-butyldimethylsilyl ether (40) (8.80 g) was dissolved in methanol (80 ml), and anhydrous potassium carbonate (2.09 g) was added to the solution. The reaction was stirred for 4 h at room temperature. A colorless oily alcohol (41) was obtained after the usual work-up, and purification. Yield: 4.11 g (67%).

11-4 Preparation of 13,14-Dihydro-16R,S-fluoro-15R,S-t-butyldimethyl-silyloxy-11-(2-tetrahydropyranyl)-oxy-PGF$_{2\alpha}$ (44)

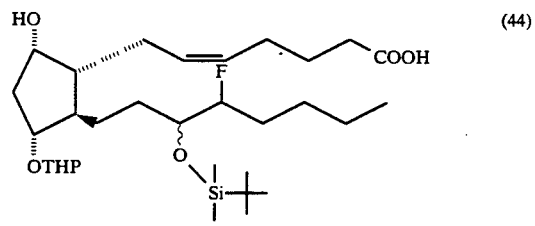

(44)

The alcohol (41) 4.11 g) was dissolved in dry dichloromethane 50 ml), and dihydropyran (4.10 ml) and p-toluenesulfonic acid (catalytic amount) were added to the solution. The reaction solution was stirred at room temperature for 10 min. The residue obtained after usual work-up was chromatographed (ethyl acetate:hexane=1:4~1:3) to give a colorless oily tetrahydropyranyl ether (42). Yield: 5.08 g (100%).

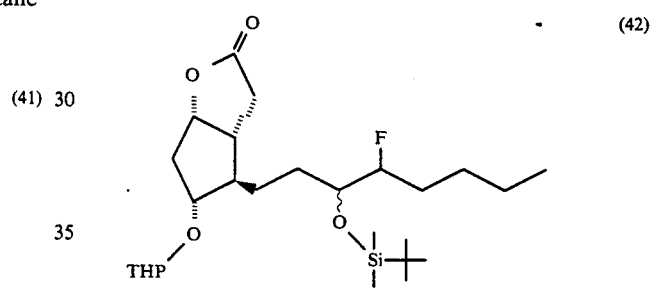

(42)

The tetrahydropyranyl ether (42) (5.08 g) was reduced with DIBAL-H (1.5M, 20 ml) in dry toluene (60 ml) at −78° C., and a colorless oily lactol (43) was obtained.

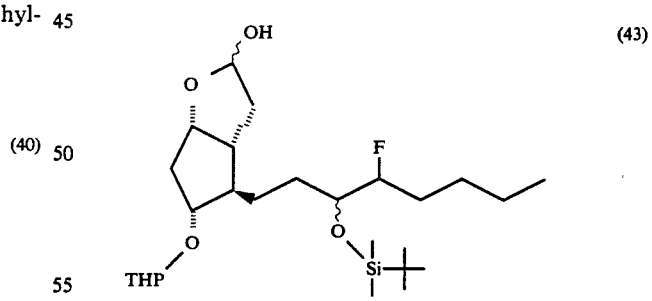

(43)

Ylide was prepared from (4-carboxybutyl) triphenylphosphonium bromide (18.51 g) according to the usual procedure, and to this ylide was added a DMSO solution of the previously prepared lactol (43). The reaction solution was stirred at room temperature for 2h. The residue obtained after the usual work-up was dissolved in ether. After insoluble material was separated by filtration, the filtrate was concentrated under reduced pressure, and a crude carboxylic acid (44) was obtained. Yield: 8.0 g.

11-5 Preparation of 13,14-Dihydro-16R,S-fluoro-15R,S-hydroxy-11-(2-tetrahydropyranyl)oxy-PGF$_{2\alpha}$ ethyl ester (46)

The crude carboxylic acid (44) (8.0 g) was dissolved in dry acetonitrile (40 ml), and DBU (3.0 ml) and ethyl iodide (6.0 ml) were added, and agitated at 60° C. for 60 min. The residue obtained after usual work-up was chromatographed (with ethylacetate:hexane=1:4~1:2) to give a colorless oily ester (45). Yield: 1.84 g.

The ester (45) (1.84 g) was dissolved in dry THF (30 ml), and tetrabutylammonium fluoride (1.0-M, 45 ml) was added. The reaction solution was stirred at room temperature for 3.5 h. The reside obtained after the usual work-up was chromatographed (ethyl acetate:hexane=1:2~1:3) to give a colorless oily alcohol (46). Yield: 1.34 g (90%).

11-6 Preparation of 13,14-Dihydro-16R,S-fluoro-15R,S-hydroxy-6-keto-11-(2-tetrahydropyranyl)oxy-PGF$_2$ ethyl ester (48)

The alcohol (46) (0.6254 g) was dissolved in dry dichloromethane (30 ml) and dry THF (3 ml), and N-bromosuccinimide (0.229 g) were added. The reaction solution was stirred for 10 min. The residue obtained after the usual work-up was chromatographed (ethyl acetate:hexane=2:3) to give a colorless oily bromo-ether (47). Yield: 0.6837 g (94%).

The bromo-ether (47) (0.8243 g) was dissolved in dry toluene (20 ml) and DBU (2.20 ml). The mixture was stirred at 65° C. overnight. After addition of water to the reaction solution, the mixture was acidified with dilute hydrochloric acid under ice cooling, and was extracted with ethyl acetate. The residue obtained after the usual work-up was chromatographed (ethyl acetate:hexane=1:1~2:1) to give a colorless oily 6-keto substance (48). Yield: 0.482 g (66%).

11-7 Preparation of 13,14-Dihydro-6,15-diketo-16R,S-fluoro-PGE$_1$ ethyl ester (50)

The dialcoholic substance (48) (0.230 g) was oxidized in acetone (20 ml) at −10° C. to −8° C. with Jones reagent (2.67M, 1.5 ml).

The residue obtained after the usual work-up was chromatographed (with ethyl acetate:hexane=1:2) to give a colorless oily keto substance (49). Yield: 0.100 g (44%)

The tetrahydropyranyl ether (49) (0.200 g) was dissolved in a mixed solvent (20 ml) of acetic acid:water:TMF (4:2:1), and the solution was stirred at 47° C. for 3 hours.

The reaction solution was concentrated under reduced pressure, and the resulting residue Was chromatographed (ethyl acetate:hexane=1:1) to give 13,14-dihydro-6,15-diketo-16R,S-fluoro-PGE$_1$ ethyl ester (50). Yield: 0.153 g (92%).

Figure 9:
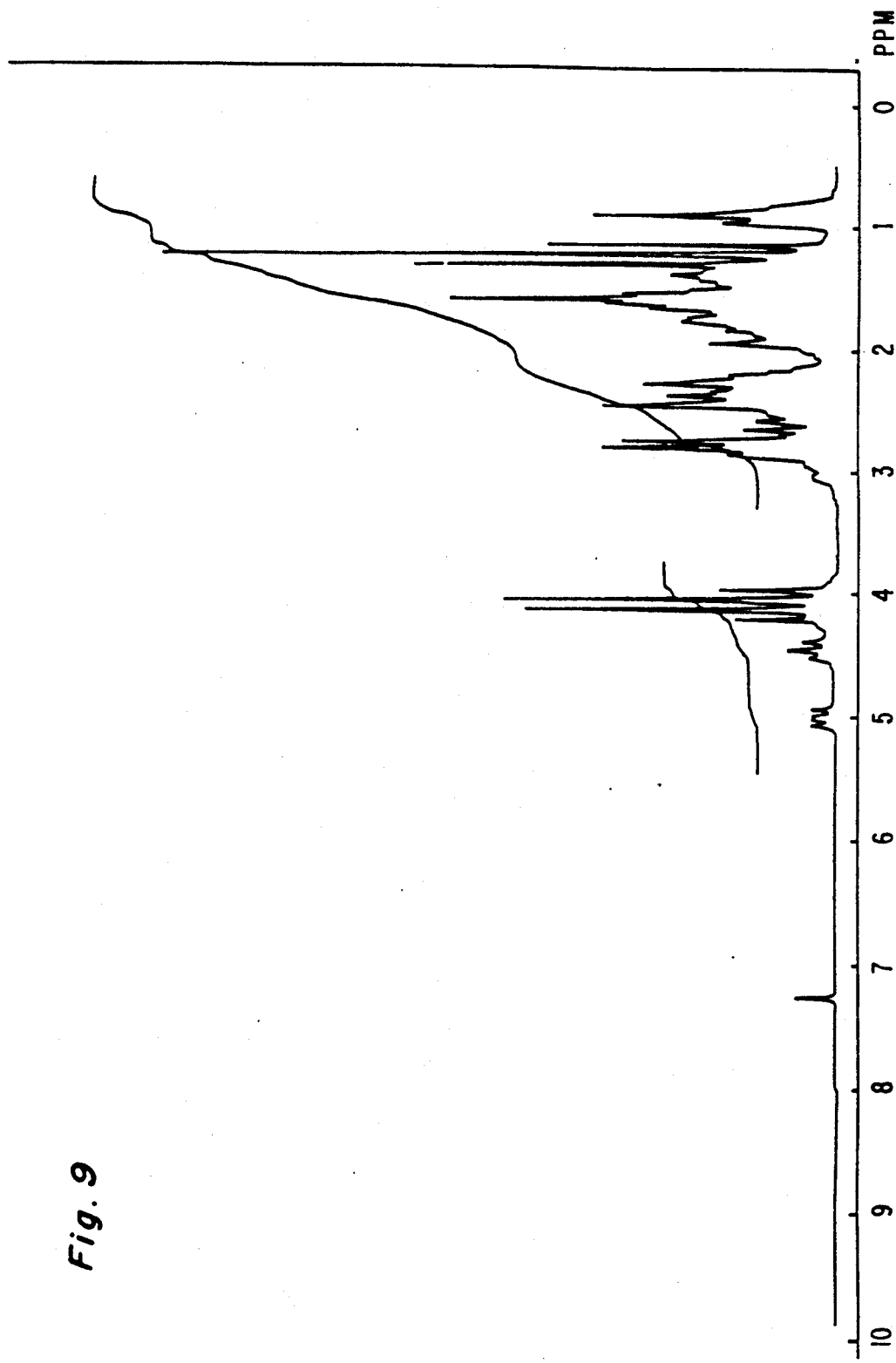

The n. m. r. spectrum of 13,14-dihydro-6,15-diketo-16R,S-fluoro-PGE$_1$ ethyl ester (50) is shown in FIG. 9.

Mass (SIMS) m/z: 415 (M+H)+, 397 ((M+H)+ −18), 377, 351, 305, 157, 111.

EXAMPLE 12 (See Chart VII)
Preparation of 13,14-Dihydro-15-keto-16R,S-fluoro-11R-dehydroxy-11R-methyl-PGE$_2$ ethyl ester (54)

12-1 Preparation of 13,14-Dihydro-15R,S-t-butyldimethylsilyloxy-16R,S-fluoro-11-(2-tetrahydropyranyl) oxy-PGE$_2$ ethyl ester (51)

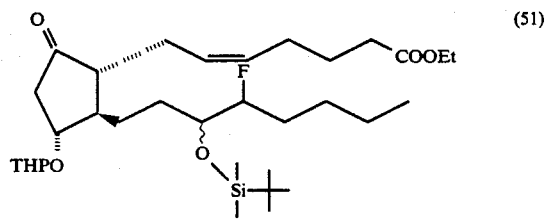

The alcohol (45) (0.506 g) was oxidized (2.67M) in acetone at −30° C. with Jones reagent. The crude product obtained after the usual work-up was chromatographed (ethyl acetate:hexane=2:9) to give a ketonic substance (51). Yield: 0.380 g (75%).

12-2 Preparation of 13,14-Dihydro-16R,S-fluoro-15R,S-hydroxy-PGA$_2$ ethyl ester (52)

The tetrahydropyranyl ether (51) was dissolved in 23 ml of a mixed solvent of acetic acid and water (20:3), and the solution was stirred at 70° C. The reactant was concentrated under reduced pressure, and then was chromatographed (ethyl acetate:hexane=1:3~1:1) to give a colorless oily enone (52). Yield: 0.078 g (32%).

12-3 Preparation of 13,14-Dihydro-15-keto-16R,S-fluoro-11R-dehydroxy-11R-methyl-PGE$_2$ ethyl ester (54)

Cuprous iodide (0.318 g) was suspended in anhydrous ether (30 ml), and methyl lithium (15-M; 2.23 ml) was added dropwise to the suspension at −13° C. to give a clear solution, to which the enone (52) (0.080 g) in ether (20 ml) was added. The reaction solution was stirred for 45 min. Then, acetic acid (0.84 ml) was added. The mixture was poured into an aqueous ammonium chloride, and extracted with ether.

The extract was washed, dried, and then concentrated under reduced pressure. The resulting crude product was chromatographed (ethyl acetate:hexane=2:5) to give a colorless oily alcoholic substance (53). Yield: 0.075 g (90%).

The alcoholic substance (53) (0.136 g) was oxidized with Jones reagent (2.67M) in acetone (20 ml) at −10° C. to −8° C. A crude product obtained after the usual work-up was chromatographed (ethyl acetate:hexane=1:4) to give colorless oily 13,14-dihydro-15-keto-16R,S-fluoro-11R-dehydroxy-11R-methyl-PGE$_2$ ethyl ester (54). Yield: 0.122 g (90%).

Figure 10:
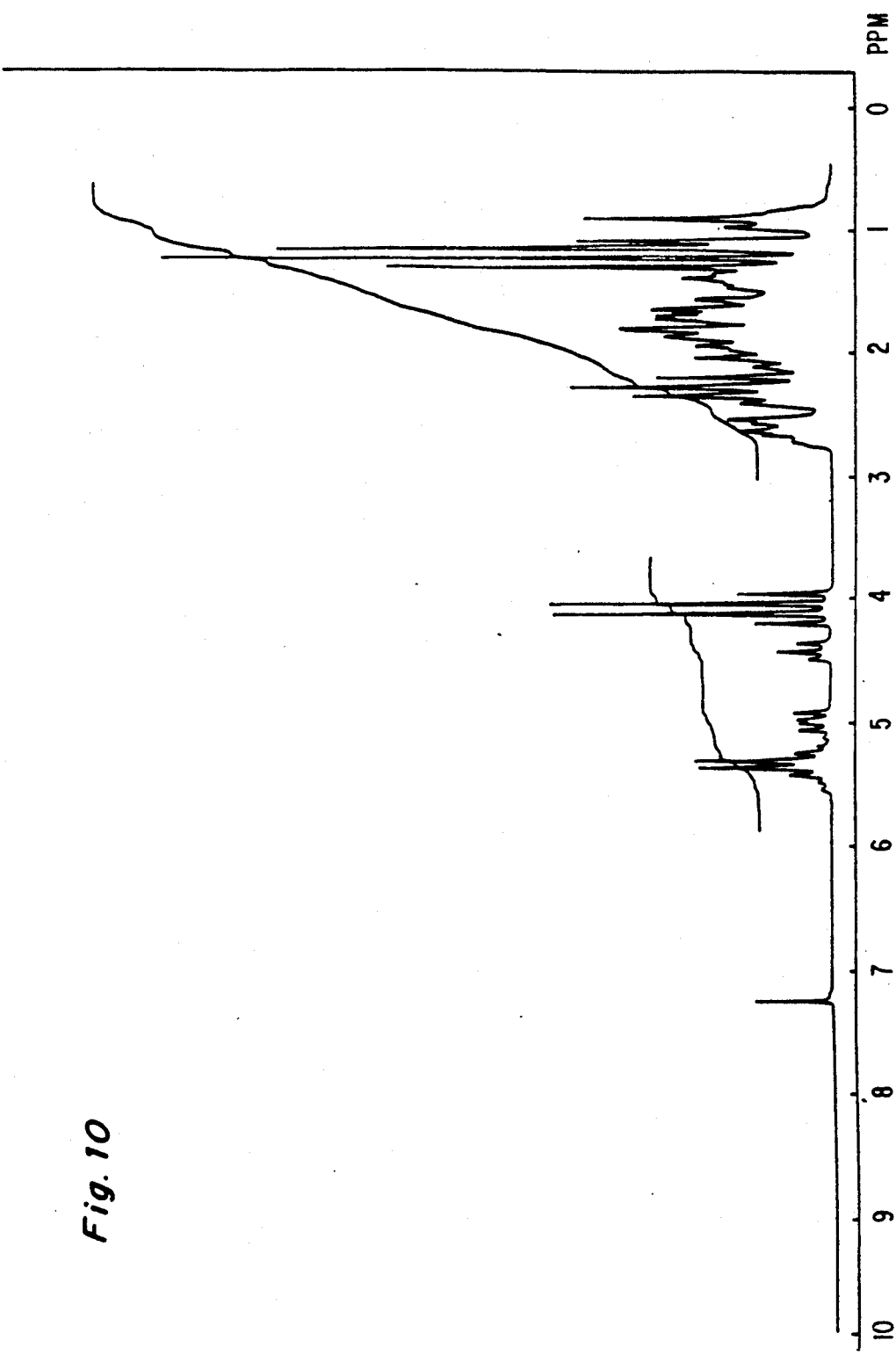

The n. m. r. spectrum of 13,14-dihydro-15-keto-16R,S-fluoro-11R-dehydroxy-11R-methyl-PGE$_2$ ethyl ester (54) is shown in FIG. 10.

Mass (SIMS) m/z:397 (M+H)$^+$, 379 ((M+H)$^+$ −18), 329, 301, 258, 237, 207, 167, 132.

EXAMPLE 13

Preparation of 13,14-Ddihydro-15-keto-16R,S-fluoro-PGE$_2$ ethyl ester (56)

Diol (46) (Chart VI) (0.501 g) was dissolved in acetone (35 ml) and was oxidized with Jones reagent at −° C. (2.67-M; 1 ml).

The crude product obtained after the usual work-up was chromatographed to give a tetrahydropyranyl ether (55). Yield: 0.347 g (70%).

The tetrahydropyranyl ether (55)(0.347 g) was dissolved in 25 ml of a mixed solvent of acetic acid:THF-:water (3:1:1), and the solution was stirred at 40° C. for 12 h.

A crude product obtained after the usual work-up was chromatographed to give 13,14-dihydro-15-keto-16R,S-fluoro-PGE$_2$ ethyl ester (56). Yield: 0.204 g (71%).

Figure 11:
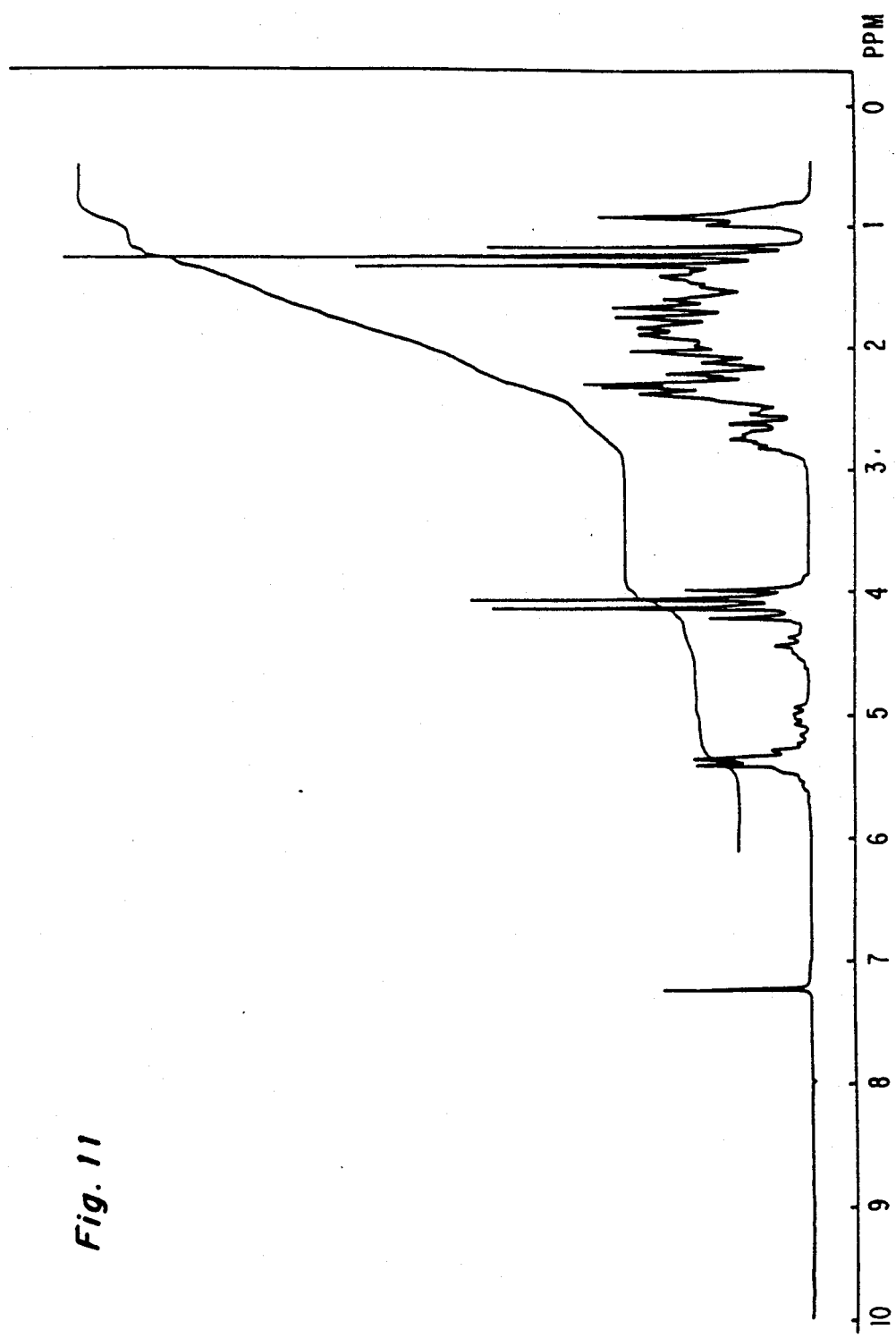

The n. m. r. spectrum of 13,14-dihydro-15-keto-16R,S-fluoro-PGE$_2$ ethyl ester (56) is shown in FIG. 11.

Mass (D I) m/z:398 (M+H)$^+$, 380 (M$^+$−18), 226, 109, 95, 81.

EXAMPLE 14

Preparation of 13,14-Dihydro-6,15-diketo-16,16-dimethyl-PGE$_1$ ethyl ester (57)

The title compound (57) was prepared following the procedure analogous to that in Example 2 to 13 with using (−)-Corey lactone (1) and dimethyl(3,3-dimethyl-2-oxoheptyl)phosphonate.

Figure 12:
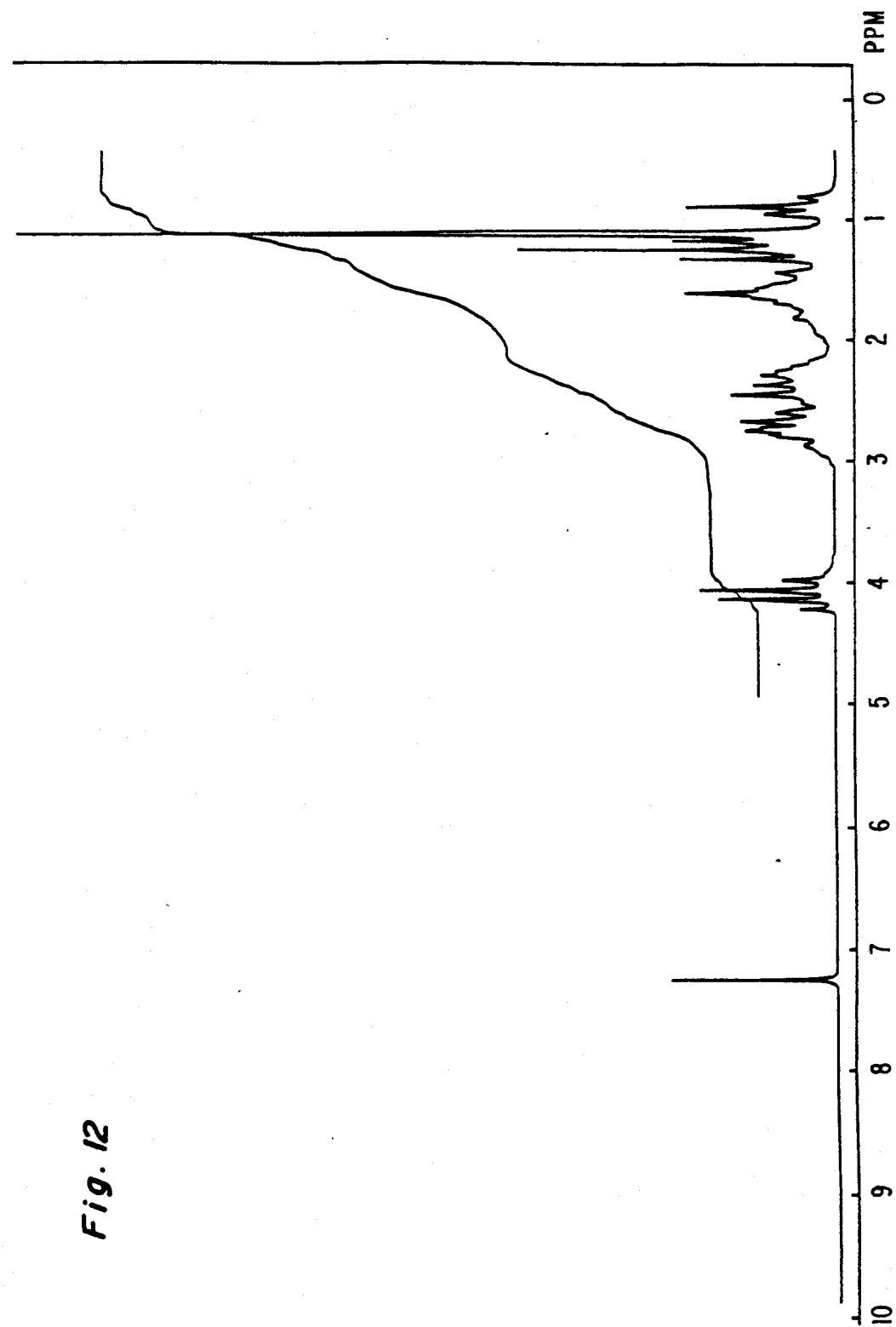

The n. m. r. spectrum of 13,14-dihydro-6,15-diketo-16,16-dimethyl-PGE$_1$ ethyl ester (57) is shown in FIG. 12.

Mass (D I) m/z:398 (M+H)$^+$, 380 (M$^+$−18), 226, 109, 95, 81.

EXAMPLE 15

Preparation of 13,14-Dihydro-15-keto-17S-methyl-PGE$_2$ ethyl ester (58)

The same procedure as in Examples 1 to 14 was followed using dimethyl (4S-methyl-2-oxoheptyl)phosphonate and (−)- Corey lactone (1), and thus 13,14-Dihydro-15-keto-S-methyl-PGE$_2$ ethyl ester (58) was synthesized.

Figure 13:
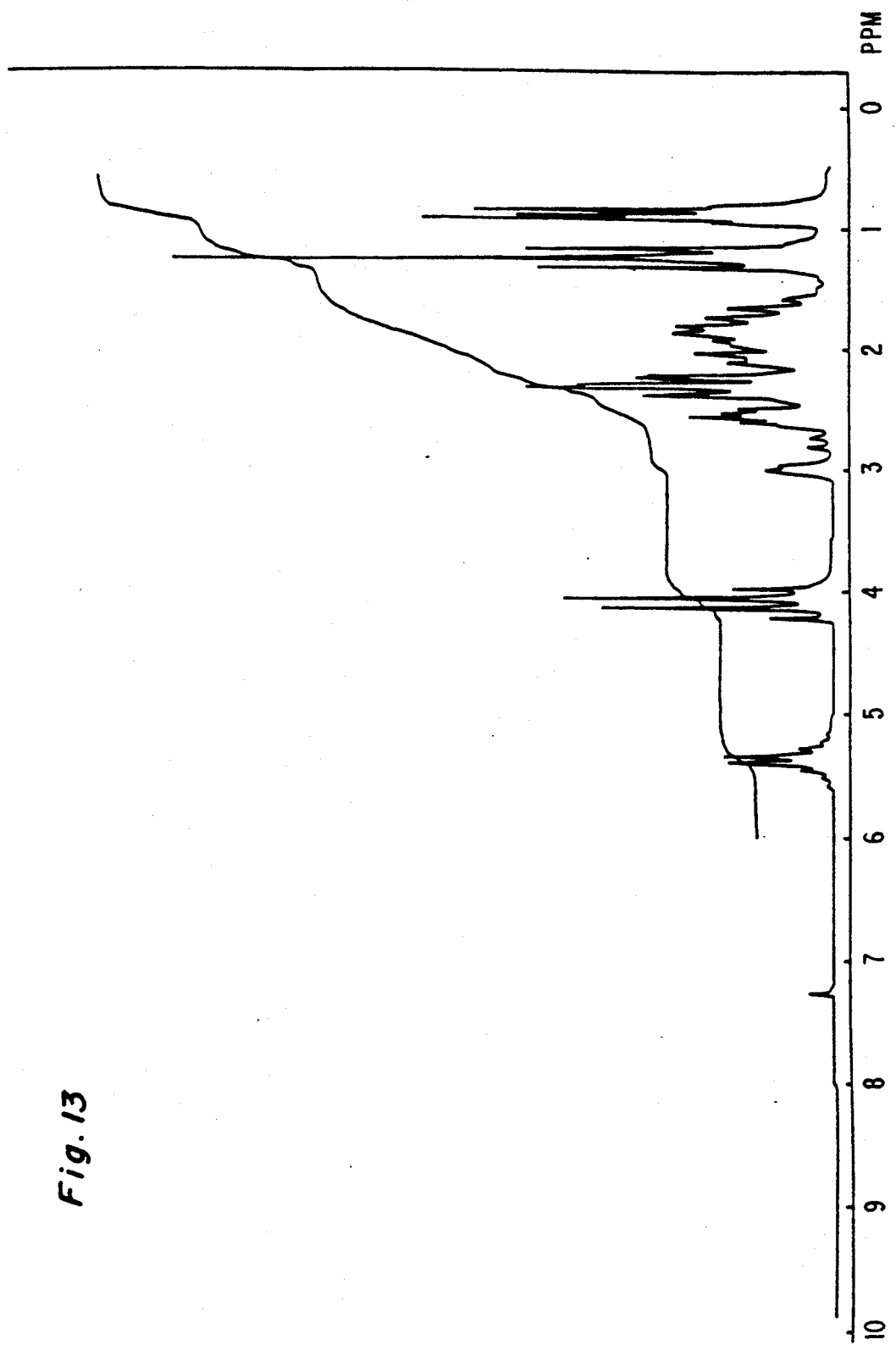

The n. m. r. spectrum of 13,14-dihydro-15-keto-S-methyl-PGE$_2$ ethyl ester (58) is shown in FIG. 13.

Mass (D I) m/z:394 (M$^+$), 376 (M$^+$−18), 222, 109, 94.

EXAMPLE 16 (See Chart VIII)

Preparation of 13,14-Dihydro-15-keto-19-methyl-PGE$_2$ ethyl ester (60), R=Et

Same procedure as in Examples 2 to 15 was followed using the unsaturated ketone (59) obtained from dimethyl (6-methyl-2-oxoheptyl)phosphonate and (−)-Corey lactone (1), and thus 13, 14-dihydro-15-keto-19-methyl-PGE$_2$ ethyl ester (60) was synthesized.

Figure 14:
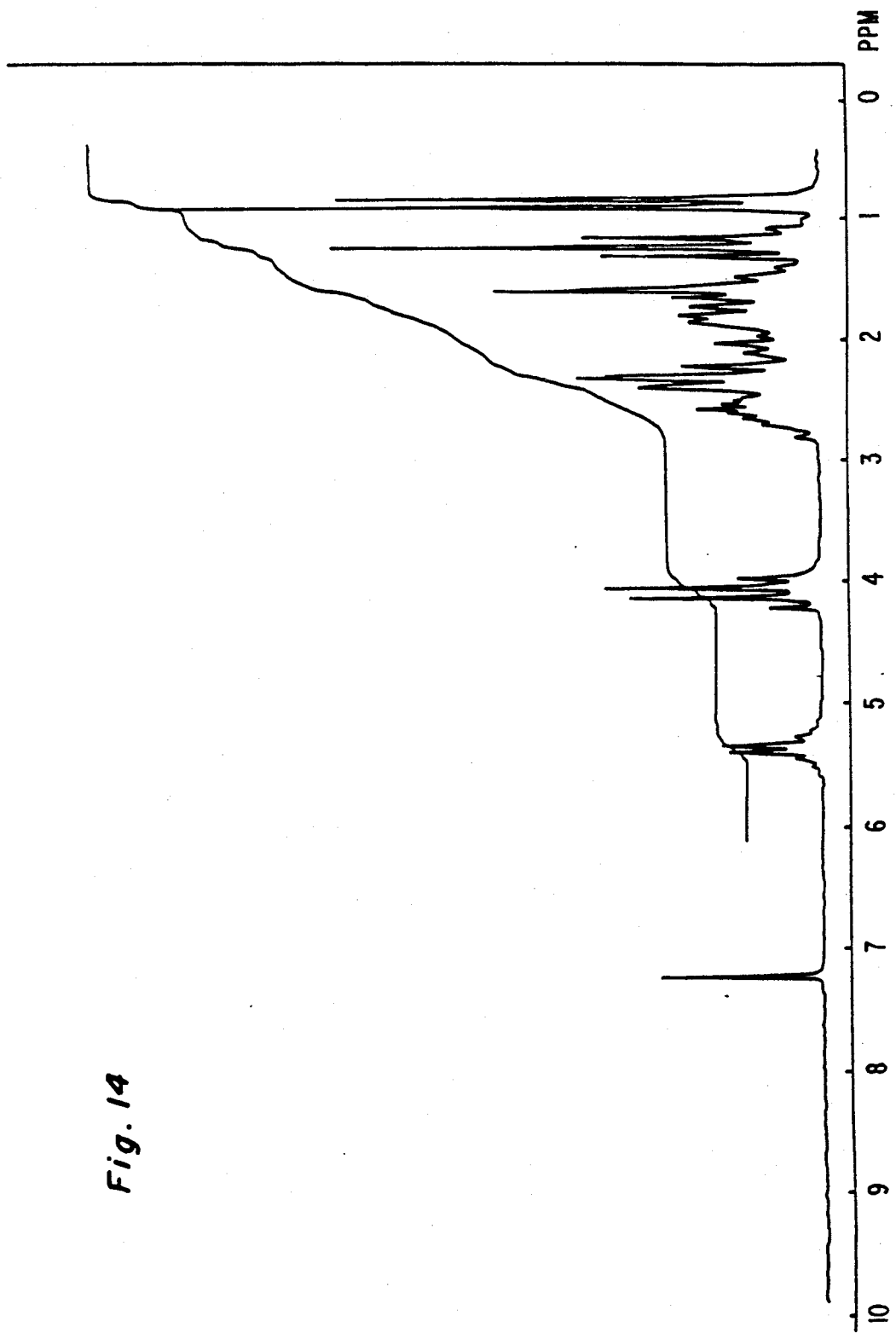

The n. m. r. spectrum of 13,14-dihydro-15-keto-19-methyl-PGE$_2$ ethyl ester (60) is shown in FIG. 14.

Mass (D I) m/z:394 (M$^+$), 376 (M$^+$−18), 331, 222, 109, 95, 94.

EXAMPLE 17 (See Chart VIII)

Preparation of 13,14-dihydro-15-keto-19-methyl-PGE$_2$ methyls ester (61), R=Me:

Preparation was carried out using the unsaturated ketone (59) and the same way as in Examples 2 to 16.

Figure 15:
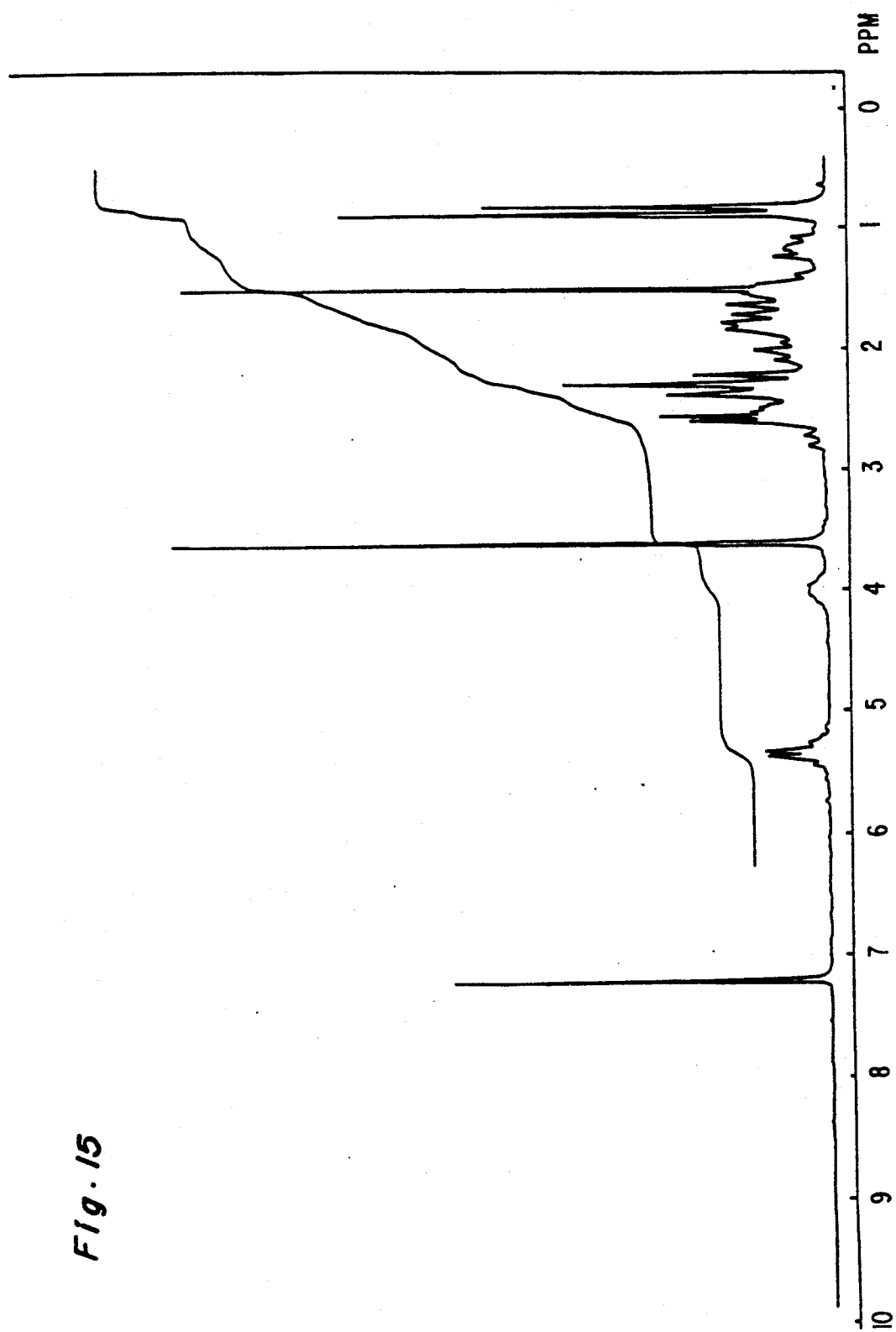

The n. m. r. spectrum of 13,14-dihydro-15-keto-19-methyl-PGE$_2$ methyl ester (61) is shown in FIG. 15.

Mass (D I) m/z:380 (M+), 362 (M+ −18), 331, 222, 109, 95, 94.

EXAMPLE 18 (See Chart VIII)

Preparation of 13,14-Dihydro-6,15-diketo-19-methyl-PGE$_1$ ethyl ester (62), R=Et Preparation was carried out using the unsaturated ketone (59) and the same way as in Examples 2 to 17.

Figure 16:
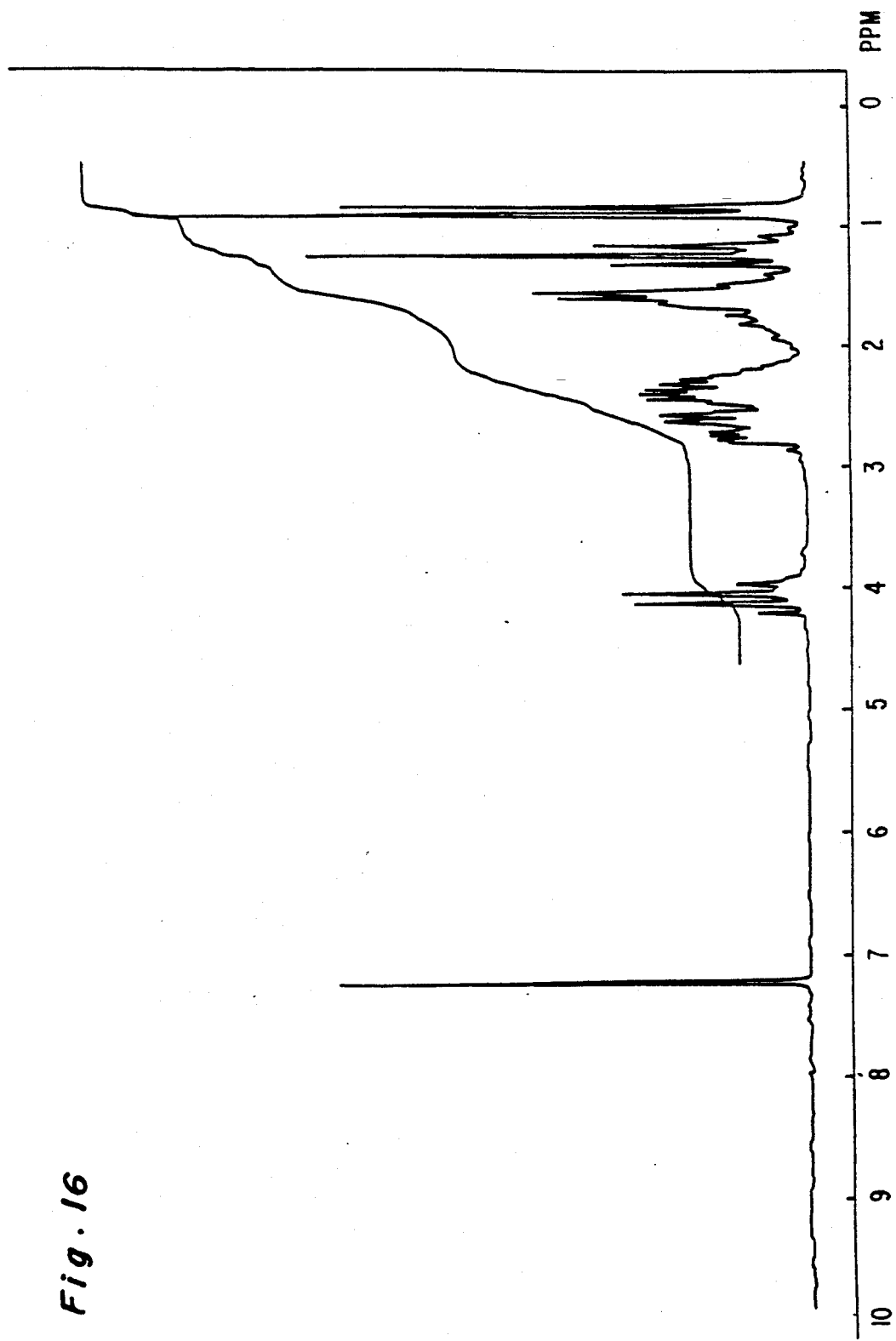

The n. m. r. spectrum of 13,14-dihydro-6,15-diketo-19-methyl-PGE$_1$ ethyl ester (62) is shown in FIG. 16.

Mass (SIMS) m/z 411 (M+M)+, 393 ((M+H)+ −18), 323, 292, 291, 217, 201, 109.

EXAMPLE 19 (See Chart VIII)

Preparation of 13,14-Dihydro-6,15-diketo-19-methyl-PGE$_1$ methyl ester (63), R=Me Preparation was carried out using the unsaturated ketone (59) and the same way as in Examples 2 to 18.

Figure 17:
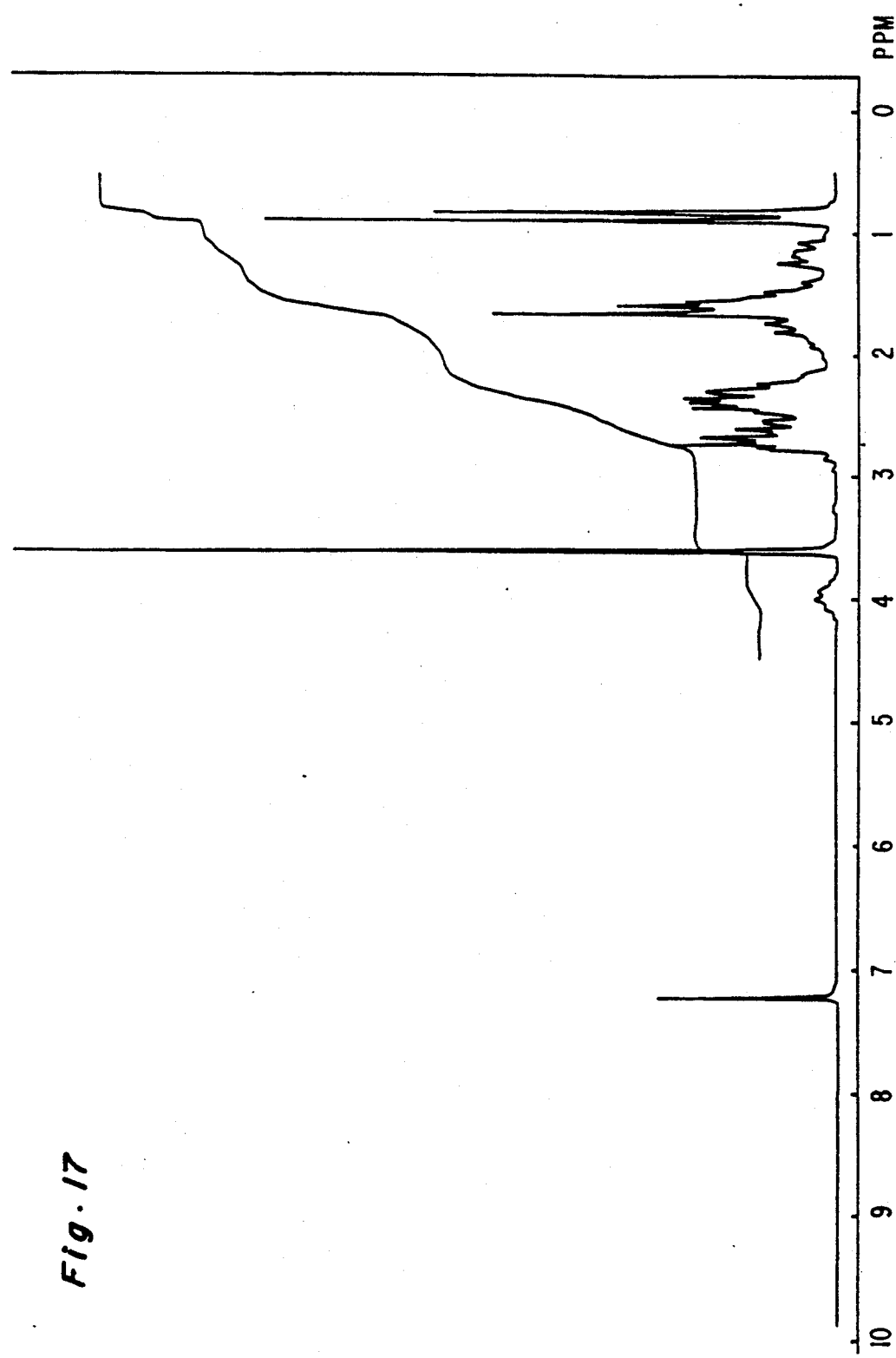

The n. m. r. spectrum of 13,14-dihydro-6,15-diketo-19-methyl-PGE$_1$ methyl ester (63) is shown in FIG. 17.

Mass (D I) m/z:369 (M+), 378 ((M+ −18), 265, 235, 143, 111.

EXAMPLE 20

Preparation of 13,14-Dihydro-15-keto-16,16-dimethyl-20-methoxy-PGE$_2$ methyl ester (64)

The same procedure as in Examples 2 to 19 was followed using dimethyl (3,3-dimethyl-7-methoxy-2-oxoheptyl)phosphonate and (−)-Corey lactone (1), and thus 13,14-dihydro-15-keto-16,16-dimethyl-20-methoxy-PGE$_2$ methyl ester (64) was prepared.

Figure 18:
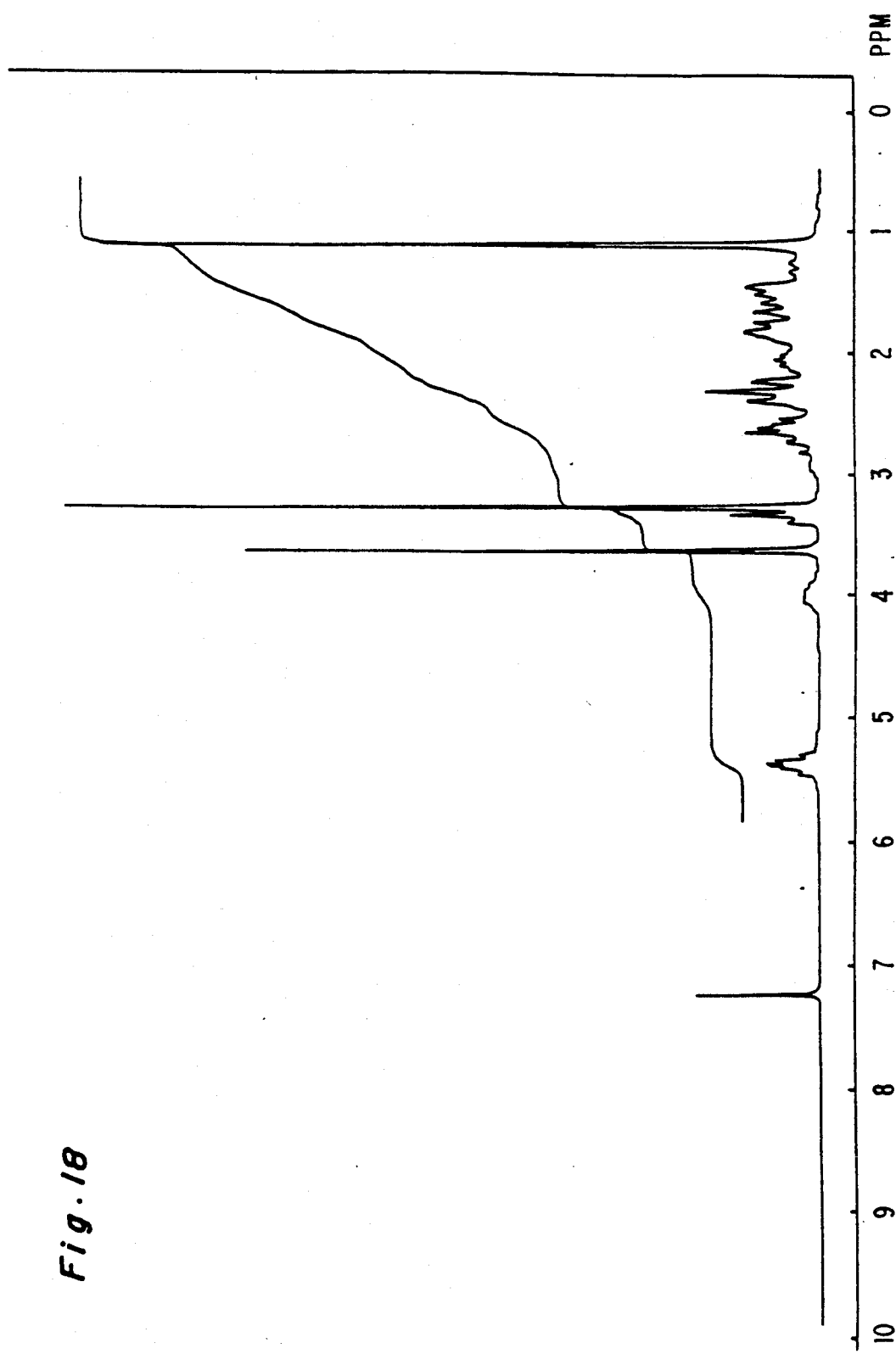

The n. m. r. spectrum of 13,14-dihydro-15-keto-16,16-dimethyl-20-methoxy-PGE$_2$ methyl ester (64) is shown in FIG. 18.

Mass (E I) m/z:424 (M+), 406 ((M−18), 375, 266, 375, 266, 245, 217, 129.

EXAMPLE 21

Preparation of 13,14-Dihydro-15-keto-16R,S-hydroxy-PGE$_2$ ethyl ester (65)

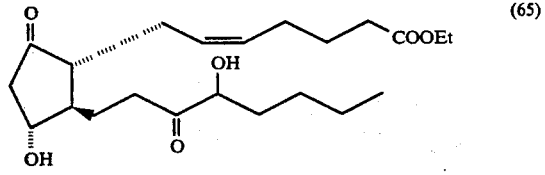

The same procedure as in Examples 2 to 20 was followed using (−)-Corey lactone (1) and dimethyl(3-(2-tetrahydropyranyl)oxy-2-oxoheptyl)phosphonate, and thus 13,14-dihydro-15 keto-16R,S-hydroxy PGE$_2$ ethyl ester (65) was synthesized.

Figure 19:
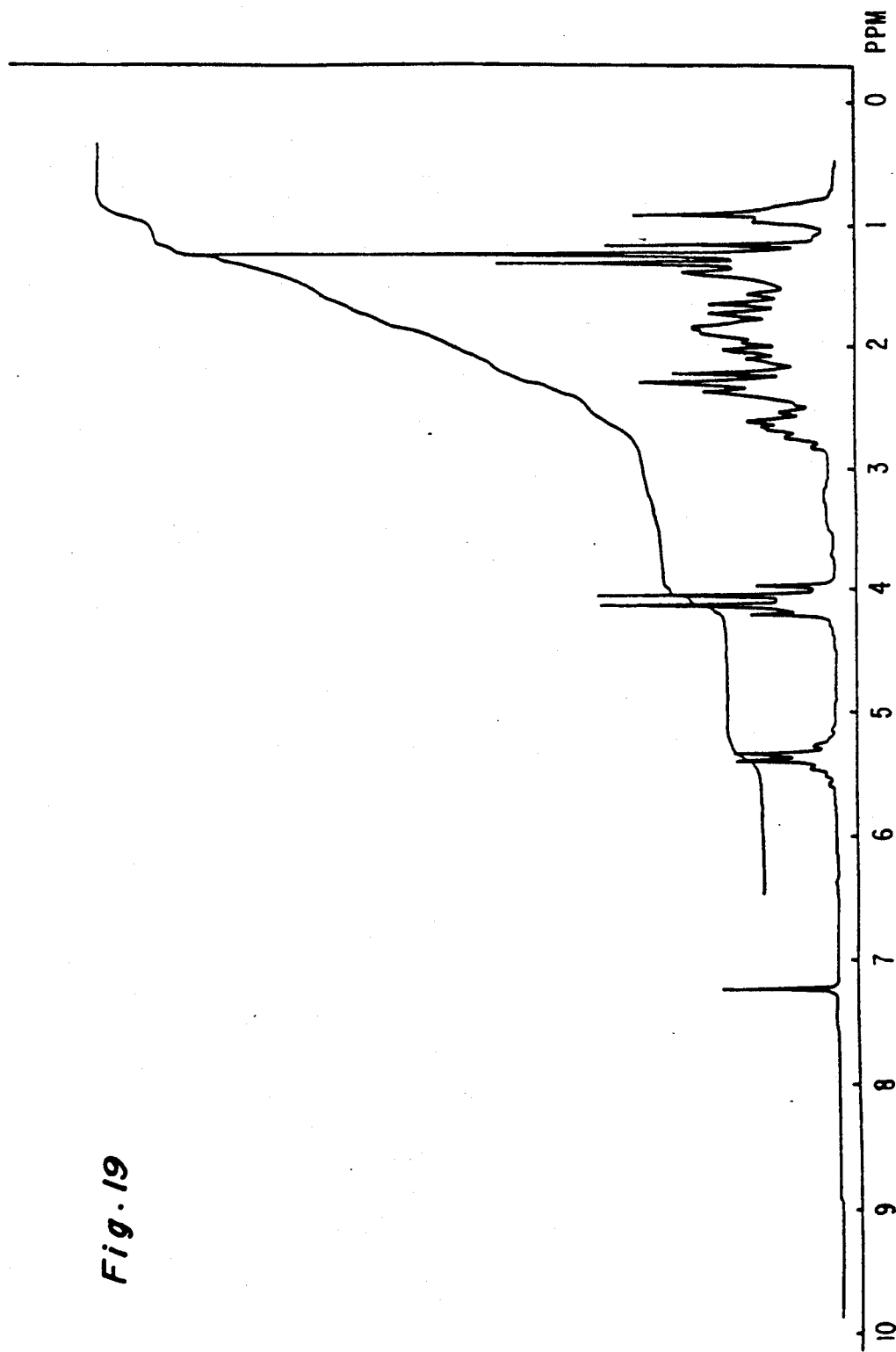

The n. m. r. spectrum of 13,14-dihydro-15 keto-16R,S-hydroxy-PGE$_2$ ethyl ester (65) is shown in FIG. 19.

Mass (D I) m/z:396 (M+), 378 ((M+ −18), 333, 309, 96, 81.

EXAMPLE 22 (See Chart IX)

Preparation of 13,14-Dihydro-15-keto-PGE$_1$ ethyl ester(66), R:Et 22-1) Preparation of 13,14-Dihydro-15,15-ethylenedioxy-11-(2-tetrahydropyranyloxy)-PGF$_{1\alpha}$ ethyl ester (64), R:Et 13,14-dihydro-15,15-ethylenedioxy-11-(2-tetrahydropyranyl)oxy-PGF$_{2\alpha}$ ethyl ester (10), R=Et, (3.56 g) was hydrogenated with platinum oxide and hydrogen in ethanol (150 ml). After the usual work-up, there was obtained 3.50 g of 13,14-dihydro-15,15-ethylenedioxy-11-(2-tetrahydropyranyl)oxy-PGE$_{1\alpha}$ ethyl ester (64).

22-2) Preparation of 13,14-Dihydro-15,15-ethylenedioxy-11-(2-tetrapyranyl)oxy-PGE$_1$ ethyl ester (65)

13,14-dihydro-15,15-ethylenedioxy-11-(2-tetrahydropyranyl)oxy-PGF$_{2\alpha}$ ethyl ester (64) (3.25 g) was oxidized with Jones reagent (2.67-M; 3.2 ml) in acetone (100 ml) at −30° C. The crude product obtained after the usual work-up was chromatographed (hexane:ethyl acetate=5:2) to give 13,14-dihydro-15,15-ethylenedioxy-11-(2-tetrahydropyranyl) oxy-PGE$_1$ ethyl ester (65). Yield 2.72 g.

22-3) Preparation of 13,14-Dihydro-15-keto-PGE$_1$ ethyl ester (66)

13,14-Dihydro-15,15-ethylenedioxy-11-(2-tetrahydropyranyl)oxy-PGE$_1$ ethyl ester (65) (2.72 g) was dissolved in a mixed solvent (90 ml) of acetic acid:water:THF (4:2:1), and the solution was agitated for 3 h at 40°∼45° C. The solvent was distilled off under reduced pressure, and the resulting crude product was chromatographed twice (hexane:ethyl acetate=1:1, and ethyl acetate:benzene=1:1) to give 13,14-dihydro-15-keto-PGE$_1$ ethyl ester (66).

Figure 20:
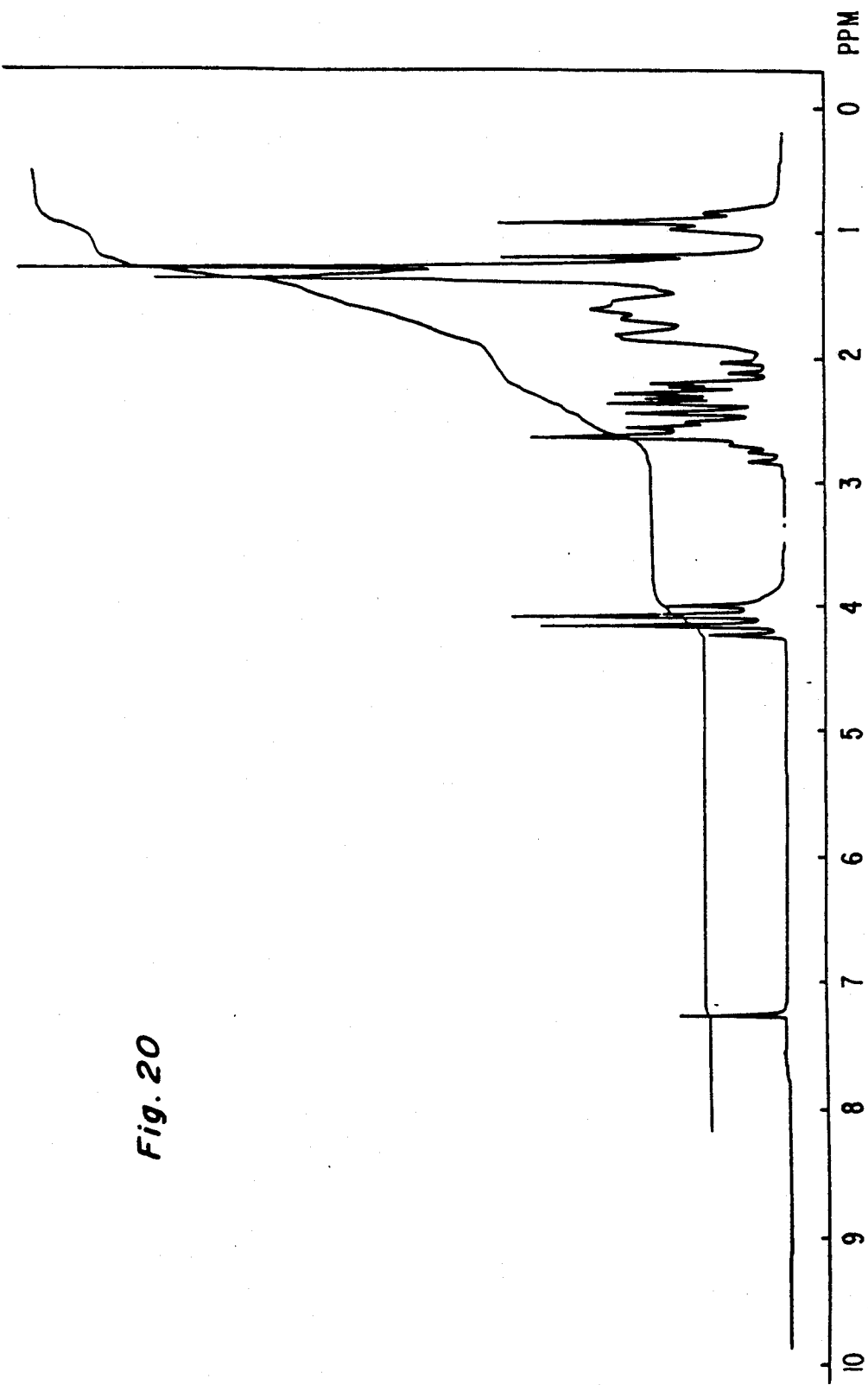

The n. m. r. spectrum of 13,14-Dihydro-15-keto-PGE$_1$ ethyl ester (66) is shown in FIG. 20.

EXAMPLE 23 (See Chart IX)

Preparation of 13, 14-Dihydro-15-keto-PGE$_1$ methyl ester (66), R:Me

The same procedure as in Example 22 was followed using 13,14-dihydro-15,15-ethylenedioxy-11-(2-tetrahydropyranyl)oxy-PGF$_{2\alpha}$ methyl ester (10), the compound obtained from the carboxylic acid (9) with diazomethane, and thus 13,14-dihydro-15-keto-PGE$_1$ methyl ester (66) was synthesized.

Figure 21:
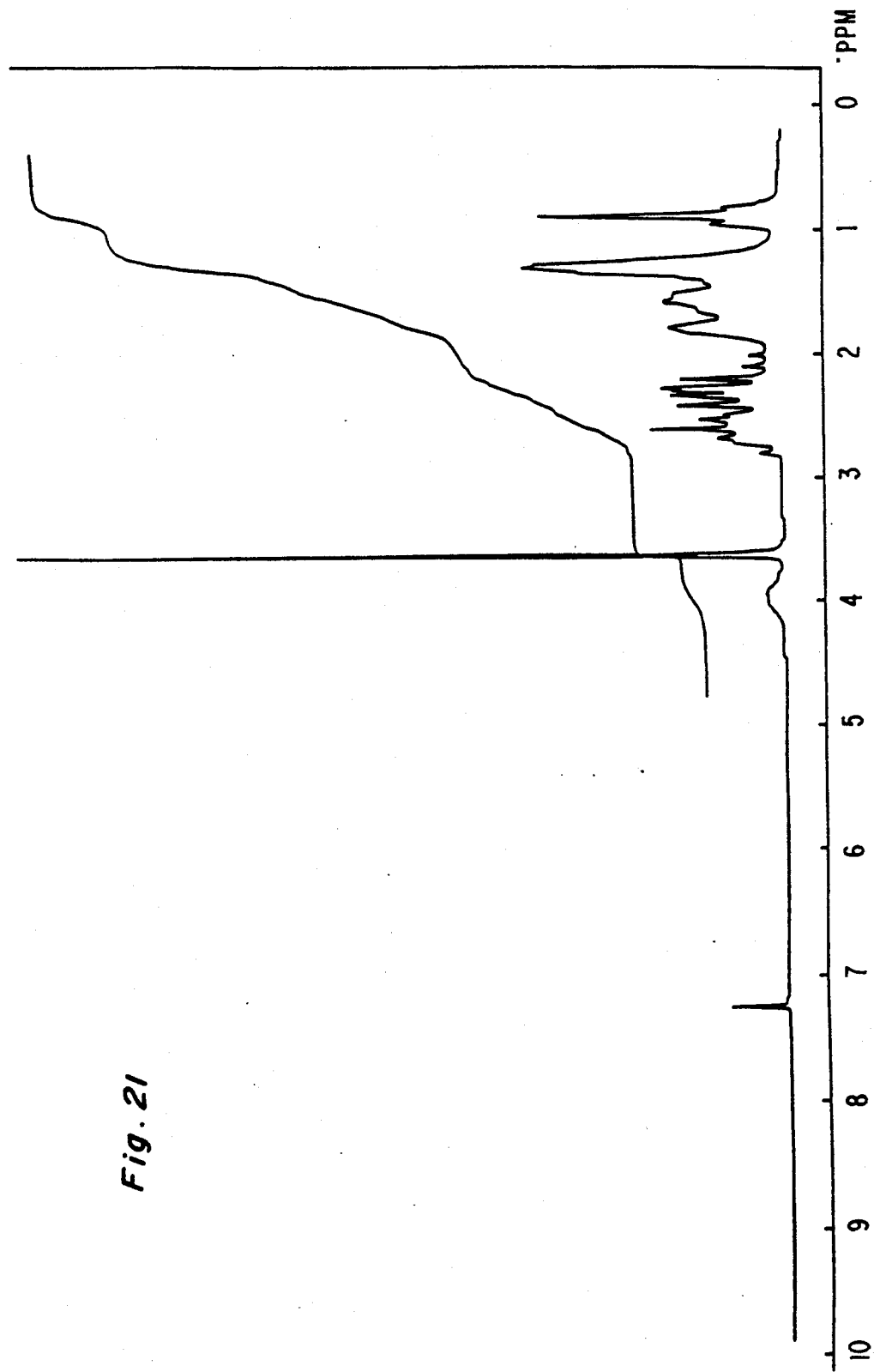

The n. m. r. spectrum of 13,14-dihydro-15-keto-PGE$_1$ methyl ester (66) is shown in FIG. 21.

EXAMPLE 24 (See Chart X)

Preparation of 13,14-Dihydro-15-keto-PGE$_2$ methyl ester (68), R:Et 24-1) Preparation of 13,14-Dihydro-15,15-ethylenedioxy-11-(2-tetrahydropyranyl)-oxy-PGE$_2$ ethyl ester (67)

The ethyl ester (10) (3.4 g) was oxidized with Jones reagent acetone (150 ml) at −40° C. and ketone (67) was obtained. Yield: 2.6 g.

24-2) Preparation of 13,14-Dihydro-15-keto-PGE$_2$ ethyl ester (68)

Ketone (67) (2.6 g) was dissolved in a mixed solvent (20 ml) of acetic acid:water:THF (4:2:1), and the solution was kept at 40°-50° C. for 3 h. Following the usual procedures, there was obtained 1.4 g of 13,14-dihydro-15-keto-PGE$_2$ ethyl ester (68).

Figure 22:
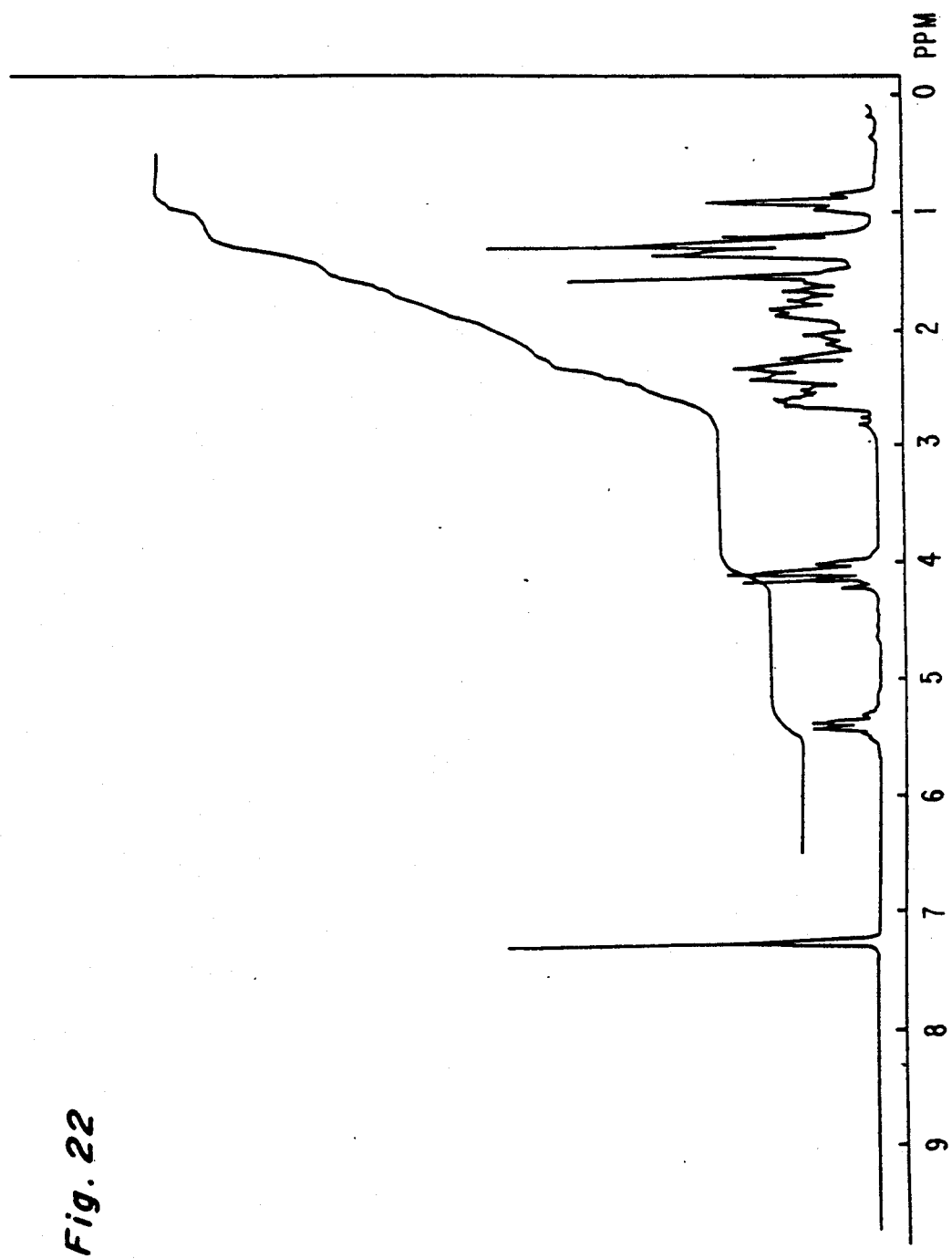

The n. m. r. spectrum of 13,14-dihydro-15-keto-PGE$_2$ ethyl ester (68) is shown in FIG. 22.

EXAMPLE 25 (See Chart X)

Preparation of 13,14-Dihydro-15-keto-PGE$_2$ methyl ester (68), R=Me

The procedure of Example 24 was repeated, except that the carboxylic acid (9) was converted to the corresponding methyl ester (10) with diazomethane, and thus 13,14-dihydro-15-keto-PGE$_2$ methyl ester (68), R=Me, was obtained.

Figure 23:
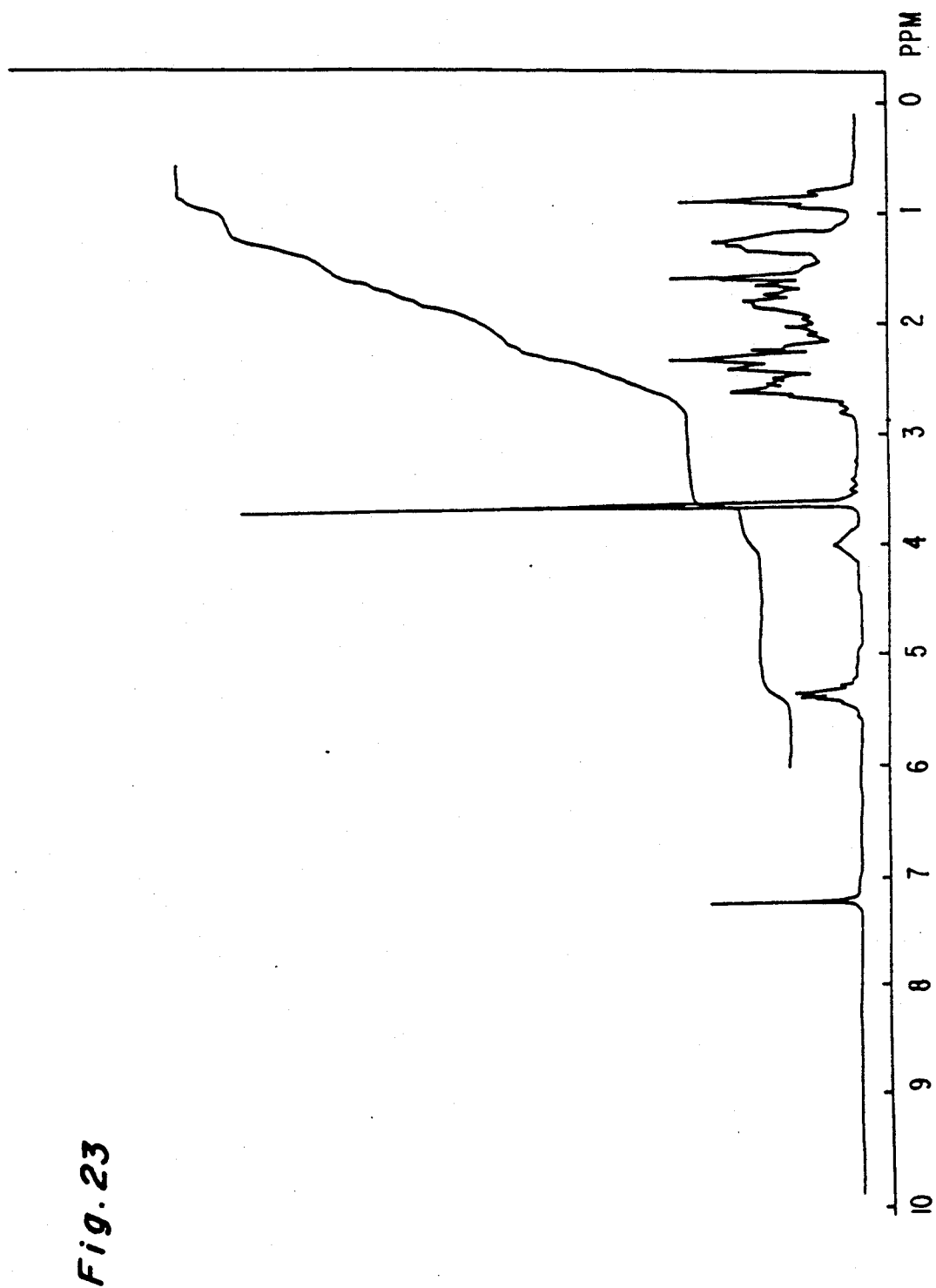

The n. m. r. spectrum of 13,14-dihydro-15-keto-PGE$_2$ methyl ester (68) is shown in FIG. 23.

EXAMPLE 26 (See Chart X)

Preparation of 13,14-Dihydro-15-keto-PGE$_2$ n-propyl ester (12), R=n-Pro

The same procedure as in Examples 24 and 25 was followed, except that the carboxylic acid was converted to the corresponding n-propyl ester (10) with DBU and n-propyl iodide in acetonitrile, and thus 13,14-dihydro-15-keto-PGE$_2$ n-propyl ester (68) was obtained.

Figure 24:
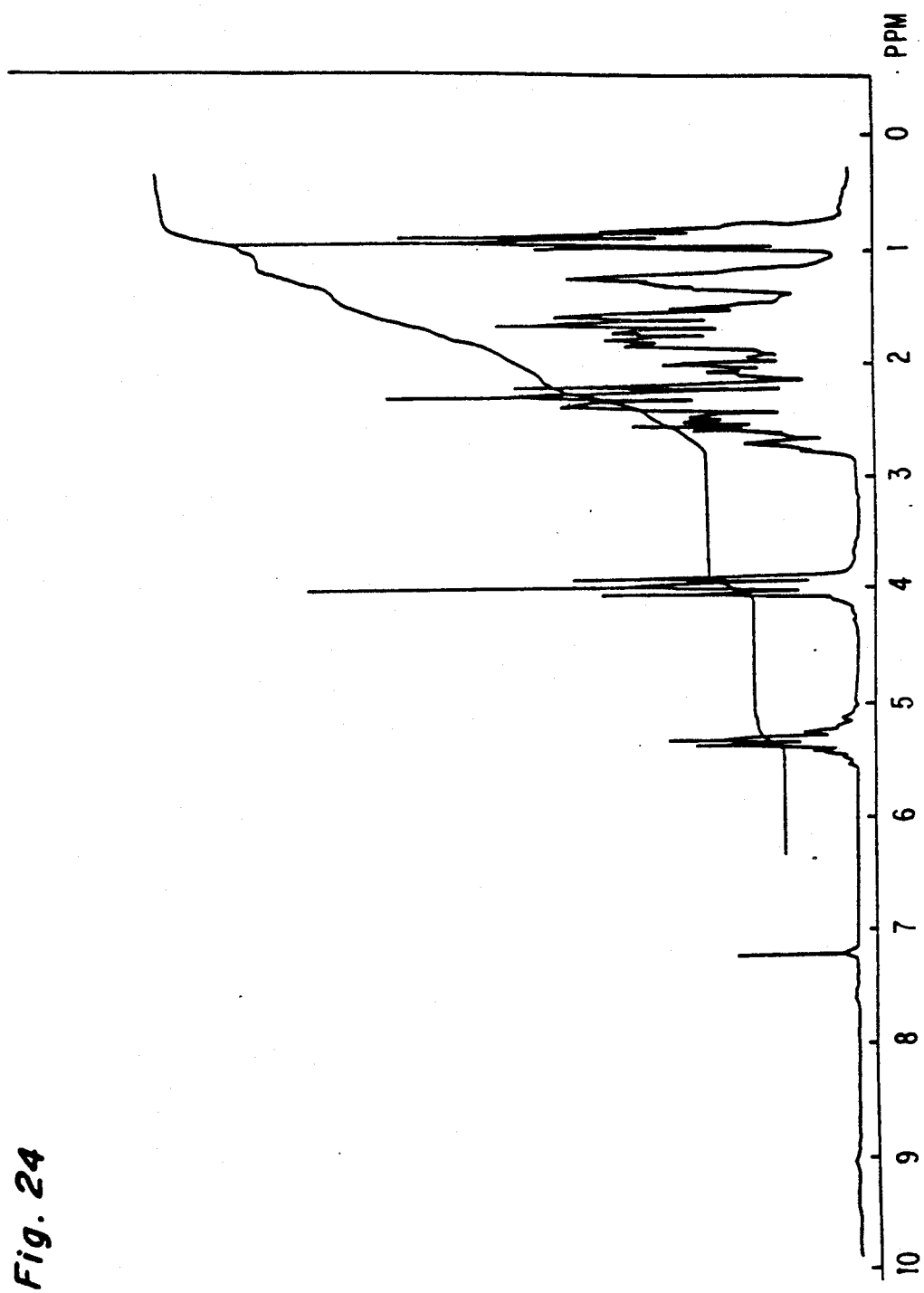

The n. m. r. spectrum of 13,14-dihydro-15-keto-PGE$_2$ n-propyl ester (68) is shown in FIG. 24.

EXAMPLE 27 (See Chart X)

Preparation of 13,14-Dihydro-15-keto-PGE$_2$ isopropyl ester (68), R=iso-Pro

The same procedure as in Examples 24, 25, and 26, 27 was followed, except that the carboxylic acid (9) was converted to the corresponding isopropyl ester (10) with DBU and isopropyl iodide in acetonitrile, and thus 13,14-dihydro-15-keto-PGE$_2$ isopropyl ester (68) was obtained.

Figure 25:
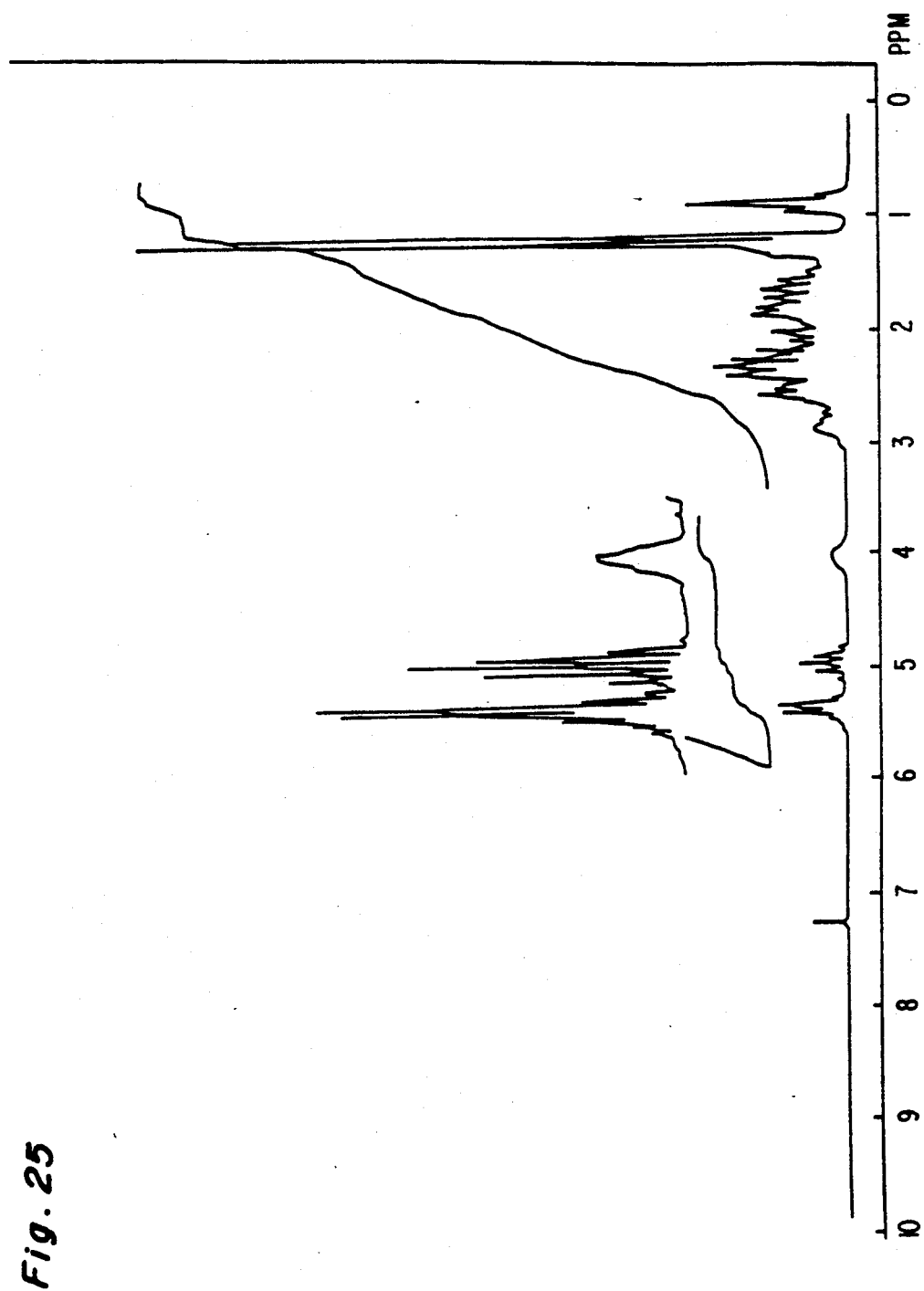

The n. m. r. spectrum of the 13,14-dihydro-15-keto-PGE$_2$ isopropyl ester (68) is shown in FIG. 25.

EXAMPLE 28 (See Chart X)

Preparation of 13,14-Dihydro-15-keto-PGE$_2$-n-butyl ester (68), R=n-Bu

The same procedure as in Examples 24, 25, 26, and was followed, except that the carboxylic acid (9) was converted to the corresponding n-butyl-ester (10) with DBU and n-butyl iodide in acetonitrile, and thus 13,14-dihydro-15-keto-PGE$_2$-n-butyl ester (68) was obtained.

Figure 26:
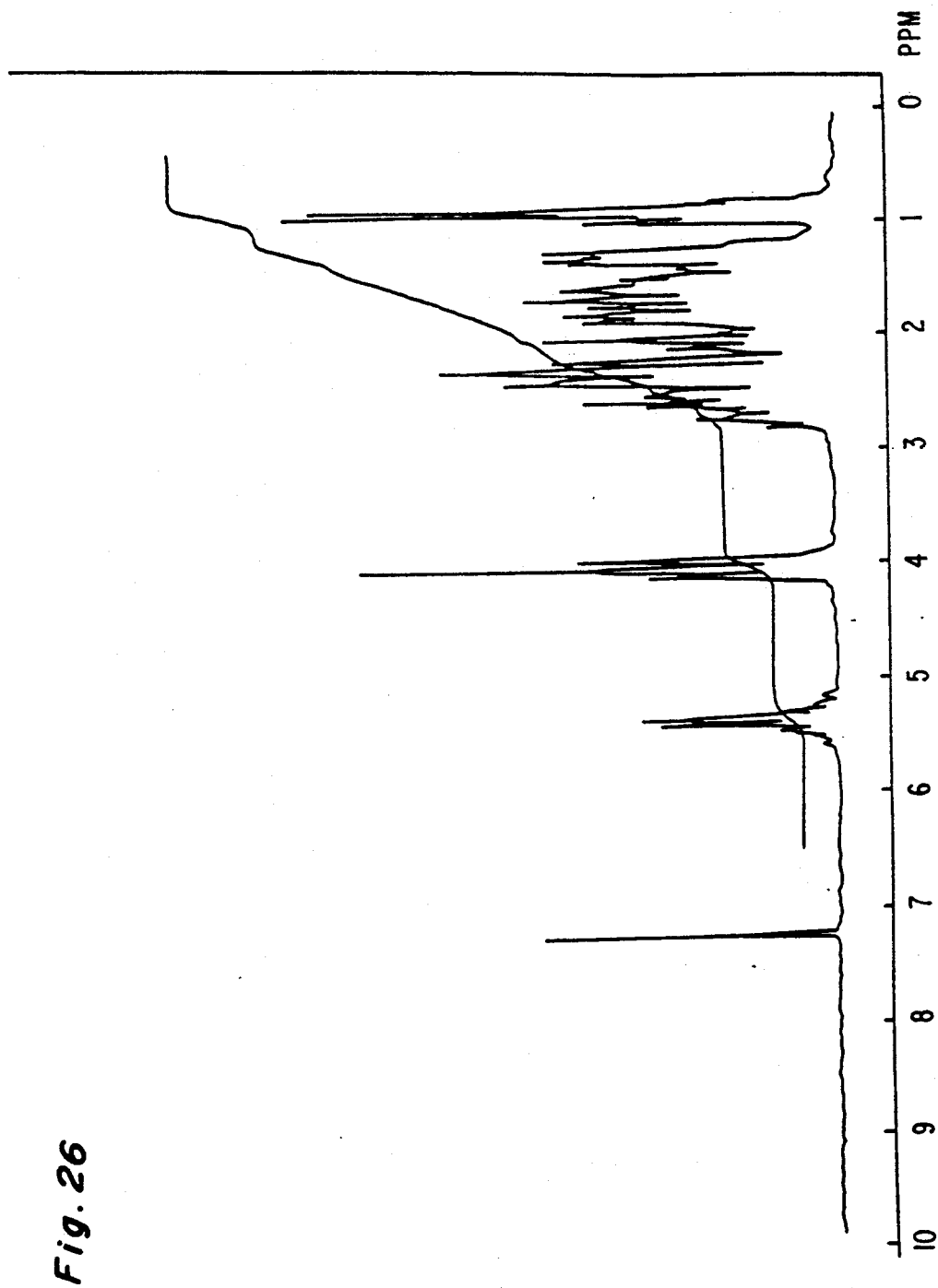

The n. m. r. spectrum of 13,14-dihydro-15-keto-PGE$_2$ n-butyl ester (68) is shown in FIG. 26.

EXAMPLE 29 (See Chart X)

Preparation of 13, 14-Dihydro-15-keto-PGE$_2$ cyclopentyl ester (68), R=cyclopentyl The same procedure as in Examples 24, 25, 26, 27, and 28 was followed, except that the carboxylic acid (9) was converted to the corresponding cyclopentyl-ester (10) with DBU and cyclopentyl iodide in acetonitrile, and thus 13,14-dihydro-15-keto-PGE$_2$ cyclopentyl ester (68) was obtained.

Figure 27:
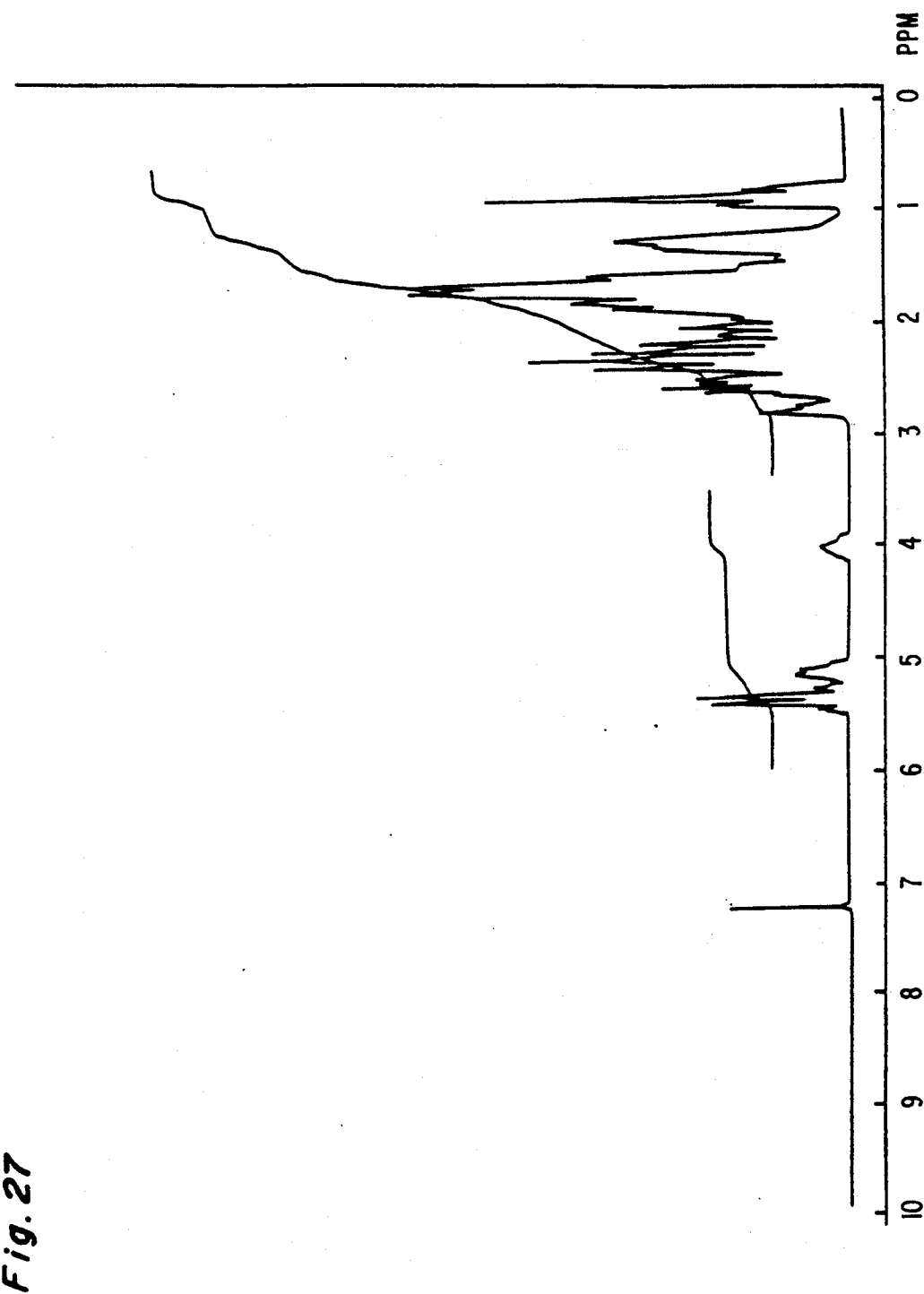

The n. m. r. spectrum of 13,14-dihydro-15-keto-PGE$_2$ cyclopentyl ester (68) is shown in FIG. 27.

EXAMPLE 30 (See Chart X)

Preparation of 13,14-Dihydro-15-keto-PGE$_2$ benzyl ester (68), R=Benzyl

The same procedure as in Examples 24, 25, 26, 27, 28, and 29 was followed, except that the carboxylic acid (9) was converted to the corresponding benzyl ester (10) with DBU and benzyl bromide in acetonitrile, and thus 13,14-dihydro-15-keto-PGE$_2$-benzil ester (68) was obtained.

Figure 28:
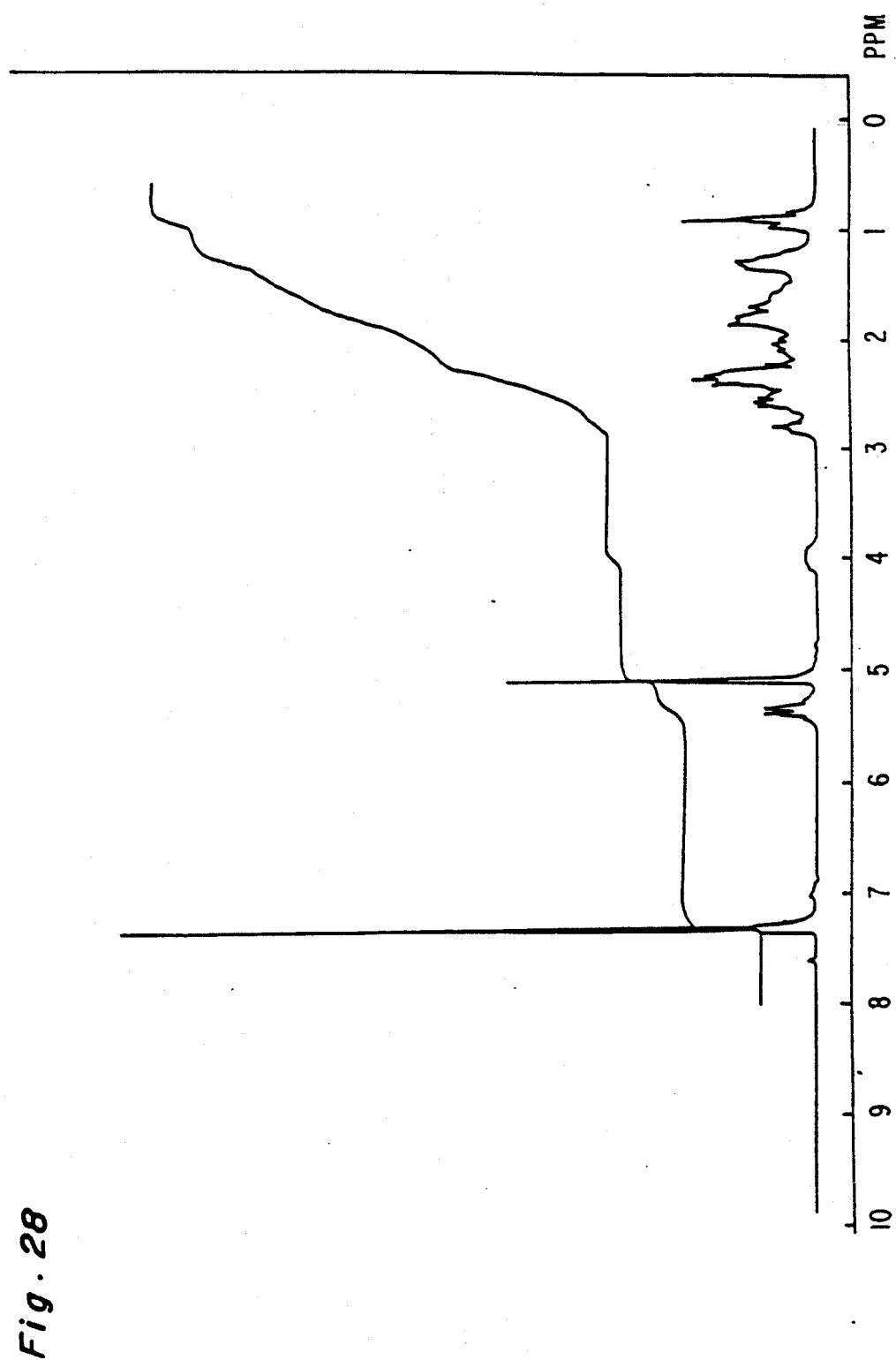

The n. m. r. spectrum of 13,14-Dihydro-15-keto-PGE$_2$ benzyl ester (68) is shown in FIG. 28.

EXAMPLE 31

Preparation of 13,14-Dihydro-15-keto-16,16-dimethyl-PGE$_2$ methyl ester (69), R=Me

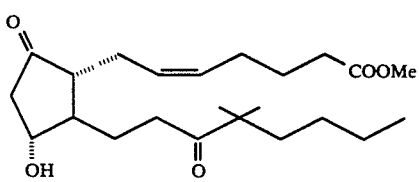

(69)

The same procedure as in Examples 24 to 30 was followed using(−)-Corey lactone (1) and a dimethyl (3,3-dimethyl-2-oxoheptyl)phosphonate obtained in the ordinary method, to produce 13,14-dihydro-15-keto-16,16-dimethyl-PGE$_2$ methyl ester (69).

Figure 29:
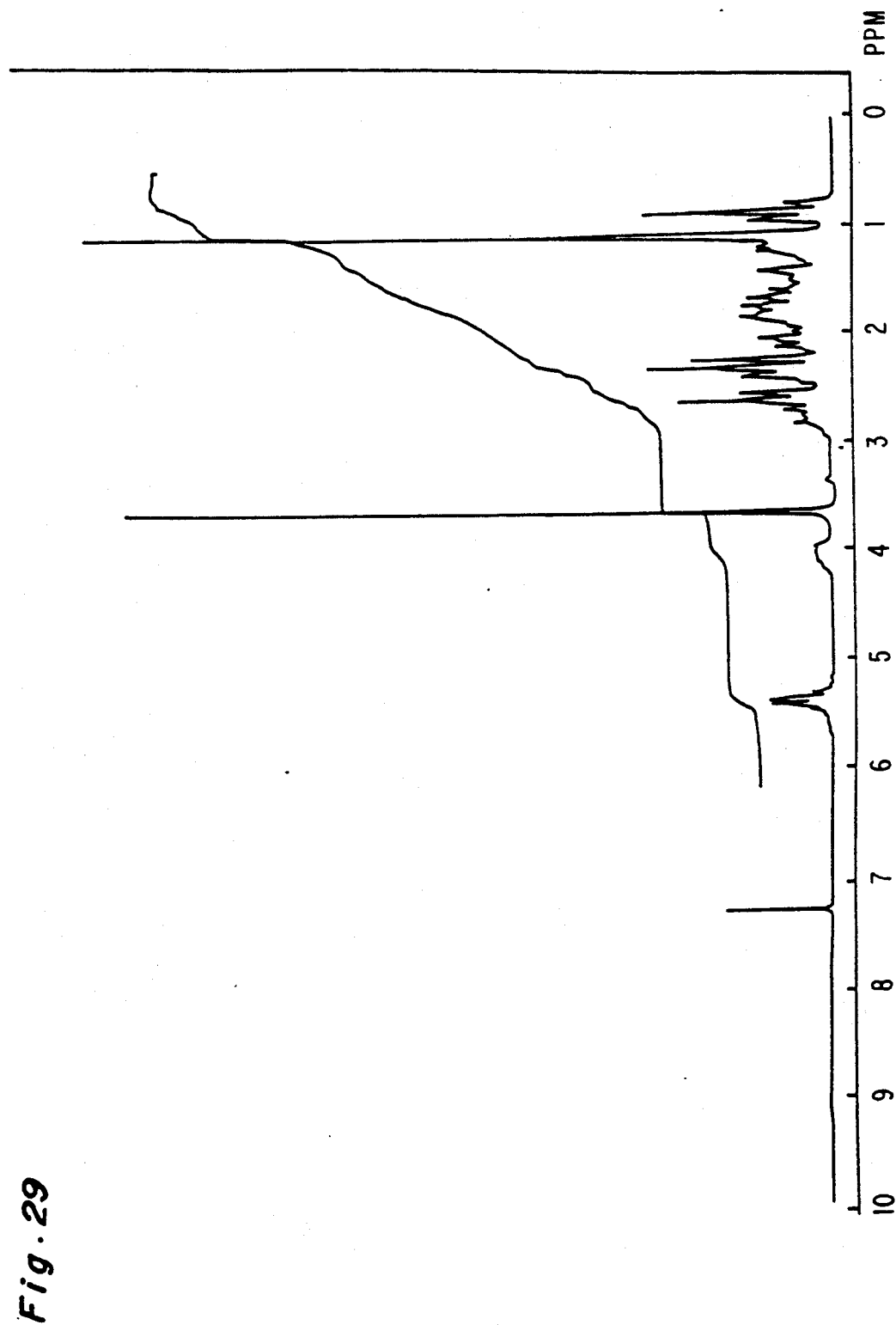

The n. m. r. spectrum of 13,14-dihydro-15-keto-16,16-dimethyl-PGE$_2$ methyl ester (69) is shown in FIG. 29.

EXAMPLE 32

Preparation of 13,14-Dihydro-15-keto-16,16-dimethyl-PGE$_2$ ethyl ester (70), R=Et

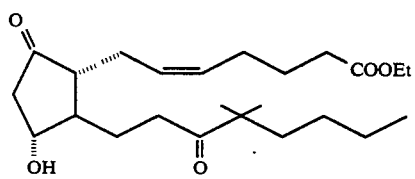

(70)

The same procedure as in Examples 24 to 31 was followed using(−)-Corey lactone (1) and dimethyl (3,3-dimethyl-2-oxoheptyl)phosphonate to produce 13,14-dihydro-15-keto-16,16-dimethyl-PGE$_2$ ethyl ester (70).

Figure 30:
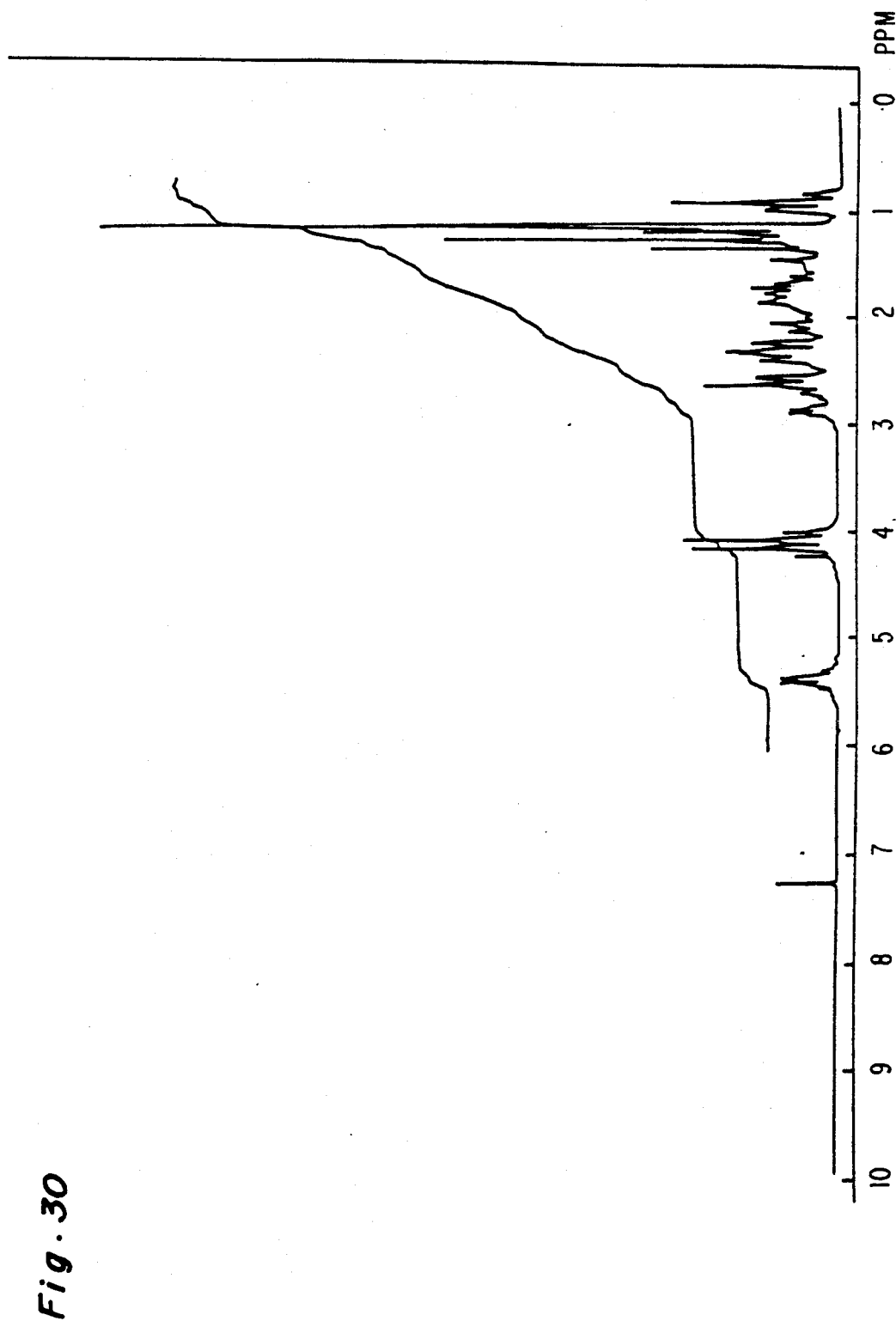

The n. m. r. spectrum of 13,14-Dihydro-15-keto-16,16-dimethyl-PGE$_2$ ethyl ester (70) is shown in FIG. 30.

EXAMPLE 33 (See Charts X and XI)

Preparation of 13,14-Dihydro-15-keto-3 R,S-methyl-PGE$_2$ ethyl ester (74)

13,14-Dihydro-15-keto-3R,S-methyl-PGE$_2$ ethyl ester (74) was obtained by following the same procedure as in Examples 24 to 30 except that ylide prepared from (3-methyl-4-carboxybutyl)triphenylphosphonium bromide, and that the lactol (8), were used to produce 13,14-dihydro-15,15-ethylenedioxy-3-methyl-11-(2-tetrahydropyranyl)oxy-PGF$_{2\alpha}$ (71).

Figure 31:
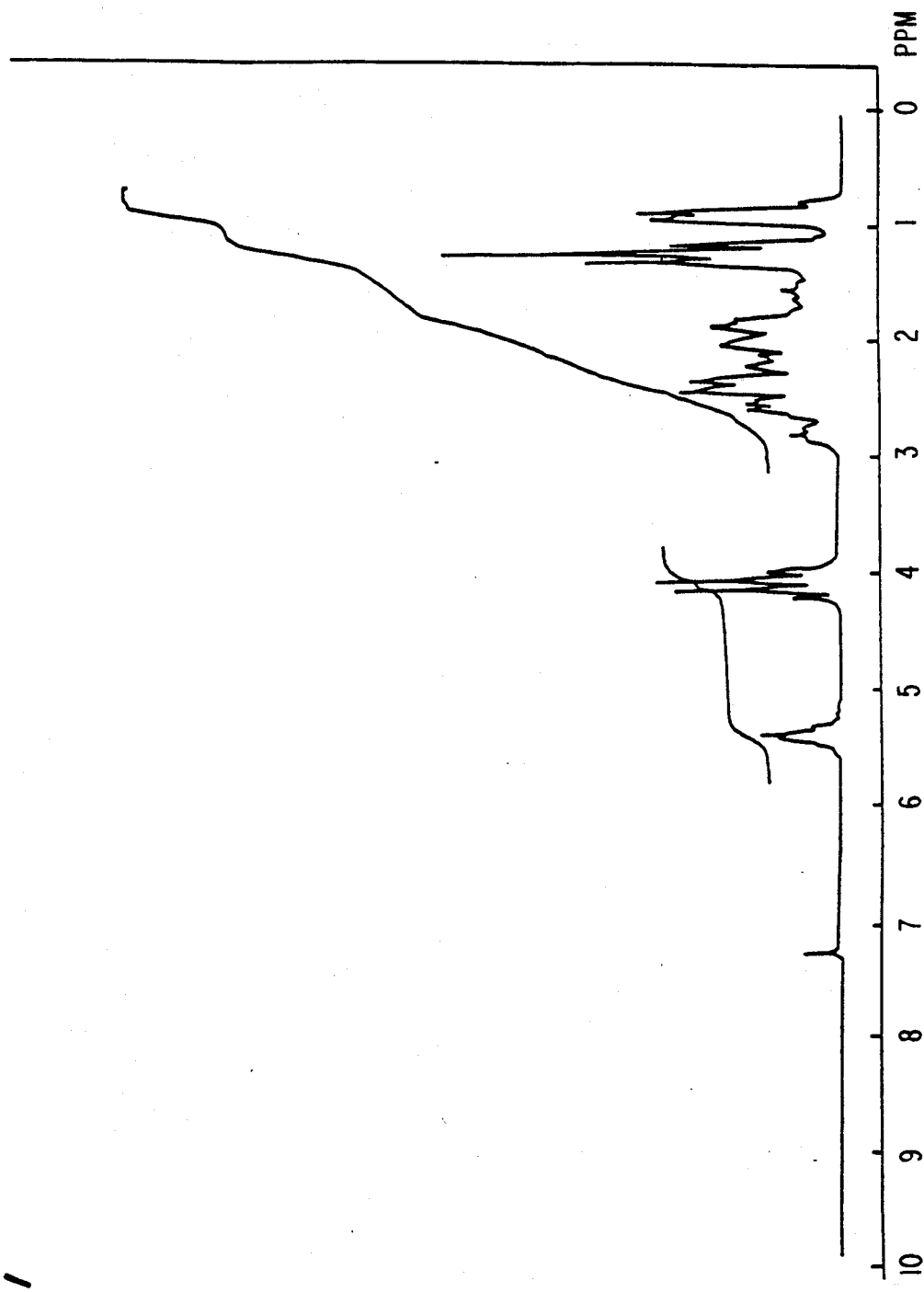

The n. m. r. spectrum of 13,14-dihydro-15-keto-3 R,S-methyl-PGE$_2$ ethyl ester (74) is shown in FIG. 31.

EXAMPLE 34 (See Charts X and XII)

Preparation of 13,14-Dihydro-15-keto-20-methoxy-PGE$_2$ methyl ester (79)

The same procedure as in Examples 24 to 30 was followed using (−)-Corey lactone (1) and dimethyl (7-methoxy-2-oxoheptyl)phosphonate produced in the ordinary method, and thus 13,14-dihydro-15-keto-20-methoxy-PGE$_2$ methyl ester (79) was obtained.

Figure 32:
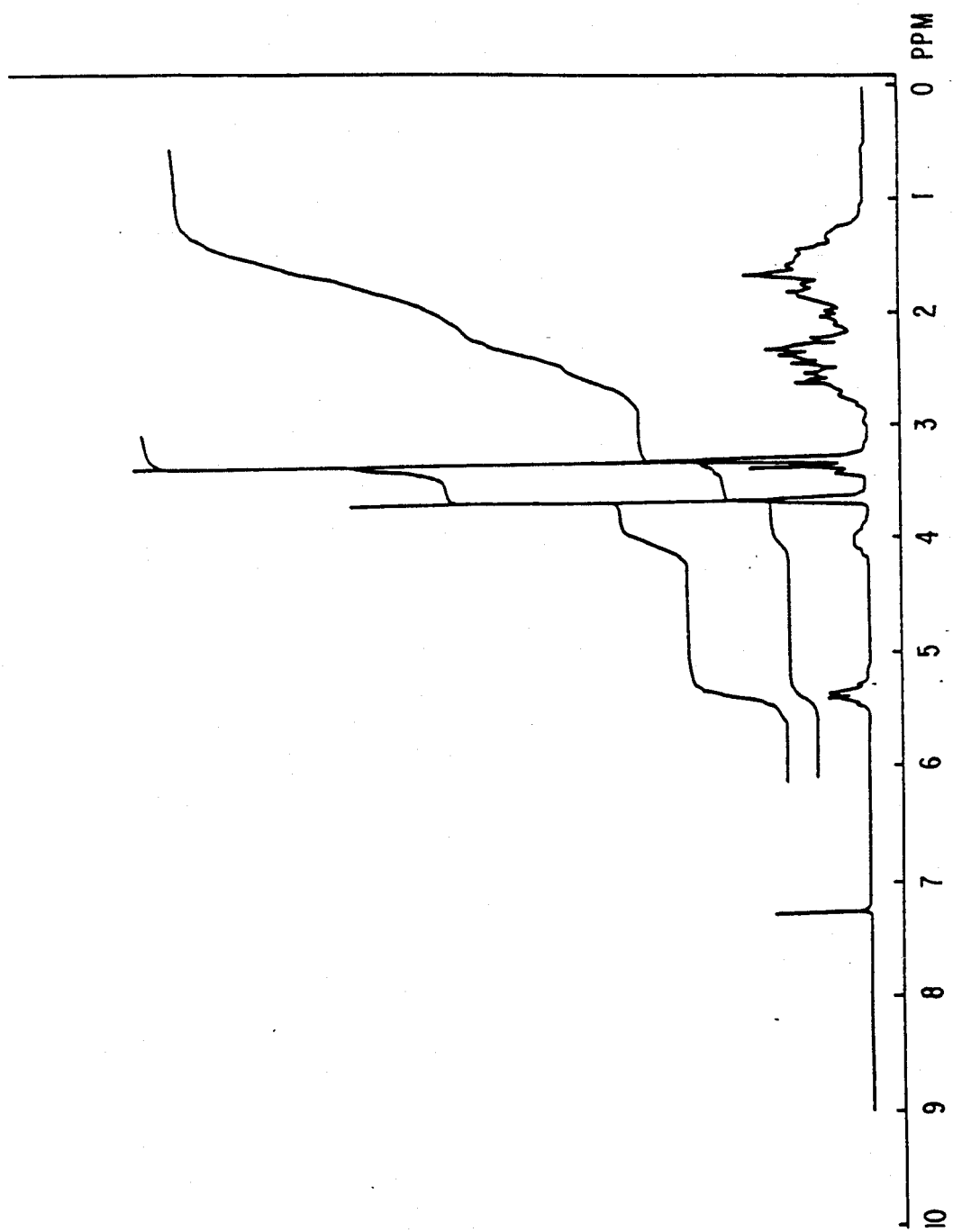

The n. m. r. spectrum of 13,14-dihydro-15keto-20-methoxy-PGE$_2$ methyl ester (79) is shown in FIG. 32.

EXAMPLE 35 (See Chart XII)

Preparation of 13,14-Dihydro-15-keto-3R,S-methyl-20-methoxy-PGE$_2$ methyl ester (80)

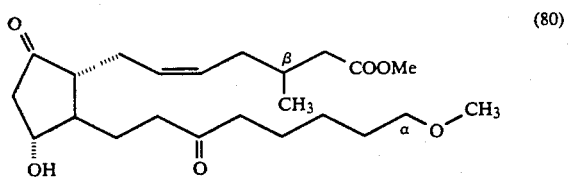

The same procedure as in Examples 24 to 30, 33 and was followed using lactol (75) and (3-methyl-4-carboxybutyl) triphenylphosphonium bromide produced in the usual manner, and thus 13,14-Dihydro-15-keto-3R,S-methyl-20methoxy-PGE$_2$ methyl ester (80) was obtained.

Figure 33:
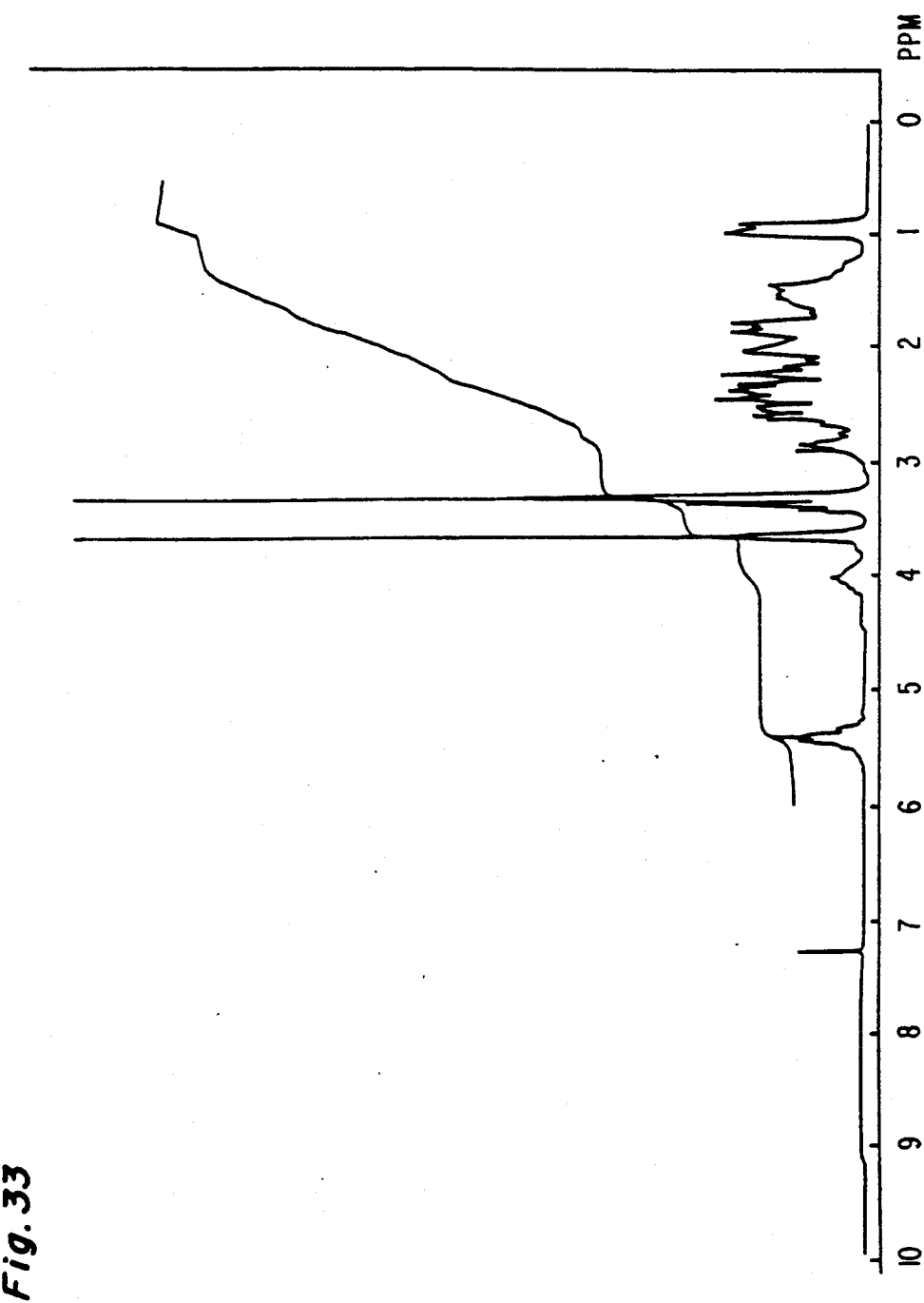

The n. m. r. spectrum of 13,14-Dihydro-15-keto-3R,S-methyl-20-methoxy-PGE$_2$ methyl ester (80) is shown in FIG. 33.

EXAMPLE 36 (See Chart XIII)

Preparation of 13,14-Dihydro-15-keto-$\Delta^2$-PGE$_2$ methyl ester (85), R=H 36-1) 11-(t-Butyldimethylsilyl)oxy-13,14-Dihydro-15,15-ethylenedioxy-2-phenylselecyl-PGF$_{2\alpha}$ methyl ester (82)

LDA was prepared from diisopropyl- amine (0.13 ml) in dry THF (3 ml), and n-butyl lithium (1.6−M; 0.58 ml), at −78° C. To LDA was added 0.1850 g of (81) in THF, and stirred for 1.5 h. A dry THF solution (2 ml) of diphenyl diselenide (0.18 g) was added, and the reaction solution was stirred at −78° C. for 30 min, then at room temperature for 1 h. Following usual procedure, there was obtained 0.1366 g of 2-phenylselenyl-PGF$_{2\alpha}$ methyl ester (82).

36-2) Preparation of 11-(t-Butyldimethylsilyl) oxy-13,14-dihydro-15,15-ethylenedioxy-$\Delta^2$-PGF$_{2\alpha}$ methyl ester (83)

The 2-Phenylselenyl-PGF$_{2\alpha}$ methyl ester (82) (0.1366 g) was dissolved in a mixed solvent (4 ml) of ethyl acetate-THF (1:1), and sodium hydrogen carbonate (0.1 g) and 30% hydrogen pereoxide (0.3 ml) were added. The reaction solution was stirred at room temperature for 15 min. Following the usual procedures, there was obtained 0.0850 g of 11-(t-butyldimethylsilyl)oxy-13,14-dihydro-15,15-ethylene dioxy-$\Delta^2$-PGF$_{2\alpha}$ methyl ester (83). Yield: 0.0850 g.

36-3) Preparation of 11-(t-butyldimethylsilyl) oxy-13,14-Dihydro-15,15-ethylenedioxy-$\Delta^2$-PGE$_2$ methyl ester (84)

The $\Delta^2$-PGF$_{2\alpha}$ methyl ester (83) (0.0717 g) was oxidized with PCC on aluminum oxide (1 g) in benzene (2 ml). Following the usual procedures, there was obtained 0.0554 g of $\Delta^2$PGE$_2$ methyl ester (84). Yield: 0.0554 g.

36-4) Preparation of 13,14-Dihydro-15-keto-$\Delta^2$-PGE methyl ester (85)

$\Delta^2$-PGE$_2$ methyl ester (84) (0.0554 g) was dissolved in acetonitrile (2 ml), and a mixture (1.5 ml) of 46%-aqueous hydrogen fluoride and acetonitrile (1:2) was added. The reaction solution was stirred at room temperature for 50 min. Following the usual procedures, there was obtained 13,14-Dihydro-15-keto-$\Delta^2$-PGE$_2$ methyl ester (85). Yield: 0.0312 g.

Figure 34:
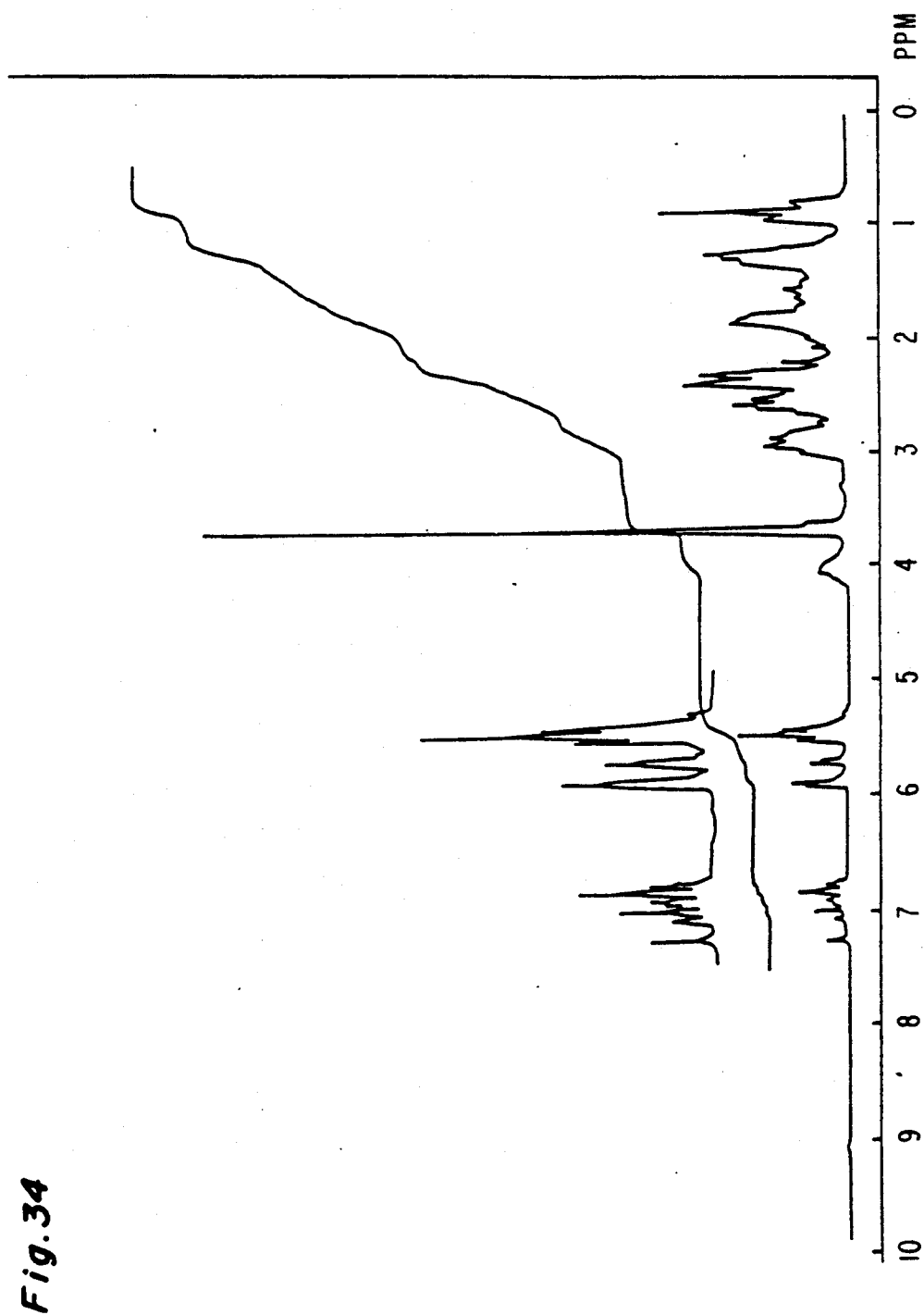

The n. m. r. spectrum of 13,14-dihydro-15 keto-$\Delta^2$-PGE$_2$ methyl ester (85) is shown in FIG. 34.

EXAMPLE 37 (See Chart XIII)

Preparation of 13,14-Dihydro-15-keto-20-methoxy-$\Delta^2$-PGE methyl ester (85), R=−OMe The same procedure as in Examples 24 to 30, 34 and 36 was followed with using(−)-Corey lactone (1) and dimethyl-(7-methoxy-2-oxoheptyl)phosphonate, and thus 13,14-dihydro-15-keto-20-methoxy-$\Delta^2$-PGE$^2$ methyl ester (85), R=−OMe, was obtained.

Figure 35:

The n. m. r. spectrum of 13,14-Dihydro-15-keto-20-methoxy-$\Delta^2$-PGE$_2$ methyl ester (85) is shown in FIG. 35.

EXAMPLE 38

Preparation of 13,14-Dihydro-15-keto-18-methoxy-19, 20-bisnor-PGE$_2$ methyl ester (86)

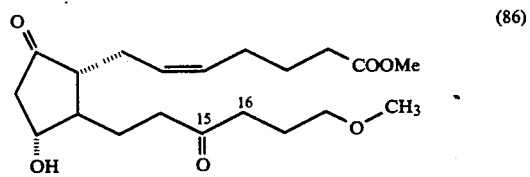

The same procedure as in Examples 24 to 30, and 34 was followed with using(−)-Corey lactone (1) and dimethyl (5-methoxy-2-oxopentyl)phosphonate, and thus 13,14-dihydro-15-keto-18-methoxy-19,20-bisnor-PGE$_2$ methyl ester (86) was obtained.

Figure 36:
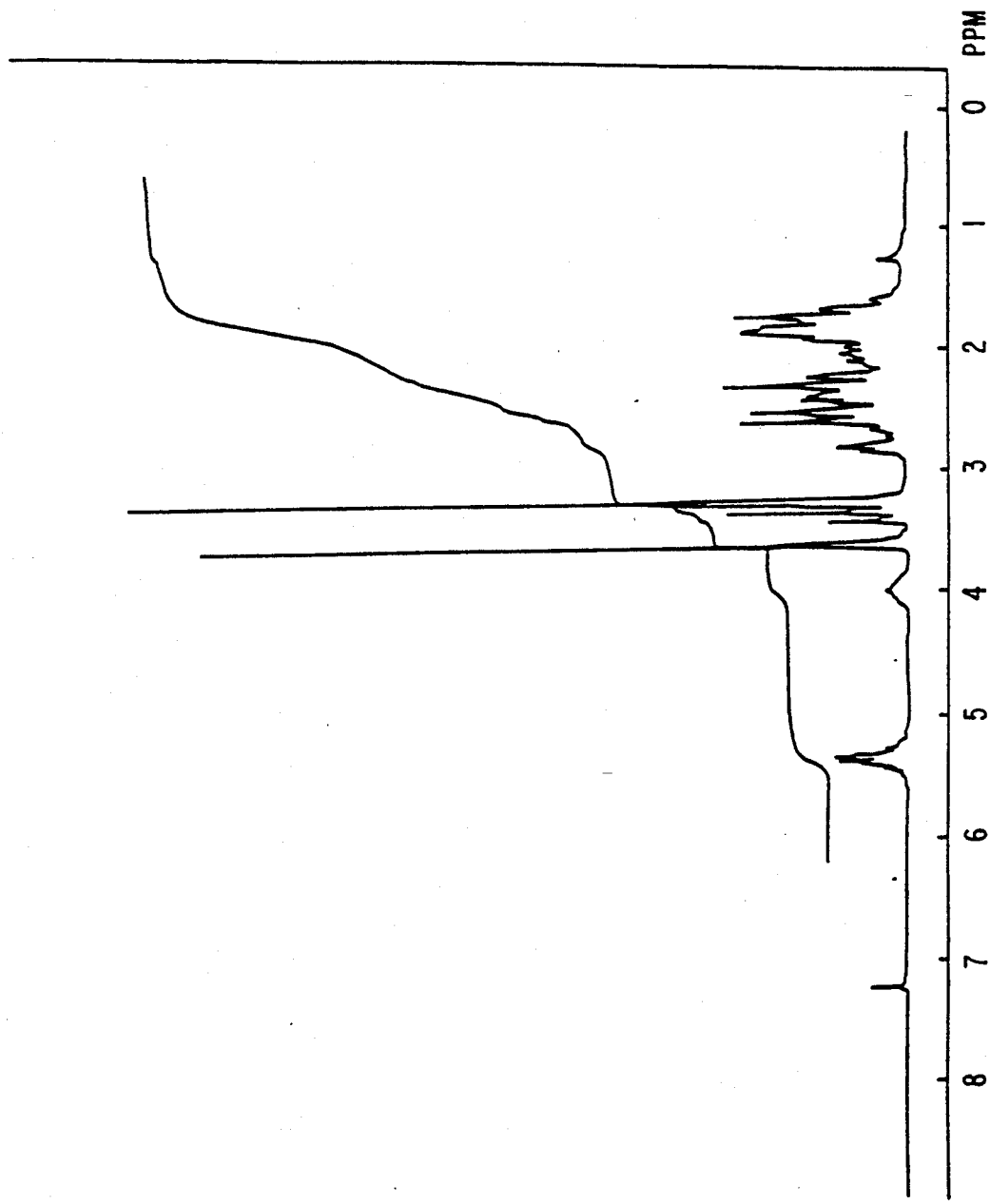

The n. m. r. spectrum of 13,14-Dihydro-15-keto-18-methoxy-19,20-bisnor-PGE$_2$ methyl ester (86) is shown in FIG. 36.

EXAMPLE 39

Preparation of 13,14-Dihydro-15-keto-20-ethyl-PGE$_2$ methyl ester (87), R=Me

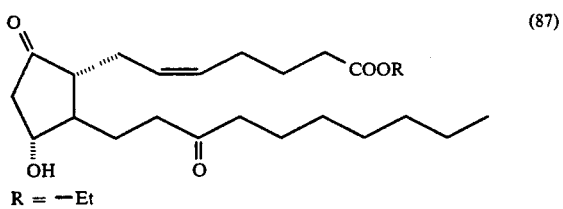

R = —Et

The same procedure as in Examples 24 to 30 was followed with using(—)-Corey lactone (1) and dimethyl(2-oxononyl)phosphonate, and thus 13,14-dihydro-15-keto-20-ethyl-PG 2 ester (87) was obtained.

Figure 37:
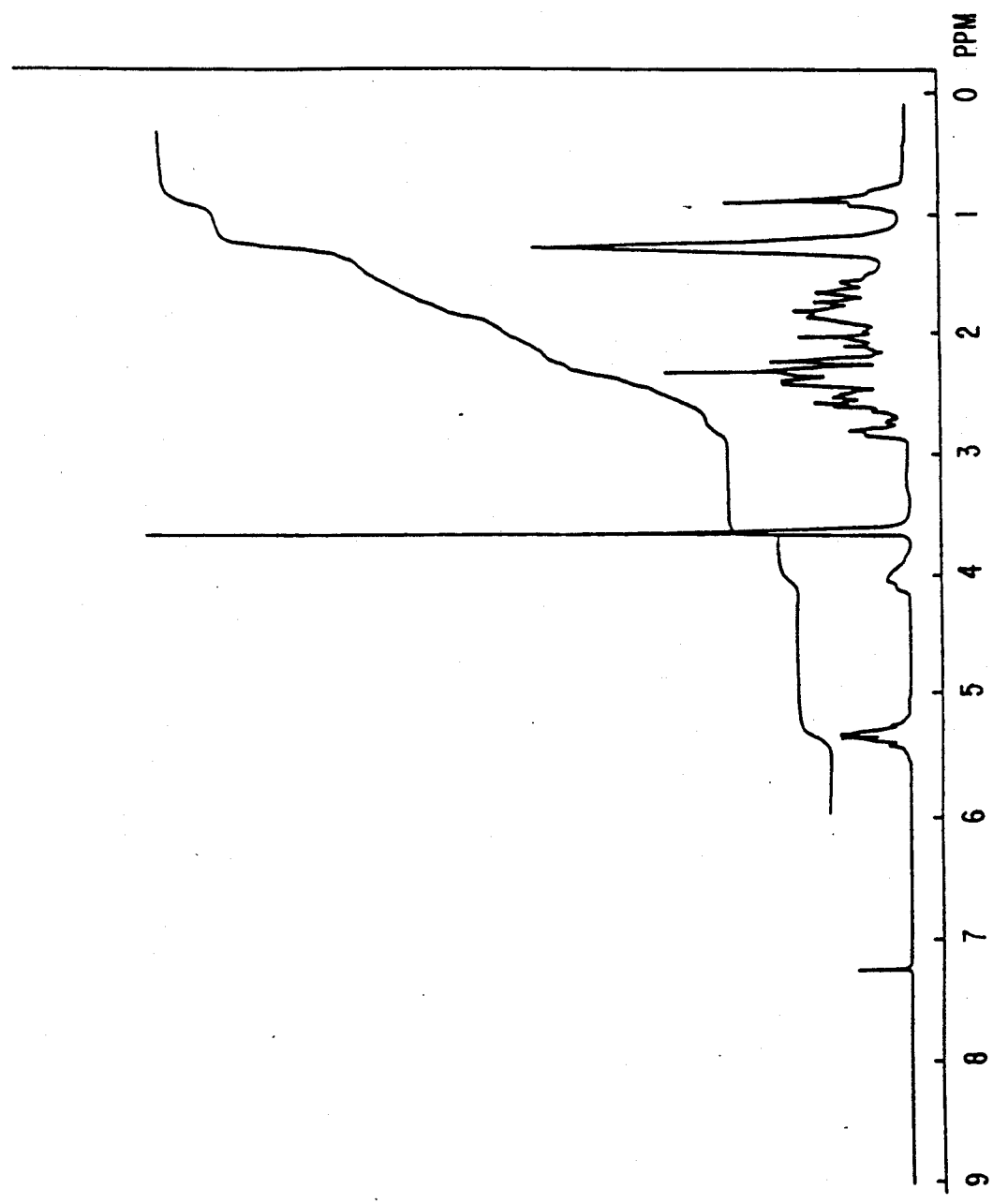

The n. m. r. spectrum of 13,14-Dihydro-15-keto-20-ethyl-PGE$_2$-methyl ester (87) is shown in FIG. 37.

EXAMPLE 40

Preparation of 13,14-Dihydro-15-keto-20-ethyl-PGE$_2$ ethyl ester (87), R=Et

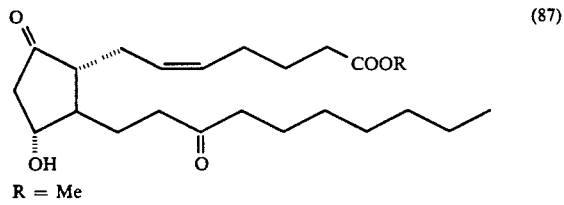

R = Me

The same procedure as in Examples 24 to 28 was followed with using(—)-Corey lactone (1) and dimethyl(2-oxononyl)phosphonate produced with the known method, and thus 13,14-Dihydro-15-keto-20-ethyl-PGE$_2$ ethyl ester (87) was obtained.

Figure 38:
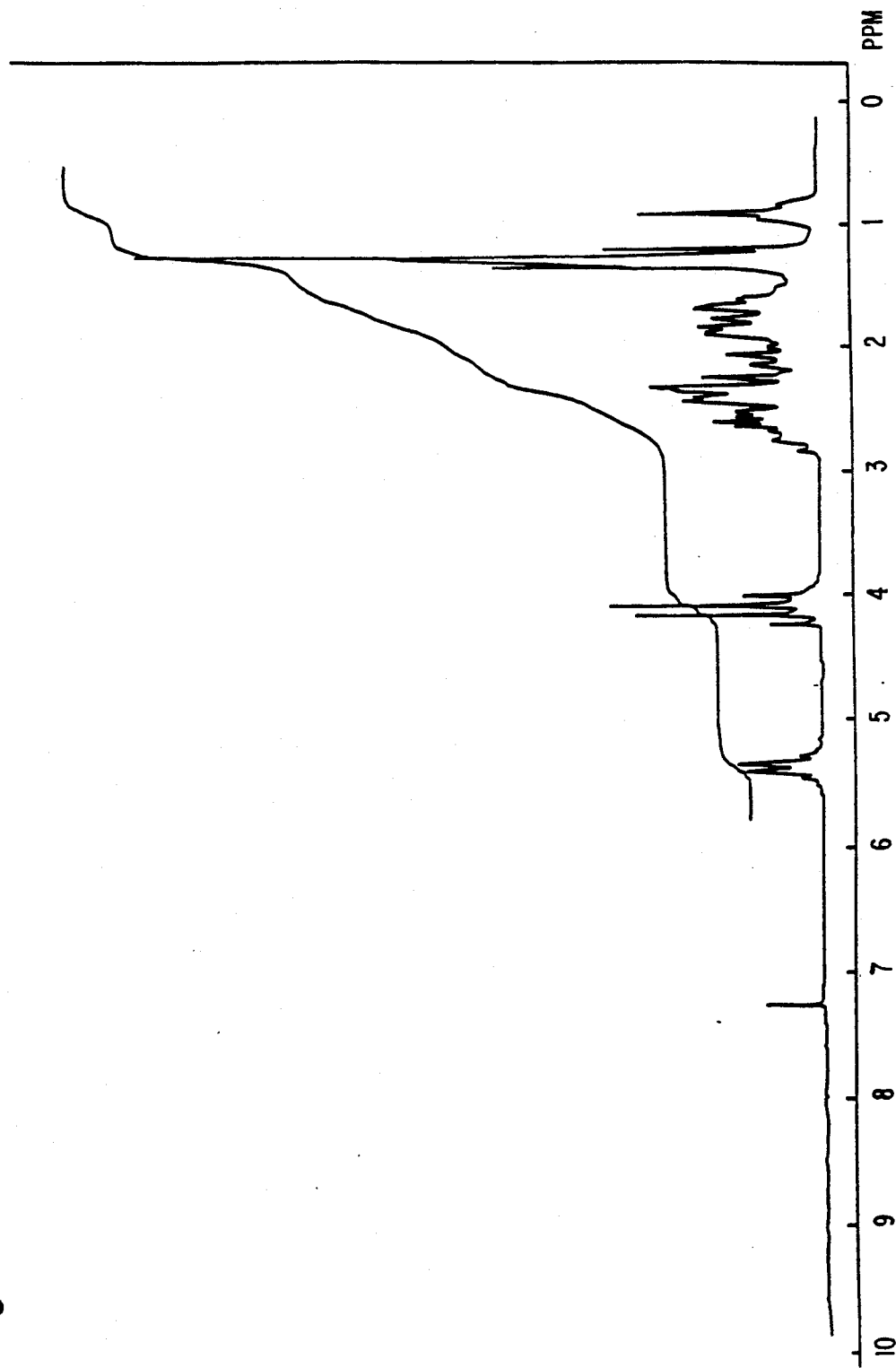

The n. m. r. spectrum of 13,14-Dihydro-15-keto-20-ethyl-PGE$_2$-ethyl ester (87), R=Et, is shown in FIG. 38.

Mass(DI) m/z:408, 390, 345.

EXAMPLE 41 (See the structural formula (87) shown in Example 40)

Preparation of 13,14-Dihydro-15-keto-20-ethyl-PGE$_1$ methyl ester (88)

13,14-Dihydro-15-keto-20-ethyl-PGE$_2$ methyl ester (87), R=Me, obtained in the same way as in Example 40 was hydrogenated with plutinum oxide and hydrogen in ethanol, and thus 13,14-Dihydro-15-keto-20-ethyl-PGE$_1$ methyl ester (88) was prepared.

Figure 39:
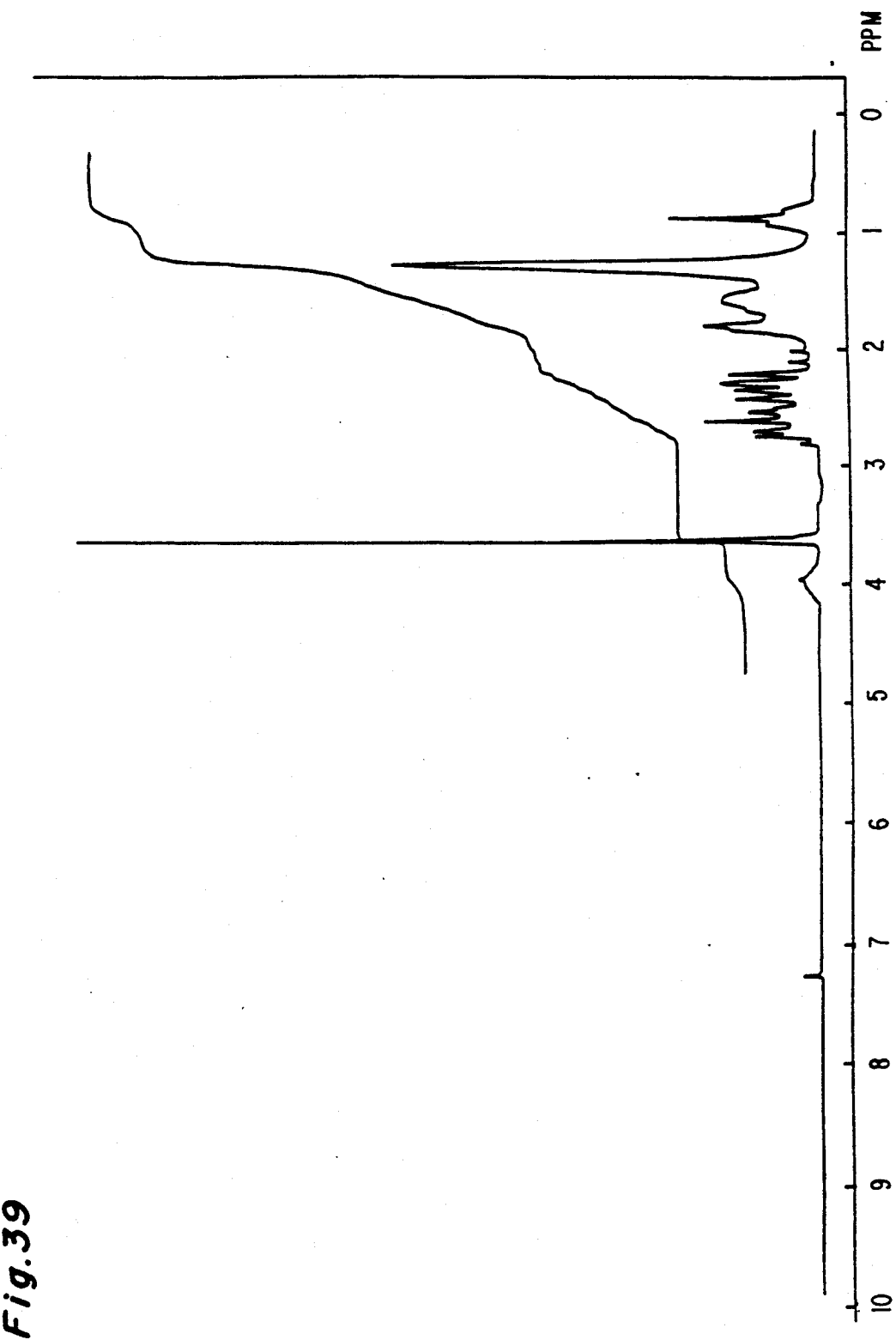
Figure 40:
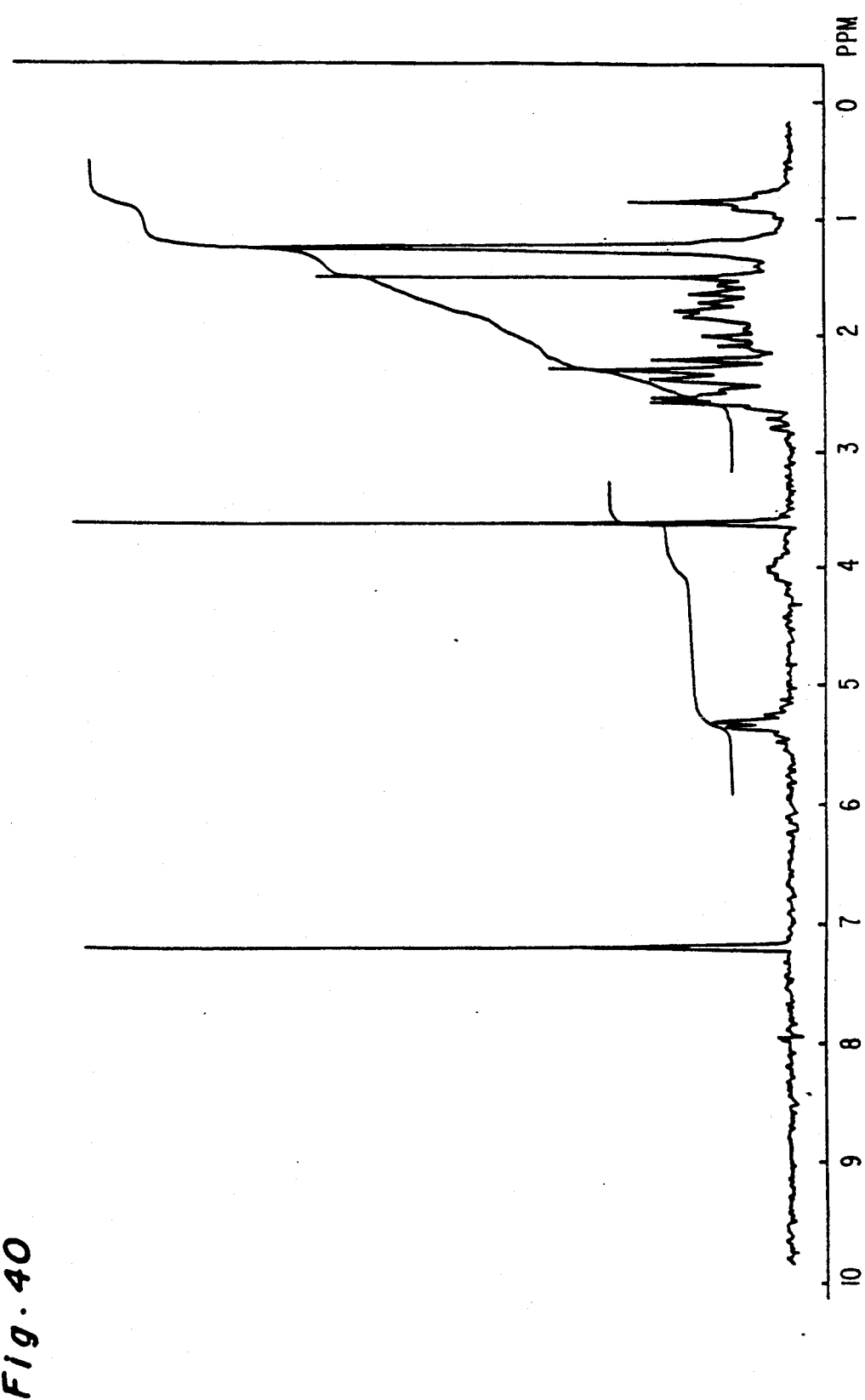

The n. m. r. spectrum of 13,14-Dihydro-15-keto-20-ethyl-PGE$_1$ methyl ester (88), R=Et, is shown in FIG. 39.

EXAMPLE 42

Preparation of 13,14-Dihydro-15-keto-20-n-propyl-PGE$_2$ methyl ester (89)

The same procedure as in Examples 24 to 30 and 40 was followed using(—)-Corey lactone 1) and dimethyl(2-oxodecyl)phosphonate produced according to the known method, and thus 13,14-Dihydro-15-keto-20-n-propyl-PGE$_2$ methyl ester (89) was synthesized.

Figure 41:
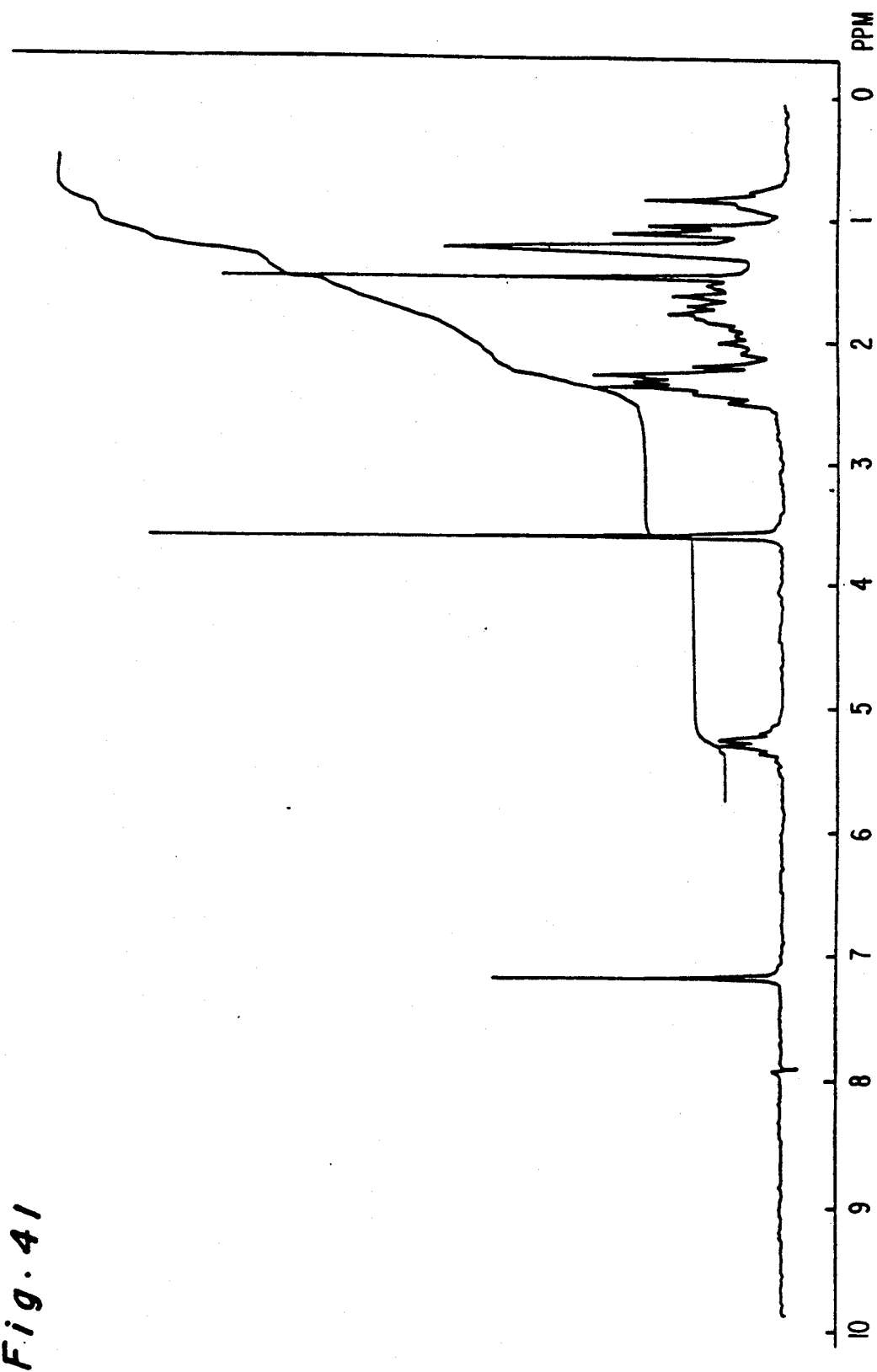

The n. m. r. spectrum of 13,14-Dihydro-15-keto-20-n-propyl-PGE$_2$ methyl ester (89) is shown in the FIG. 41. Mass (SIMS):409, 391, 369.

EXAMPLE 43 (See Chart XIV)

Preparation of 13,14-Dihydro-15-keto-20-ethyl-11R-dehydroxy-11R-methyl-PGE$_2$ methyl ester (98)

43-1) Tosylation of 1S-2-Oxa-3-oxo-6R-(3,3-ethylenedioxy-1-decyl)-7R-hydroxy-cis-bicyclo (3,3,0)octane (90)

Preparation of tosylate (91)

Alcohol (90) (1.723 g) was treated with p-toluenesulfonyl chloride (2.893 g) in pyridine (5 ml) to give the tosylate(91). Yield: 1.812 g (74%).

43-2) Preparation 1S-2-Oxa-3-oxo-6S-(3,3-ethylenedioxy-1-decyl)-cis-bicyclo(3,3,0)oct-7-ene (92)

DBU (5.6 ml) was added to a toluene solution (1.9 of the tosylate (91) (1.812 g), and the reaction solution was kept at 60 ° C. for 7 h. A crude product obtained after the usual work-up was chromatographed (hexane-ethyl acetate=3:1) to give the olefin (92).

Yield: 0.7594 g (63%).

43-3) DIBAL-H reduction of 1S-2-Oxa-3-oxo-6S-(3,3-ethylenedioxy-1-decyl)-cis-bicyclo(3,3,0)-oct-7-ene (92)

Preparation of lactol (93)

The olefin (92) (0.7594 g) was treated with DIBAL-H (1.5—M; 6.2 ml) to produce the lactol (93).

43-4) Preparation of methyl 15,15-Ethylenedioxy-20-ethyl-9S-hydroxy-cis-$\Delta^5$-$\Delta^{10}$-prostanoate (95)

The lactol (93) was added to a ylide generated from (4-carboxybutyl)triphenylphosphonium bromide and sodium methylsulfinyl carbanion, in DMSO, whereby prostanoic acid (94) was obtained. The acid (94) was esterified with diazomethane, and thus methyl 20-ethyl-prostanoate (95) was obtained.

Yield: 0.6600 g (67%).

43-5) Preparation of 15,15-Ethylenedioxy-20-ethyl-13,14-dihydro-PGA$_2$ methyl ester (96)

The methyl 20-ethyl-prostanoate (95) (0.6600 g) was oxidized with Jones reagent in acetone (400 ml) at —20° C. The crude material obtained after the usual work-up was chromatographed (hexane-ethyl acetate=3:1) to give 15,15-ethylenedioxy-20-ethyl-13,14-dihydro-PGA$_2$ methyl ester (96).

Yield: 0.6182 g (99%).

43-6) Preparation of 15,15-Ethylenedioxy-20-ethyl-13,14-dihydro-11R-dehydroxy-11R-methyl PGE$_2$ methyl ester (97)

The enone (96) (0.6100 g) was treated with lithium dimethylcuprate obtained from copper (I) iodide (0.8380 g) and methyl lithium (1.5—M; 5.8 ml), in ether (15 ml, and there was obtained 15,15-ethylenedioxy-20-ethyl-13,14-dehydroxy-11R-dihydroxy-11R-methyl PGE$_2$ methyl ester (97).

Yield: 0.5720 g (94%).

43-7) Preparation of 13,14-Dihydro-15-keto-20-ethyl-11R-dehydroxy-11R-methyl-PGE₂ methyl ester (98)

15,15-Ethylenedioxy-20-ethyl-13,14-dihydro-11R-dehydroxy-11R-methyl-PGE₂ methyl ester (97) (0.2300 g) was dissolved in 25 ml of a mixed solvent of acetic acid:water:THF (3:1:1), and the solution was kept at 50° C. for 2 h. A crude product obtained after the usual work-up was chromatographed to give 13,14-dihydro-15-keto-20-ethyl-11R-dehydroxy-11R-methyl-PGE₂ methyl ester (98).

Yield: 0.200 g.

Figure 42:
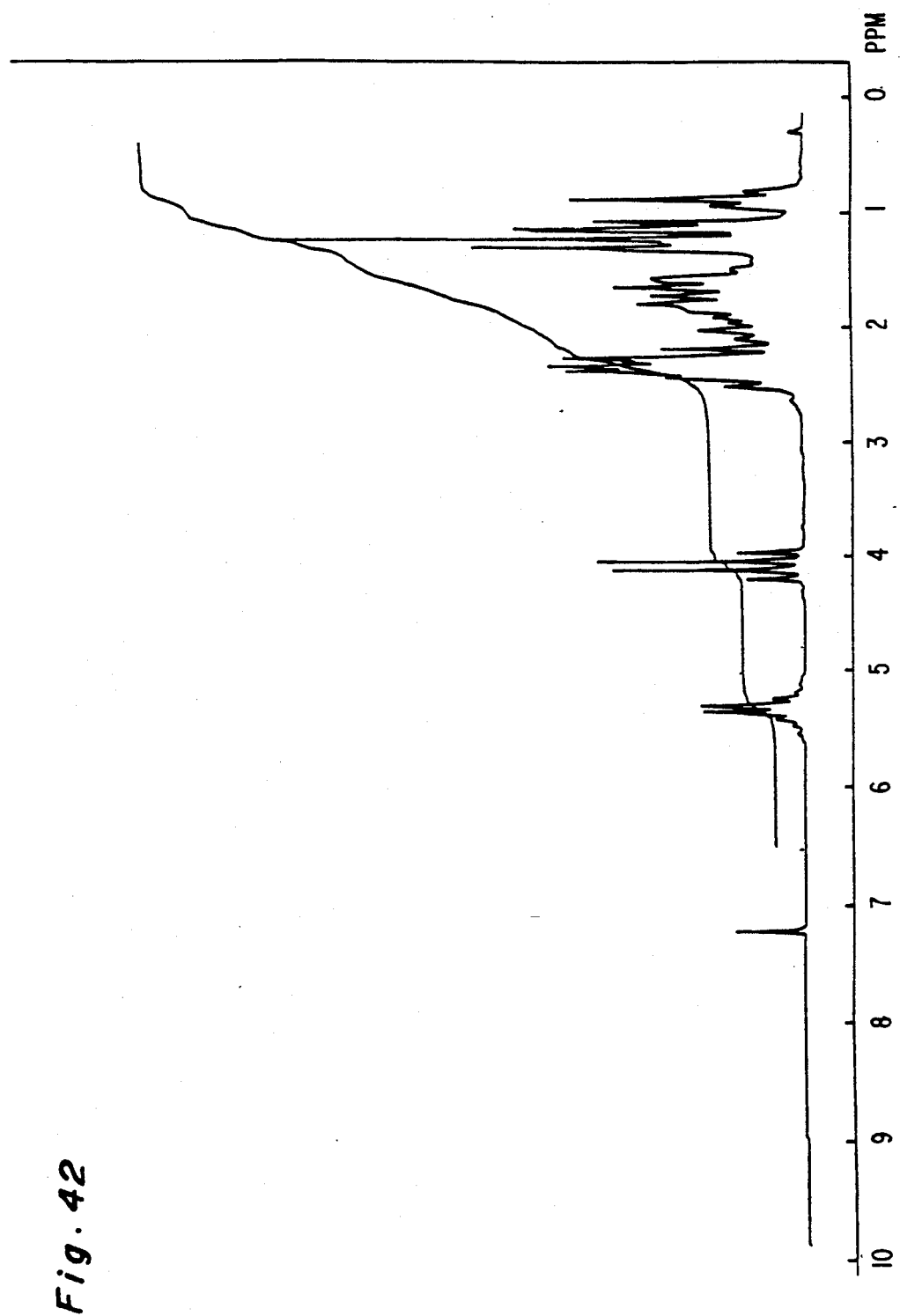

The n. m. r. spectrum of 13,14-dihydro-15-keto-20-ethyl-11R-dehydroxy-11R-methyl-PGE₂ methyl ester (98) is shown in FIG. 42.

Mass (DI) m/z: 392, 374, 361, 343.

EXAMPLE 44

Preparation of 13,14-Dihydro-15-keto-11R-dehydroxy-11R-methyl-PGE₂ ethyl ester (99)

The same procedure as in Example 43 was followed with using (—)-Corey lactone (1), dimethyl(2-oxoheptyl)phosphonate, and (4-carboxybutyl)triphenylphosphonium bromide, and 13,14-dihydro- 15-keto-11R-dehydroxy-11R-methyl-PGE₂ ethyl ester (99) was produced.

The n. m. r. spectrum of 13,14-dihydro-15-keto-1R-dehydroxy-11R-methyl-PGE₂ ethyl ester (99) is shown in FIG. 42.

Mass (SIMS) m / z:387, 360, 333, 315.

EXAMPLE 45 (See Chart XV)

Preparation of 13,14-Dihydro-15-keto-20-isopropylidene-PGE₂ methyl ester (103):

1S-2-Oxa-3-oxo-6R-(8-isopropylidene-3-keto-1-trans-octenyl)-7R-(4-phenylbenzoyl)oxy-cis-bicyclo(3, 3, 0)-octane (100), a compound produced from(—)-Corey lactone (1) and dimethyl (2-oxo-7-isopropylideneheptyl)phosphonate, was converted to the corresponding silylenolether (101) with dimethylphenyl silane (0.9 ml) and Wilkinson catalyst (50 mg)in THF (40 ml). The silylenolether (101) was ketalized in benzene in the usual manner, and thus there was obtained 1S-2-oxa-3-oxo-6R-(8-isopropylidene-3,3-ethylenedioxy-1-octyl)-7R-(4-phenylbenzoyl)oxy-cis-bicyclo(3, 3, 0)octane (102)

Yield: 2.32 g (82%).

Subsequently, the same procedure as in Examples 24 to 30, 40, 41, and 42 was followed to produce 13,14-dihydro-15-keto-20-isopropylidene-PGE₂ methyl ester (103).

Figure 43:
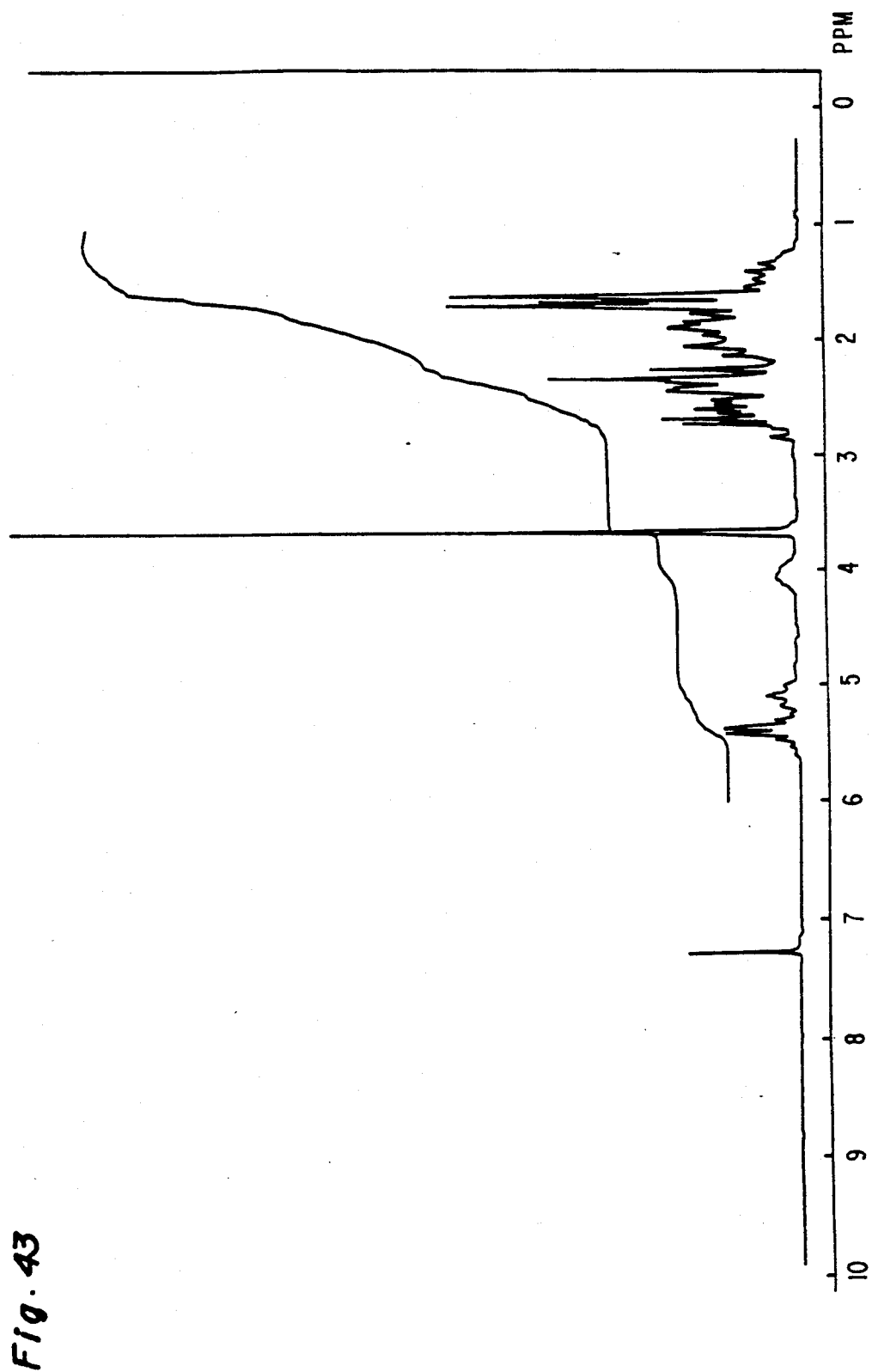

The n. m. r. spectrum of 13,14-dihydro-15-keto-20-isopropylidene-PGE₂ methyl ester (103) is shown in FIG. 43.

EXAMPLE 46 (See Chart XVI)

Preparation of 13,14-Dihydro-6,15-diketo-PGE₁ n-butyl ester (107), R=n-Bu

46-1) Preparation of the bromo-ether (104):

Bromo-ether formation from 15,15-ethylenedioxy-13,14-dihidro-11-(2-tetrahydropyranyl)oxy-PGF₂α n-butyl ester (10)

The butyl ester (10) (1.165 g) was dissolved in a THF-dichloromethane mixture (3 ml +30 ml), and the solution was ice-cooled. After addition of N-bromosuccinimide (0.405 g), the solution was stirred for 1 h. The reaction solution was poured in aqueous dilute sodium sulfite, and extracted with dichloromethane. The extract was dried, then concentrated under reduced pressure. The resulting crude product was chromatographed and thus bromo-ether (104) was obtained.

46-2) Preparation of 15,15-Ethylenedioxy-13,14-dihydro-6-keto-11-(2-tetrahydropyranyl)oxy-PGF₂α n-butyl ester (105)

Bromo-ether (104) (1.057 g) was dissolved in dry toluene (6 ml) and DBU (2.6 ml), and then agitated at 55° C. for 18 h. After being diluted with ethyl acetate, the mixture was adjusted to pH 3. Then, the organic layer of the solution was processed in the usual way.

Yield: 0.7132 g (75%).

46-3) Preparation of 15,15-Ethylenedioxy-13,14-dihydro-6-keto-11-(2-tetrahydropyranyl)oxy-PGE₂ n-butyl ester (106)

In acetone (40 ml), 6-keto-PGF₂α (105) (0.7132 g) was oxidized at −40° C. with Jones reagent, whereby 13,14-dihydro-15,15-ethylenedioxy-6-keto-11-(2-tetrahydropyranyl)oxy-PGE₂ n-butyl ester (106) (0.4404 g) was obtained.

Yield: 0.4404 g (62%).

46-4) Preparation of 13,14-Dihydro-6,15-diketo-PGE₂ n-butyl ester (107)

13, 14-Dihydro-15,15-ethylenedioxy-6-keto-11-(2-tetrahydropyranyloxy)-PGE₂ n-butyl ester (106) (0.4404 g) was kept at 55° C. in a mixed solvent of acetic acid:THF:water (3:1:1) for 3.5 h, whereby there was obtained 13,14-dihydro-6,15-diketo-PGE₂ n-butyl ester (107).

Yield: 0.200 g (59%).

Figure 44:
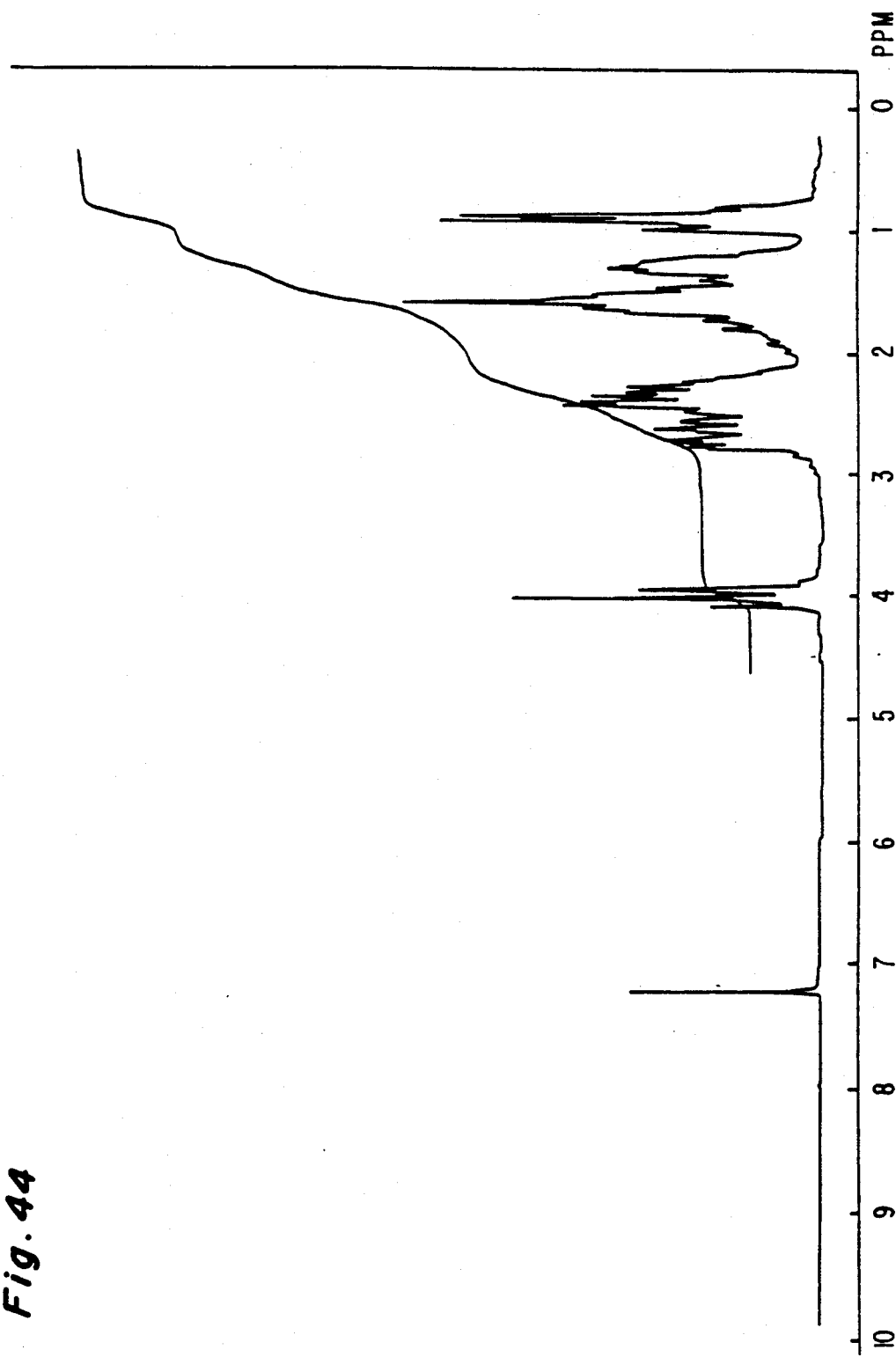

The n. m. r. spectrum of 13,14-dihydro-6,15-diketo-PGE₂ n-butyl ester (107) is shown in the FIG. 44.

EXAMPLE 47

Preparation of 13,14-Dihydro-6,15-diketo-20-methyl-PGE₂ ethyl ester (108)

The procedure of Example 46 was repeated with using(—)-Corey lactone (1) and dimethyl(2-oxooctyl)phosphonate, and thus 13,14-dihydro-6,15-diketo-20-methyl-PGE₂ ethyl ester (108) was obtained.

Figure 45:
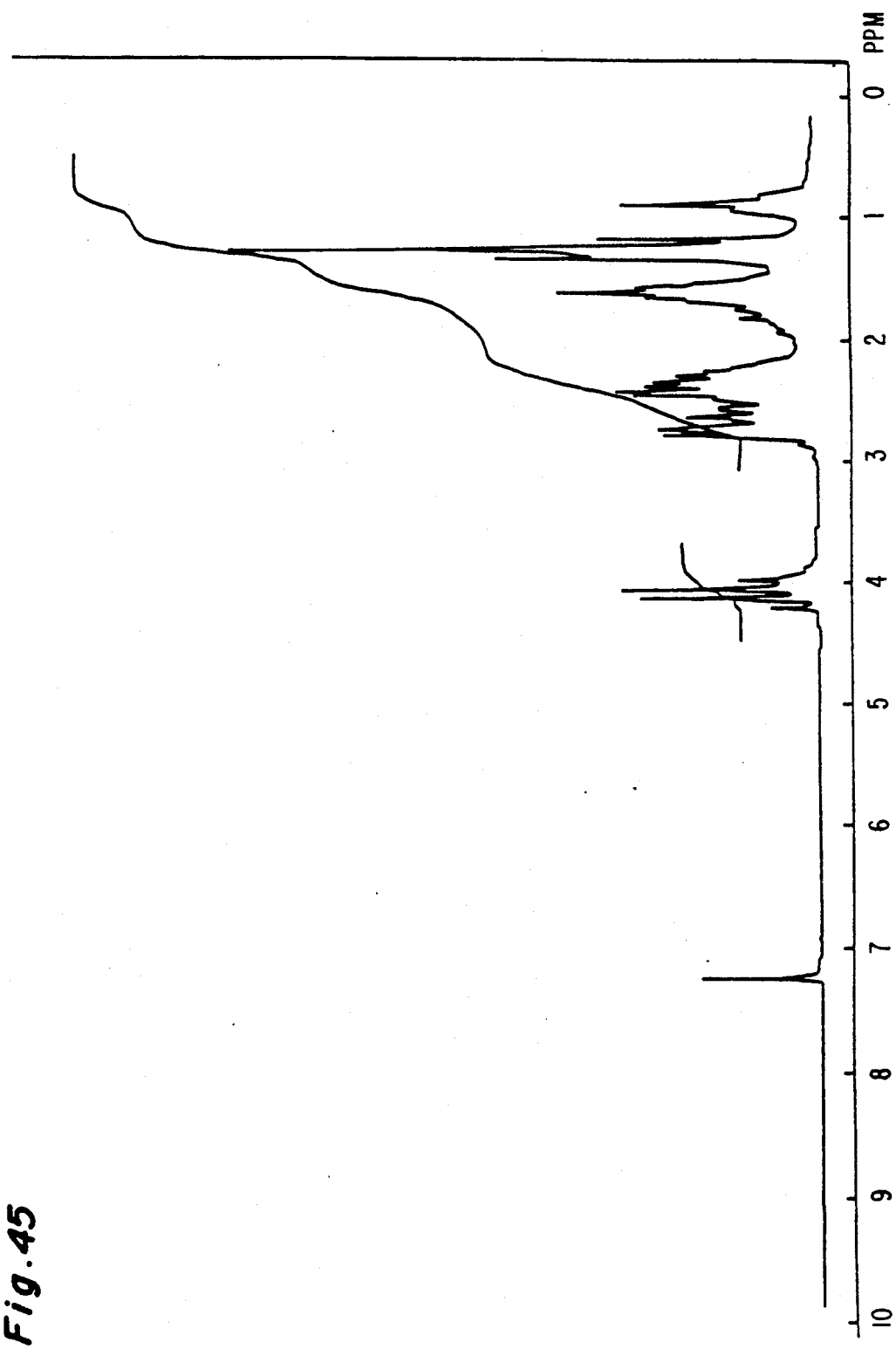

The n. m. r. spectrum of 13,14-dihydro-6,15-diketo-20-methyl-PGE₂ ester (108) is shown in FIG. 45.

EXAMPLE 48 (See Chart XVII)

Preparation of 13,14-Dihydro-6,15-diketo-11R-dehydroxy-11 R-methyl PGE₁ ethyl ester (115), R=Et

48-1) Preparation of 15,15-Ethylenedioxy-13,14-dihydro-11R-dehydroxy-11R-methyl-PGF₂α ethyl ester (110)

15,15-Ethylenedioxy-13,14-dihydro-11R-dehydroxy-11R-methyl PGE₂ ethyl ester (109) (1.775 g), the compound obtained in the same way as in Example 43, was dissolved in a THF-methanol mixed solvent, and 0.1600 g of NaBH₄ was added. The solution was kept at −18° C. overnight. A crude product obtained after the usual work-up was chromatographed (hexane-ethyl acetate=3.5:1) to give. 9α-hydroxy substance (110):0.9464 g; 9β-hydroxy substance (111):0.5867 g.

The 9β-hydroxy substance (111) was oxidized with Jones reagent whereby 15,15-ethylenedioxy-13,14-dihydro-11R-dehydroxy-11R-methyl PGE$_2$ ethyl ester (109) was recovered, which was again reduced with NaBH$_4$. These reaction were repeated to amount to 1.446 g of 13,14-dihydro-15,15-ethylenedioxy-11R-dehydroxy-11 R-methyl-PGF$_{2\alpha}$ ethyl ester (110).

48-2) Preparation of Bromo-ether (112)

13,14-Dihydro-15,15-ethylenedioxy-11R-dehydroxy-11R-methyl-PGF$_{2\alpha}$ ethyl ester (110) (1.446 g) was dissolved in a mixed solvent of THF (12 ml) and dichloromethane (3.5 ml), and NBS (0.6453 g) was added at −18° C. Following the usual procedure, there was obtained 1.932 g of bromo-ether (112).

48-3) Preparation of 15,15-Ethylenedioxy-13,14-dihydro-11R-dehydroxy-6-keto-11R-methyl-PGF$_{2\alpha}$ ethyl ester (113)

The bromo-ether (112) (1.932 g) was dissolved in DBU (6 ml) and toluene (3 ml), and the solution was kept at 75° C. A crude product obtained after the usual work-up was chromatographed (hexane-ethyl acetate=3:1) to give the title compound (113).
Yield: 1.230 g.

48-4) Preparation of 15,15-Ethylenedioxy-13,14-dihydro-11R-dehydroxy-6-keto-11R-methyl-PGE$_1$ ethyl ester (114)

6-Keto-11R-methyl-PGF$_{2\alpha}$ ethyl ester (113) (1.230 g) was oxidized with Jones reagent in acetone, whereby 15,15-ethylenedioxy-13,14-dihydro-11R-dehydroxy-6-keto-11R-methyl-PGE$_1$ ethyl ester (114) was obtained.
Yield: 0.7614 g (62%).

48-5) Preparation of 13,14-Dihydro-6,15-diketo-11R-dehydroxy-11R-methyl-PGE$_1$ ethyl ester (115)

15,15-Ethylenedioxy-11R-dehydroxy-11R-methyl-PGE$_1$ ethyl ester (114) (0.7614 g) was dissolved in a mixed solvent of acetic acid:THF:water (3:1:1), and the solution was kept at 50° C. for 5. Following the usual procedure, there was obtained 0.6290 g of 13,14-dihydro-6,15-diketo-11R-methyl-PGE$_1$ ethyl ester (115), R=Et.

Figure 46:
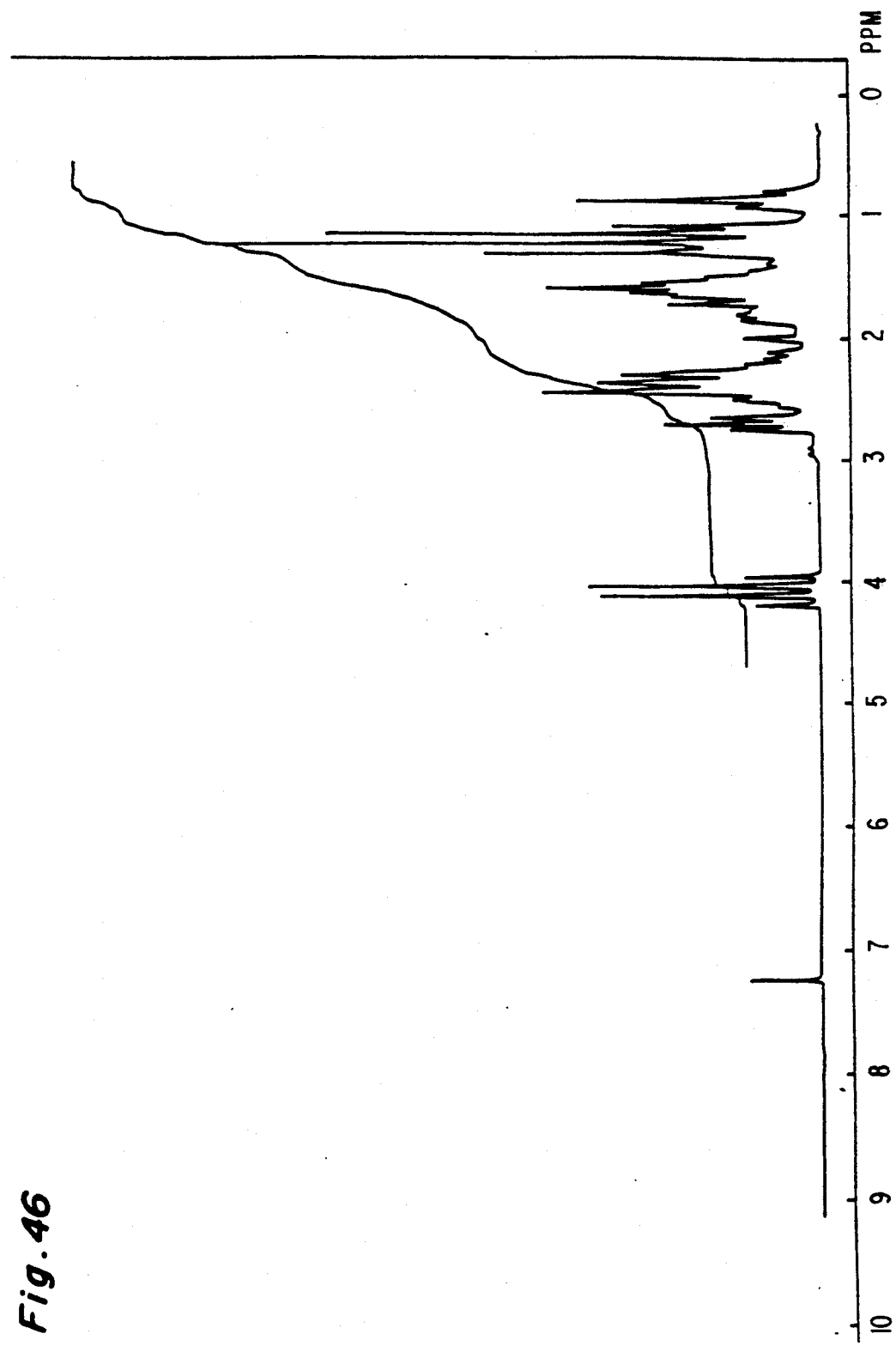

The n. m. r. spectrum of 13,14-dihydro-6,15-diketo-11R-methyl-PGE$_1$ ethyl ester (115) is shown in FIG. 46.
Mass (SIMS):395 (M +1)+, 377, 349.

EXAMPLE 49 (See Chart XVII)

Preparation of 13,14-Dihydro-6,15-diketo-11R-dehydroxy-11R-methyl-PGE$_1$ methyl ester (115), R=Me The same procedure as in Example 48 was followed except that diazomethane was used for methyl-esterification, and thus there was obtained 13,14-dihydro-6,15-diketo-11R-dehydroxy-11R-methyl-PGE$_1$ methyl ester (115), R=Me.

Figure 47:
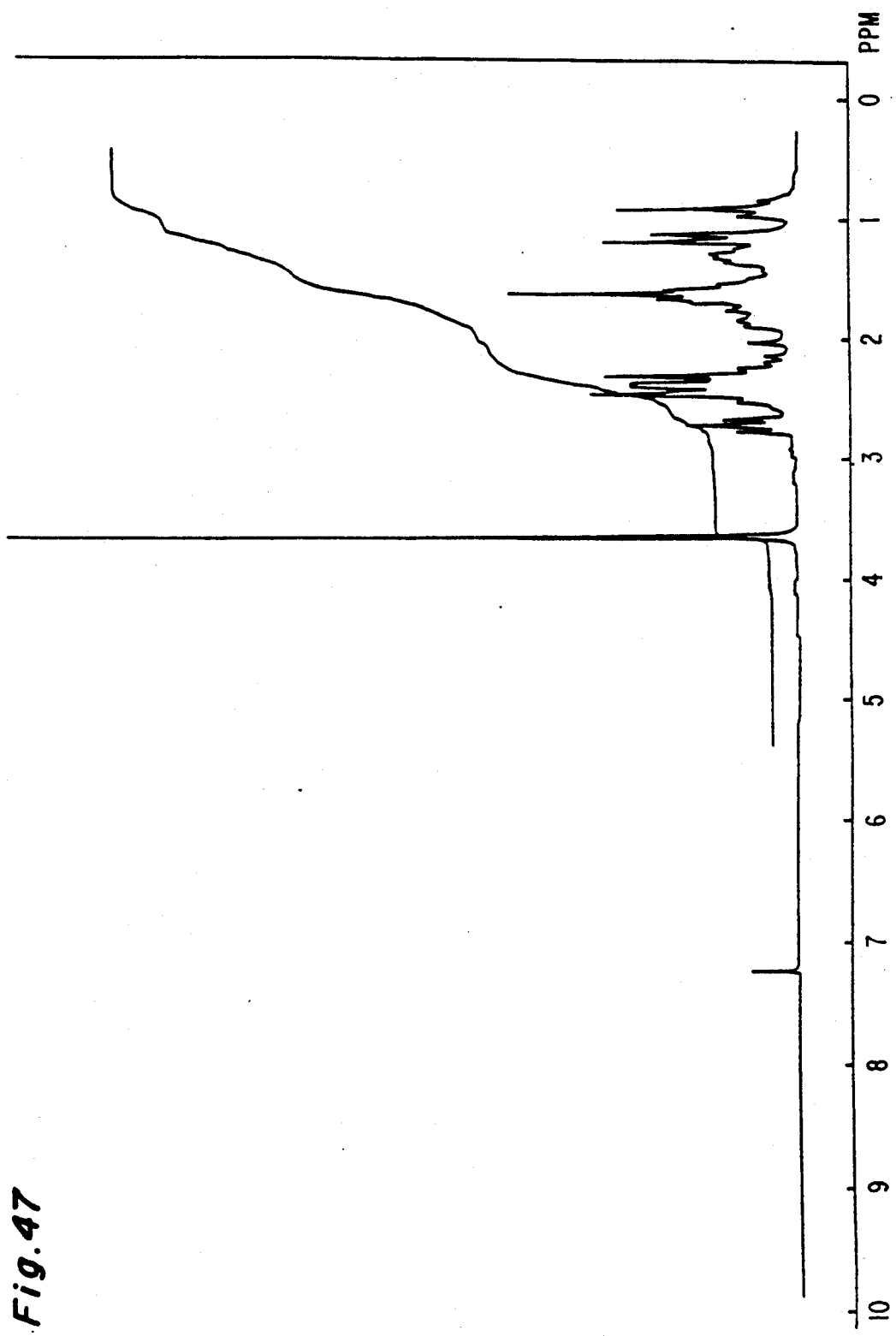

The n. m. r. spectrum of 13,14-dihydro-6,15-diketo-11R-dehydroxy-11R-methyl-PGE$_1$ methyl ester (115), R=Me, is shown in FIG. 47.
Mass (DI):380, 362, 349, 331.

50 (See Chart XVIII)

Preparation of 13,14-Dihydro-15-keto-16R,S-fluoro-PGE$_2$ methyl ester (125), R=Me

50-1) Preparation of 1S-2-Oxa-3-oxo-6R-(4-fluoro-3-keto-1-octyl-7R-hydroxy-cis-bicyclo(3, 0, 0) octane (118)

A saturated ketone (117) (5.20 g) obtained after catalytic hydrogenation of the unsaturated ketone (116) produced from(−)-Corey lactone (1) and dimethyl(3-fluoro-2-oxoheptyl)phosphonate was dissolved in a mixed solvent (18 ml) of THF and methanol (3:1), and potassium carbonate (1.54 g) was added. The solution was stirred for 3 h.

The crude product obtained after the usual work-up was chromatographed (hexane:ethyl acetate=1:1) to yield an alcohol (118).
Yield: 1.81 g (57%).

50-2) Preparation of 1S-2-Oxa-3-oxo-6R-(4R,S-fluoro-3-oxo-1-octyl)-7R-(2-tetrahydropyranyl)oxy-cis-bicyclo-(3, 3, 0) octane (119)

The alcohol (118) 1.81 g) was converted to the corresponding tetrahydropyranyl ether (119) with dihydrapyran and p-toluenesulfonic acid in dichloromethane.
Yield: 2.33 g.

50-3) Preparation of 1S-2-Oxa-3-oxo-6R-(4R,S-fluoro-3R,S-hydroxy-1-octyl)-7R-(2-tetrahydropyranyl) oxy-cis-bicyclo-(3, 3, 0)octane (120)

The tetrahydropyranyl ether (119) (2.33 g) was reduced with NaBH$_4$ in methanol. Alcoholic-lactone (120) was thus obtained.

50-4) Preparation of Lactol (121)

The alcoholic-lactone (120) (0.84 g) was reduced with DIBAL-H (1.5-M, 6 ml) in toluene (20 ml) to the corresponding lactol (121).

50-5) Preparation of 16R,S-fluoro-13,14-dihydro-15R,S-hydroxy-11R-(2-tetrahydropyranyl)oxy-PGF$_{2\alpha}$ methyl ester (123), R=Me Ylide produced from (4-carboxybutyl)triphenyl~-phosphonium bromide (3.50 g) in the ordinary method was let to react with the previously synthesized lactol (121) in DMSO. A carboxylic acid (122) obtained according to the ordinary procedure was treated with diazomethane. Methyl ester (123) was thus obtained.
Yield: 0.470 g (44%).

50-6) Preparation of 13,14-Dihydro-15-keto-16R,S-fluoro-PGE$_2$ methyl ester (125), R=Me The methyl ester (123) (0.470) was oxidized with Jones reagent in acetone (25 ml) at −30° C. After the usual work-up, the crude product was chromatographed (hexane:ethyl acetate=5:2) to yield 0.298 g of 13,14-dihydro-15-keto-16R,S-fluoro-11R-(2-tetrahydropyranyl)oxy-PGE$_2$ methyl ester (124).

The methyl ester (124) (0.298 g) was dissolved in a mixed solvent (25 ml) of acetic acid, THF, and water (4:12), and the solution was kept at 45° C. for 3 h. Then, a crude product obtained after the usual work-up was chromatographed (benzene - ethyl acetate=2:3) to give 13,14-dihydro-15-keto-16R,S-fluoro-PGE$_2$ methyl ester (125), R=Me.

Yield: 0.202 g.

Figure 48:
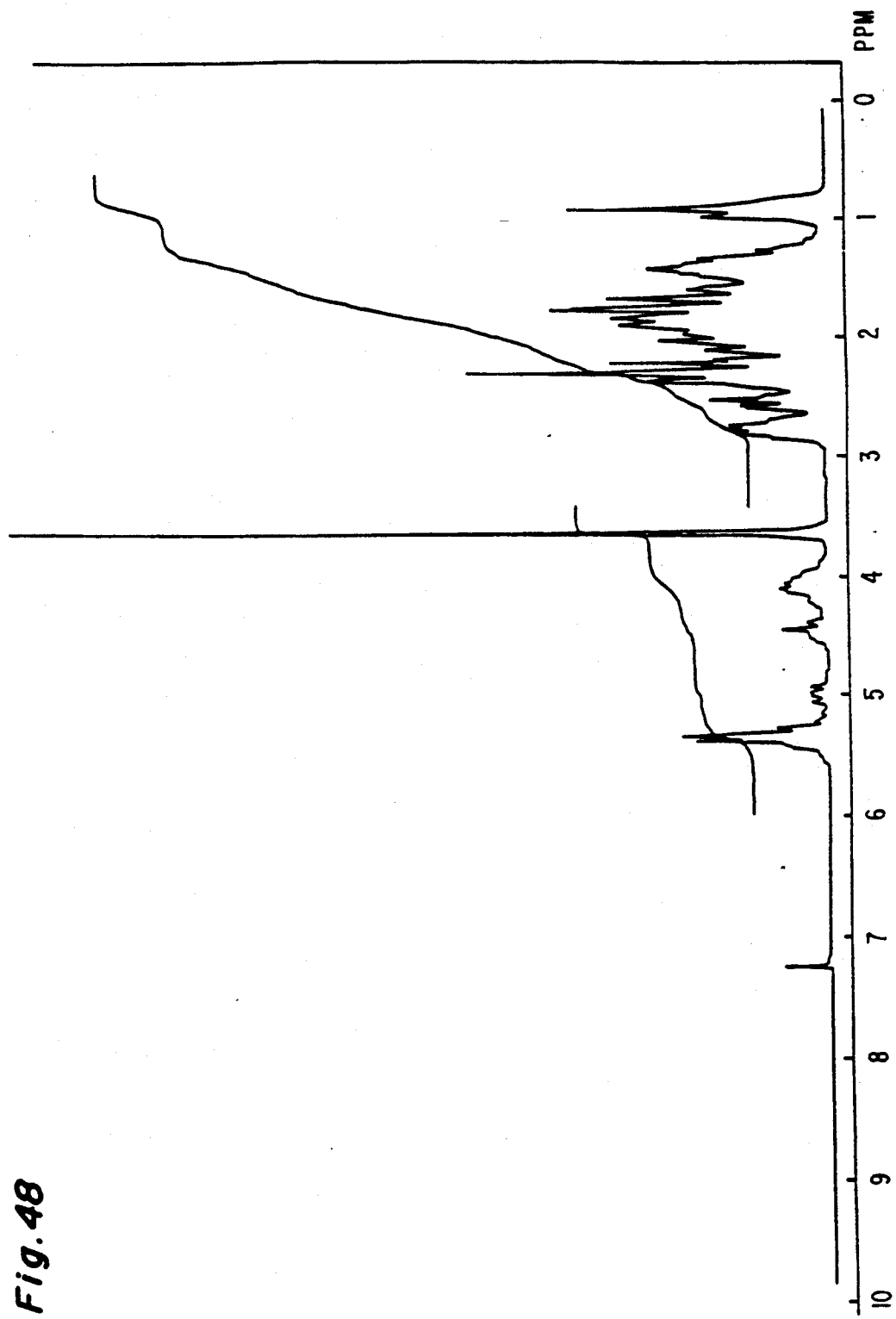

The n. m. r. spectrum of 13,14-dihydro-15-keto-16R,S-fluoro-PGE$_2$ methyl ester (125) is shown in FIG. 48. Mass (DI) 384, 366, 346, 335.

EXAMPLE 51 (See Chart XIX)

Preparation of 13,14-Dihydro-6,15-diketo-16R,S-fluoro-11R-dehydroxy-11R-methyl-PGE$_1$ ethyl ester (135)

51-1) Tosylation of 16R,S-Fluoro-13,14-dihydro-15R,S-(t-butyldimethylsilyl)oxy-PGF$_{2\alpha}$ ethyle ster (126)

Preparation of tosylate (127): 16R,S-Fluoro-13,14-dihydro-15R,S-(t-butyldimethylsilyl)oxy-PGF$_{2\alpha}$ ethyl ester (126) (1.00 g) produced from(−)-Corey lactone (1) and dimethyl(3-fluoro-2-oxoheptyl)phosphonate according to the known method was tosylated with tosyl chloride (4.00 g) in pyridine (10 ml) at 0° C.

Yield: 1.04 g.

51-2) Preparation of 16R,S-fluoro-13,14-dihydro-15R,S-(t-butyldimethylsilyl)oxy-PGA$_2$ ethyl ester (128)

The tosylate (127) (1.04 g) was oxidized with Jones reagent (2.67- M, 2 ml) in acetone (30 ml) at −20° C. A crude product obtained after usual processing was chromatographed (hexane-ethyl acetate=5:1) to give R,S-fluoro-13,14-dihydro-15R,S-(t-butyldimethylsilyl)oxy-PGA$_2$ ethyl ester (128).

Yield: 0.627 g.

51-3) Preparation of 16R,S-Fluoro-13,14-dihydro-11R-dehydroxy-11R-methyl- 15R,S-(t-butyldimethylsilyl)oxy-PGE$_2$ ethyl ester (129)

To lithium dimethylcuprate, prepared in ether (70 ml) from copper (I) iodide (1.28 g) and methyl lithium (1.5-M; 9.0 ml) was added an ether solution (40 ml) of the enone (128) (1.114 g). The mixture was stirred for 30 min. Then, after usual processing, there was obtained 16R,S-fluoro-13,14-dihydro-11R-dehydroxy-11R-methyl-15R,S-t-butyldimethylsilyl)oxy-PGE$_2$ ethyl ester (129).

Yield: 0.931 g.

51-4) Preparation of 16R,S-Fluoro-13,14-dihydro-11R-dehydroxy-11R-methyl-15R,S-(t-butyl dimethylsilyl)oxy-PGF$_{2\alpha}$ ethyl ester (130)

The ketone (129) (0.931 g) was reduced with NaBH$_4$ (0.688 g) in methanol (40 ml), and thus 9$\alpha$-hydroxy-PGF derivative (130) and 9$\beta$-hydroxy-PGF derivative (131) were obtained.

The 9$\beta$-hydroxy-PGF derivative (131) was oxidized by Jones reagent to the ketone (129), and then reduction of the ketone (129) with NaBH$_4$ was carried out again. A total yield of 0.677 g of 16R,S-fluoro-13,14-dihydro-11R-dehydroxy-11R-methyl-15R,S-(t-butyldimethylsilyl)oxy-PGF$_{2\alpha}$ ethyl ester (130) was obtained.

51-5) Preparation of 16R,S-Fluoro-13,14-dihydro-11R-dehydroxy-15R,S-hydroxy-11R-methyl-PGF$_{2\alpha}$ ethyl ester (132)

Tetrabutylammonium fluoride (1.0-M; 8 ml) was added to a THF solution of 15R,S-(t-butyldimethylsilyl)oxy-PGF$_{2\alpha}$ ethyl ester (130) (0.677 g), and the mixture was stirred at room temperature overnight. A crude product obtained after the usual processing was chromatographed (hexane-ethyl acetate=3:1) to give 16R,S-fluoro-13,14-dihydro-11R-dehydroxy-15R,S-hydroxy-11R-methyl-PGF$_2$a ethyl ester (132) (0.503 g).

51-6) Preparation of 13,14-Dihydro-6,15-diketo-11R-dehydroxy-11R-methyl-PGE ethyl ester (135)

The same procedure as in Examples 48 and 49 was followed with using 16R,S-fluoro-13,14-dihydro-11R-dehydroxy-15R,S- hydroxy-11R-methyl-PGF$_{2\alpha}$ ethyl ester (132), and thus there was obtained 13,14-dihydro-6,15-diketo-11R-dehydroxy-11R-methyl-PGE$_1$ ethyl ester (135).

Figure 49:
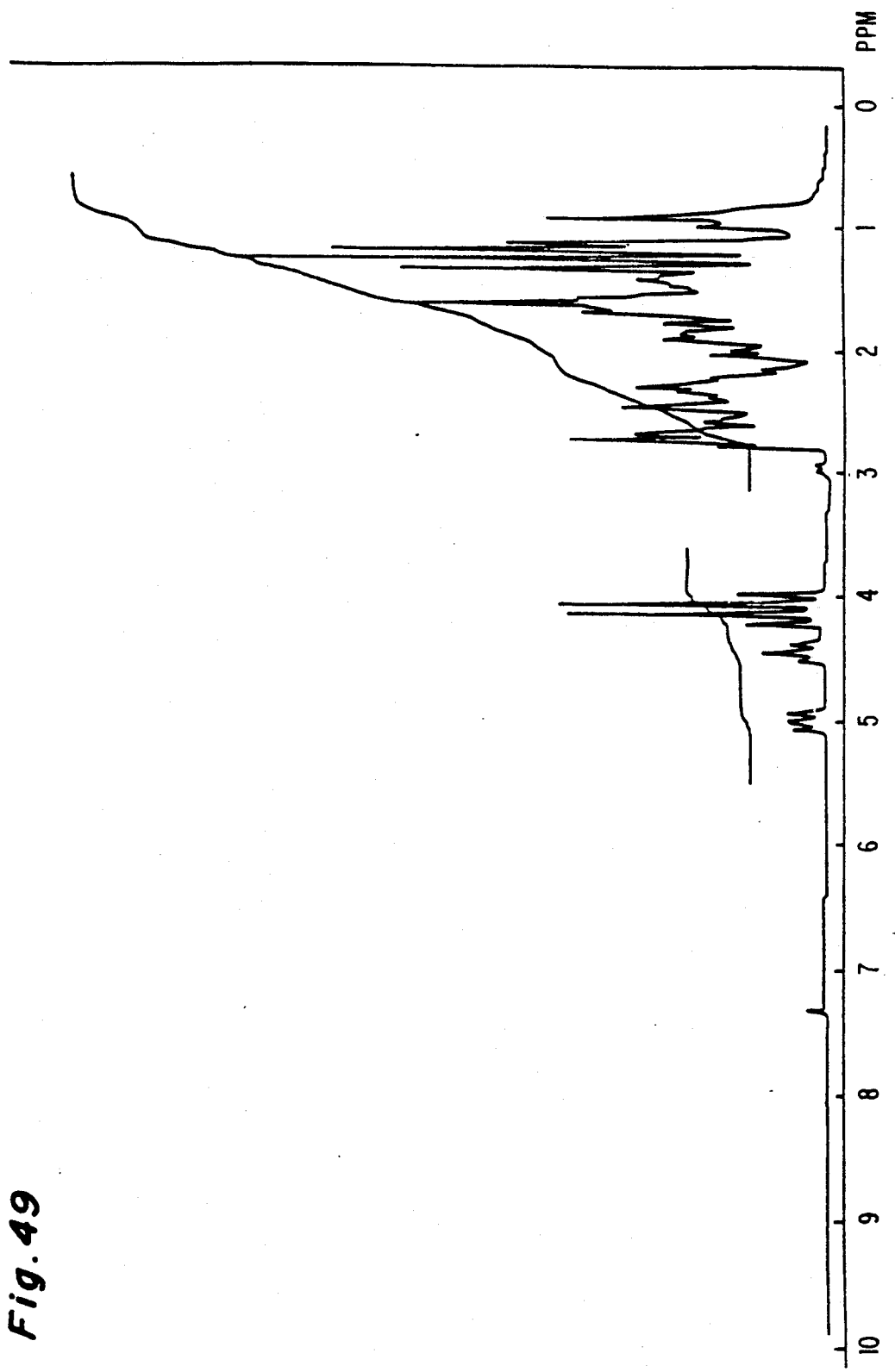

The n. m. r. spectrum of 13,14-dihydro-6,15-diketo-11R-dehydroxy-11R-methyl-PGE$_1$ ethyl ester (135) is shown in FIG. 49.

Mass (DI):412, 394, 367.

EXAMPLE 52 (See Chart XX)

Preparation of 13,14-Dihydro-6,15-diketo-11R-dehydroxy-11R-hydroxymethyl-19-methyl-PGE$_1$ methyl ester (138)

52-1) Preparation of 15,15-Ethylenedioxy-13,14-dihidro-11R-dehydroxy-11R-hydroxymethyl-PGE$_2$ methyl ester (137)

15,15-Ethylenedioxy-13,14-dihydro-19-methyl-PGA$_2$ methyl ester (136) (0.410 g) produced from (−)-Corey lactone (1) and dimethyl(6-methyl-2-oxoheptyl)phosphonate, and 0.255 g of benzophenone were dissolved in 80 ml of methanol. The solution was irradiated through a pyrex filter with a 300 W high pressure mercury lamp. After the ordinary work-up and purification, there was obtained 15,15-ethylene dioxy-13,14-dihidro-11R-dehydroxy-11R-hydroxymethyl-PGE$_2$ methyl ester (137).

52-1) Preparation of 13,14-Dihydro-6,15-diketo-11R-dehydroxy-11R-hydroxymethyl-PGE$_1$ methyl ester (138)

The same procedure as in Examples 47, 48, and 49 was applied on the compound (137), and thus 13,14-dihydro-6,15-diketo-11R-dehydroxy-11R-hydroxymethyl-PGE$_1$ methyl ester (138) was obtained.

Figure 50:
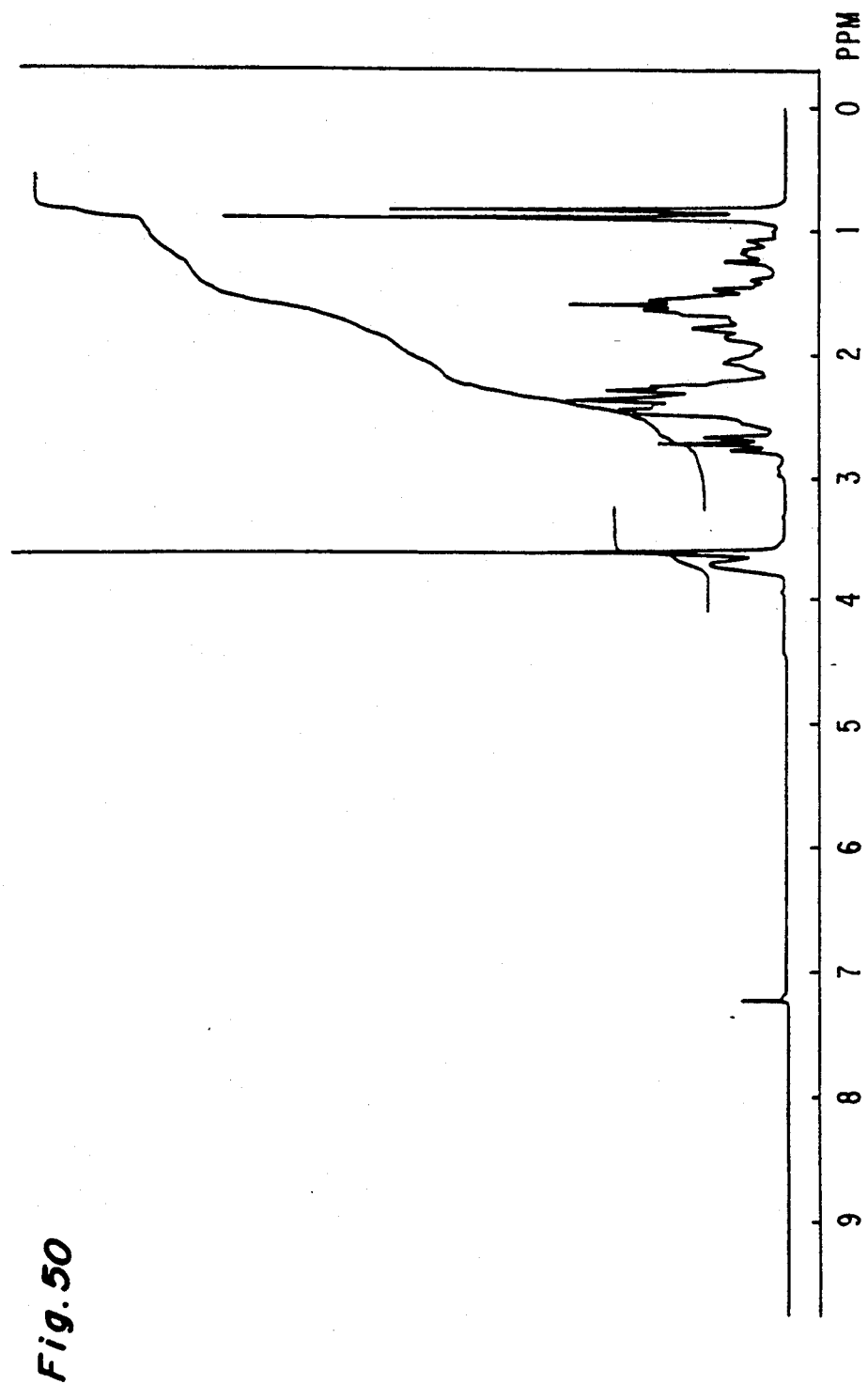
Figure 51:
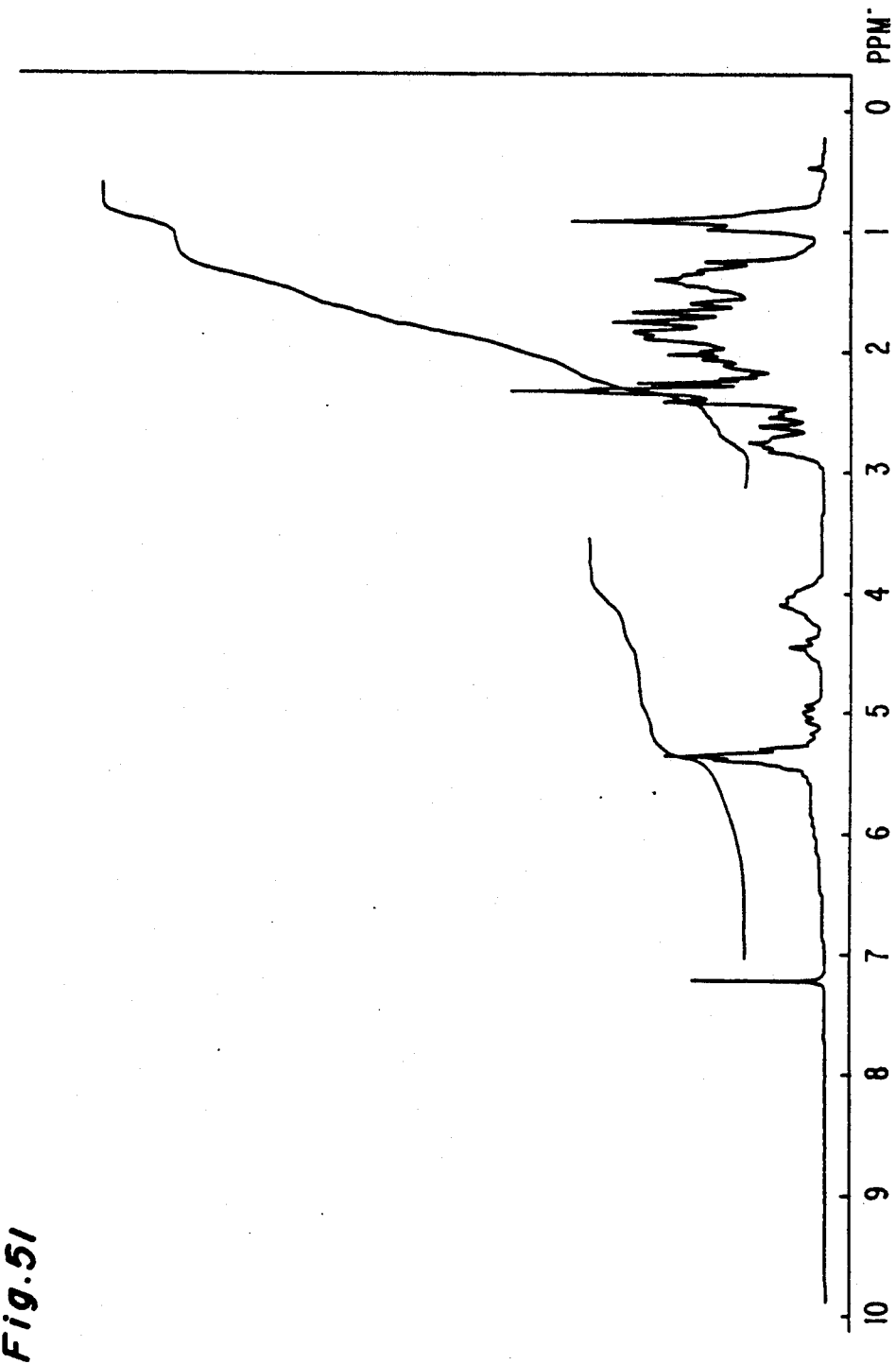

In FIG. 51 there is shown the n. m. r. spectrum of 13,14-dihydro-6,15-diketo-11R-dehydroxy-11R-hydroxymethyl-PGE$_1$ methyl ester (138) is shown in FIG. 50.

Mass m/z 410 (M+), 392(M+ −18), 379, 361.

EXAMPLE 53 (See Chart XXI)

Preparation of 13,14-Dihydro-15-keto-16R,S-fluoro-PGE$_2$ (140)

53-1) Preparation of 13,14-Dihydro-15-keto-16R,S-fluoro-11R-(2-tetrahydropyranyl)oxy-PGE$_2$ The carbonic acid (122) was oxidized in aceton (25 ml) with Jones reagent (2.67-M, 1.1 ml) at −15 ° C. A crude product obtained after the usual work-up was chromatographed to give 13,14-dihydro-15-keto-16R,S-fluoro-11R-(2-tetrahydropyranyl)oxy-PGE$_2$ (139). Yield: 0.247 g.

53-2) Preparation of 13,14-Dihydro-15-keto-16R,S-fluoro-PGE₂ (140)

13,14-Dihydro-15-keto-16R,S-fluoro-11R-(2-tetrahydropyranyl)oxy-PGE₂ (139) (0.247 g) was dissolved in a mixture (25 ml) of acetic acid—water—THF (4:2:1) to be kept at 45° C. for 3 h. A crude product obtained after the usual work-up was chromatographed to give 13,14-dihydro-15-keto 16R,S-fluoro-PGE₂ (140). Yield: 0.148 g.

The n. m. r. spectrum of 13,14-dihydro-15-keto-R,S-fluoro-PGE₂ (140) is shown in FIG. 51.

Mass 352 (M⁺ − 18) 282, 281, 226.

EXAMPLE 54

Preparation of 13,14-Dihydro-15-keto-20-methyl-methyl ester (141)

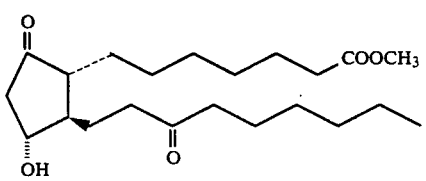
(141)

13,14-Dihydro-15-keto-20-methyl-PGE₁ methyl ester was prepared using (−)-Corey lactone together with dimethyl(2-oxooctyl)phosphonate according to the procedure as in Example 41.

Figure 52:
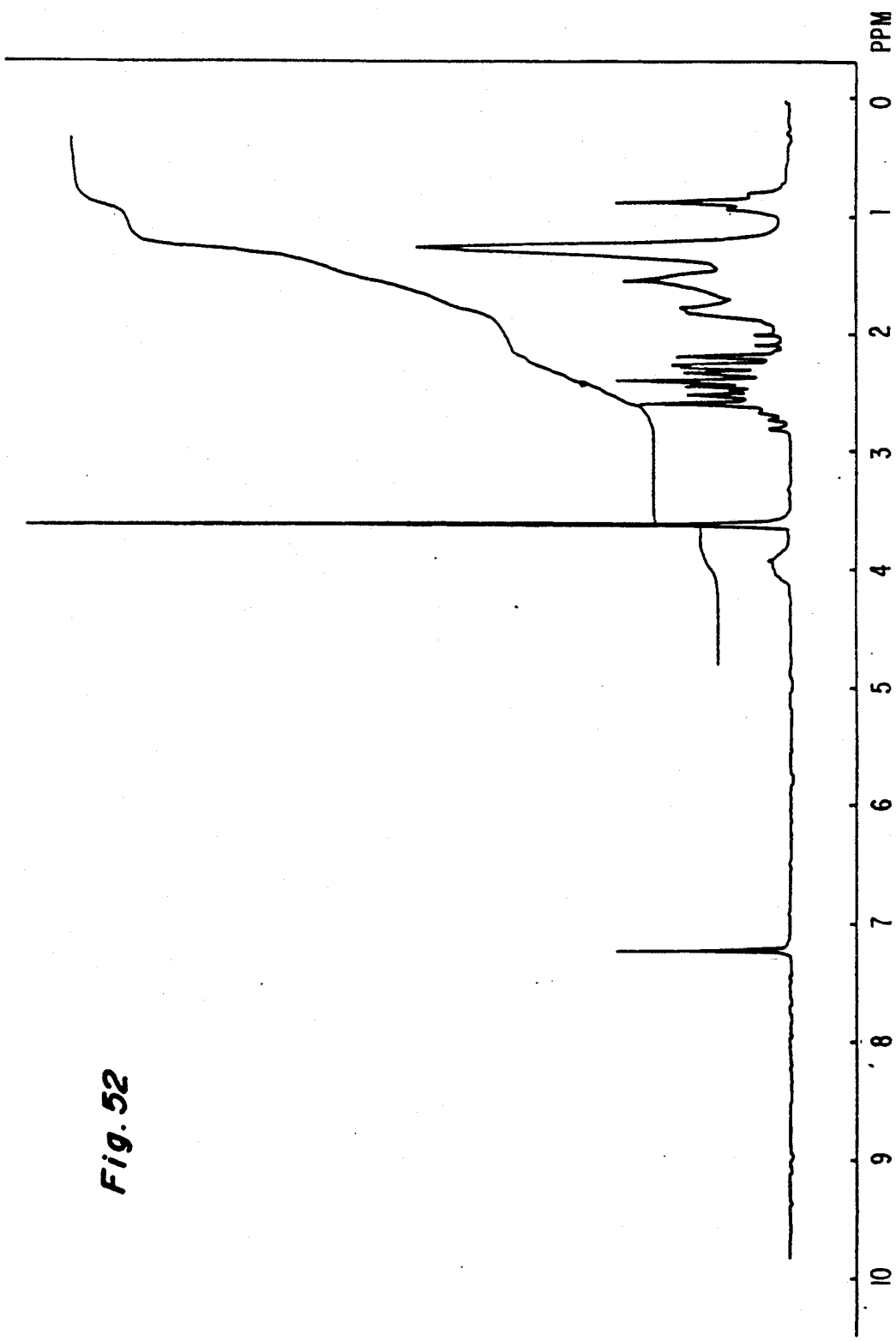

The n.m.r. spectrum of the titled compound (141) was shown in FIG. 52.

Mass (DI) m/z 382(M+) , 364, 333.

EXAMPLE 55 (See Chart XXII)

Preparation of 13,14-Dihydro-15-keto-Δ²-PGE₁ methyl ester (146)

According to the same manner as in Example 36 13,14-dihydro-15-keto-Δ²-PGE₁ methyl ester (146) was prepared using 13,14-dihydro-15,15-ethylenedioxy-11-(2-tetrahydropyranyl)oxy-PGF₁α methyl ester (142) which can be obtained by catalitic hydrogenation of the compound (10).

Figure 53:
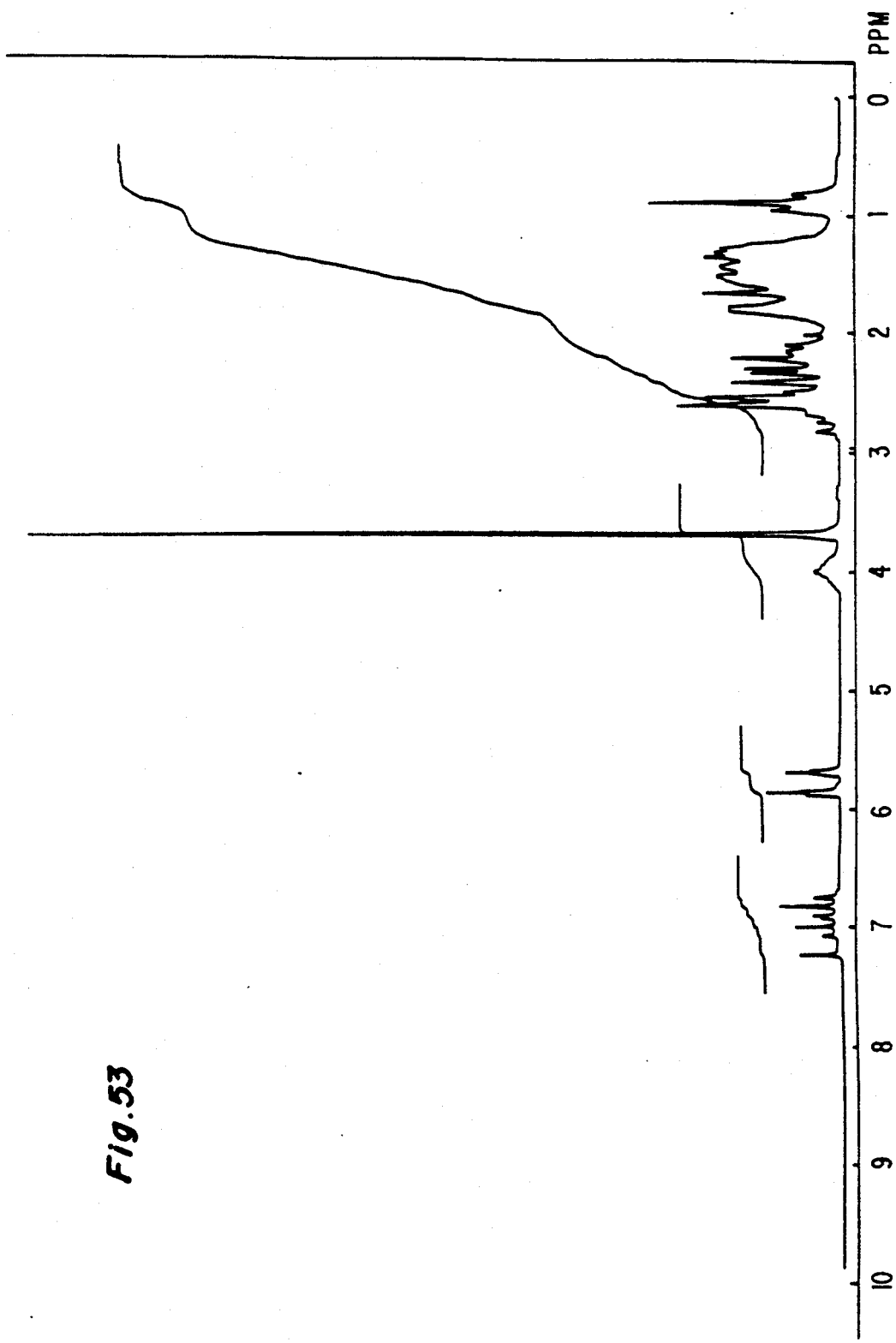

The n.m.r. spectrum of the titled compound (146) is shown in FIG. 53.

Mass (DI) z/m 366, 348, 316.

EXAMPLE 56 (See Chart XXI)

Preparation of 13,14-Dihydro-15-keto-Δ²-PGE₁ (149)

56-1 Preparation of 13,14-Dihydro-15,15-ethylenedioxy-11-(2-tetrahydropyranyl)oxy-Δ²-PGF₁α (145):

To the solution of 13,14-dihydro-15,15-ethylenedioxy-11-(2-tetrahydropyranyl)oxy-Δ²-PGF₁α methyl ester (144) (0.7687 g) in THF (15 ml) 0.5-M aqueous solution of litium hydroxide (20 ml) was added, and stirred at room temperature over night. A crude carboxylic acid (147) was obtained after a usual work-up. Yield: 0.8779 g.

56-2 Preparation of 13,14-Dihydro-15,15-ethylenedioxy-11-(2-tetrahydropyranyl)oxy-Δ²-PGE₁α (148)

Carboxylic acid (147) (0.8779 g) was oxidized with Jones reagent (2.67-M, 1.7 ml) at −35° C. in acetone (50 ml ). A crude product obtained after a usual work-up was chromatographed (3–5% isopropanol-hexane) to give 13,14-dihydro-15,15-ethylenedioxy-11-(2-tetrahydropyranyl) oxy-Δ²-PGE₁(148). Yield: 0.5972 g.

56-3 Preparation of 13,14-Dihydro-15-keto-Δ²-PGE₁α (149)

In a mixed solvent of acetic acid:THF:water (3:1:1) (15 ml) Δ²-PGE₁ (148) (0.5972 g) was dissolved and maintained at 40° C. for 3.5 hours. A crude compound obtained by a usual work-up was chromatographed twice (acid washed Mallincklodt silica-gel, hexane:ethyl acetate=3:1–1:1, and then 8% isopropanol-hexane) to give 13,14-dihydro-15-keto-Δ²-PGE₁ (149). Yield: 0.2473.

Figure 54:

The n.m.r. of the titled compound (149) was shown in FIG. 54.

Mass (DI) z/m 352(M+), 334, 316.

EXAMPLE 57

Preparation of 13,14-Dihydro-15-keto-16R,S-fluoro-20-methyl-PGE₂ methyl ester (150)

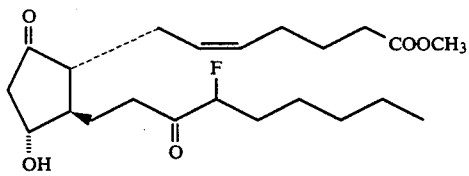
(150)

Using (−)-Corey lactone and dimethyl(3R,S-fluoro-2-oxooctyl)phosphonate, 13,14-dihydro-15-keto-16R,S-fluoro-20-methyl-PGE₂ methyl ester (150) was prepared according to the same manner as in Example 50.

Figure 55:
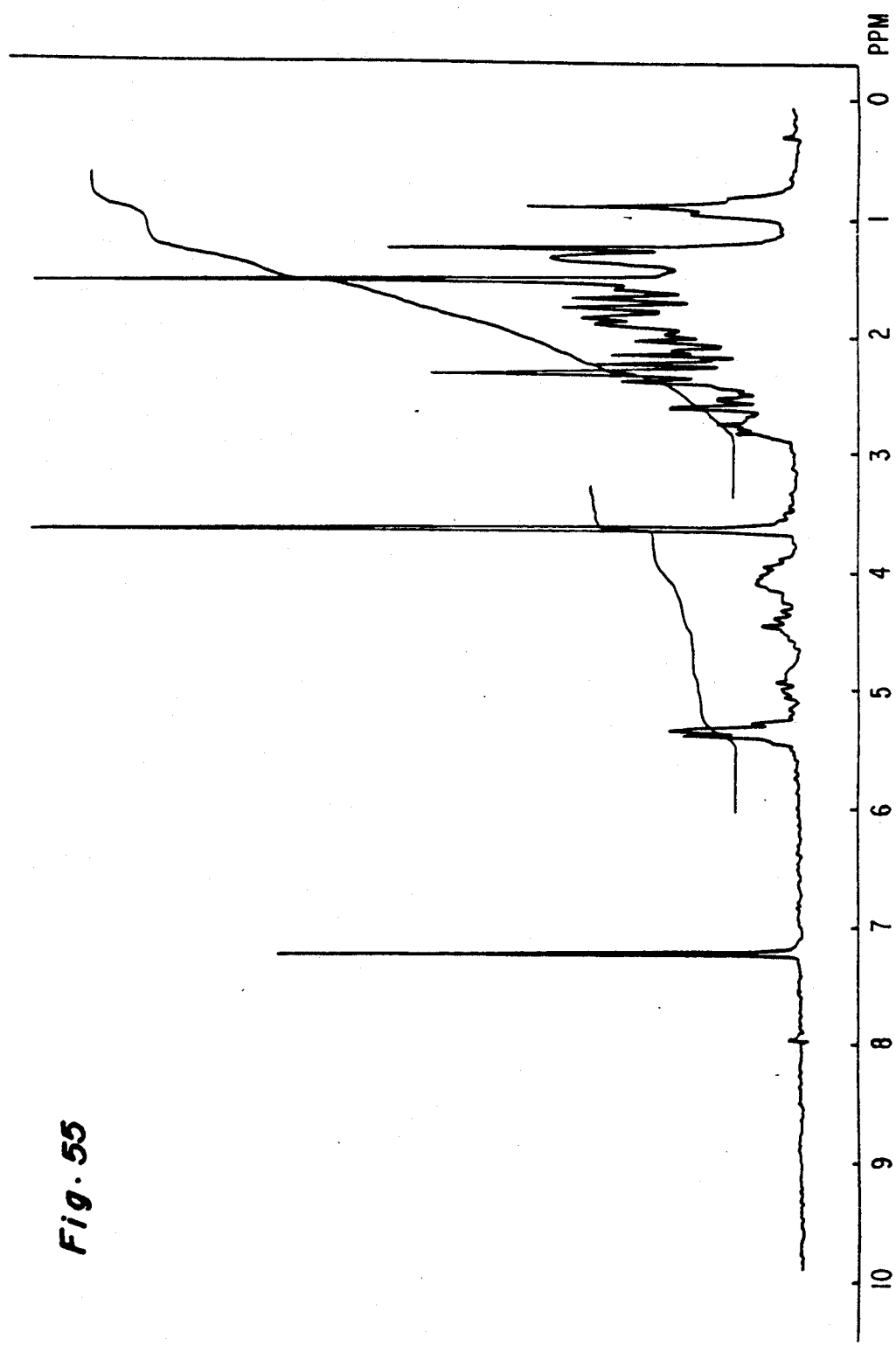

The n.m.r. spectrum of the titled compound (150) was shown in FIG. 55.

Mass (DI) m/z 398 (M+), 380.

EXAMPLE 58 (See Chart XXII)

Preparation of 13,14-Dihydro-15-keto-16,16-difluoro-PGE₂ methyl ester (154)

58-1 Preparation of 1S-2-Oxa-3-oxo-6R-(4,4-difluoro-3-oxo-trans-1-octenyl)-7R-(4-phenylbenzoyl)oxy-cis-bicyclo(3,3,-0)octane (151)

Aldehyde (2) was obtained by the oxidation of (−)-Corey lactone 1) (6.33 g) with Collins reagent. Separately thallium ethoxide (4.26 g) was dissolved in benzene, to which the solution of dimethyl(3,3-difluoro-2-oxoheptyl)phosphonate (4.64 g) in benzene was added at cool temperature, and the mixture was stirred for 30 min. To the resultant the solution of the aldehyde (2) in benzene as prepared above was added, and stirred at room temperature for 3 h. After the mixture was neutralized with acetic acid, a saturated aqueous solution of potassium iodide was added and passed through a celite column. After a usual work-up the desired unsaturated ketone (151) was obtained. Yield: 3.88 g.

58-2 Preparation of 1S-2-Oxa-3-oxo-6R-(4,4-difluoro-3R,S-hydroxy-1-octyl)-7R-(4-phenylbenzoyl)oxy-cis-bicyclo(3,3,0)octane (153)

The unsaturated ketone (151) (3.88 g) was hydrogenated with palladium on carbon (5%) in ethyl acetate (40 ml) to give the saturated ketone (152). The saturated ketone (152) was reduced with NaBH₄ in a mixed solvent of methanol-THF (70:30) to give the alcohol (153). Yield: 4.02 g.

58-3 Preparation of 1S-2-Oxa-3-oxo-6R-(4,4-difluoro-15R,S-t-butyldimethylsilyloxy-1-octyl)-7R-hydroxy-cis-bicyclo(3,3,0)octane (155)

The alcohol (153) was treated with imidazol and t-butyldimethylsilyl chloride in DMF to give 1S-2-oxa-3-oxo-6R-(4,4-difluoro-15R,S-t-butyldimethylsilyl-oxy-1-octyl)-7R-(4-phenylbenzoyl)oxy-cis-bicyclo(3,3,0) octane (154). The resultant (154) was methonolysised with potassium carbonate (1.14 g) in methanol (20 ml) to give 1S-2-oxa-3-oxo-6R-(4,4-difluoro-15R,S-t-butyl-dimethylsilyl-oxy-1-octyl)-7R-hydroxy-cis-bicyclo(3,3,0)octane (155). Yield: 2.89 g.

58-4 Preparation of 1S-2-Oxa-3-oxo-6R-(4,4-difluoro-15R,S-t-butyldimethylsilyloxy-1-octyl)-7R-(2-tetrahydropyranyl)oxy-cis-bicyclo(3,3,0)octane (156)

The alcohol (155) was converted to the tetrahydropyranyl ether (156) according to a known method. Yield: 3.38 g.

58-5 Preparation of 16,16-difluoro-13,14-dihydro-15R,S-t-butyldimethylsilyloxy-11-(2-tetrahydropyranyl)oxy-PGF$_{2\alpha}$ methyl ester (157)

The desired silylether (157) was obtained from the tetrahydropyranyl ether (156) (3.38 g) according to the procedure in Examples 50 and 51. Yield: 3.02 g.

58-6 Preparation of 16,16-Difluoro-13,14-dihydro-15R,S-hydroxy-11R-(2-tetrahydropyranyl)oxy-PGF$_{2\alpha}$ methyl ester (158)

The silyl ether (157) (0.882 g) was treated with tetrabutylammonium fluoride (1.1-M, 10.6 ml) in THF (25 ml) to give the desired diol (158). Yield: 0.710 g.

58-7 Preparation of 13,14-Dihydro-15-keto-16,16-difluoro-PGE$_2$ methyl ester (160)

Collins reagent was prepared from chromic anhydride (2.57 g) and pyridine (4.15 ml) in dichloromethane (40 ml). To the resultant was added the solution of the diol (158) (0.360 g) in dichloromethane (15 ml). After the usual work-up and purification, 13,14-dihydro-15-keto-16,16-difluoro-11-(2-tetrahydropyranyl)oxy-PGE$_2$ methyl ester (159) was obtained. Yield: 0.277 g. The obtained compound (159) (0.208 g) was dissolved in a mixed solvent of acetic acid: THF:water (4:2:1) (30 ml) and maintained at 45° C. for 3.5 h. A crude compound obtained after a usual work-up was chromatographed to give 13,14-dihydro-15-keto-16,16-difluoro-PGE$_2$ methyl ester (160). Yield: 0.208 g.

Figure 56:
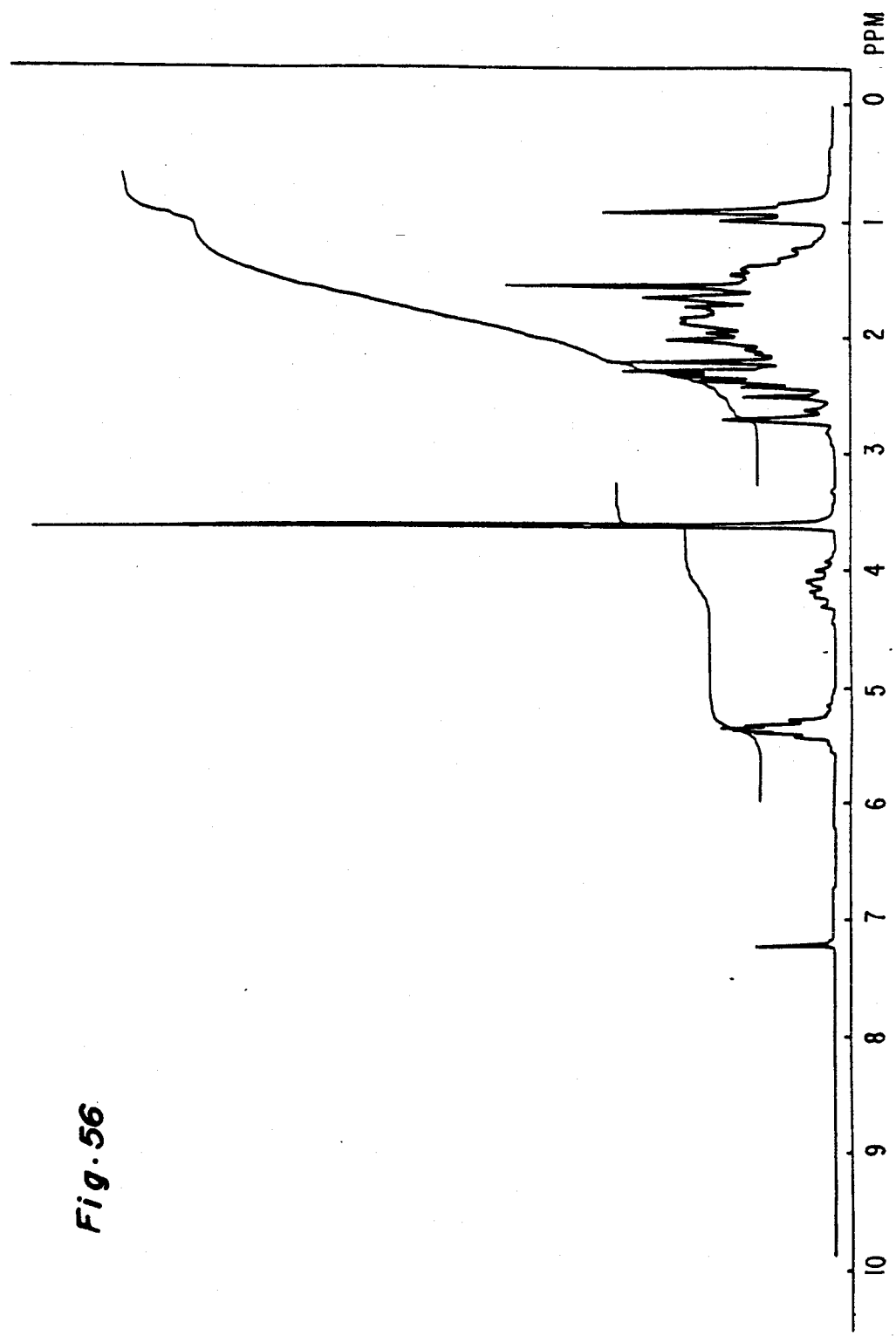

The n.m.r. spectrum of the titled compound (160) is shown in FIG. 56.

Mass (DI) z/m 402(M+), 384(M+ −18), 364.

EXAMPLE 59 (See Charts XXIV and XXV)

Preparation of 13,14-dihydro-15-keto-5,6-dehydro-20-methoxy-PGE$_2$ methyl ester To a solution of 8-methoxy-3,3-ethylenedioxy-1-iodooctane (167) (0.985 g) in ether (15 ml) t-butyllitium (2.3-M, 2.87 ml) was added dropwise at −78° C., and the resultant mixture was stirred for 3 h, to which an ether solution of copper (I) iodide and tributylphosphine was added all at once, and stirred for 20 min. To the reaction mixture was added a solution of 4R-t-butyl-dimethylsilyloxy-2-cyclopentene-1-on (168) (0.637 g) in THF (21 ml) dropwise over 15 min. After 15 min HMPA (2.61 ml) was added to the resultant followed by the addition of triphenyltin chloride (1.217 g) in THF (6 ml) after 30 min, and then stirred for 15 min. The reaction mixture was cooled at 30° C., to which a solution of 6-carboxymethoxy-1-iodo-2-hexyne (169) (3.19 g) in HPMA (2.61 ml) was added, and stirred for 4.5 h and then at room temperature for 12 h. The reaction mixture was poured into a saturated ammonium chloride solution with vigorous agitation. The organic layer was collected. The aqueous layer was extracted with ether, and the extracted layer was put together with the organic layer, which was then washed with a saturated aqueous solution of sodium chloride. After dried the organic layer was concentrated under reduced pressure to give a crude product. The crude product was chromatographed to give 11-t-butyldimethylsilyloxy-15,15-ethylenedioxy-13,14-dihydro-5,6-dehydro-20-methoxy-PGE$_2$ methyl ester (170). Yield: 0.3700 g.

n.m.r.: 0.08(3H,s), 0.10(3H,s , 1.3–2.8(24H, m), 3.30 (3H,s), 3.32(2H,t), 3.74(3H,s), 3.90(4H,s), 4.10(1H,m).

59-2 Preparation of 13,14-dihydro-15-keto-5,6-dehydro-20-methoxy-PGE$_2$ methyl ester (171)

A mixture (3ml) of hydrofluoric acid (46%): acetonitrile (1:2) cooled at 0° C. was added to 11-t-butyldimethylsilyloxy-15,15-ethylenedioxy-13,14-dihydro-5,6-dehydro-20-methoxy-PGE$_2$ methyl ester (170) (0.035 g), and stirred at room temperature for 25 min, to which water was poured, and the reaction product was extracted with ethyl acetate. The obtained organic layer was neutralized with a saturated aqueous solution of sodium bicarbonate, and concentrated under reduced pressure to give a crude product, which was chromatographed to give 13,14-dihydro-15-keto-5,6-dehydro-20-methoxy-PGE$_2$ methyl ester (171). Yield: 0.0081 g.

Figure 57:
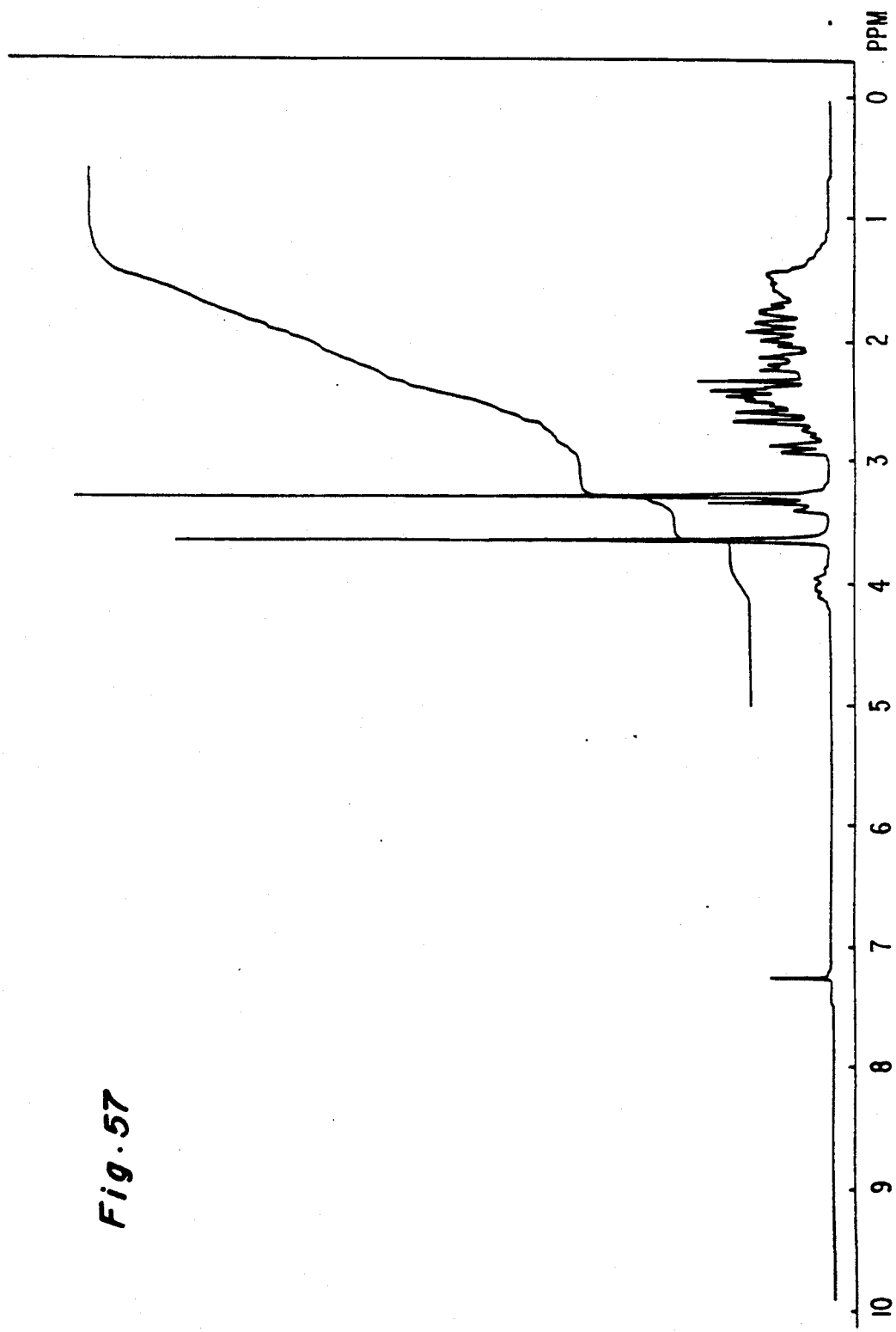

The n.m.r. spectrum of the obtained compound (171) was shown in FIG. 57.

The n.m.r. data of compounds in the above Examples are shown as follows, wherein the compounds number in brackets.

(6) δ:0.88 (3H, 6Hz), 1.1–3.0(19H, m), 3.8–4.1(1H, m), 3.90(4H, s), 4.93(1H, dt, J=6Hz, J=3Hz)

(7) 0.88(3H, 6Hz), 1.0–2.9(24H, m), 350(1H, m), 3.88(4H, s), 3.6–4.1(2H, m), 4.63(1H, bs), 4.8–5.06(1H, m)

(11) 0.88(3H, t, J=6Hz), 1.24(3H, t, J=7.5Hz), 1.0–2.7(30H, m), 3.3–3.6(1H, m), 3.89(4H, s), 3.6–4.35(5H, m), 4.10(2H, q, 8.75Hz), 4.35–4.7(1H, m)

(23) 0.7–1.0(6H, m), 1.0–3.0(18H, m), 3.8–4.1(1H), 3.90(4H, s), 4.92(1H, dt, J=6Hz, J=3Hz)

(30) 0.73–1. 6H, m), 1.24(3H, t, J=7Hz), 1.0–2.5(29H, m), 3.3–4.7(7H, m), 3.88(4H, s), 4.11(2H, q, J=7Hz)

(38) 0.88(3H, t, J=6Hz), 1.1–3.6(16H, m), 4.43(0.5H, t, J=6Hz), 4.9–5.3(2.5H, m), 7.3–8.2(9H, m)

(39) 0.90(3H, t, J=6Hz), 1.1–3.2(17H, m), 3.3–3.8(1H, m), 3.8–4.16(0.5H, m), 4.33–4.75(0.5H, m), 4.9–5.16(1H, bs), 5.16–5.33(1H, m), 7.3–8.2(9H, m)

(40) 0.07(6H, S), 0.87(9H, S), 0.7–1.05(3H), 1.05–3.2(16H, m), 3.5–3.85(1H, m), 3.85–4.15(0.5H, m), 4.3-4.6(0.5H, m), 4.95-5.15(1H, m) 5.15-5.33(1H, m), 7.3-8.2(9H, m)

(41) 0.07(6H, s), 0.88(9H, S), 0.75-1.05(3H), 1.05-3.0(17H, m), 3.45-3.85(1H, m), 3.85-4.15(1.5H, m), 4.4-4.65(0.5H, m), 4.93(1H, dd, J=6Hz, J=3Hz)

(42) 0.05(6H, s), 0.88(9H,s), 0.75-1.05(3H), 1.05-3.0(22H, m), 3.3-5.1(7H, m)

(45) 0.07(6H, s), 0.88(9H, S), 0.75-1.0(3H), 1.23(3H, t, J=7Hz), 1.05-2.6(29H, m), 3.2-4.7(7H, m), 4.07(2H, q, J=7Hz), 5.1-5.65(2H, m)

(46) 0.88(3H, t, J=6Hz), 1.23(3H, t, J=7Hz), 1.1-2.6(30H, m), 3.3-4.2(6H, m), 4.10(2H, q, J=7Hz), 4.60(1H, 5.1-5.7(2H, m)

(47) 0.90(3H, t, J=6Hz), 1.25(3H, t, J=6Hz), 1.03-2.70(29H, m), 3.25-4,70(9H, m), 4.07(2H, q, J=6Hz)

(52) 0.92(3H, t, J=6Hz), 1.24(3H, t, J=6Hz), 1.05-2.75(21H, m), 3.3-3.8(1H, m), 4.10(2H, q, 6Hz), 4.10(0.5H), 4.4-4.7(0.5H, m), 5.67(2H, m), 6.10(1H, dd, J=6Hz, J=3Hz), 7.57(1H, dd, J=6Hz, J=3Hz)

(92) 0.88(3H, t, J=6Hz), 1.1-1.8(16H, m), 2.2-3.0(4H, m), 3.88(4H, s), 5.4-5.57(1H, m), 5.80(1H, dd, J=6Hz, J=3Hz), 6.02(1H, dd, J=6Hz, 3Hz)

(95) 0.88(3H, t, J=6Hz), 1.0-2.6(27H, m), 3.62(3H, s), 3.88(4H, S), 4.5-4.7(1H, m), 5.1-5.6(2H, 1 m), 5.6-6.0(2H, m)

(96) 0.87(3H, t, J=6Hz), 1.1-2.7(26H, m), 3.62(3H, S), 3.87(4H, S), 5.15-5.60(2H, m), 6.07(1H, dd, J=6Hz, J=3Hz), 7.53(1H, dd, J=6Hz, J=3Hz)

(97) 0.87(3H, t, J=6Hz), 1.10(3H, d, J=5Hz), 1.0-2.7(29H, m), 3.62(3H, S), 3.7-4.0(4H), 5.1-5.6(2H, m)

(104) 0.7-1.03(6H, m), 1.03-2.6(34H, m), 3.3-4.3(6H, m), 3.88(4H, S), 4.08(2H, q, J=7Hz), 4.60(1H, m)

(112) 0.88(3H, t, J=6Hz), 0.97(3H, d, J=6Hz), (3H, t, J=7Hz), 1.1-2.5(25H, m), 3.90(4H, s), 4.10(2H, q, J=7Hz), 3.8-4.7(3H, m)

(118) 0.90(3H, t, J=6Hz), 1.1-3.1(17H, m), 3.93(1H, q, J=6Hz), 4.41(0.5H, t, J=6Hz), 4.7-5.1(1.5H, m)

(127) 0.05(6H, s), 0.88(9H, s), 0.75-1.0(3H), 1.23(3H, t, J=7Hz), 1.05-2,4(23H, m), 2,42(3H, s), 4.08(2H, q, J=7Hz), 3.9-4.7(4H, m), 5.35(2H, m), 7.27(2H, d, J=9Hz), 7.75(2H, d, J=9Hz)

(129) 0.05(6H, s), 0.88(9H, s), 0.7-1.0(3H), 1.23(3H, t, J=7Hz), 1.05-2.65(20H, m), 3.4-3.85(1H, m), q, J=7Hz), 3.85-4.15(0.5H), 4.35-4.65(0.5H, m) 5.35(2H, m), 6.08(1H, dd, J=6Hz, J=3Hz), 7.53(1H, dd, J=6Hz, J=3Hz)

(137) 0.85(6H, d, J=7Hz), 1.0-2.7(25H, m), (3H, S), 3.5-3.75(2H), 3.88(4H, s), 5.1-5.6(2H, m)

The above data were determined by n.m.r. measuring apparatus R-90H available from Hitachi Seisakusho.

TEST EXAMPLE 1

Antiulcer Activity

As test samples, we used the PGE as obtained in Examples 2 to 52 as described herein, 13,14-dihydro-15-keto-PGE$_2$ (produced by Funakoshi & Co.) being employed as a control reference.

Each group of test animals used consisted of 8 to 10 male rats of the Crj: Wistar strain, weighing 180 to 230 g. Test animals were fasted for 24 hours before the oral administration of the test samples; in the case of development of confinement-stress induced ulcers through immersion in water, 10 minutes after oral administration of the test specimens, the animals were confined in a stress cage developed by Univ. of Tokyo, then immersed up to the ensiform process of sternum in water at 23° C. for 4 hours and sacrificed; in the case of formation of indomethacin-induced ulcers, shortly after the materials were given, animals were given indomethacin orally at a dose of 10 mg/kg and sacrificed after 5 hours.

The stomacks were taken out, followed by fixation with 1% formalin, and incised along the greater curvature to carry our investigation under an illuminated magnifier for ulceration. The degree and extent of lesion and ulcer were rated based on the ulceration index being classified into the following five numerical categories:

0:normal, with no lesion detected;
1:bleeding or erosion of mucosa;
2:development of less than 5 small ulcers (not greater than 2 mm in diameter);
3: generation of not less than 5 small ulcers or a large ulcer (not less than 2 mm in diameter);
4: generation of not less than 2 large ulcers.

On the basis of the criteria that the rats with the ulceration index of not less than "2", the ulcer inhibition rate (ED$_{50}$) was calculated from ulcer-generation ratio in the control and the ratio in the test specimens.

The results are shown in Table 1 (confinement-stress induced ulcers through immersion in water) and Table 2 (indomethacin-induced ulcers).

TABLE 1

(Hydrorestraint Stress Ulcer Preventing Effect)

| Material tested | Dosage (mg/kg) | Animal used (no. of heads) | Ulcer index (aver. ± SE) | Inhibition factor (%) | ED$_{50}$ (mg/kg) |
|---|---|---|---|---|---|
| Control | — | 10 | 3.0 ± 0.2 | — | — |
| (1) | 20 | 8 | 2.5 ± 0.3 | 6.3 | >20 |
| (2) | 15 | 8 | 0.5 ± 0.3 | 87.5 | 4.0 |
|  | 5 | 8 | 1.4 ± 0.4 | 58.3 |  |
| (3) | 10 | 8 | 0.3 ± 0.1 | 100.0 | 1.5 |
|  | 3 | 8 | 1.1 ± 0.3 | 86.1 |  |
|  | 1 | 8 | 2.1 ± 0.4 | 25.0 |  |
| (4) | 5 | 8 | 1.6 ± 0.3 | 44.4 | 7.0 |
|  | 1 | 8 | 2.1 ± 0.4 | 16.7 |  |
| (5) | 5 | 8 | 1.5 ± 0.3 | 44.0 | 6.5 |
|  | 1 | 8 | 2.2 ± 0.4 | 14.3 |  |
| (6) | 10 | 8 | 1.4 ± 0.2 | 72.2 | 5.5 |
|  | 3 | 8 | 2.4 ± 0.3 | 28.0 |  |
| (7) | 10 | 8 | 1.1 ± 0.2 | 75.0 | 4.5 |
|  | 3 | 8 | 1.9 ± 0.3 | 37.5 |  |
| (8) | 1 | 10 | 1.5 ± 0.5 | 62.5 | 0.60 |
|  | 0.3 | 10 | 2.0 ± 0.3 | 30.6 |  |
| (9) | 1 | 10 | 1.5 ± 0.3 | 75.0 | 0.45 |
|  | 0.3 | 10 | 1.9 ± 0.2 | 37.5 |  |
| (10) | 3 | 10 | 0.9 ± 0.4 | 78.4 | 1.5 |
|  | 1 | 10 | 2.0 ± 0.4 | 25.5 |  |
| (11) | 10 | 10 | 1.1 ± 0.2 | 85.7 | 2.4 |
|  | 3 | 10 | 1.4 ± 0.2 | 57.1 |  |
|  | 1 | 10 | 2.0 ± 0.4 | 25.0 |  |
| (12) | 10 | 10 | 1.1 ± 0.2 | 75.3 | 6.2 |
|  | 3 | 10 | 2.6 ± 0.3 | 13.6 |  |
| (13) | 10 | 8 | 1.5 ± 0.4 | 50.0 | 10 |
|  | 3 | 8 | 2.6 ± 0.3 | 13.2 |  |
| (14) | 1 | 10 | 1.3 ± 0.2 | 77.8 | 0.35 |
|  | 0.3 | 10 | 1.7 ± 0.3 | 44.4 |  |
|  | 0.1 | 10 | 1.9 ± 0.4 | 22.2 |  |
| (15) | 6 | 10 | 0.8 ± 0.3 | 79.9 | 3.5 |
|  | 3 | 10 | 1.8 ± 0.3 | 37.5 |  |
| (16) | 1 | 10 | 1.7 ± 0.3 | 44.4 | 2.0 |
|  | 0.3 | 10 | 2.5 ± 0.3 | 0 |  |
| (17) | 0.1 | 10 | 0.5 ±0.2 | 95.7 | 0.005 |
|  | 0.03 | 10 | 1.5 ± 0.3 | 81.4 |  |
|  | 0.01 | 10 | 1.7 ± 0.2 | 67.1 |  |
|  | 0.003 | 10 | 2.2 ± 0.4 | 39.0 |  |
| (18) | 0.3 | 10 | 0.5 ± 0.2 | 95.9 | 0.03 |
|  | 0.1 | 10 | 0.7 ± 0.2 | 89.0 |  |
|  | 0.03 | 10 | 1.7 ± 0.3 | 49.3 |  |
| (19) | 0.3 | 10 | 1.1 ± 0.3 | 83.3 | 0.06 |
|  | 0.1 | 10 | 1.6 ± 0.3 | 63.0 |  |
|  | 0.03 | 10 | 2.5 ± 0.4 | 33.3 |  |

TABLE 1-continued
(Hydrorestraint Stress Ulcer Preventing Effect)

| Material tested | Dosage (mg/kg) | Animal used (no. of heads) | Ulcer index (aver. ± SE) | Inhibition factor (%) | ED$_{50}$ (mg/kg) |
|---|---|---|---|---|---|
| (20) | 3 | 10 | 0.9 ± 0.2 | 87.7 | 0.80 |
|  | 1 | 10 | 1.7 ± 0.2 | 58.3 |  |
|  | 0.3 | 10 | 2.4 ± 0.3 | 22.2 |  |
| (21) | 3 | 10 | 0.9 ± 0.2 | 87.5 | 0.80 |
|  | 1 | 10 | 1.6 ± 0.3 | 52.4 |  |
| (22) | 3 | 10 | 1.2 ± 0.3 | 70.0 | 1.8 |
|  | 1 | 10 | 2.0 ± 0.4 | 30.0 |  |
| (23) | 3 | 10 | 2.0 ± 0.2 | 50.0 | 3.0 |
|  | 1 | 10 | 2.9 ± 0.3 | 12.5 |  |
| (24) | 10 | 10 | 1.4 ± 0.2 | 87.1 | 2.0 |
|  | 3 | 10 | 1.7 ± 0.2 | 61.4 |  |
| (25) | 10 | 8 | 1.4 ± 0.2 | 62.5 | 8.0 |
|  | 3 | 8 | 2.3 ± 0.4 | 12.5 |  |
| (26) | 10 | 8 | 1.1 ± 0.2 | 72.2 | 4.0 |
|  | 3 | 8 | 1.6 ± 0.3 | 44.4 |  |
| (27) | 6 | 8 | 1.6 ± 0.2 | 56.0 | 5.0 |
|  | 3 | 8 | 2.1 ± 0.3 | 31.8 |  |
| (28) | 6 | 8 | 1.3 ± 0.3 | 70.2 | 4.0 |
|  | 3 | 8 | 1.9 ± 0.2 | 36.0 |  |
| (29) | 6 | 10 | 2.0 ± 0.4 | 42.2 | >6 |
|  | 3 | 10 | 2.5 ± 0.3 | 30.0 |  |
| (30) | 6 | 8 | 1.1 ± 0.2 | 57.8 | 5.0 |
|  | 3 | 8 | 2.3 ± 0.4 | 29.7 |  |
| (31) | 0.3 | 10 | 1.0 ± 0.2 | 75.0 | 0.14 |
|  | 0.1 | 10 | 2.2 ± 0.3 | 37.5 |  |
|  | 0.03 | 10 | 2.6 ± 0.4 | 12.5 |  |
| (32) | 1 | 10 | 0.8 ± 0.2 | 82.3 | 0.2 |
|  | 0.3 | 10 | 1.5 ± 0.3 | 57.0 |  |
|  | 0.1 | 10 | 2.0 ± 0.4 | 27.9 |  |
| (33) | 5 | 10 | 1.2 ± 0.3 | 55.0 | 3.9 |
|  | 1 | 10 | 2.6 ± 0.3 | 25.0 |  |
| (34) | 10 | 10 | 0.8 ± 0.3 | 90.0 | 1.3 |
|  | 3 | 10 | 1.4 ± 0.4 | 60.0 |  |
|  | 1 | 10 | 2.0 ± 0.4 | 40.0 |  |
| (35) | 3 | 10 | 1.2 ± 0.3 | 77.5 | 0.9 |
|  | 1 | 10 | 1.5 ± 0.3 | 55.0 |  |
|  | 0.3 | 10 | 2.3 ± 0.3 | 21.3 |  |
| (36) | 1 | 10 | 1.5 ± 0.3 | 57.0 | 0.8 |
|  | 0.3 | 10 | 2.4 ± 0.4 | 22.6 |  |
| (37) | 6 | 10 | 1.0 ± 0.2 | 79.7 | 3.0 |
|  | 3 | 10 | 1.9 ± 0.2 | 45.9 |  |
|  | 1 | 10 | 2.7 ± 0.4 | 8.1 |  |
| (38) | 3 | 10 | 1.0 ± 0.2 | 79.7 | 1.5 |
|  | 1 | 10 | 1.9 ± 0.2 | 45.9 | 1.5 |
|  | 0.3 | 10 | 2.7 ± 0.4 | 8.1 |  |
| (39) | 3 | 10 | 0.7 ± 0.2 | 85.3 | 0.5 |
|  | 1 | 10 | 1.0 ± 0.2 | 77.5 |  |
|  | 0.3 | 10 | 2.0 ± 0.3 | 30.2 |  |

TABLE 2
(Indomethacin Ulcer Preventing Effect)

| Material tested | Dosage (mg/kg) | Animal used (no. of heads) | Ulcer index (aver. ± SE) | Inhibition factor (%) | ED$_{50}$ (mg/kg) |
|---|---|---|---|---|---|
| Control | — | 10 | 2.5 ± 0.3 | — | — |
| (1) | 20 | 8 | 2.4 ± 0.4 | 4.0 | >20 |
| (2) | 20 | 9 | 0.4 ± 0.2 | 100.0 | 6.0 |
|  | 6 | 8 | 1.4 ± 0.3 | 50.0 |  |
|  | 3 | 9 | 1.9 ± 0.4 | 30.0 |  |
| (3) | 10 | 9 | 1.0 ± 0.3 | 71.4 | 4.4 |
|  | 3 | 9 | 1.7 ± 0.4 | 42.9 |  |
| (8) | 3 | 10 | 1.7 ± 0.3 | 42.9 | 3.8 |
|  | 1 | 10 | 2.3 ± 0.4 | 14.3 |  |
| (9) | 3 | 10 | 1.5 ± 0.3 | 50.5 | 3.0 |
|  | 1 | 10 | 2.1 ± 0.4 | 37.5 |  |
| (11) | 10 | 10 | 2.0 ± 0.2 | 50.0 | 10.0 |
|  | 3 | 10 | 2.6 ± 0.3 | 0 |  |
| (12) | 10 | 10 | 0.8 ± 0.2 | 71.4 | 7.4 |
|  | 3 | 10 | 1.6 ± 0.3 | 48.0 |  |
| (14) | 3 | 10 | 0.6 ± 0.1 | 80.0 | 1.5 |
|  | 1 | 10 | 2.0 ± 0.3 | 32.0 |  |
| (16) | 10 | 10 | 1.0 ± 0.2 | 60.0 | 8.2 |
|  | 3 | 10 | 2.3 ± 0.3 | 10.0 |  |
| (18) | 1 | 10 | 0.2 ± 0.2 | 100.0 | 0.17 |
|  | 0.3 | 10 | 1.4 ± 0.1 | 62.5 |  |
|  | 0.1 | 10 | 1.8 ± 0.2 | 38.3 |  |
| (19) | 10 | 10 | 0.4 ± 0.1 | 85.7 | 3.6 |
|  | 3 | 10 | 1.9 ± 0.2 | 42.9 |  |
| (20) | 10 | 10 | 0.6 ± 0.1 | 87.5 | 3.5 |
|  | 3 | 10 | 1.3 ± 0.2 | 44.4 |  |
| (21) | 10 | 10 | 1.5 ± 0.3 | 80.0 | 6.0 |
|  | 3 | 10 | 2.5 ± 0.4 | 0 |  |
| (23) | 10 | 10 | 1.5 ± 0.3 | 50.0 | 10.0 |
|  | 3 | 10 | 2.0 ± 0.3 | 25.0 |  |
| (30) | 10 | 10 | 0.6 ± 0.1 | 71.5 | 0.9 |
|  | 3 | 10 | 2.1 ± 0.4 | 24.0 |  |
|  | 1 | 10 | 2.4 ± 0.5 | 10.0 |  |
| (33) | 10 | 10 | 1.6 ± 0.2 | 62.0 | 6.3 |
|  | 3 | 10 | 2.3 ± 0.3 | 30.0 |  |
| (34) | 10 | 10 | 1.9 ± 0.2 | 70.0 | 6.0 |
|  | 3 | 10 | 2.2 ± 0.4 | 20.0 |  |
| (35) | 10 | 10 | 1.0 ± 0.2 | 72.5 | 4.8 |
|  | 3 | 10 | 2.3 ± 0.4 | 29.3 |  |

Materials tested in Table 1 is shown hereinafter:
(1) 13, 14-dihydro-15-keto-PGE$_2$,
(2) 13, 14-dihydro-15-keto-PGE$_2$ methyl ester,
(3) 13, 14-dihydro-15-keto-PGE$_2$ ethyl ester,
(4) 13, 14-dihydro-15-keto-PGE$_2$-n-propyl ester,
(5) 13, 14-dihydro-15-keto-PGE$_2$ isopropyl ester,
(6) 13, 14-dihydro-15-keto-PGE$_1$ methyl ester,
(7) 13, 14-dihydro-15-keto-PGE$_1$ ethyle ester,
(8) 13, 14-dihydro-6,15-diketo-PGE$_1$ methyl ester,
(9) 13, 14-dihydro-6,15-diketo-PGE$_1$ ethyl ester,
(10) 13, 14-dihydro-6,15-diketo-PGE$_1$ n-butyl esterm
(11) (±)13, 14-dihydro-6,15-diketo-PGE$_1$ ethyl ester,
(12) 13, 14-dihydro-15-keto-3R,S-methyl-PGE$_2$ methyl ester,
(13) 13, 14-dihydro-15-keto-3R,S-methyl-PGE$_2$ ethyl ester,
(14) 13, 14-dihydro-15-keto-16R,S-fluoro-11-dehydroxy-11R-methyl-PGE$_2$ ethyl ester,
(15) 13, 14-dihydro-15-keto-11-dehydroxy-11R-methyl-PGE$_2$ ethyl ester,
(16) 13, 14-dihydro-15-keto-16R,S-hydroxy-PGE$_2$ ethyl ester,
(17) 13, 14-dihydro-15-keto-16R,S-fluoro-PGE$_2$,
(18) 13, 14-dihydro-15-keto-16R,S-fluoro-PGE$_2$ methyl ester,
(19) 13, 14-dihydro-15-keto-16 R,S-fluoro-PGE$_2$ ethyl ester,
(20) 13, 14-dihydro-15-keto-16R,S-methyl-PGE$_2$ methyl ester,
(21) 13, 14-dihydro-15-keto-16R,S-methyl-PGE$_2$ ethyl ester,
(22) 13, 14-dihydro-15-keto-3R,S,16R,S-dimethyl-PGE$_2$ methyl ester,
(23) 13, 14-dihydro-15-keto-19-methyl-PGE$_2$ methyl ester,
(24) 13, 14-dihydro-15-keto-19-methyl-PGE$_2$ ethyl ester,
(25) 13, 14-dihydro-15-keto-20-isopropylidene-PGE$_2$ methyl ester,
(26) 13, 14-dihydro-15-keto-20-ethyl-PGE$_2$ methyl ester,
(27) 13, 14-dihydro-15-keto-20-ethyl-PGE$_2$ ethyl ester,

(28) 13, 14-dihydro-15-keto-20-ethyl-11-dehydroxy-11R-methyl-PGE$_2$ methyl ester, methyl ester, ester,
(29) 13, 14-dihydro-15-keto-20-n-propyl-PGE$_2$ methyl ester,
(30) 13, 14-dihydro-15-keto-20-ethyl-PGE$_1$, ethyl ester,
(31) 13, 14-dihydro-6,15-diketo-16R,S-fluoro-PGE$_1$ ethyl ester,
(32) 13, 14-dihydro-6,15-diketo-16R,S-fluoro-11-dehydroxy-11R-methyl-PGE$_1$ ethyl ester,
(33) 13, 14-dihydro-6,15-diketo-16R,S-methyl-PGE$_1$ methyl ester,
(34) 13, 14-dihydro-6,15-diketo-16R,S-methyl-PGE$_1$ ethyl ester,
(35) 13,14-dihydro-6,15-diketo-19-methyl-PGE$_1$ methyl ester,
(36) 13, 14-dihydro-6, 15-diketo-19-methyl-PGE$_1$ ethyl ester,
(37) 13, 14-dihydro-6, 15-diketo-20-methyl-PGE$_1$ ethyl ester,
(38) 13, 14-dihydro-6, 15-diketo-11-dehydroxy-11R-methyl-PGE$_1$ methyl ester,
(39) 13,14-dihydro-6,15-diketo-11-dehydroxy-11R-methyl-PGE$_1$ ethyl ester.

From the foregoing results, it can be seen that while 13, 14-dihydro-15-keto-PGE$_2$, as a physiologically and pharmacologically inactive metabolite, shows no antiulcerative effect, it can have antiulcerative effect if it is made into an ester compound of 13, 14-dihydro-15-keto-PGE or a compound similar thereto.

TEST EXAMPLE 2

The following 4 materials were measured as to their respective effects of ulcer prevention, intestinal constriction, tracheorelaxation, and uteroconstriction, and examined in comparison to one another. The results are shown in Table 3.

TABLE 3

| Material tested | Ulcer inhibiting effect ED$_{50}$ (mg/kg) | Intestinal constriction effect | Tracheal relaxation effect | Uterus constriction effect |
| --- | --- | --- | --- | --- |
| A | 0.5 | + | + | + |
| B | 0.4 | + | + | ± |
| C | >20 | − | ± | ± |
| D | 1.5 | − | − | − |

Materials tested:
A: PGE$_2$ (product of Funakoshi Yakuhin K.K.)
B: PGE$_2$ ethyl ester (produced by Applicant Co.)
C: 13, 14-dihydro-15-keto-PGE$_2$ (product of Funakoshi Yakuhin K.K.)
D: 13, 14-dihydro-15-keto-PGE$_2$ ethylester

(1) Antiulcerative Effect

The procedure of Test Example 1 was followed in determining values for hydrorestraint stress-ulcer preventing effect in terms of ED$_{50}$.
++: alvin flux developed at a concentration lower than 1 mg/kg;
+: alvin flux developed at concentrations of 1~10 mg/kg;
−: no flux developed at a concentration higher than 10 mg/kg.

(2) Intestinal Constriction Effect

A male Wister rat (of 250~300 g in weight) was struck to death, and immediately its carotid artery was cut to dehematize. An ileum portion located about 10 cm from the cecum was extracted, and after its contents were washed away with a Tyrode liquid, a 1.5~2 cm long part of it was cut off and hung in a Magnus tube.

The constriction of the ileum was brought to rest for 15~20 minutes until the ileum was allowed to be stabilized, and subsequently the ileum was constricted with $10^{-6}$ g/ml of acetylcholine. After constrictions of same magnitude were had two times, the material to be tested was cumulatively administered at one-minute intervals.

Constrictions with the material tested were expressed in terms of ratios, based on constriction per $10^{-6}$ of acetylcholine, and values for ED$_{50}$ were determined.
+: ED$_{50}$ < $10^{-6}$M
±: $10^{-4}$M ≦ ED$_{50}$ ≦ $10^{-6}$M
−: $10^{-4}$M < ED$_{50}$

3) Tracheal Relaxation

A male gunea pig (of about 300 g in weight) was struck to death, and its artery was cut to dehematize. Its trachea, after having been extracted, was cut open lengthwise on the opposite side to the trachea smooth muscle, and seven tracheal rings were connected by string in a chain-like pattern, same being hung in a Magnus tube.

Trachea was brought to rest for 60~90 minutes and until tracheal equilibrium was reached. Thereafter, $5.4 \times 10^{-4}$M of histamine was administered in such manner that it was cumulatively administered at 6 minutes' intervals after a constriction peak was reached. Tracheal relaxation with the material tested was expressed in terms of ratio of constrictional inhibition under histamine administering, and values for IC$_{50}$ were determined.
+: $IC_{50} < 10^{-7}M$
±: $10^{-5}M \leq IC_{50} \leq 10^{-7}M$
−: $10^{-5}M < IC_{50}$

(4) Uterine Constriction

A female rat (of 150 g in weight) was dehematized to death, and its uterus was taken out, which was cut to a length of 1.5-2.5 cm. The cut uterus was hung in a magnus tube. The uterus was constricted several times with 1 mU Oxytocin. After stable uterine movement was obtained, the material to be tested was independently administered. Constrictions with the material were expressed in terms of ratios based on constriction by 1 mU of oxytocin=100, and values for EC$_{50}$ were determined on the following standards.
+: EC$_{50}$ < $10^{-7}$M
±: $10^{-5}M \leq EC_{50} \leq 10^{-7}M$
−: $10^{-5}M < ED_{50}$ From the results of the foregoing tests it can be seen that PGE$_2$ and PGE$_2$ ethylester can, in addition to their ulcer inhibiting effects, concurrently produce intestinal constriction, tracheal relaxation, and uterus constriction. Whilst, no pharmacological or physiological effect, such as ulcer inhibiting effect, can be found with 13,14-dihydro-15-keto-PGE$_2$. However, it can be recognized that 13,14-dihydro-15-keto-PGE$_2$ ethylester, an ester compound of said 3, 14-dihydro-15-keto-PGE$_2$, can produce a high degree of ulcer inhibiting effect, though it has no such effet as intestinal, uterus constriction, tracheal relaxation and the like.
Chart I
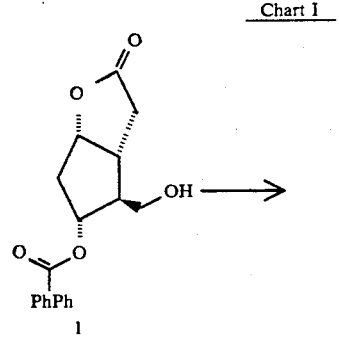
1
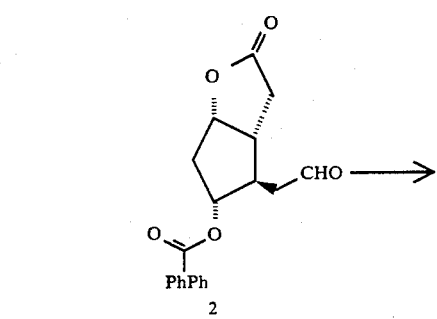
2
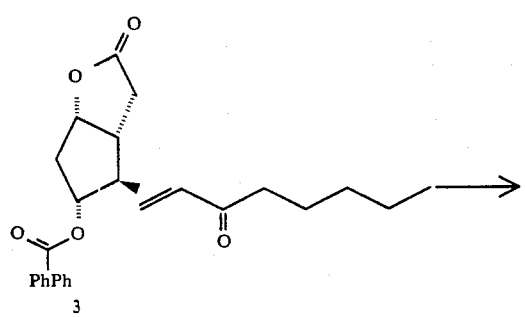
3
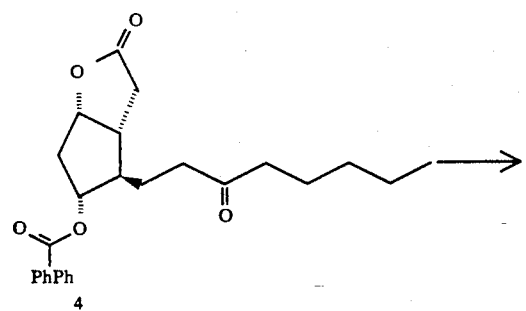
4
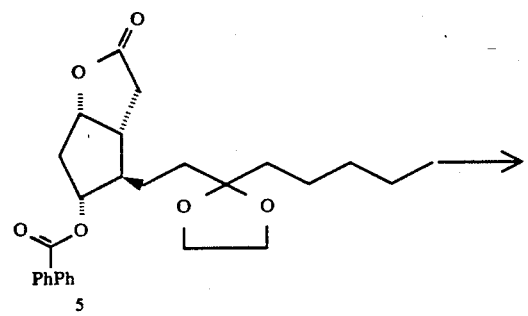
5
-continued
Chart I
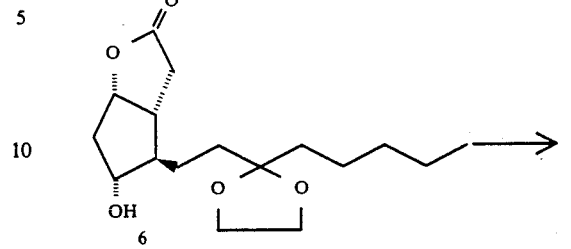
6
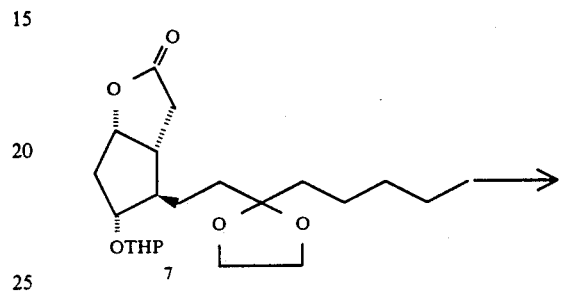
7
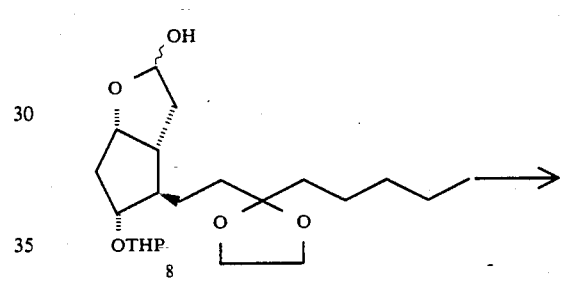
8
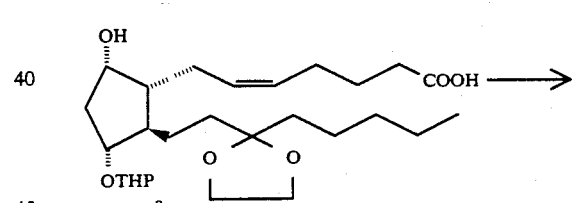
9
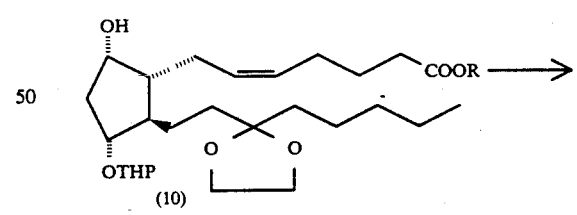
(10)
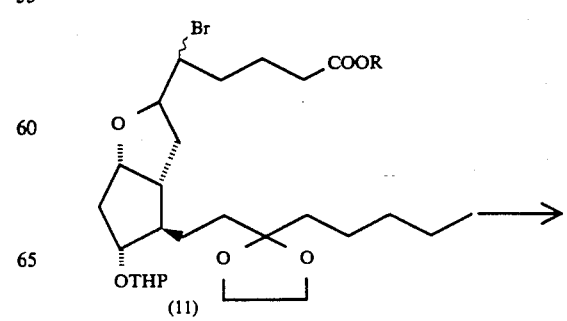
(11)

5,225,439
Chart I -continued
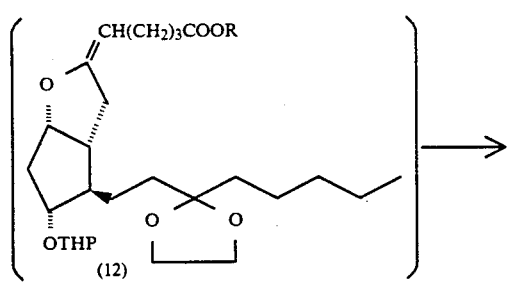
(12)
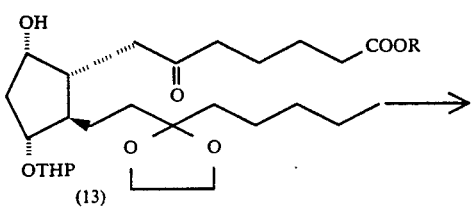
(13)
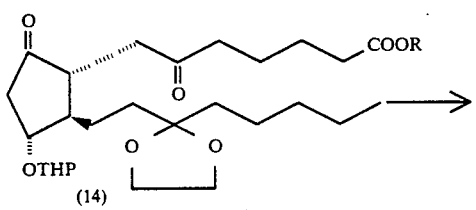
(14)
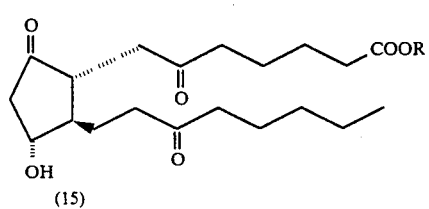
(15)
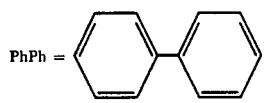
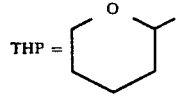
Chart II
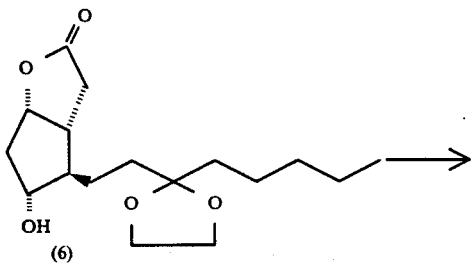
(6)
Chart II -continued
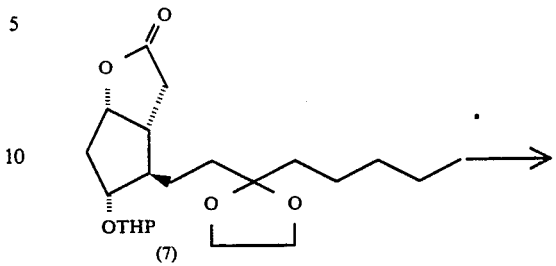
(7)
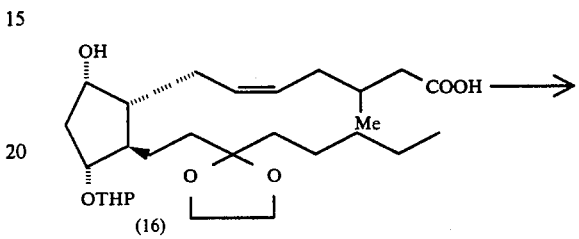
(16)
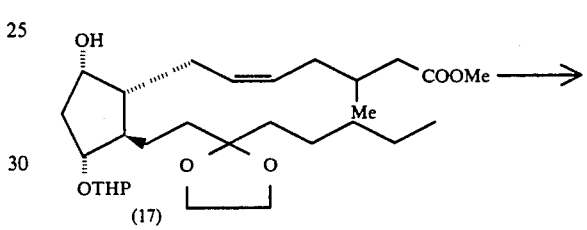
(17)
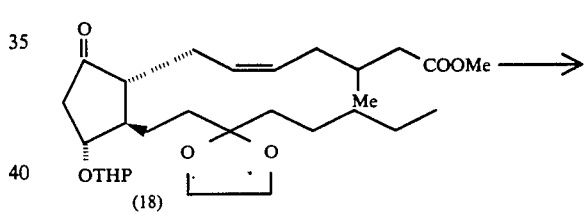
(18)
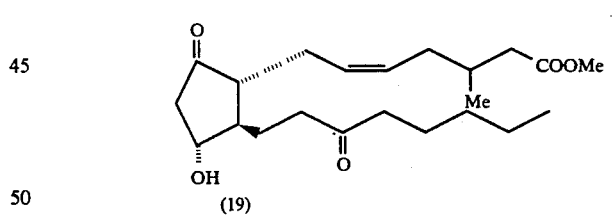
(19)
Chart III
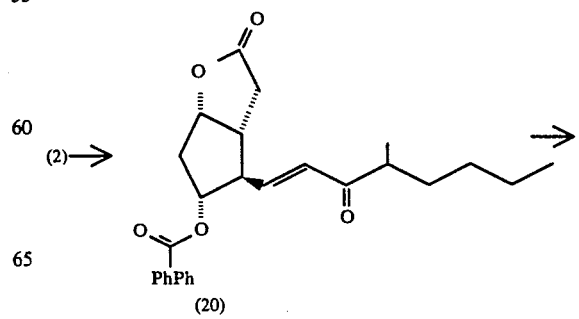
(20)

5,225,439
53
-continued
Chart III
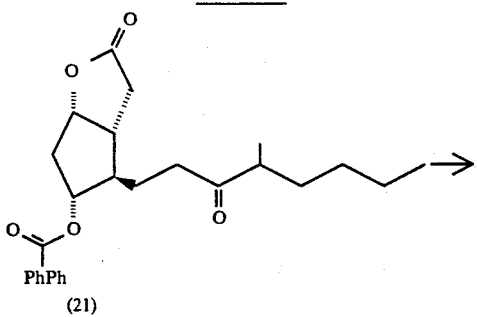
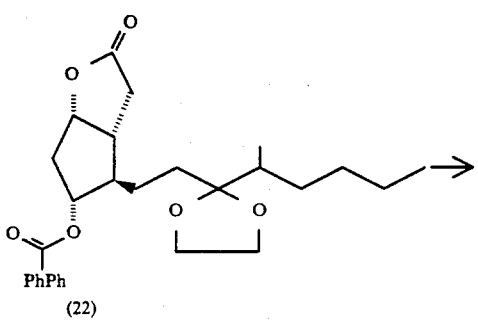
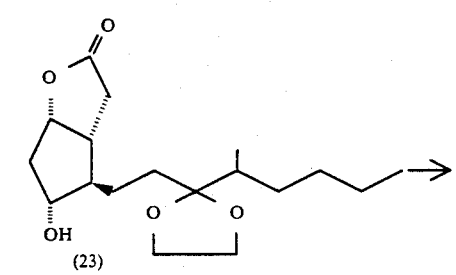
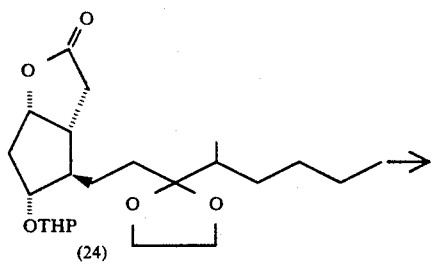
54
-continued
Chart III
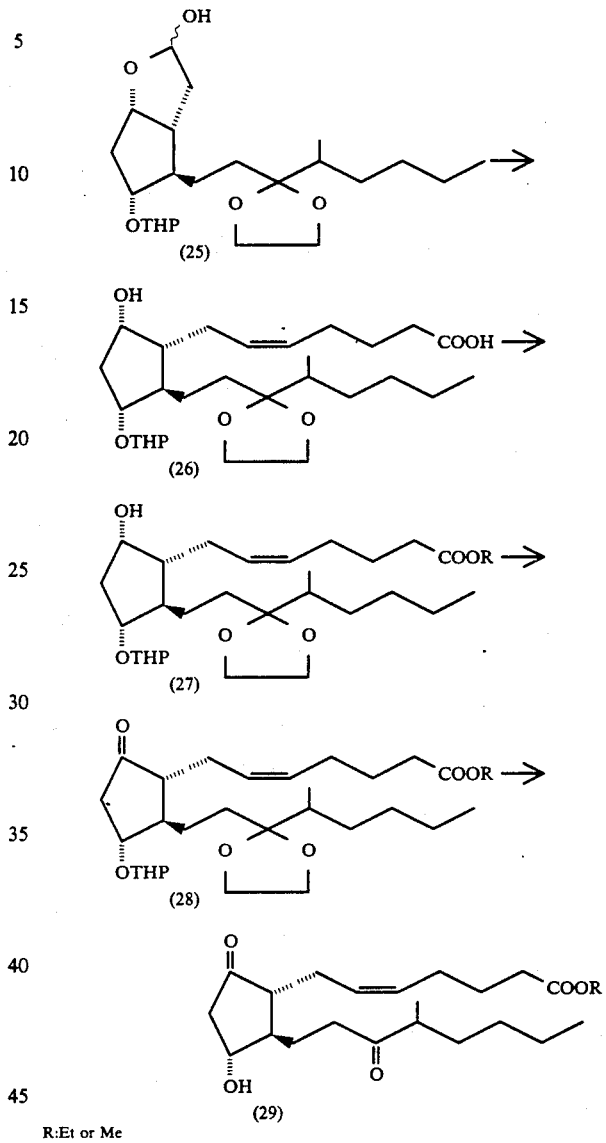
R:Et or Me
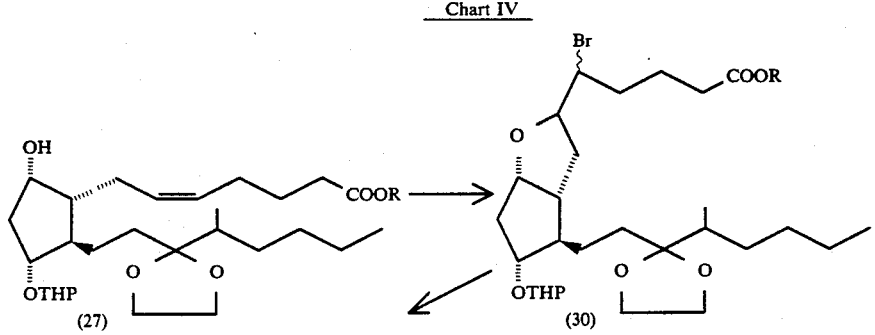
Chart IV

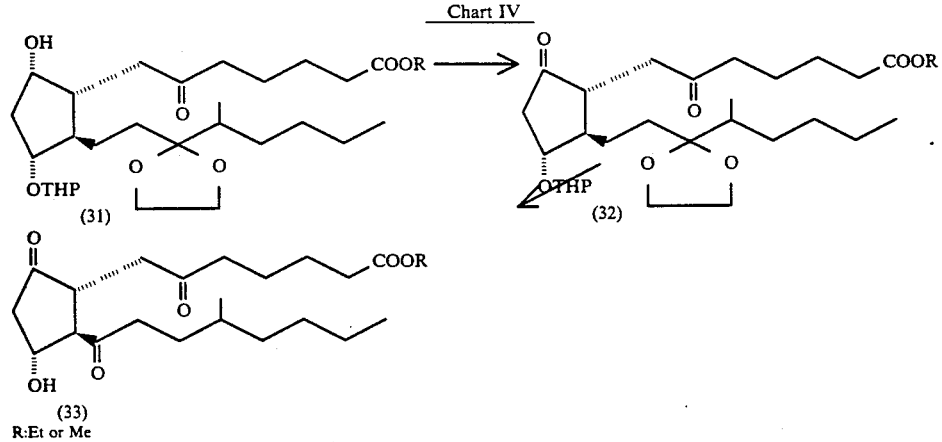
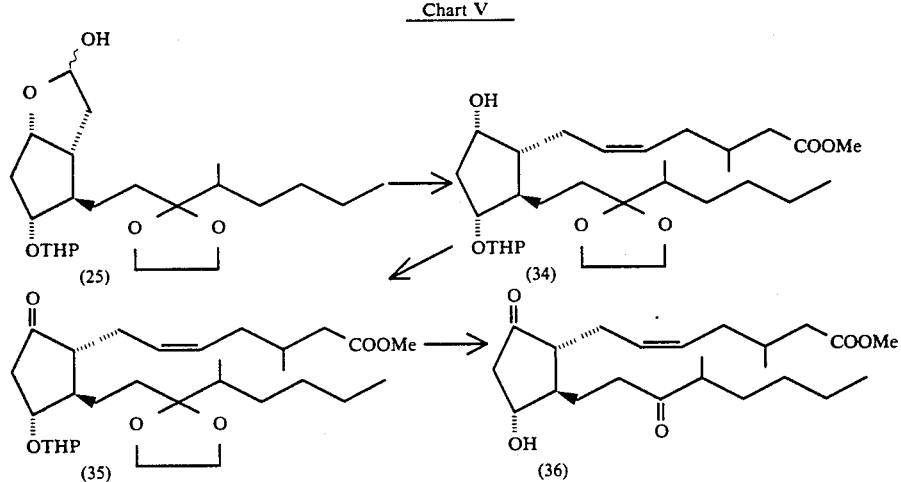
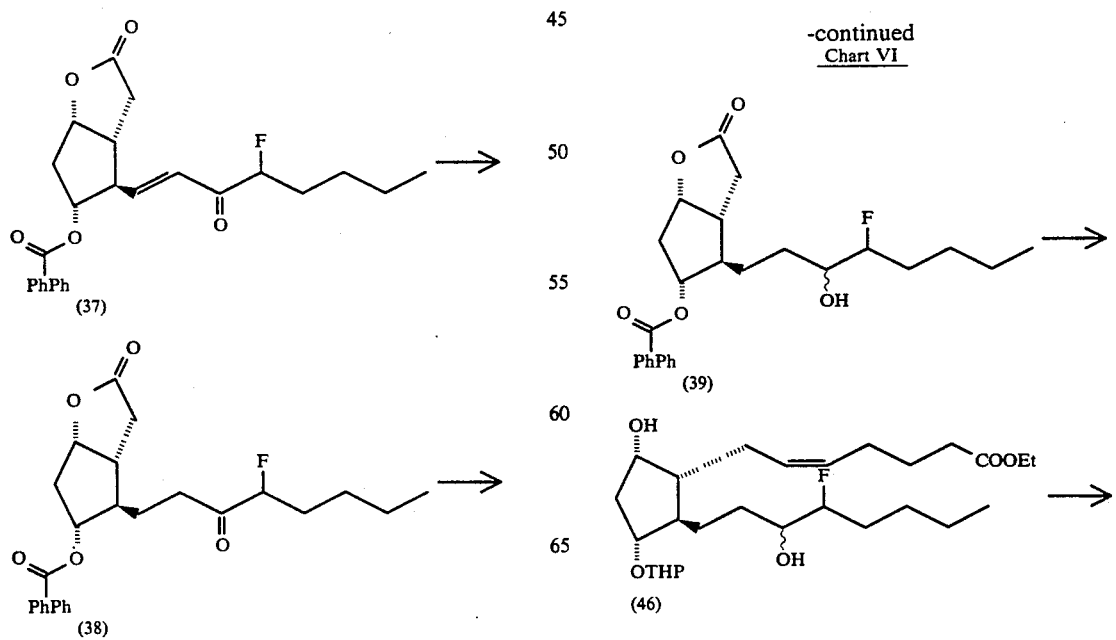

57
-continued
Chart VI
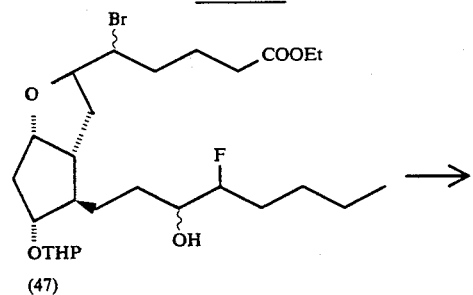
(47)
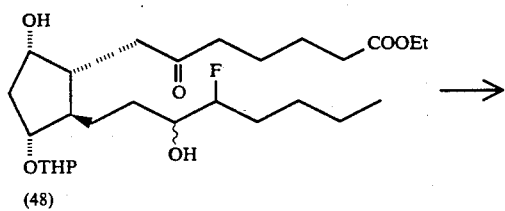
(48)
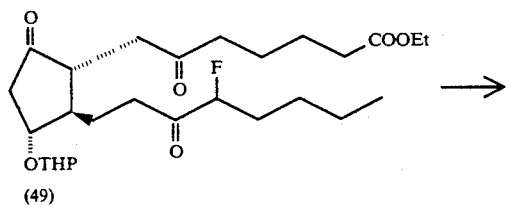
(49)
58
-continued
Chart VI
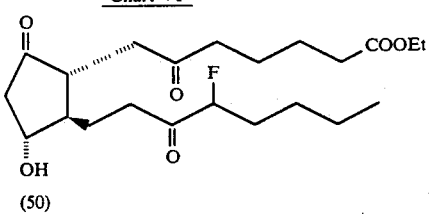
(50)
Chart VII
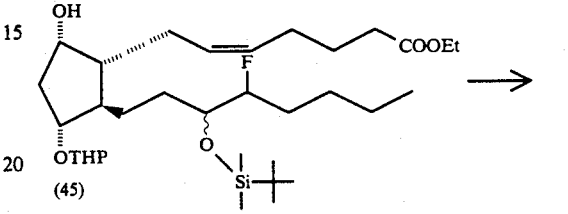
(45)
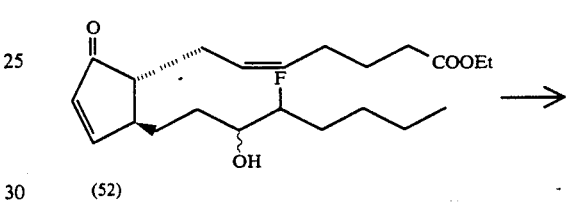
(52)
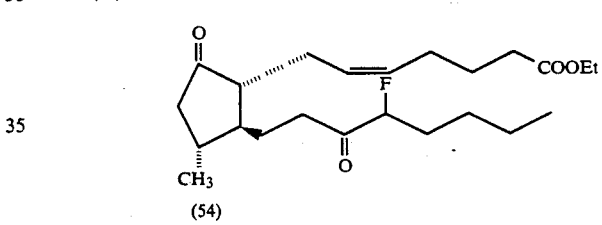
(54)
Chart VIII
(2) →
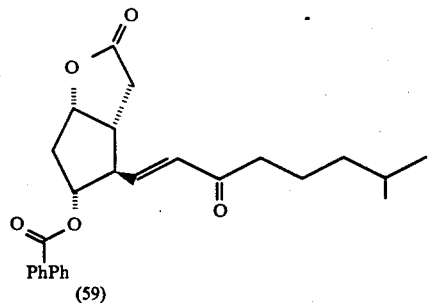
(59)
↓
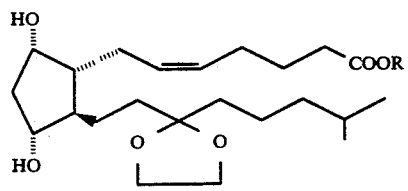
↓   ↓ 

-continued
Chart VIII
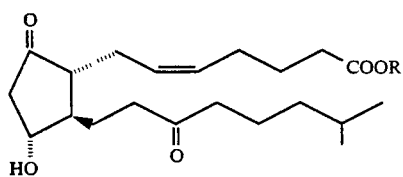
R: Et (60)
Me (61)
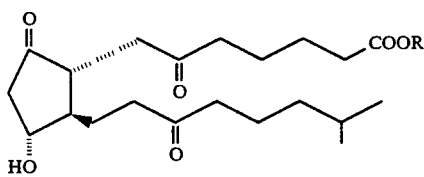
R: Et or Me
R: Et (62)
Me (63)
Chart IX
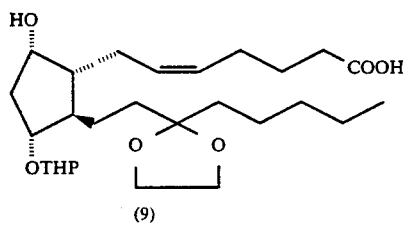
(9)
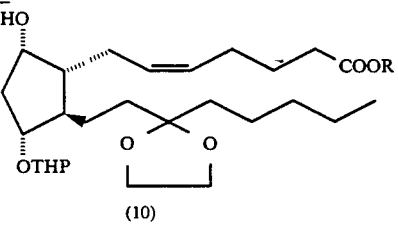
(10)
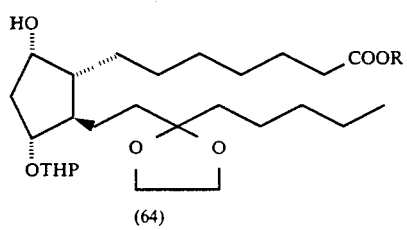
(64)
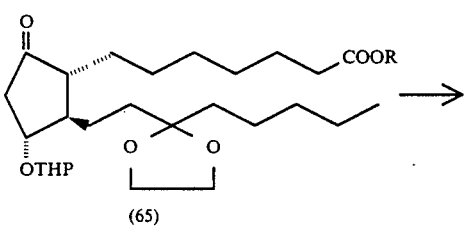
(65)
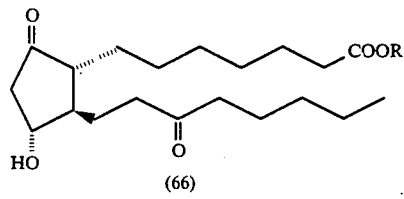
(66)
R: Et or Me
Chart X
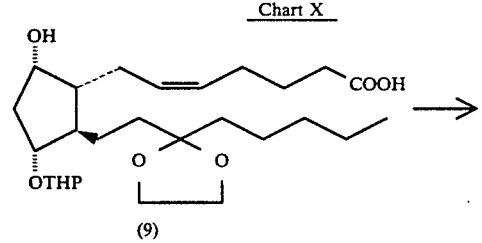
(9)
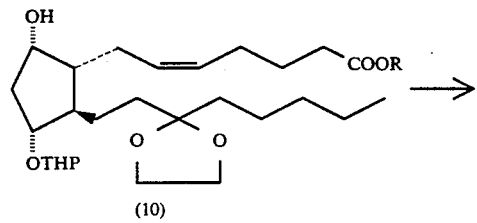
(10)
-continued
Chart X
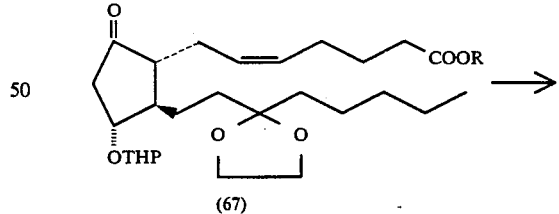
(67)
(68)
THP = 
R = Et, Me, n-Pro, iso-Pro iso-Pro, n-Bu, Cyclopentyl, Benzyl Chart XI
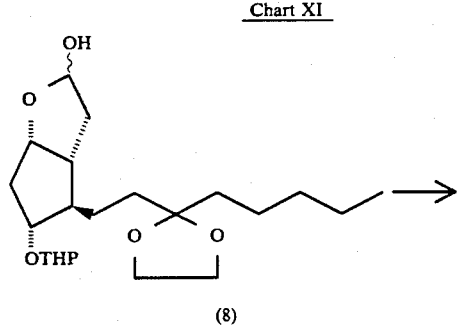
(8)
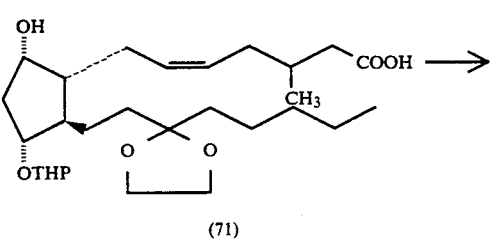
(71)
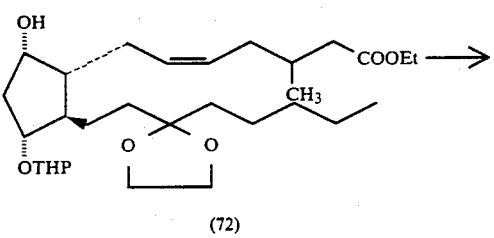
(72)
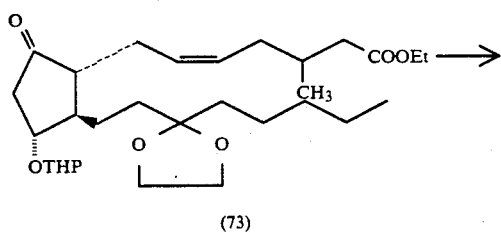
(73)
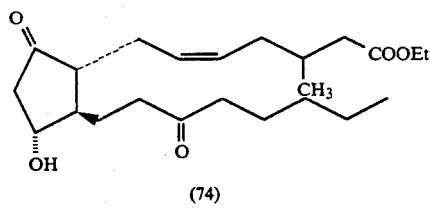
(74)
Chart XII
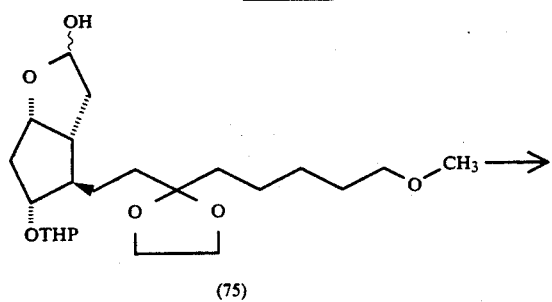
(75)
Chart XII -continued
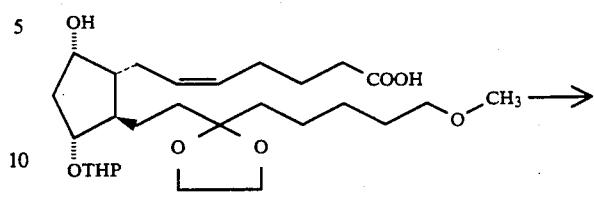
(76)
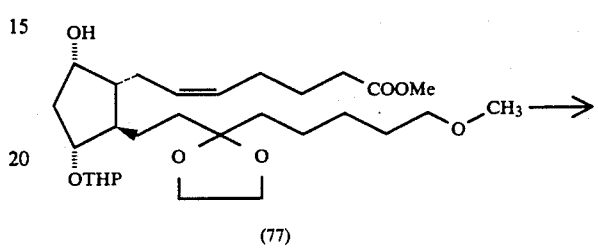
(77)
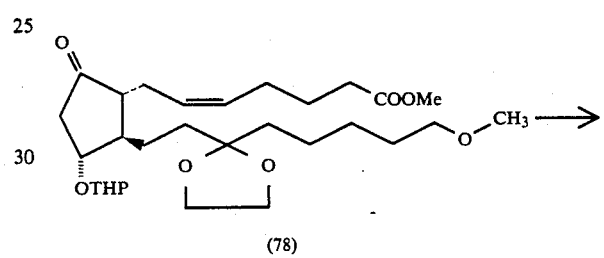
(78)
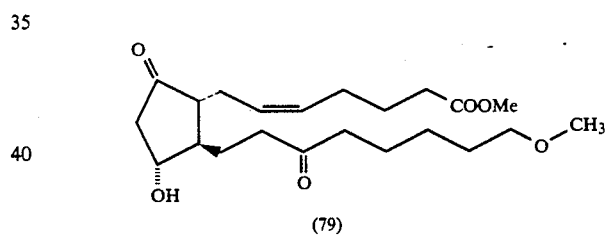
(79)
Chart XIII
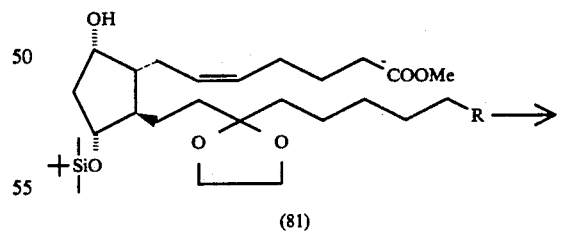
(81)
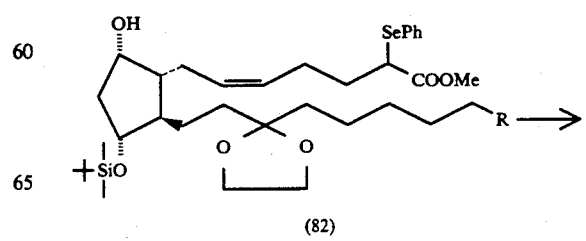
(82)

-continued
Chart XIII
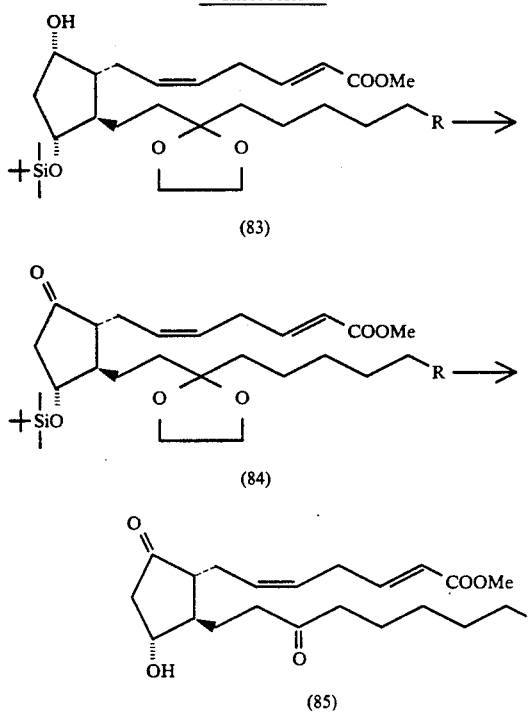
-continued
Chart XIV
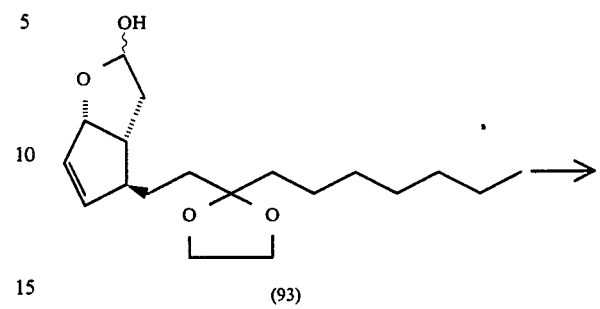
(93)
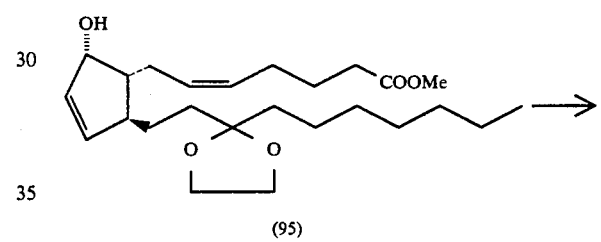
(94)
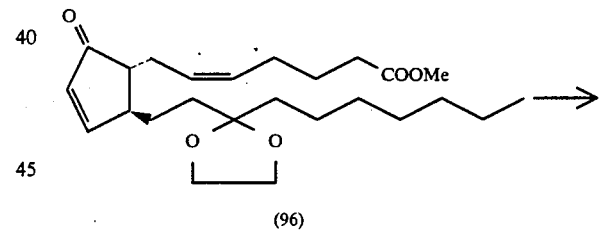
(95)
Chart XIV
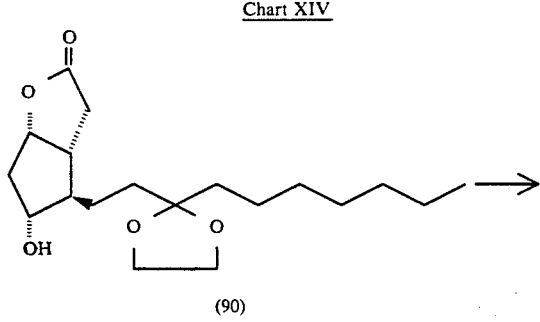
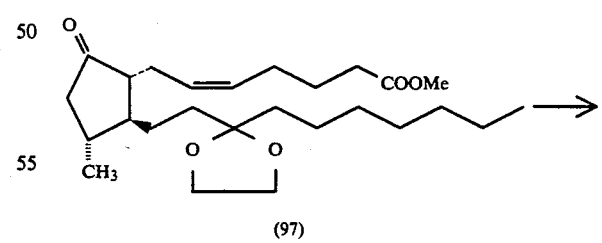
(96)
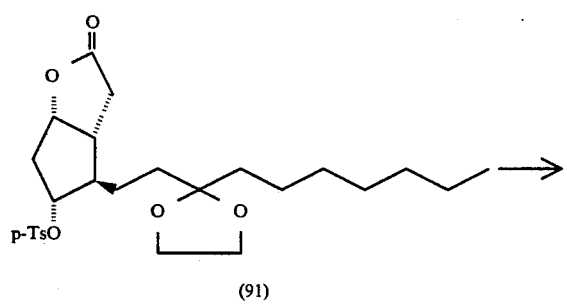
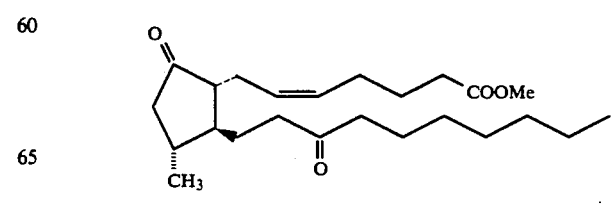
(97)
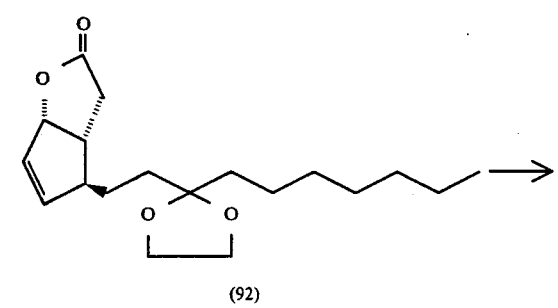
(98)

Chart XV
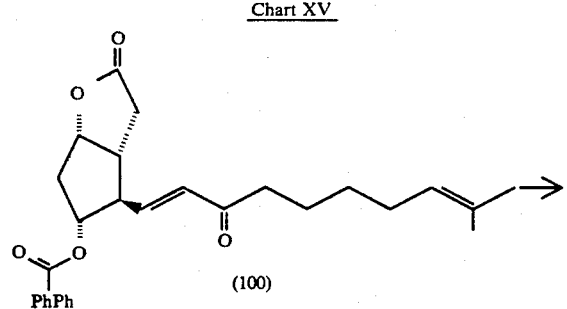
(100)
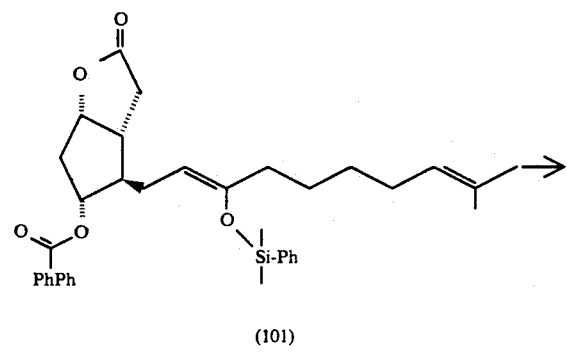
(101)
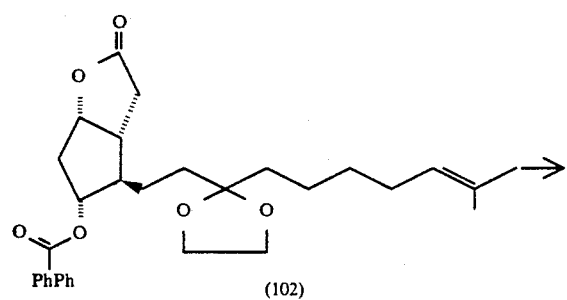
(102)
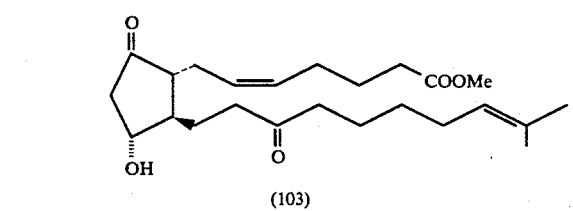
(103)
Chart XVI
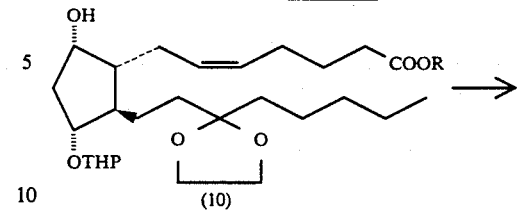
(10)
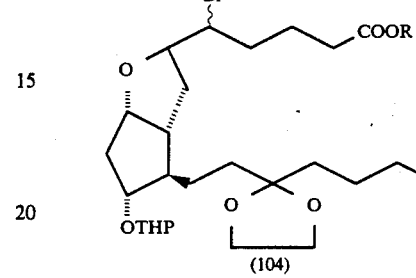
(104)
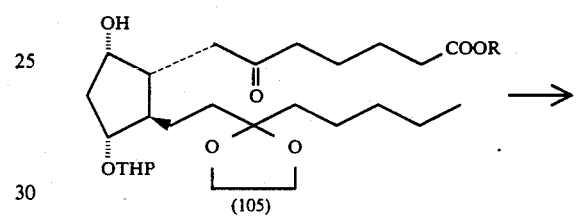
(105)
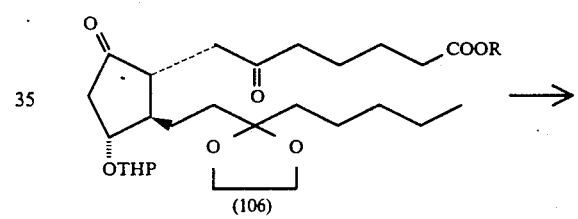
(106)
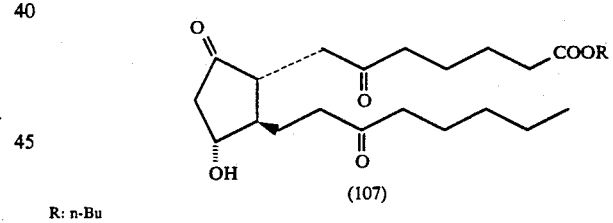
(107)
R: n-Bu

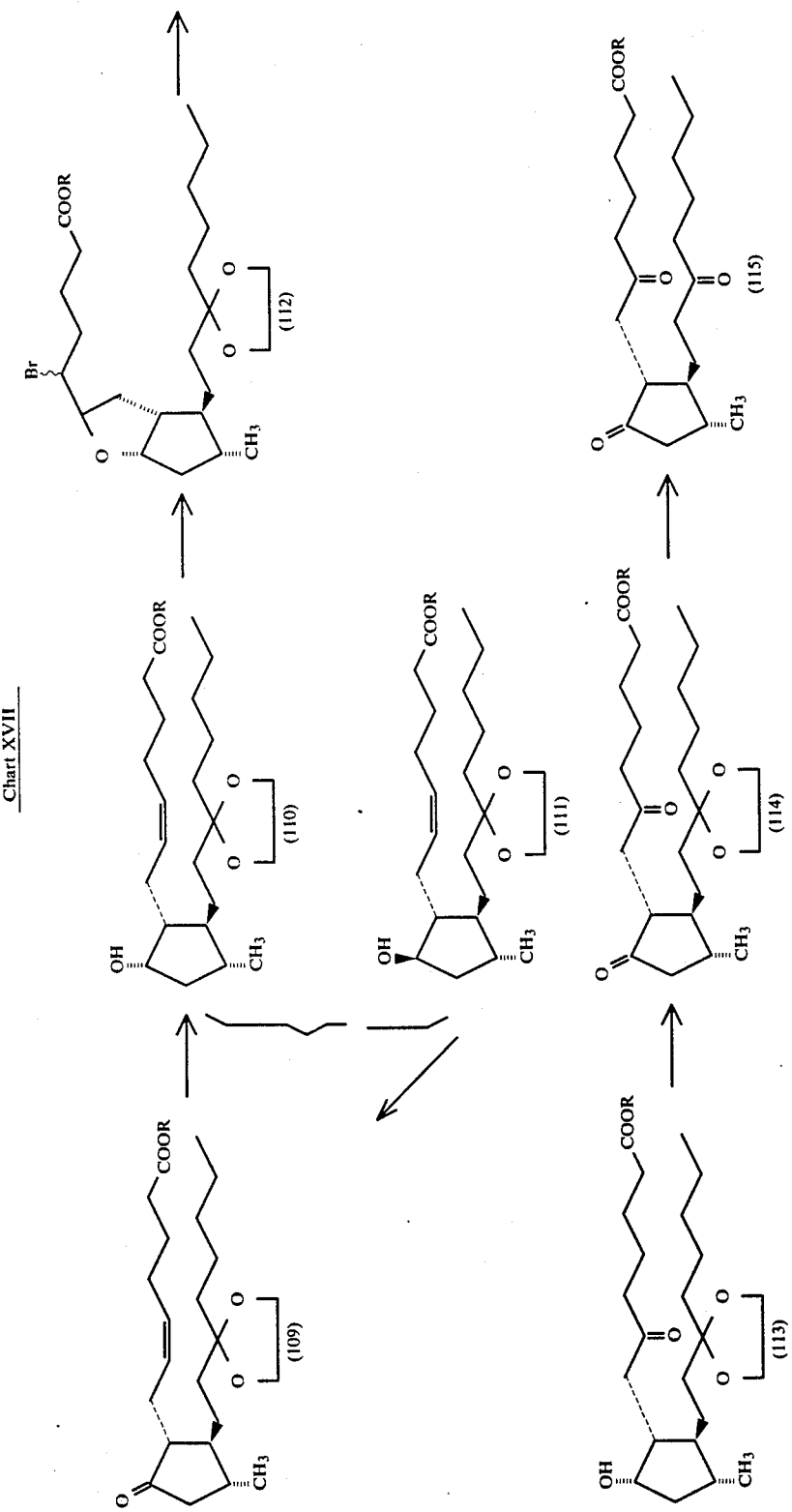

Chart XVIII
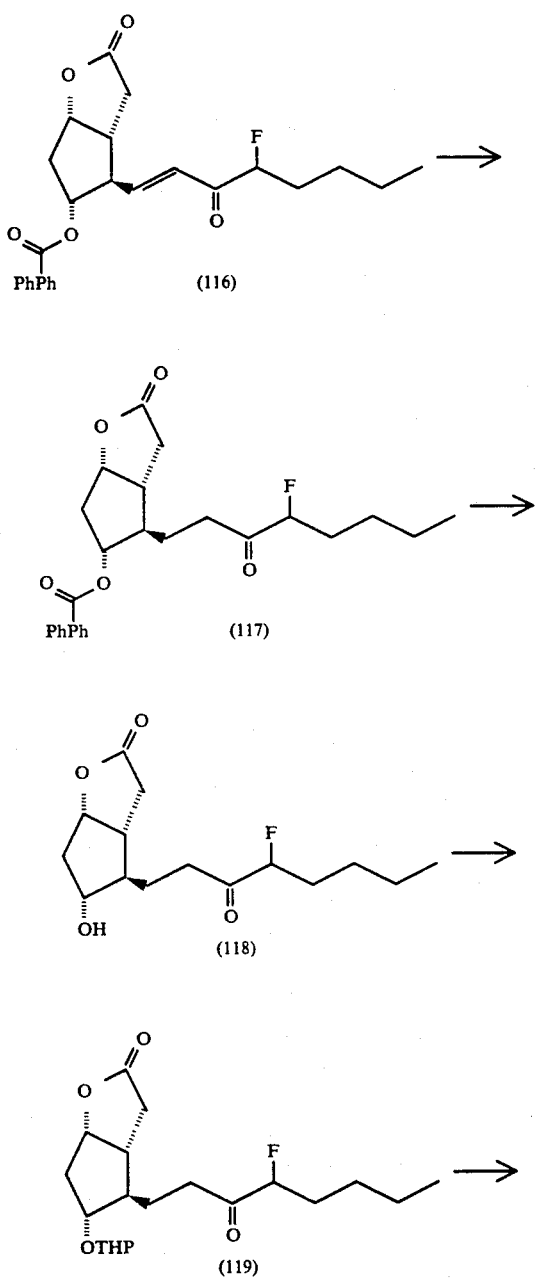
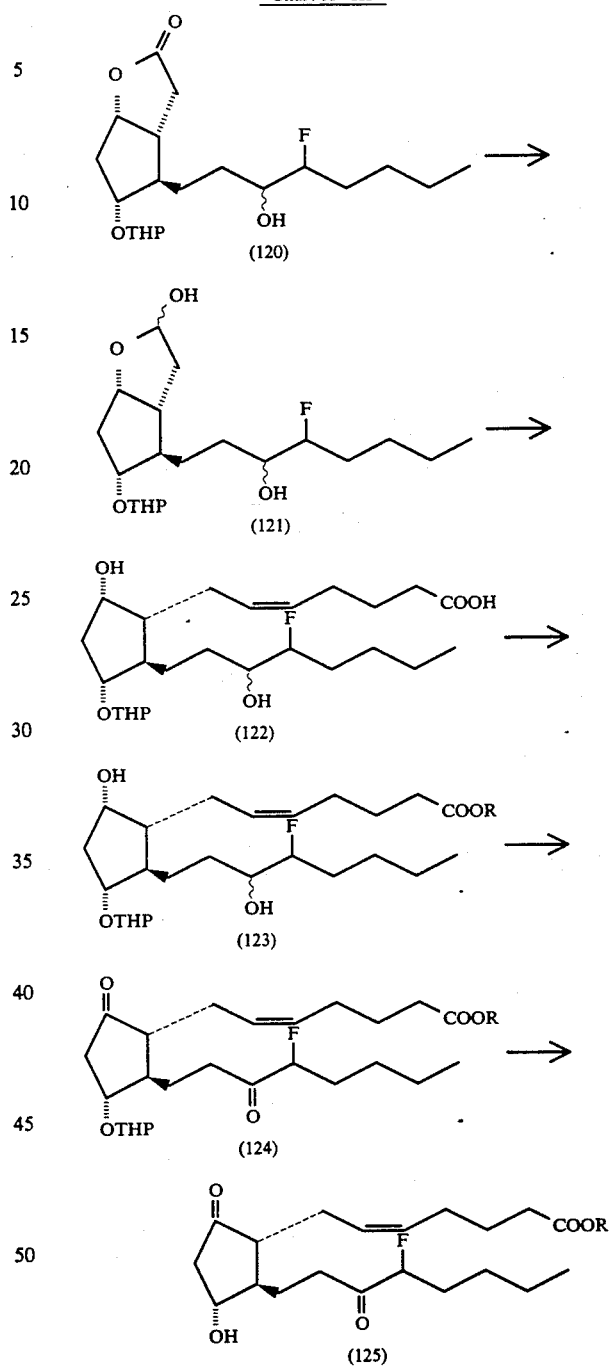
-continued
Chart XVIII

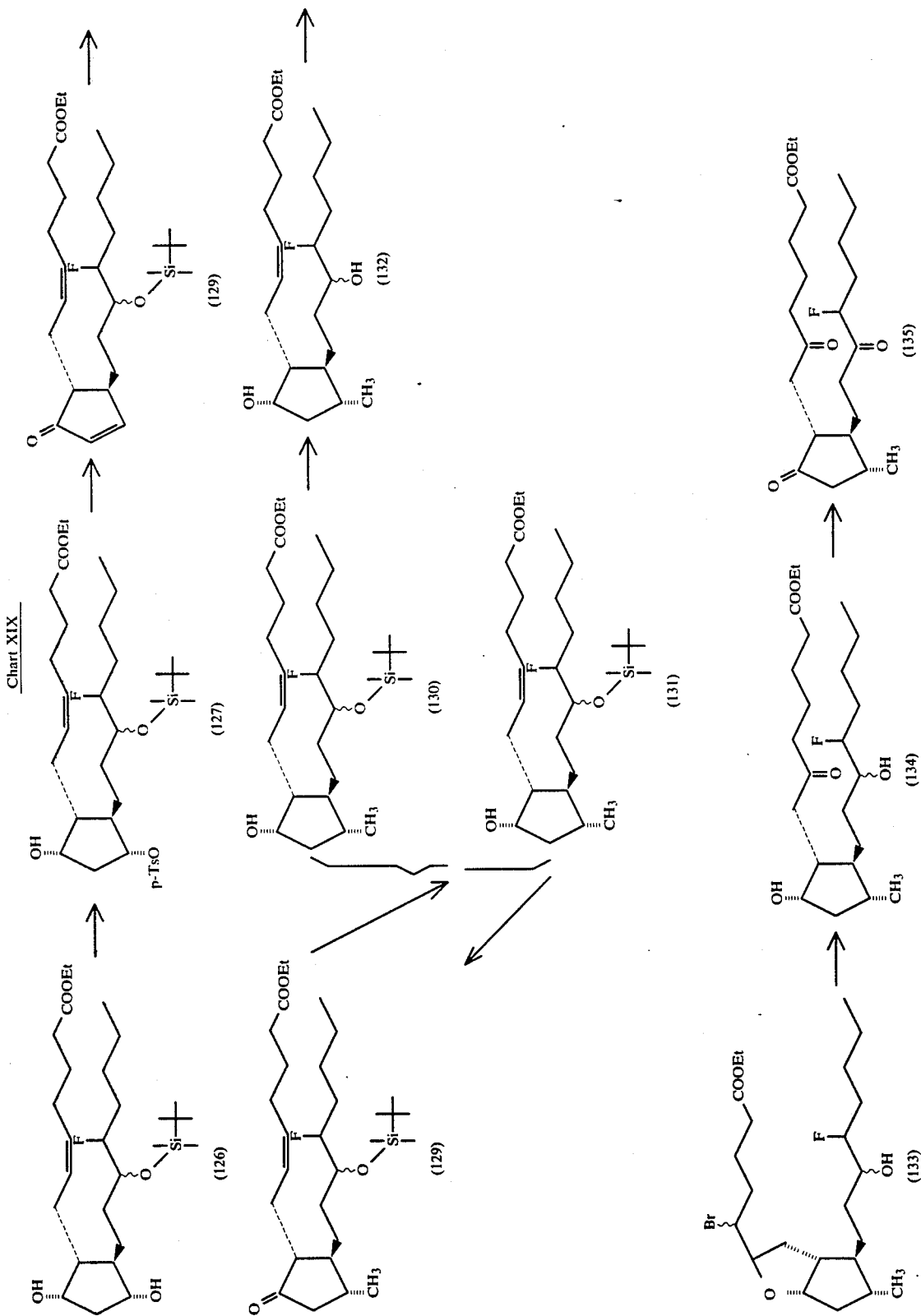

Chart XX
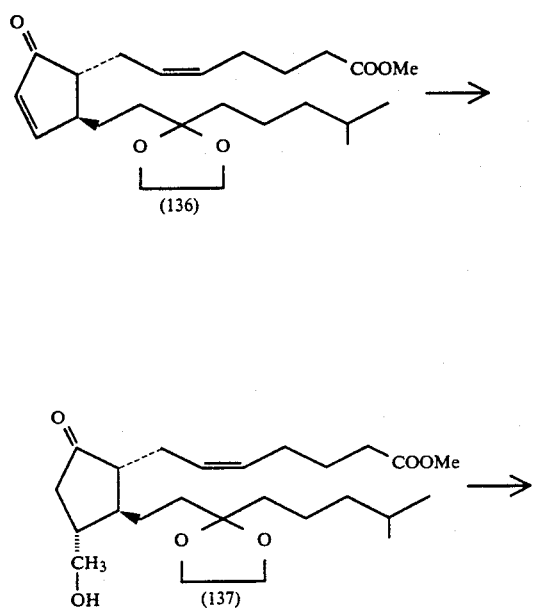
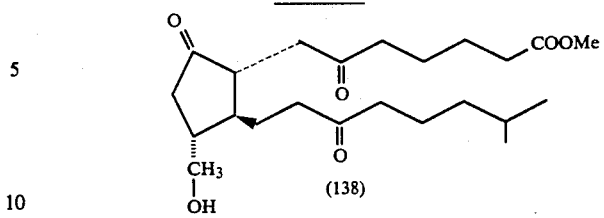
Chart XXI
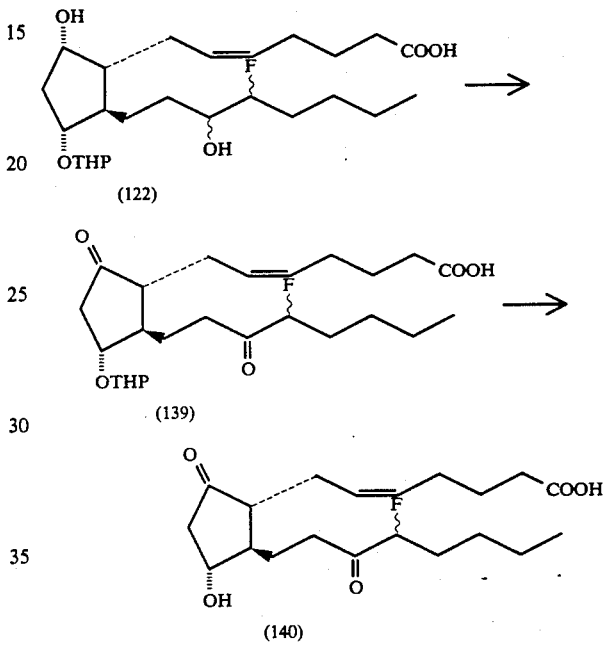

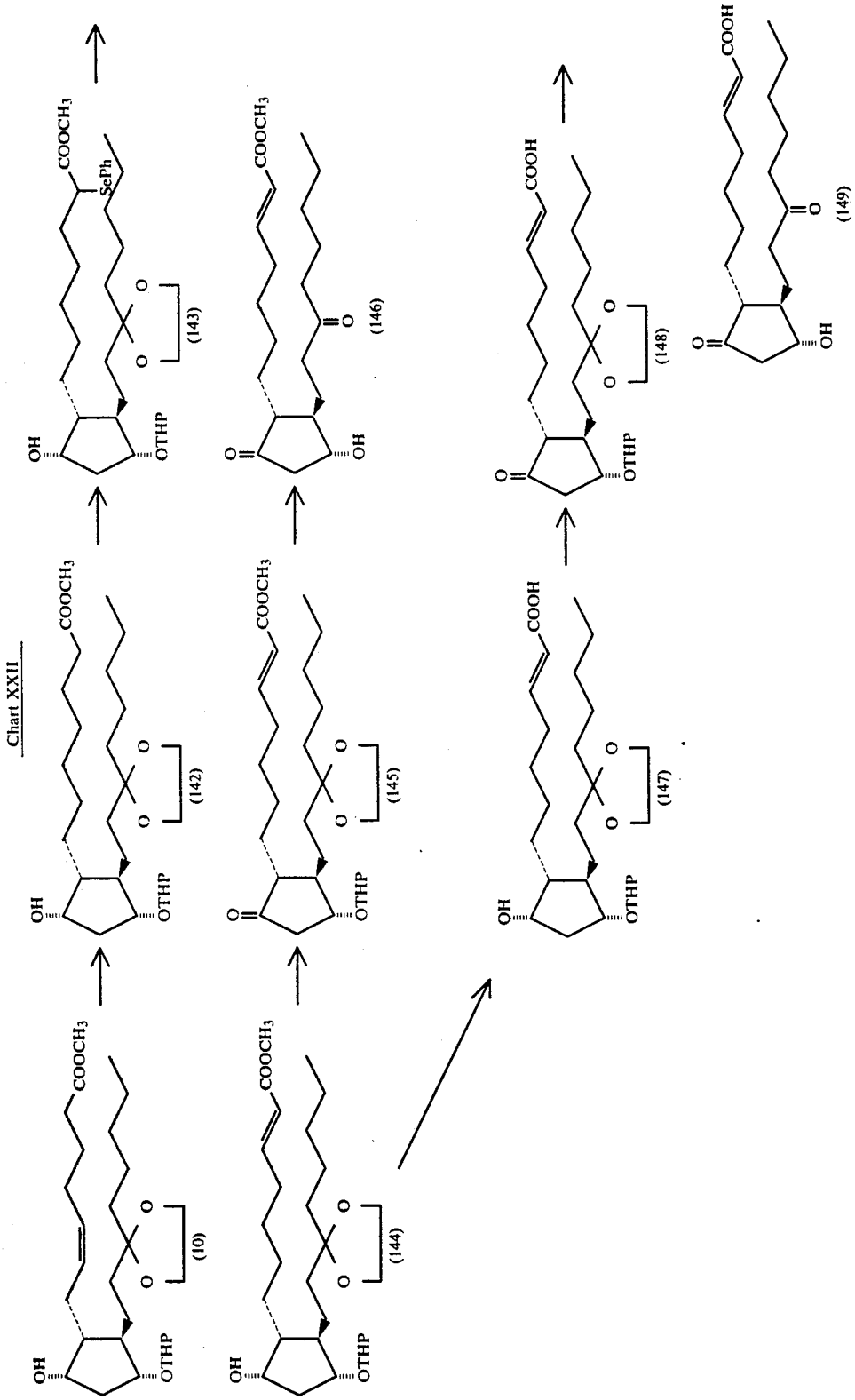

Chart XXIII
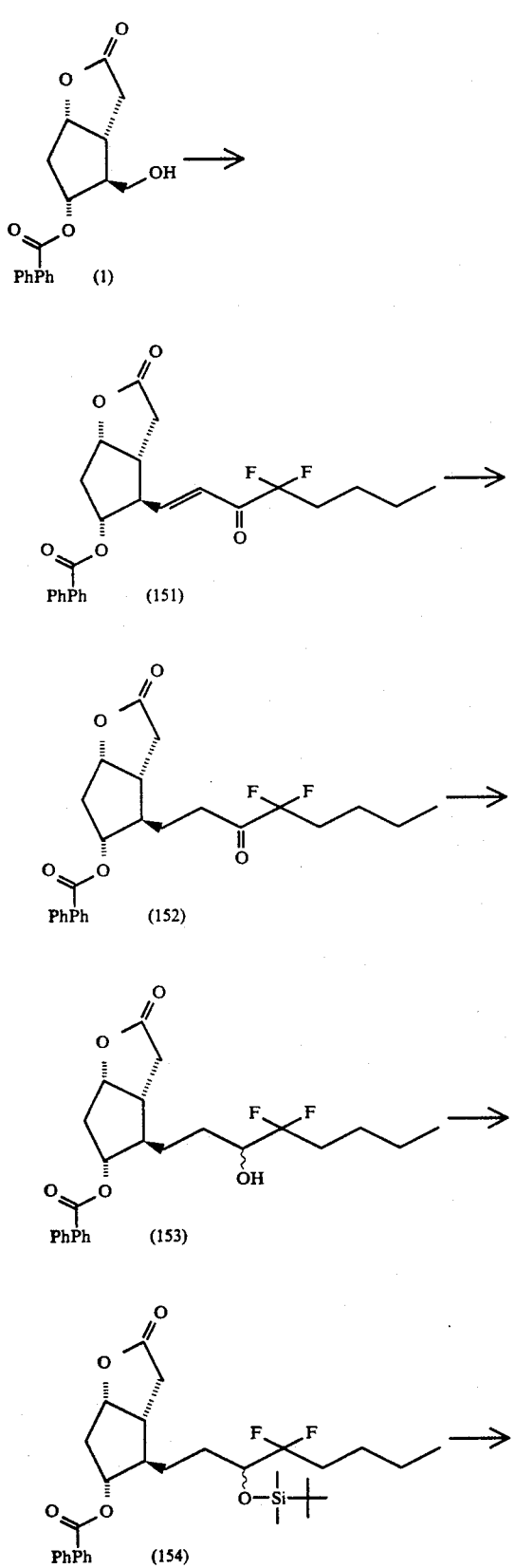
-continued
Chart XXIII
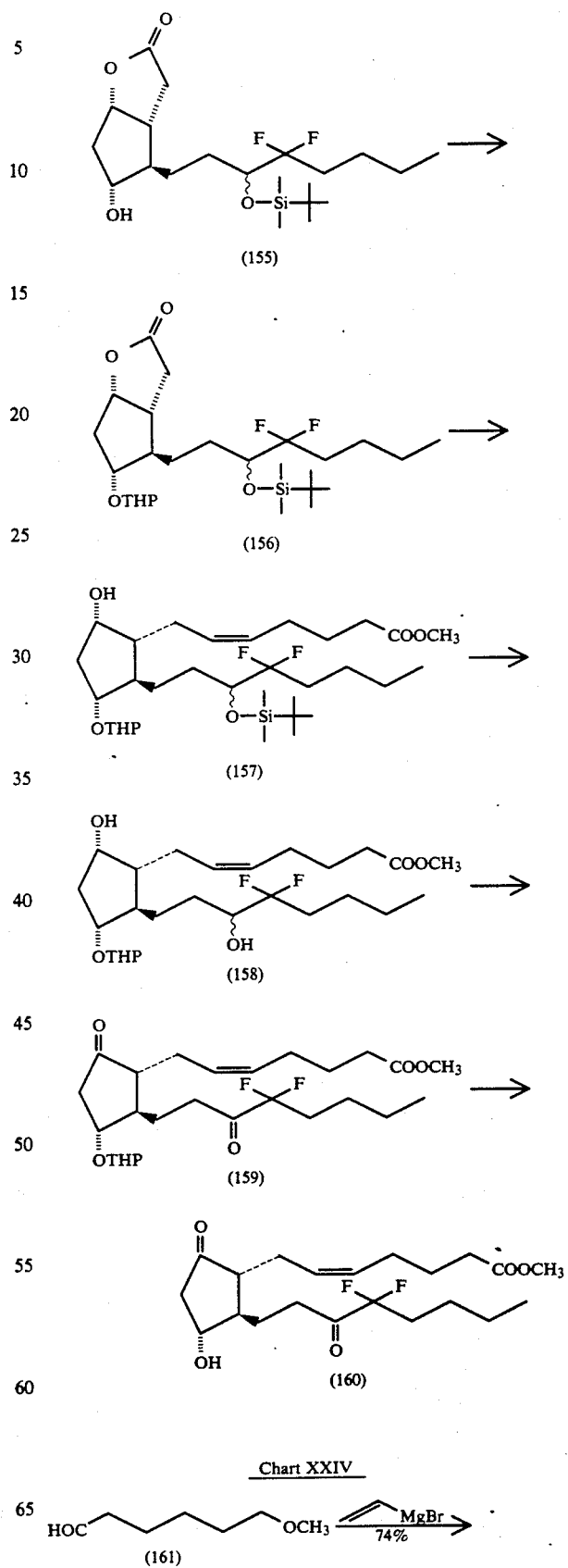
Chart XXIV

-continued
Chart XXIV

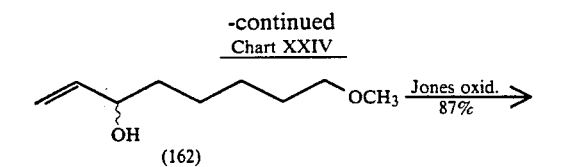
(162)

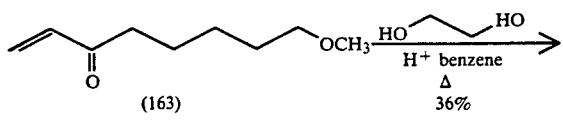
(163)

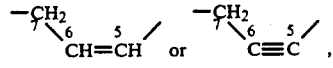
(164)

(165)

(166)

(167)

Chart XXV

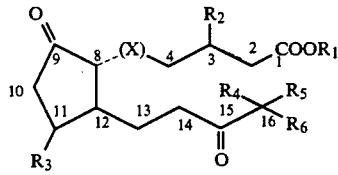
(168)

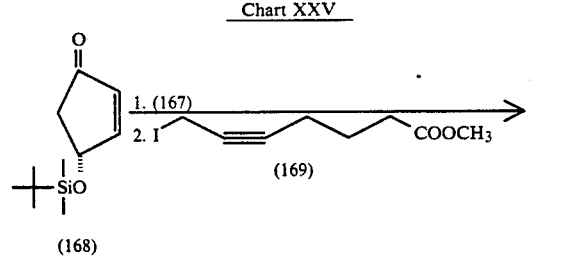
(170)

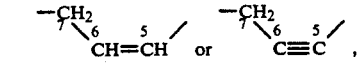

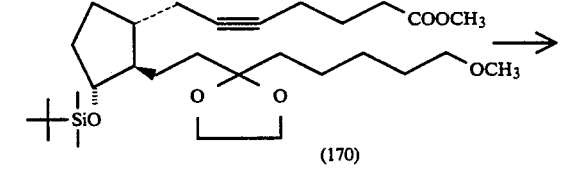
(171)

What is claimed is:
1. Prostaglandins E represented by a general formula:

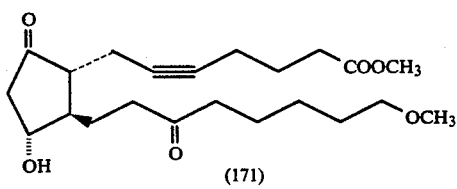

in which
X represents:

$-\underset{7}{C}H_2\underset{6}{\diagdown}\underset{CH=CH}{5}\diagup$ or $-\underset{7}{C}H_2\underset{6}{\diagdown}\underset{C\equiv C}{5}\diagup$, $R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;

$R_2$ represents: a hydrogen atom or a methyl group;
$R_3$ represents: a hydroxyl or hydroxymethyl group;
$R_4$ represents: a hydroxyl group;
$R_5$ represents: a hydrogen atom or a methyl group; and
$R_6$ represents: a $C_1-C_9$ alkyl group which may have a branch or a double bond, or a $C_1-C_9$ alkyl group having an alkoxy substituent group, in which the $C_2-C_3$ bond is a single or a double bond.

2. An anti-ulcer composition comprising an anti-ulcer effective amount of a prostaglandin E represented by a general formula:

(I)

in which
represents:

$-\underset{7}{C}H_2\underset{6}{\diagdown}\underset{CH=CH}{5}\diagup$ or $-\underset{7}{C}H_2\underset{6}{\diagdown}\underset{C\equiv C}{5}\diagup$, $R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;

$R_2$ represents: a hydrogen atom or a methyl group;
$R_3$ represents: a hydroxyl or hydroxymethyl group;
$R_4$ represents: a hydroxyl group;
$R_5$ represents: a hydrogen atom or a methyl group; and
$R_6$ represents: a $C_1-C_9$ alkyl group which may have a branch or a double bond, or a $C_1-C_9$ alkyl group having an alkoxy substituent group, in which the $C_2-C_3$ bond is a single or a double bond.

3. Prostaglandins E represented by a general formula:

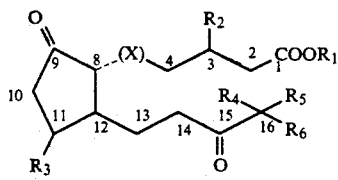
(I)

in which X represents:

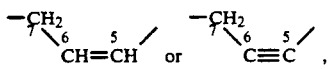

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;
$R_2$ represents: a hydrogen atom or a methyl group;
$R_3$ represents: a hydroxyl or hydroxymethyl group;
$R_4$ represents: a hydrogen atom or a methyl group;
$R_5$ represents: a hydrogen atom or a methyl group; and
$R_6$ represents: a $C_1$–$C_9$ alkyl group having an alkoxy substituent group,
in which the $C_2$–$C_3$ bond is a single or a double bond.

4. Prostaglandins E as described in claim 3, being 13,14-dihydro-15-keto-5,6-dehydro-20-methoxy-$PGE_2$ or alkyl ester thereof.

5. An anti-ulcer composition comprising an anti-ulcer effective amount of a prostaglandin E represented by a general formula:

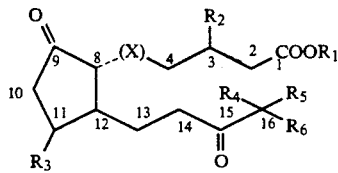
(I)

in which
X represents:

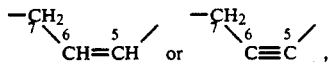

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;
$R_2$ represents: a hydrogen atom or a methyl group;
$R_3$ represents: a hydroxyl or hydroxymethyl group;
$R_4$ represents: a hydrogen atom or a methyl group;
$R_5$ represents: a hydrogen atom or a methyl group; and
$R_6$ represents: a $C_1$–$C_9$ alkyl group having an alkoxy substituent group,
in which the $C_2$–$C_3$ bond is a single or a double bond.

6. An anti-ulcer composition as described in claim 5, wherein the prostaglandin E is 13,14-dihydro-15-keto-5,6-dehydro-20-methoxy-$PGE_2$ or alkyl ester thereof.

7. Prostaglandins E represented by a general formula:

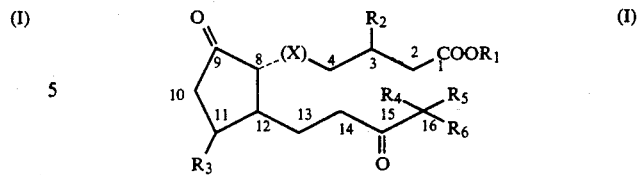
(I)

in which
X represents:

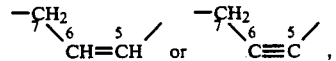

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;
$R_2$ represents: a hydrogen atom or a methyl group;
$R_3$ represents: a hydroxyl or hydroxymethyl group;
$R_4$ represents: a hydrogen atom or a methyl group;
$R_5$ represents: a hydrogen atom or a methyl group; and
$R_6$ represents: a $C_1$–$C_9$ alkyl group which may have a branch or a double bond,
in which the $C_2$—$C_3$ bond is a double bond.

8. Prostaglandins E as described in claim 7, being 13,14-dihydro-15-keto-$\Delta^2$-$PGE_2$ or alkyl ester thereof.

9. An anti-ulcer composition comprising an anti-ulcer effective amount of a prostaglandin E represented by a general formula:

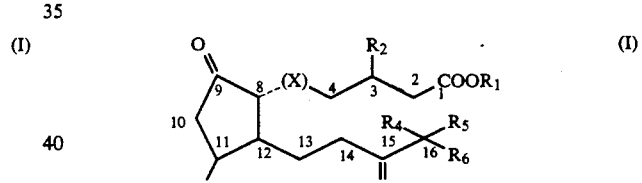
(I)

in which
X represents:

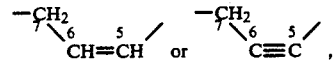

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;
$R_2$ represents: a hydrogen atom or a methyl group;
$R_3$ represents: a hydroxyl or hydroxymethyl group;
$R_4$ represents: a hydrogen atom or a methyl group;
$R_5$ represents: a hydrogen atom or a methyl group; and
$R_6$ represents: a $C_1$–$C_9$ alkyl group which may have a branch or a double bond,
in which the $C_2$–$C_3$ bond is a double bond.

10. An anti-ulcer composition as described in claim 9, wherein the prostaglandin E is 13,14-dihydro-15-keto-$\Delta^2$-$PGE_2$ or alkyl ester thereof.

11. Prostaglandins E represented by a general formula:

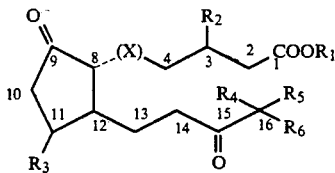

in which
X represents:

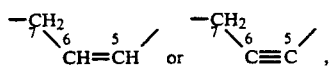

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;

$R_2$ represents: a hydrogen atom or a methyl group;

$R_3$ represents: a hydroxyl or hydroxymethyl group;

$R_4$ represents: a methyl group;

$R_5$ represents: a hydrogen atom or a methyl group; and $R_6$ represents: a $C_1$–$C_9$ alkyl group which may have a branch or a double bond, in which the $C_2$–$C_3$ bond is a single bond.

12. Prostaglandins E as described in claim 11, wherein $R_5$ is a methyl group.

13. Prostaglandins E as described in claim 11, wherein $R_6$ is a $C_6$–$C_9$ alkyl group.

14. Prostaglandins E as described in claim 11, wherein $R_6$ is a hexyl group.

15. Prostaglandins E as described in claim 11, wherein the carboxyl group on the terminal position of the α-chain is esterified with an alkyl group.

16. An anti-ulcer composition comprising an anti-ulcer effective amount of a prostaglandin E represented by a general formula:

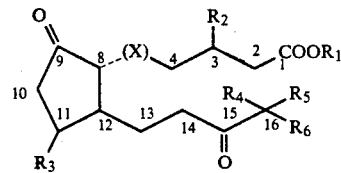

in which
X represents:

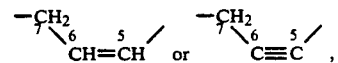

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;

$R_2$ represents: a hydrogen atom or a methyl group;

$R_3$ represents: a hydroxyl or hydroxymethyl group;

$R_4$ represents: a methyl group;

$R_5$ represents: a hydrogen atom or a methyl group; and $R_6$ represents: a $C_1$–$C_9$ alkyl group which may have a branch or a double bond, in which the $C_2$–$C_3$ bond is a single bond.

17. An anti-ulcer composition as described in claim 16, wherein $R_5$ is a methyl group.

18. An anti-ulcer composition as described in claim 16, wherein $R_6$ is a $C_6$–$C_9$ alkyl group.

19. An anti-ulcer composition as described in claim 16, wherein $R_6$ is a hexyl group.

20. An anti-ulcer composition as described in claim 16, wherein the carboxyl group on the terminal position of the α-chain is esterified with an alkyl group.

21. An anti-ulcer composition as described in claim 16, wherein the prosaglandin E is 13,14-dihydro-15-keto-6R,S-methyl-$PGE_2$ alkyl ester.

22. A method of treating an ulcer comprising administering to a patient in need of such treatment an anti-ulcer effective amount of a prostaglandin E represented by a general formula:

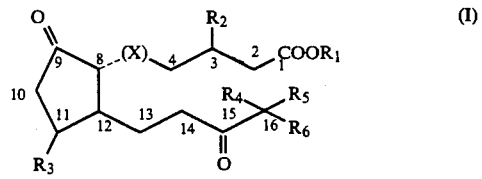

in which
X represents

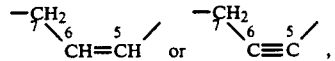

$R_1$ represents: a hydrogen atom, a physiologically acceptable salt residue, or an ester residue selected from the group consisting of alkyl, benzyl, hydroxyalkyl, alkoxyalkyl, alkylsilyl and tetrahydropyranyl group;

$R_2$ represents: a hydrogen atom or a methyl group;

$R_3$ represents: a hydroxyl or hydroxymethyl group;

$R_4$ represents: a hydrogen atom, a methyl group or a hydroxyl group;

$R_5$ represents: a hydrogen atom or a methyl group; and $R_6$ represents: a $C_1$–$C_9$ alkyl group which may have a branch or a double bond, or a $C_1$–$C_9$ alkyl group having an alkoxy substituent group, in which the $C_2$–$C_3$ bond is a single or a double bond; provided that when $R_4$ and $R_5$ are each hydrogen, $R_6$ is a $C_5$–$C_9$ alkyl group which may have a branch or a double bond, or a $C_1$–$C_9$ alkyl group having an alkoxy substituent group.

* * * * *